US012622922B2

(12) United States Patent
Moon et al.

(10) Patent No.: US 12,622,922 B2
(45) Date of Patent: May 12, 2026

(54) COMPOSITIONS AND METHODS FOR METAL CONTAINING FORMULATIONS CAPABLE OF MODULATING IMMUNE RESPONSE

(71) Applicant: The Regents of the University of Michigan, Ann Arbor, MI (US)

(72) Inventors: James J. Moon, Ann Arbor, MI (US); Xiaoqi Sun, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 670 days.

(21) Appl. No.: 17/259,819

(22) PCT Filed: Jul. 12, 2019

(86) PCT No.: PCT/US2019/041659
§ 371 (c)(1),
(2) Date: Jan. 12, 2021

(87) PCT Pub. No.: WO2020/014644
PCT Pub. Date: Jan. 16, 2020

(65) Prior Publication Data

US 2022/0072023 A1 Mar. 10, 2022

Related U.S. Application Data

(60) Provisional application No. 62/697,092, filed on Jul. 12, 2018.

(51) Int. Cl.

| | |
|---|---|
| ***A61K 31/7084*** | (2006.01) |
| ***A61K 9/1271*** | (2025.01) |
| ***A61K 9/16*** | (2006.01) |
| ***A61K 31/167*** | (2006.01) |
| ***A61K 31/192*** | (2006.01) |

(Continued)

(52) U.S. Cl.

CPC ........ *A61K 31/7084* (2013.01); *A61K 9/1271* (2013.01); *A61K 9/1611* (2013.01); *A61K 9/1641* (2013.01); *A61K 31/167* (2013.01); *A61K 31/192* (2013.01); *A61K 31/196* (2013.01); *A61K 31/198* (2013.01); *A61K 31/353* (2013.01); *A61K 31/366* (2013.01); *A61K 31/395* (2013.01); *A61K 31/409* (2013.01); *A61K 31/42* (2013.01); *A61K 31/4745* (2013.01); *A61K 31/519* (2013.01); *A61K 31/52* (2013.01); *A61K 31/5415* (2013.01); *A61K 31/573* (2013.01); *A61K 31/655* (2013.01); *A61K 31/7034* (2013.01); *A61K 31/7048* (2013.01); *A61K 31/7068* (2013.01); *A61K 33/242* (2019.01); *A61K 38/2006* (2013.01); *A61K 39/00* (2013.01); *A61K 39/0008* (2013.01); *A61K 39/001106* (2018.08); *A61K 39/001109* (2018.08); *A61K 39/001156* (2018.08); *A61K 39/001157* (2018.08); *A61K 39/00116* (2018.08); *A61K 39/001182* (2018.08); *A61K 39/001184* (2018.08); *A61K 39/001186* (2018.08); *A61K 39/001197* (2018.08); *A61K 39/001198* (2018.08); *A61K 39/39* (2013.01); *A61K 39/3955* (2013.01); *A61K 47/6915* (2017.08); *A61P 37/06* (2018.01); *A61K 2039/55505* (2013.01); *A61K 2039/55511* (2013.01); *A61K 2039/55516* (2013.01); *A61K 2039/55522* (2013.01); *A61K 2039/55533* (2013.01); *A61K 2039/55544* (2013.01); *A61K 2039/55555* (2013.01); *A61K 2039/55561* (2013.01); *A61K 2039/55572* (2013.01); *A61K 2039/55577* (2013.01); *A61K 2039/55583* (2013.01); *A61K 2039/60* (2013.01)

(58) Field of Classification Search
None
See application file for complete search history.

(56) References Cited

U.S. PATENT DOCUMENTS

| | | | |
|---|---|---|---|
| 4,588,585 | A | 5/1986 | Mark et al. |
| 4,656,127 | A | 4/1987 | Mundy |

(Continued)

FOREIGN PATENT DOCUMENTS

| | | |
|---|---|---|
| CN | 103998058 | 8/2014 |
| CN | 105848649 | 8/2016 |

(Continued)

OTHER PUBLICATIONS

Abellan-Pose, Raquel, et al. "Polyaminoacid nanocapsules for drug delivery to the lymphatic system: Effect of the particle size." International Journal of Pharmaceutics 509.1-2 (2016): 107-117. (Year: 2016).*

(Continued)

*Primary Examiner* — Bethany P Barham
*Assistant Examiner* — Peter Anthopolos
(74) *Attorney, Agent, or Firm* — Casimir Jones, S.C.; Robert A. Goetz

(57) ABSTRACT

This disclosure provides compositions and methods for stimulating the innate immune response in a subject with agents capable of stimulating an innate immune response in a subject upon administration to the subject (e.g., damage-associated molecular patterns (DAMPs) and pathogen-associated molecular patterns (PAMPs)). In particular, the present invention is directed to compositions of DAMPs/PAMPs and metals ions, as well as systems and methods utilizing such nanoparticles (e.g., in diagnostic and/or therapeutic settings).

19 Claims, 38 Drawing Sheets

Specification includes a Sequence Listing.

(51) Int. Cl.

| | |
|---|---|
| *A61K 31/196* | (2006.01) |
| *A61K 31/198* | (2006.01) |
| *A61K 31/353* | (2006.01) |
| *A61K 31/366* | (2006.01) |
| *A61K 31/395* | (2006.01) |
| *A61K 31/409* | (2006.01) |
| *A61K 31/42* | (2006.01) |
| *A61K 31/4745* | (2006.01) |
| *A61K 31/519* | (2006.01) |
| *A61K 31/52* | (2006.01) |
| *A61K 31/5415* | (2006.01) |
| *A61K 31/573* | (2006.01) |
| *A61K 31/655* | (2006.01) |
| *A61K 31/7034* | (2006.01) |
| *A61K 31/7048* | (2006.01) |
| *A61K 31/7068* | (2006.01) |
| *A61K 33/242* | (2019.01) |
| *A61K 38/20* | (2006.01) |
| *A61K 39/00* | (2006.01) |
| *A61K 39/39* | (2006.01) |
| *A61K 39/395* | (2006.01) |
| *A61K 47/69* | (2017.01) |
| *A61P 37/02* | (2006.01) |
| *A61P 37/04* | (2006.01) |
| *A61P 37/06* | (2006.01) |

(56) References Cited

U.S. PATENT DOCUMENTS

| | | | | |
|---|---|---|---|---|
| 5,252,327 | A * | 10/1993 | Bernhardt | A61K 33/26 424/229.1 |
| 5,354,308 | A | 10/1994 | Simon et al. | |
| 5,466,680 | A * | 11/1995 | Rudy | A61K 33/14 514/921 |
| 5,674,192 | A | 10/1997 | Sahatjian et al. | |
| 5,693,014 | A | 12/1997 | Abele et al. | |
| 5,733,303 | A | 3/1998 | Israel et al. | |
| 5,755,722 | A | 5/1998 | Barry et al. | |
| 5,792,105 | A | 8/1998 | Lin et al. | |
| 5,800,391 | A | 9/1998 | Kontos | |
| 5,800,508 | A | 9/1998 | Goicoechea et al. | |
| 5,800,519 | A | 9/1998 | Sandock | |
| 5,843,089 | A | 12/1998 | Sahatjian et al. | |
| 5,849,589 | A | 12/1998 | Tedder et al. | |
| 5,851,228 | A | 12/1998 | Pinheiro | |
| 5,857,998 | A | 1/1999 | Barry | |
| 5,866,561 | A | 2/1999 | Ungs | |
| 5,868,719 | A | 2/1999 | Tsukernik | |
| 5,876,445 | A | 3/1999 | Andersen et al. | |
| 5,885,613 | A | 3/1999 | Holland et al. | |
| 5,895,653 | A * | 4/1999 | Eibl | A61K 39/39 424/282.1 |
| 5,908,413 | A | 6/1999 | Lange et al. | |
| 5,913,894 | A | 6/1999 | Schmitt | |
| 5,933,145 | A | 8/1999 | Meek | |
| 5,935,114 | A | 8/1999 | Jang et al. | |
| 6,406,705 | B1 * | 6/2002 | Davis | A61K 39/12 424/282.1 |
| 6,743,778 | B2 | 6/2004 | Kohno | |
| 6,774,180 | B2 | 8/2004 | Kozlowski et al. | |
| 7,053,150 | B2 | 5/2006 | Kozlowski et al. | |
| 7,283,337 | B2 | 10/2007 | Sakai et al. | |
| 7,566,695 | B2 | 7/2009 | Dasseux et al. | |
| 7,592,326 | B2 | 9/2009 | Karaolis | |
| 7,709,458 | B2 | 5/2010 | Karaolis et al. | |
| 2002/0009457 | A1 * | 1/2002 | Bowersock | A61K 39/39 264/4.1 |
| 2003/0077829 | A1 | 4/2003 | Maclachlan | |
| 2003/0171277 | A1 | 9/2003 | Fogelman et al. | |
| 2004/0131643 | A1 * | 7/2004 | Grewal | A61K 39/107 424/643 |
| 2004/0131650 | A1 * | 7/2004 | Trouve | A61K 9/0019 424/401 |
| 2005/0008689 | A1 | 1/2005 | Semple et al. | |
| 2006/0069030 | A1 | 3/2006 | Bachovchin | |
| 2006/0252077 | A1 | 11/2006 | Buzby | |
| 2009/0081293 | A1 | 3/2009 | Murase et al. | |
| 2011/0046056 | A1 | 2/2011 | Bianchi et al. | |
| 2013/0231459 | A1 | 9/2013 | Dasseux et al. | |
| 2014/0205653 | A1 | 7/2014 | Dubensky, Jr. et al. | |
| 2015/0056224 | A1 | 2/2015 | Dubensky, Jr. et al. | |
| 2015/0238599 | A1 * | 8/2015 | Choi | A61K 33/04 424/278.1 |
| 2016/0074507 | A1 | 3/2016 | Manel et al. | |
| 2016/0287623 | A1 | 10/2016 | Gajewski et al. | |
| 2016/0346204 | A1 | 12/2016 | Lin et al. | |
| 2017/0037400 | A1 | 2/2017 | Barber | |
| 2018/0117171 | A1 | 5/2018 | Mooney et al. | |
| 2019/0269706 | A1 | 9/2019 | Lin et al. | |
| 2020/0254095 | A1 | 8/2020 | Lin et al. | |

FOREIGN PATENT DOCUMENTS

| | | | |
|---|---|---|---|
| CN | 107823653 | 3/2018 | |
| EP | 0412883 | 11/1996 | |
| JP | 2010-530013 | 9/2010 | |
| WO | WO 1991/02087 | 2/1991 | |
| WO | WO 1992/15712 | 9/1992 | |
| WO | WO 2005/026372 | 3/2005 | |
| WO | WO 2007/054279 | 5/2007 | |
| WO | WO 2008/151150 | 12/2008 | |
| WO | WO 2013185052 | 12/2013 | |
| WO | WO 2014179335 | 11/2014 | |
| WO | WO 2015161762 | 10/2015 | |
| WO | WO 2016096577 | 6/2016 | |
| WO | WO 2016100261 | 6/2016 | |
| WO | WO-2016154544 A1 * | 9/2016 | A61K 31/7088 |
| WO | WO 2016201450 | 12/2016 | |
| WO | WO 2017011622 | 1/2017 | |
| WO | WO 2017011920 | 1/2017 | |
| WO | WO 2017027646 | 2/2017 | |
| WO | WO 2021/237209 | 11/2021 | |

OTHER PUBLICATIONS

Kaminskas, Lisa M., et al. "PEGylation of polylysine dendrimers improves absorption and lymphatic targeting following SC administration in rats." Journal of Controlled Release 140.2 (2009): 108-116. (Year: 2009).*

Hanson, Melissa C., et al. "Nanoparticulate STING agonists are potent lymph node-targeted vaccine adjuvants." The Journal of clinical investigation 125.6 (2015): 2532-2546 and S1-S4. (Year: 2015).*

Wang, Chenguang, et al. "Manganese increases the sensitivity of the cGAS-STING pathway for double-stranded DNA and is required for the host defense against DNA viruses." Immunity 48.4 (Apr. 17, 2018): 675-687. (Year: 2018).*

Kim, C. K., and J. H. Han. "Lymphatic delivery and pharmacokinetics of methotrexate after intramuscular injection of differently charged liposome-entrapped methotrexate to rats." Journal of Microencapsulation 12.4 (1995): 437-446. (Year: 1995).*

Wu, Hong, Lin Zhu, and Vladimir P. Torchilin. "pH-sensitive poly (histidine)-PEG/DSPE-PEG co-polymer micelles for cytosolic drug delivery." Biomaterials 34.4 (2013): 1213-1222. (Year: 2013).*

Putnam, David, et al. "Polyhistidine—PEG: DNA nanocomposites for gene delivery." Biomaterials 24.24 (2003): 4425-4433. (Year: 2003).*

Lee, Eun Seong, et al. "Poly (I-histidine)—PEG block copolymer micelles and pH-induced destabilization." Journal of Controlled Release 90.3 (2003): 363-374. (Year: 2003).*

Khan, Arshad Ali, et al. "Advanced drug delivery to the lymphatic system: lipid-based nanoformulations." International journal of nanomedicine (2013): 2733-2744. (Year: 2013).*

Chaigne-Delalande, Benjamin, and Michael J. Lenardo. "Divalent cation signaling in immune cells." Trends in immunology 35.7 (2014): 332-344. (Year: 2014).*

(56) References Cited

OTHER PUBLICATIONS

Iwasaki, Takashi, et al. "Cellular uptake and in vivo distribution of polyhistidine peptides." Journal of Controlled Release 210 (2015): 115-124. (Year: 2015).*
Zhang, Lei, et al. "Histidine-rich cell-penetrating peptide for cancer drug delivery and its uptake mechanism." Langmuir 35.9 (Jan. 23, 2019): 3513-3523. (Year: 2019).*
Abdelaziz, H. M., et al. "Poly (Amino Acid) Nanoparticles as a Promising Tool for Anticancer Therapeutics." Polymeric Nanoparticles as a Promising Tool for Anti-cancer Therapeutics. Academic Press, 2019. 167-204. (Year: 2019).*
Allison. The mode of action of immunological adjuvants. Dev Biol Stand. 1998;92:3-11.
Aroh et al., Innate Immune Activation by cGMP-AMP Nanoparticles Leads to Potent and Long-Acting Antiretroviral Response against HIV-1. J Immunol. Dec. 1, 2017;199(11):3840-3848.
Ashokan et al., Multifunctional calcium phosphate nano-contrast agent for combined nuclear, magnetic and near-infrared in vivo imaging. Biomaterials. Sep. 2013;34(29):7143-57.
Barany & Merrifield, The Peptides, Gross & Meienhofer, eds. (N.Y., Academic Press), (1979) TOC only. 17 pages.
Bergmann et al., An endogenously synthesized decamer peptide efficiently primes cytotoxic T cells specific for the HIV-1 envelope glycoprotein. Eur J Immunol. Nov. 1993;23(11):2777-81.
Bergmann et al., Flanking residues alter antigenicity and immunogenicity of multi-unit CTL epitopes. J Immunol. Oct. 15, 1996;157(8):3242-9.
Bonifaz et al., Efficient targeting of protein antigen to the dendritic cell receptor DEC-205 in the steady state leads to antigen presentation on major histocompatibility complex class I products and peripheral CD8+ T cell tolerance. J Exp Med. Dec. 16, 2002;196(12):1627-38.
Bonifaz et al., In vivo targeting of antigens to maturing dendritic cells via the DEC-205 receptor improves T cell vaccination. J Exp Med. Mar. 15, 2004;199(6):815-24.
Brunsvig et al., Telomerase peptide vaccination: a phase I/II study in patients with non-small cell lung cancer. Cancer Immunol Immunother. Dec. 2006;55(12):1553-64.
Campani et al. Lipid-based core-shell nanoparticles: Evolution and potentialities in drug delivery. Opennano, vol. 3, Dec. 11, 2017, pp. 5-17.
Conlon et al., Mouse, but not human STING, binds and signals in response to the vascular disrupting agent 5,6-dimethylxanthenone-4-acetic acid. J Immunol. May 15, 2013;190(10):5216-25.
Dupuis et al., Dendritic cells internalize vaccine adjuvant after intramuscular injection. Cell Immunol. May 25, 1998;186(1):18-27.
El-Hariri et al., The mitigating effects of phosphatidylcholines on bile salt- and lysophosphatidylcholine-induced membrane damage. J Pharm Pharmacol. Aug. 1992;44(8):651-4.
EP Search Report, EP Patent Application No. 19833966.5, dated Mar. 10, 2022, 4 pages.
Gabrilovich et al., IL-12 and mutant P53 peptide-pulsed dendritic cells for the specific immunotherapy of cancer. J Immunother Emphasis Tumor Immunol. Nov. 1996;19(6):414-8.
Gevaert et al., Protein identification methods in proteomics. Electrophoresis. Apr. 2000;21(6):1145-54.
Gluzman. SV40-transformed simian cells support the replication of early SV40 mutants. Cell. Jan. 1981;23(1):175-82.
Goodwin et al., Investigation of phosphorylated adjuvants co-encapsulated with a model cancer peptide antigen for the treatment of colorectal cancer and liver metastasis. Vaccine. May 2, 2017;35(19):2550-2557.
Guthals et al., Shotgun protein sequencing with meta-contig assembly. Mol Cell Proteomics. Oct. 2012;11(10):1084-96.
Hadrup et al., Parallel detection of antigen-specific T-cell responses by multidimensional encoding of MHC multimers. Nat Methods. Jul. 2009;6(7):520-6.
Hawiger et al., Dendritic cells induce peripheral T cell unresponsiveness under steady state conditions in vivo. J Exp Med. Sep. 17, 2001;194(6):769-79.
Heemskerk et al., The cancer antigenome. EMBO J. Jan. 23, 2013;32(2):194-203.
Hombrink et al., High-throughput identification of potential minor histocompatibility antigens by MHC tetramer-based screening: feasibility and limitations. PLoS One. 2011;6(8):e22523. 1-11.
Honda et al., Actinin-4, a novel actin-bundling protein associated with cell motility and cancer invasion. J Cell Biol. Mar. 23, 1998;140(6):1383-93.
Huang et al., Preparation and Biocompatibility Evaluation of PEG-PLL/RGD-PEG-DSPE/Phospholipid/CaP Nanoparticles. J Biomed Nanotechnol. Jan. 1, 2018;14(1):98-113.
International Search Report & Written Opinion, International Patent Application No. PCT/US2019/041659, dated Nov. 13, 2019, 15 pages.
Kang et al., Necroptotic cancer cells-mimicry nanovaccine boosts anti-tumor immunity with tailored immune-stimulatory modality. Biomaterials. May 2018;164:80-97.
Kim et al., Anticancer flavonoids are mouse-selective STING agonists. ACS Chem Biol. Jul. 19, 2013;8(7):1396-401.
Knuschke et al., Immunization with biodegradable nanoparticles efficiently induces cellular immunity and protects against influenza virus infection. J Immunol. Jun. 15, 2013;190(12):6221-9.
Kornher et al., Mutation detection using nucleotide analogs that alter electrophoretic mobility. Nucleic Acids Res. Oct. 11, 1989;17(19):7779-84.
Krieg. Therapeutic potential of Toll-like receptor 9 activation. Nat Rev Drug Discov. Jun. 2006;5(6):471-84.
Kuppuswamy et al., Single nucleotide primer extension to detect genetic diseases: experimental application to hemophilia B (factor IX) and cystic fibrosis genes. Proc Natl Acad Sci USA, 1991; 88(4): 1143-1147.
Lee et al., Critical Reviews in Therapeutic Drug Carrier Systems, 1991, p. 1-105.
Luckow et al., Trends in the Development of Baculovirus Expression Vectors. Bio/Technology. 1988;6:47-55.
Mark et al., Site-specific mutagenesis of the human fibroblast interferon gene. Proc Natl Acad Sci U S A. Sep. 1984;81(18):5662-6.
Merrifield. Solid Phase Peptide Synthesis. I. The Synthesis of a Tetrapeptide. J. Am. Chem. Soc. 1963, 85, 14, 2149-2154.
Merrifield. Solid phase synthesis. Science. Apr. 18, 1986;232(4748):341-7.
Mi et al. "PEGlyated polyanion hybrid calcium phosphate micellar MRI probe for in vivo noninvasive solid tumor diagnosis" Proceedings of the 16th International Symposium on Recent Advances in Drug Delivery. Drug Delivery: The Penetrating Challenges, article P51, 2013, pp. 179-180.
Muranshi. Absorption enhancers. Crit Rev Ther Drug Carrier Syst. 1990;7(1):1-33.
Nyren et al., Solid phase DNA minisequencing by an enzymatic luminometric inorganic pyrophosphate detection assay. Anal Biochem. Jan. 1993;208(1):171-5.
Prezant et al., Trapped-oligonucleotide nucleotide incorporation (TONI) assay, a simple method for screening point mutations. Hum Mutat. 1992;1(2):159-64.
Reddy et al., Apolipoprotein A-I mimetics. Curr Opin Lipidol. Aug. 2014;25(4):304-8.
Sokolov. Primer extension technique for the detection of single nucleotide in genomic DNA. Nucleic Acids Res. Jun. 25, 1990;18(12):3671.
Staehler et al., Correlation of T-cell response, clinical activity and regulatory T-cell levels in renal cell carcinoma patietns treated with IMA901, a novel multipeptide vaccine. ASCO meeting 2007; Abstract No. 3017. Journal of Clincal Oncology. 2007; 25(18): 3017.
Stahl-Hennig et al., Synthetic double-stranded RNAs are adjuvants for the induction of T helper 1 and humoral immune responses to human papillomavirus in rhesus macaques. PLoS Pathog. Apr. 2009;5(4):e1000373. 1-15.
Stewart & Young, Solid Phase Peptide Synthesis, (Rockford, Ill., Pierce), 2d Ed. 1984. TOC only. 8 pages.
Suhrbier. Multi-epitope DNA vaccines. Immunol Cell Biol. Aug. 1997;75(4):402-8.

(56) References Cited

OTHER PUBLICATIONS

Syvanen et al., A primer-guided nucleotide incorporation assay in the genotyping of apolipoprotein E. Genomics. Dec. 1990;8(4):684-92.
Syvanen et al., Identification of individuals by analysis of biallelic DNA markers, using PCR and solid-phase minisequencing. Am J Hum Genet. Jan. 1993;52(1):46-59.
Tang et al., Effect of size and pegylation of liposomes and peptide-based synthetic lipoproteins on tumor targeting. Nanomedicine. Aug. 2017;13(6):1869-1878.
Ugozzoli et al., Detection of specific alleles by using allele-specific primer extension followed by capture on solid support. Genet Anal Tech Appl. Aug. 1992;9(4):107-12.
Van Rooij et al., Tumor exome analysis reveals neoantigen-specific T-cell reactivity in an ipilimumab-responsive melanoma. J Clin Oncol. Nov. 10, 2013;31(32):e439-42.
Wang et al., Manganese Increases the Sensitivity of the cGAS-STING Pathway for Double-Stranded DNA and Is Required for the Host Defense against DNA Viruses. Immunity. Apr. 17, 2018;48(4):675-687.e7.
Yan et al., Synthesis and immunostimulatory properties of the phosphorothioate analogues of cdiGMP. Bioorg Med Chem Lett. Oct. 15, 2008;18(20):5631-4.
Koshy, S. et al. Liposomal Delivery Enhances Immune Activation by STING Agonists for Cancer Immunotherapy, Adv Biosyst . Feb. 2017; 1(1-2):1600013. doi: 10.1002/adbi.201600013.
Dulbecco, R. and Vogt, M. Plaque formation and isolation of pure lines with poliomyelitis viruses, J Exp Med. Feb. 1954; 99(2): 167-82.
Ziady et al., "Transfection of Airway Epithelium by Stable PEGylated Poly-L-lysine DNA Nanoparticles in Vivo", Molecular Therapy vol. 8, No. 6, Dec. 2003, pp. 936-947, DOI: 10.1016/j.ymthe.2003.07.007.

* cited by examiner

CDN-Zn@ liposome

CDN@ CaP/PEI-PEG

C

D

FIG. 15B-F
b
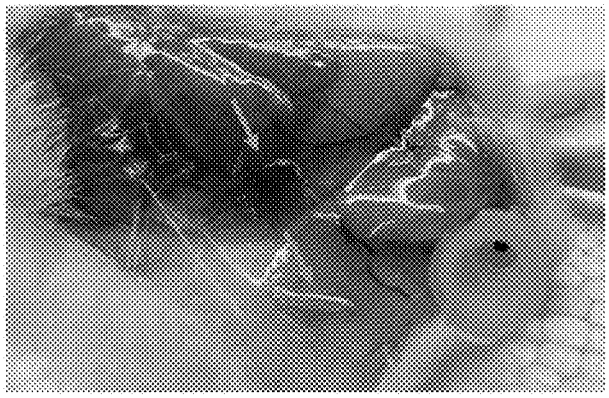
Trypan Blue@4aH11-Co hydrogel
(6h after injection)
c Control (0/5)
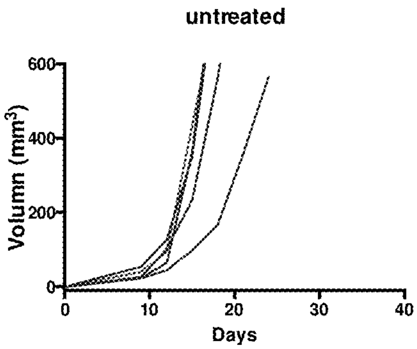
d Free CDA (2/5)
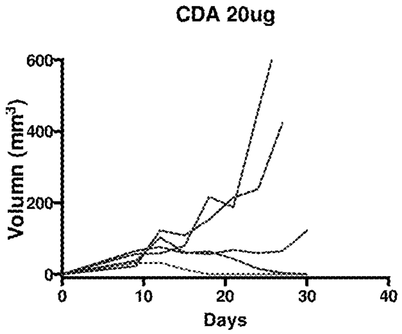
e CDA@4aH11-Co hydrogel (3/5)
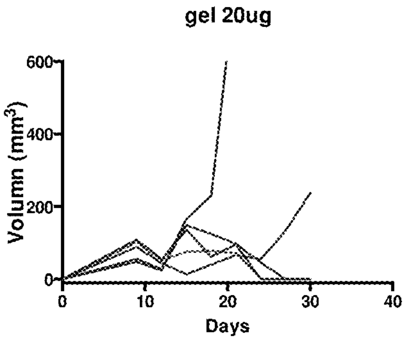
f
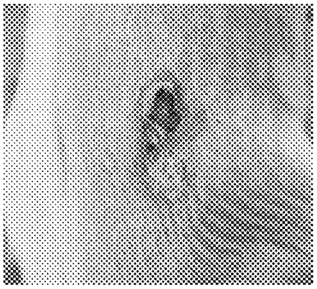
Representative tumor picture after
Treatment with CDA@4a H11-Co hydrogel)

CDN concentration (ug/ml)

CDN concentration (ug/ml)

DSG-NTA (−)-Catechin (CH)

(−)-Catechin gallate (CG)

(−)-Epigallo CG(EGCG)

Punicalagin (PC)

Tannic acid (TA)

Punicalin

Vescalagin

Procyanidin C1

Geraniin

Theaflavin 3,3'-digallate

COMPOSITIONS AND METHODS FOR METAL CONTAINING FORMULATIONS CAPABLE OF MODULATING IMMUNE RESPONSE

CROSS REFERENCE TO RELATED APPLICATIONS

The application is a national stage of International (PCT) Patent Application Serial No. PCT/US2019/041659, filed Jul. 12, 2019, which claims priority to U.S. Provisional Patent Application 62/697,092, filed Jul. 12, 2018 the entire contents of which are incorporated herein by reference.

STATEMENT REGARDING FEDERALLY SPONSORED RESEARCH OR DEVELOPMENT

This invention was made with government support under CA210273 awarded by the National Institutes of Health. The government has certain rights in the invention.

FIELD OF THE INVENTION

This disclosure provides compositions and methods for stimulating the innate immune response in a subject with agents capable of stimulating an innate immune response in a subject upon administration to the subject (e.g., damage-associated molecular patterns (DAMPs) and pathogen-associated molecular patterns (PAMPs)). In particular, the present invention is directed to compositions of DAMPs/PAMPs and metals ions, as well as systems and methods utilizing such nanoparticles (e.g., in diagnostic and/or therapeutic settings).

BACKGROUND OF THE INVENTION

The innate immune system is humans' first line of defense, and activation of which can induce pro-inflammation cytokines secretion and orchestrate adaptive immune systems. DAMPs and PAMPs represent two major innate immune stimulators. DAMPs are endogenous host biomolecules released upon tissue damage and include heat-shock proteins and HMGB1 (high-mobility group box 1), ATP, uric acid, hyaluronan fragments, heparin sulfate and tumor-derived DNA. PAMPs are conserved pathogen components recognized by various pathogen recognition receptors (PRRs) and induce anti-pathogen inflammation. PAMPs include ligands of Toll-Like receptors (TLRs), NOD-Like receptors (NLRs), RIG-I-Like receptors (RLRs), cytosolic DNA sensors (CDS), stimulator of IFN genes (STING) agonists, purine containing or purine derived agents, and C-type lectin receptors (CLRs).

DAMPs and PAMPs can induce pro-inflammatory cytokines production and immune cell pro-inflammation phenotypic change, which are critical for both cancer and autoimmune disease. On one hand, the pro-inflammation phenotypic change could break the immune-suppressive tumor microenvironment, tuning "cold tumor" to "hot tumor". Therefore, TLR-3, TLR4, TLR7, TLR9, NLRP3 and STING agonists are currently in clinical trials for cancer immunotherapy. Especially, tumor-derived DNA-cGAS-STING pathway has been recently found to be critical for tumor immune surveillance and shown dramatic cancer immunotherapy effect in preclinical studies, which led to a number of phase I clinical trials of STING agonists. On the other hand, DAMPs and PAMPs are extensively involved in occurrence and progress of autoimmune diseases. Inhibition of abnormal innate immune activation is emerging to be effective therapy for many uncurable autoimmune diseases. Modulating DAMP and PAMP mediated immune responses will provide new therapeutic approaches for diverse human diseases, including cancer and autoimmune diseases.

This present invention addresses this need.

SUMMARY

Immune checkpoint blockades can allow patients' own immune system to fight against cancer. However, the current average response rate to immune check point blockades is only around 30%. This may be attributed to that some tumors, characterized as "cold tumors", are less visible to the immune system. The characters of such tumors include low inflammatory responses, less mutation burden, and deficient tumoral-infiltration of T cells and other pro-inflammatory immune cells. In contrast, "hot tumors", with more inflammatory signatures available for immune system recognize, have better therapeutic response rate to cancer immunotherapy. Therefore, it is critical to understand how to turn "cold tumors" into "hot tumors".

Accumulating evidence indicates that immune surveillance of tumors, mediated by the innate immune system, recognizes the presence of tumor by sensing tumor cell-derived DNA by STING pathway. The activation of STING pathway could elicit innate immune cascade, such as type-I interferon response and other pro-inflammation phenotypic change, which further elicit adaptive antitumor reaction. Therefore, STING is regarded as the "trigger" of the reversion from "cold tumor" to "hot tumor". For example, intra-tumoral administration of STING agonists could elicit antitumor immune response to both local and metastatic tumors. In a clinical setting, type-1 interferon response is found to be a signature of better cancer therapy prognosis similar to antigen-specific T cells infiltration. Therefore, developing STING agonists with great in-vivo stability, favorable pharmacokinetics properties and acceptable safety profiles is of great significance and high translational value.

However, most human STING agonists under current evaluations are based on cyclic dinucleotides and their derivates. Their small molecular weight, poor pharmacokinetics parameter and serious side effects greatly limit their systemic application.

Experiments conducted during the course of developing embodiments for the present invention demonstrated that CDNs, including cdi-AMP, cGAMP, and cGMP, assemble into homogeneous nanoparticles in the presence of $Zn^{2+}$. It was also shown that such CDNs assembled into homogenous nanoparticles in the presence of $Zn^{2+}$ are further stabilized with lipid vesicles. Additional experiments demonstrated that CDNs can be formulated into nanoparticles in the presence of calcium phosphate and copolymers of cationic poly (ethylene imine) (PEI) and polyethylene glycol (PEG). It was further shown that such CDN-nanoparticle assemblies (e.g., CDNs formulated into nanoparticles in the presence of calcium phosphate and copolymers of PEI-PEG) (e.g., CDNs formulated into nanoparticles in the presence of of $Zn^{2+}$ and liposomes) provide increased cancer cell uptake and more accurate targeting to the tumor microenvironment (e.g., TME), thereby enabling increased STING agonist delivery efficacy and lower toxicity.

For CDN-Zn embodiments, such results indicate the following unique characteristics in comparison with previous drug delivery systems: 1) reversible assembly for sustained drug released without losing bioactivity, 2) high loading efficacy and loading capacity, 3) increased cellular uptake, 4) pH-sensitive release at low pH, 5) good biocompatibility, 6) flexible surface chemistry for surface modification and functionalization, and 7) low cost and ease of scale-up.

For CDN@CaP/PEI-PEG embodiments, such results indicate the following unique characteristics in comparison with previous drug delivery systems: 1) Increased cellular uptake, 2) high loading efficacy, 3) pH-sensitive release at low pH, 4) biocompatibility, and 5) low cost and easy of scale-up.

Such results have significant clinical importance, as these nanoparticles associated with CDNs can induce immune responses against specific tumors through systemic administration thereby avoiding the need for direct local injection into tumors.

Additional experiments conducted during the course of developing embodiments for the present invention determined that specific metal ions can significantly enhance STING activation and type-I IFN response of STING agonists. For example, it was shown that in optimized conditions, $Mn^{2+}$ or $Co^{2+}$ enhanced STING activation of cGAMP by over sixty times. It was further shown that administration of a STING agonist combined with $Mn^{2+}$ or $Co^{2+}$ into murine tumors significantly improved treatment effect, characterized as elevated serum type-I IFN level, higher tumor eradication efficacy and longer animal survival. After the treatment, 80% of tumor-bearing mice eradicated established tumors, and they were resistant to second tumor challenging after 80 days, demonstrating long-term immunity against tumor relapse. Furthermore, it was found that this phenomenon was generalizable for various other innate immune pathways, including but not limited to the TLR 3/4/7/8/9 ligands, NOD1/2 ligands, TLR 7/8 ligands, RIG-I & CDS agonist and inflammasome-inducers. For example, $Co^{3+}$ dramatically increased polyIC-mediated production of IFNb, TNFa, IL6 and IL2 by dendritic cells, while $Mn^{2+}$ increased polyIC-mediated IFNb production. $Mn^{2+}$ increased MPLA-mediated production of IFNb and TNFa, while $Ni^{2+}$ increased MPLA-mediated production of TNFa. $Mn^{2+}$ increased R848-mediated production of IFNb and TNFa, while $Ni^{2+}$ increased R848-mediated production of TNFa. In addition, $Ni^{2+}$ and $Mn^{2+}$ increased CpG-mediated production of IFNb and TNFa.

Based on such results, several pharmaceutically acceptable formulations were developed to precisely deliver metals-innate immune stimulator combinations to desired targets and promote immune activation. For example, liposome-coated nanoparticle, CDA-Mn-His11-DOPE@liposome (Mn-CDA/H11@lip) could be used for systemic delivery of STING agonist and eradicated 60% established CT26 colon tumor. Co-CDA/His33-PEG could greatly prolong the production of IFNb production, which was detectable even 4 days after injection. Furthermore, experiments were conducted that tested whether chelating intracellular metal ions could inhibit the innate immune response. By unbiased screening, several chelators were identified that could effectively inhibit DNA-induced cGAS-STING-Type-I IFN/NFkB responses and poly IC-induced TLR3-cGAS-STING-Type-I IFN, which may be useful for autoimmune disease treatment. Overall, such results represent a simple but effective approach to solve some unmet medical challenges, such as improving the efficacy of vaccine adjuvants, developing cancer immunotherapy and controlling autoimmune diseases.

Accordingly, such results and embodiments indicate a new class of drug delivery systems for both local and systemic delivery of agents capable of stimulating an innate immune response in a subject upon administration to the subject.

As such, this disclosure provides compositions and methods for stimulating an innate immune response in a subject upon administration to the subject through administration of agents capable of stimulating an innate immune response in the subject. In particular, the present invention is directed to such compositions comprising agents capable of stimulating an innate immune response in a subject upon administration to the subject, methods for synthesizing such compositions, as well as systems and methods utilizing such compositions (e.g., in diagnostic and/or therapeutic settings).

Accordingly, in certain embodiments, the present invention provides compositions comprising one or more DAMPs or PAMPs, and either a) calcium phosphate and copolymers of cationic poly (ethylene imine) (PEI) and polyethylene glycol (PEG), poly (histidine)-polyethylene glycol (PH-PEG), lipid-poly-histidine, poly (lysine)-polyethylene glycol PEG (PK-PEG), or anionic poly (glutamic acid)-polyethylene glycol (PGA-PEG); or
b) one or more cations selected from the group consisting of $Zn^{2+}$, $Mn^{2+}$, $Ca^{2+}$, $Fe^{2+}$, $Fe^{3+}$, $Cu^{2+}$, $Ni^{2+}$, $Co^{2+}$, $Pb^{2+}$, $Sn^{2+}$, $Ru^{2+}$, $Au^{2+}$, $Mg^{2+}$, $VO^{2+}$, $Al^{3+}$, $Co^{3+}$, $Cr^{3+}$, $Ga^{3+}$, $Tl^{3+}$, $Ln^{3+}$, $MoO^{3+}$, $Cu^{+}$, $Au^{+}$, $T^{+}$, $Ag^{+}$, $Hg^{2+}$, $Pt^{2+}$, $Pb^{2+}$, $Hg^{2+}$, $Cd^{2+}$, $Pd^{2+}$, $Pt^{4+}$, $Na^{+}$, $K^{+}$, and relative phosphate or carbonate salt.

In some embodiments, the composition is capable of stimulating an innate immune response in a subject upon administration to the subject. In some embodiments, the subject is suffering from or at risk of suffering from cancer. In some embodiments, the composition is used to elicit an immune response for vaccine applications. In some embodiments, the composition is capable of stimulating an innate immune response in at least one cancer cell upon administration to the subject, wherein the subject is suffering from cancer. In some embodiments, stimulating an innate immune response comprises stimulating an innate cytokine response mediated through cytokines. In some embodiments, the innate cytokine response is mediated through type 1 interferon.

Accordingly, in certain embodiments, the present invention provides methods for treating cancer in a subject, the method comprising administering a pharmaceutically effective amount of a composition comprising agents capable of stimulating an innate immune response in a subject upon administration to the subject (e.g., DAMPs/PAMPs) to the subject. In some embodiments, the innate immune response is an innate cytokine response mediated through cytokines in the subject. In some embodiments, the innate cytokine response is mediated through type 1 interferon in the subject.

Such methods are not limited to a particular manner of administration. In some embodiments, the administration is systemic administration. In some embodiments, the administration is local administration.

In some embodiments, the composition is co-administered with a chemotherapeutic agent. In some embodiments, the chemotherapeutic agent is one or more of the following: aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (TAXOL), pilocarpine, prochloroperazine, rituximab, tamoxifen, taxol, topotecan hydrochloride, trastuzumab, vinblastine, vincristine and vinorelbine tartrate.

Such compositions are not limited to specific DAMPs or PAMPs agonists. In some embodiments, the DAMP and PAMP agonists are selected from STING agonists, purine containing or purine derived agents, Toll-Like receptor (TLR) agonists, NOD-Like receptor (NLRs) agonists, RIG-I-Like receptor (RLR) agonists, cytosolic DNA sensor (CDS) agonists, C-type lectin receptor (CLR) agonists, and inflammasome inducers. In some embodiments, the DAMP and PAMP agonists are selected from TLR-3 agonists, TLR-4 agonists, TLR-5 agonists, TLR-7 agonists (e.g., Imiquimod), TLR-8 agonists (e.g., Resiquimod), TLR-9 agonists, and NLRP3 agonists.

Such compositions are not limited to specific purine containing or purine derived agents. In some embodiments the purine containing or purine derived agents are selected from 2'3'-cGAMP, 3'3'-cGAMP, c-di-AMP, c-di-GMP, cAIMP, cAIMP Difluor, cAIM(PS)2, Difluor (Rp/Sp), 2'2'-cGAMP, 2'3'-cGAM(PS)2 (Rp/Sp), 3'3'-cGAMP Fluorinated, c-di-AMP Fluorinated, 2'3'-c-di-AMP, 2'3'-c-di-AM (PS)2 (Rp,Rp), c-di-GMP Fluorinated, 2'3-c-di-GMP, c-di-IMP, cGAMP, 2'3'-cGAMP, 2'2'-cGAMP, 3'3'-cGAMP, cGAM(PS)2,2'3'-cGAM(PS)2 (Rp/Sp), 2'2'-cGAM(PS)2, 2'3'-cGAM(PS)2, cGAMP Fluorinated, 3'3'-cGAMP Fluorinated, 2'3'-cGAMP Fluorinated, 2'2'-cGAMP Fluorinated, c-di-AMP, 2'3-cdAMP, 2'2'-cdAMP, 3'3'-cdAMP, c-di-AM (PS)2,2'3'-c-di-AM(PS)2 (Rp,Rp), 2'2'-c-di-AM(PS)2,3'3'-c-di-AM(PS)2, c-di-AMP Fluorinated, 2'3'-cdAMP Fluorinated, 2'2'-cdAMP Fluorinated, 3'3'-cdAMP Fluorinated, cdGMP, 2'3'-cdGMP, 2'2'-cdGMP, 3'3'-cdGMP, c-di-GM (PS)2,2'3'-c-di-GM(PS)2,2'2'-c-di-GM(PS)2,3'3'-c-di-GM (PS)2, cdGMP Fluorinated, 2'3-cdGMP Fluorinated, 2'2'-cdGMP Fluorinated, 3'3'-cdGMP Fluorinated, cAIMP, 2'3'-cAIMP, 2'2'-cAIMP, 3'3'-cAIMP, cAIMP Difluor (3'3'-cAIMP Fluorinated, 2'3'-cAIMP Fluorinated, 2'2'-cAIMP Fluorinated, cAIM(PS)2 Difluor, 3'3-cAIM(PS)2 Difluor (Rp/Sp), 2'3'-cAIM(PS)2 Difluor, 2'2'-cAIM(PS)2 Difluor, c-di-IMP, 2'3'-cdIMP, 2'2'-cdIMP, 3'3'-cdIMP, c-di-IM(PS) 2,2'3'-c-di-IM(PS)2,2'2'-c-di-IM(PS)2,3'3'-c-di-IM(PS)2, c-di-IMP Fluorinated, 2'3'-cdIMP Fluorinated, 2'2'-cdIMP Fluorinated, 3'3'-cdIMP Fluorinated, Imiquimod, Resiquimod, 6-(4-amino-imidazoquinolyl)-norleucines,

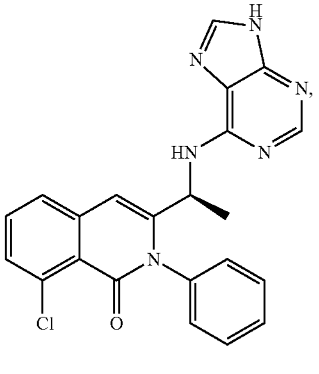

-continued

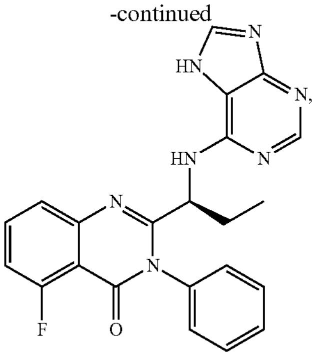

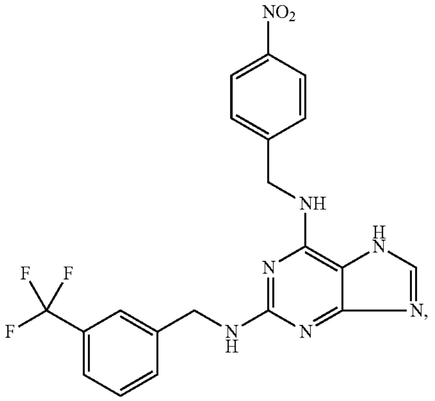

RNA, siRNA, microRNA, interference RNA, mRNA, replicon mRNA, RNA-analogues, DNA, and purine based PI3K inhibitors.

Such compositions are not limited to a particular type or kind of STING agonist. In some embodiments, the STING agonist is a small molecular agonist of STING. In some embodiments, the small molecular agonists of STING are cyclic dinucleotides. For example, in some embodiments, the cyclic dinucleotides include cGAMP, cdiAMP, cdiGMP, and cAIMP.

Additional examples of cyclic purine dinucleotides are described in some detail in, e.g., U.S. Pat. Nos. 7,709,458 and 7,592,326; WO2007/054279; and Yan et al., Bioorg. Med. Chem Lett. 18:5631 (2008), each of which is hereby incorporated by reference. In some embodiments, additional STING agonists are selected from 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, and retusin 7-methyl ether, or any derivatives thereof. In some embodiments, the small molecular agonists of STING include, but are not limited to, 2'3'-cGAMP, 3'3'-cGAMP, c-di-AMP, c-di-GMP, cAIMP, cAIMP Difluor, cAIM(PS)2, Difluor (Rp/Sp), 2'2'-cGAMP, 2'3'-cGAM(PS)2 (Rp/Sp), 3'3'-cGAMP Fluorinated, c-di-AMP Fluorinated, 2'3'-c-di-AMP, 2'3'-c-di-AM (PS)2 (Rp,Rp), c-di-GMP Fluorinated, 2'3'-c-di-GMP, c-di-IMP, SB11285, STING-agonist-C11, STING agonist-1, STING agonist G10, and Gemcitabine.

In some embodiments, the small molecular agonist of STING is selected from
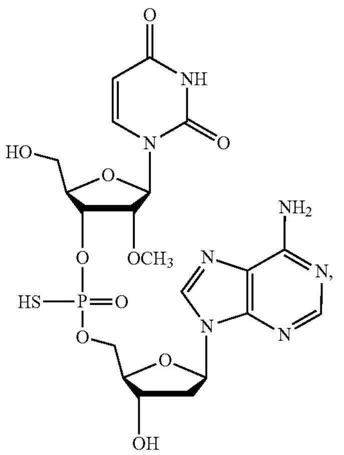
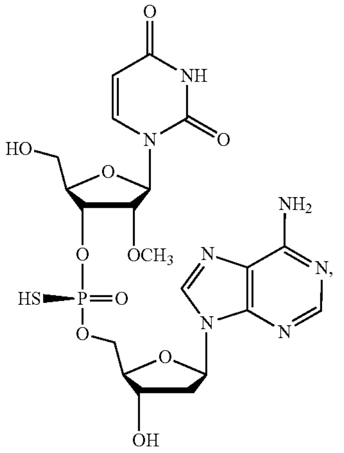
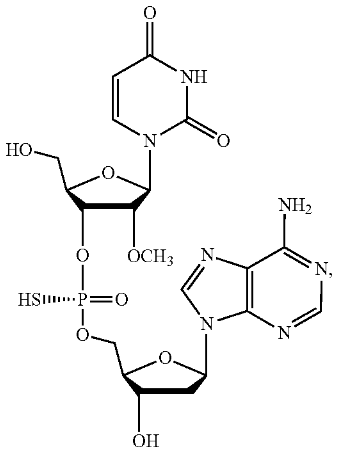
-continued
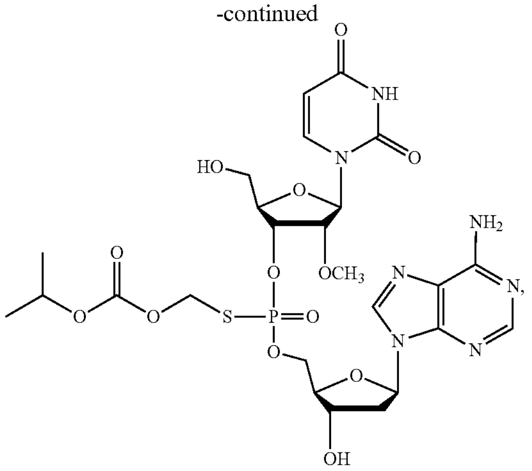
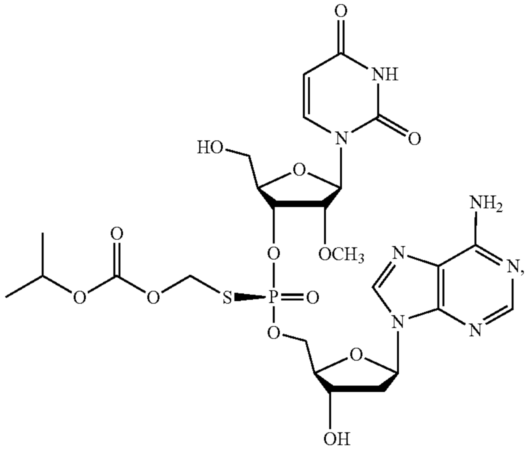
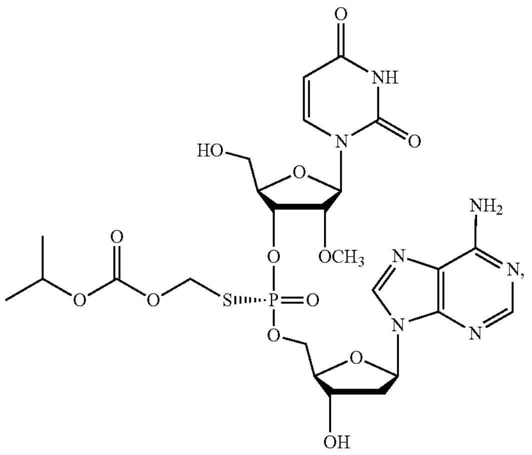

SB11285 (Spring Bank Pharmaceuticals), Gemcitabine

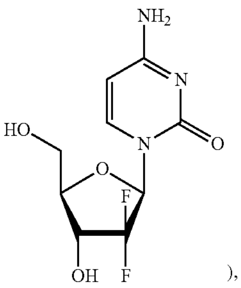

),

STING-agonist-C11

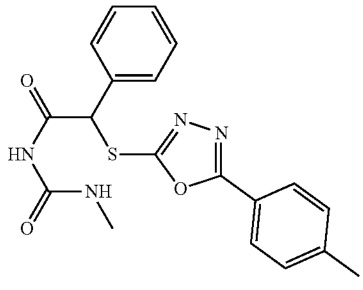

), $C_{19}H_{18}N_4O_3S$
Mol. Wt.: 382.44

STING agonist-1

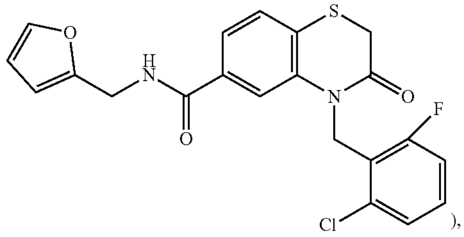 [SMILES: O=C(NCc1ccco1)c1ccc2c(c1)N(Cc1c(F)cccc1Cl)C(=O)CS2]

),

STING agonist G10

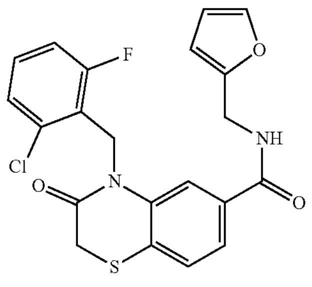

$C_{21}H_{16}ClFN_2O_3S$
Mol. Wt.: 430.88

2'3'-cGAMP, 3'3'-cGAMP, c-di-AMP, c-di-GMP, cAIMP, cAIMP Difluor, cAIM(PS)2, Difluor (Rp/Sp), 2'2'-cGAMP, 2'3'-cGAM(PS)2 (Rp/Sp), 3'3'-cGAMP Fluorinated, c-di-AMP Fluorinated, 2'3'-c-di-AMP, 2'3'-c-di-AM(PS)2 (Rp, Rp), c-di-GMP Fluorinated, 2'3'-c-di-GMP, c-di-IMP, cGAMP, 2'3'-cGAMP, 2'2'-cGAMP, 3'3'-cGAMP, cGAM (PS)2,2'3'-cGAM(PS)2 (Rp/Sp), 2'2'-cGAM(PS)2,2'3'-cGAM(PS)2, cGAMP Fluorinated, 3'3'-cGAMP Fluorinated, 2'3'-cGAMP Fluorinated, 2'2'-cGAMP Fluorinated, c-di-AMP, 2'3'-cdAMP, 2'2'-cdAMP, 3'3'-cdAMP, c-di-AM (PS)2,2'3'-c-di-AM(PS)2 (Rp,Rp), 2'2'-c-di-AM(PS)2,3'3'-c-di-AM(PS)2, c-di-AMP Fluorinated, 2'3'-cdAMP Fluorinated, 2'2'-cdAMP Fluorinated, 3'3'-cdAMP Fluorinated, cdGMP, 2'3'-cdGMP, 2'2'-cdGMP, 3'3'-cdGMP, c-di-GM (PS)2,2'3'-c-di-GM(PS)2,2'2'-c-di-GM(PS)2,3'3'-c-di-GM (PS)2, cdGMP Fluorinated, 2'3'-cdGMP Fluorinated, 2'2'-cdGMP Fluorinated, 3'3'-cdGMP Fluorinated, cAIMP, 2'3'-cAIMP, 2'2'-cAIMP, 3'3'-cAIMP, cAIMP Difluor (3'3'-cAIMP Fluorinated, 2'3'-cAIMP Fluorinated, 2'2'-cAIMP Fluorinated, cAIM(PS)2 Difluor, 3'3'-CAIM (PS)2 Difluor (Rp/Sp), 2'3'-cAIM(PS)2 Difluor, 2'2'-cAIM(PS)2 Difluor, c-di-IMP, 2'3'-cdIMP, 2'2'-cdIMP, 3'3'-cdIMP, c-di-IM(PS)2,2'3'-c-di-IM(PS)2,2'2'-c-di-IM(PS)2,3'3'-c-di-IM(PS)2, c-di-IMP Fluorinated, 2'3'-cdIMP Fluorinated, 2'2'-cdIMP Fluorinated, and 3'3'-cdIMP Fluorinated, and amidobenzimidazole (ABZI)-based compounds.

As noted, to use as a cancer drug, CDNs have two key limitations: 1) poor pharmacokinetics and serious off-target side effects. Regarding poor pharmacokinetics, if administrated via intratumor injection, CDNs would easily diffuse away because of the small molecule weight and high hydrophilicity: if administrated via intravenous injection, CDNs would show low bioavailability to tumor tissue due to in-vivo instability, low lipophilicity and fast excretion. Regarding serious off-target side effects, as an immunological sensor to virus infections, STING is widely distributed across body. As such, high dose of STING agonists or systemically administrated STING agonists would nonspecifically activate the innate immune system and cause cytokine storm. The present invention addresses such limitations through providing prodrugs of such small molecular agonists of DAMPs and/or PAMPs (including STING agonists).

Indeed, in some embodiments, the small molecular agonist of DAMP and/or PAMP is a prodrug of a small molecular agonist of the DAMP and/or PAMP. For example, in some embodiments, the prodrug of a small molecular agonist of a DAMP and/or PAMP is a prodrug of any of the small molecular agonists of DAMP and/or PAMP recited herein. In some embodiments, the prodrug of a small molecular agonist of DAMP and/or PAMP is attached with hydrophobic moieties that assist with loading into nanoparticles and/or assist with tissue retention.

In some embodiments, the CDNs are modified with a cleavable lipid moiety to make CDN prodrugs. For example, as shown in the schemes below, three synthesis routes for lipid-CDN prodrugs are contemplated. Each are activated by different mechanisms, esterase-based activation for route 1, phosphoramidase-based activation for route 2, and reduce environment-sensitive activation for route 3.

Scheme 1. Synthesis route for lipid-CDN prodrugs.
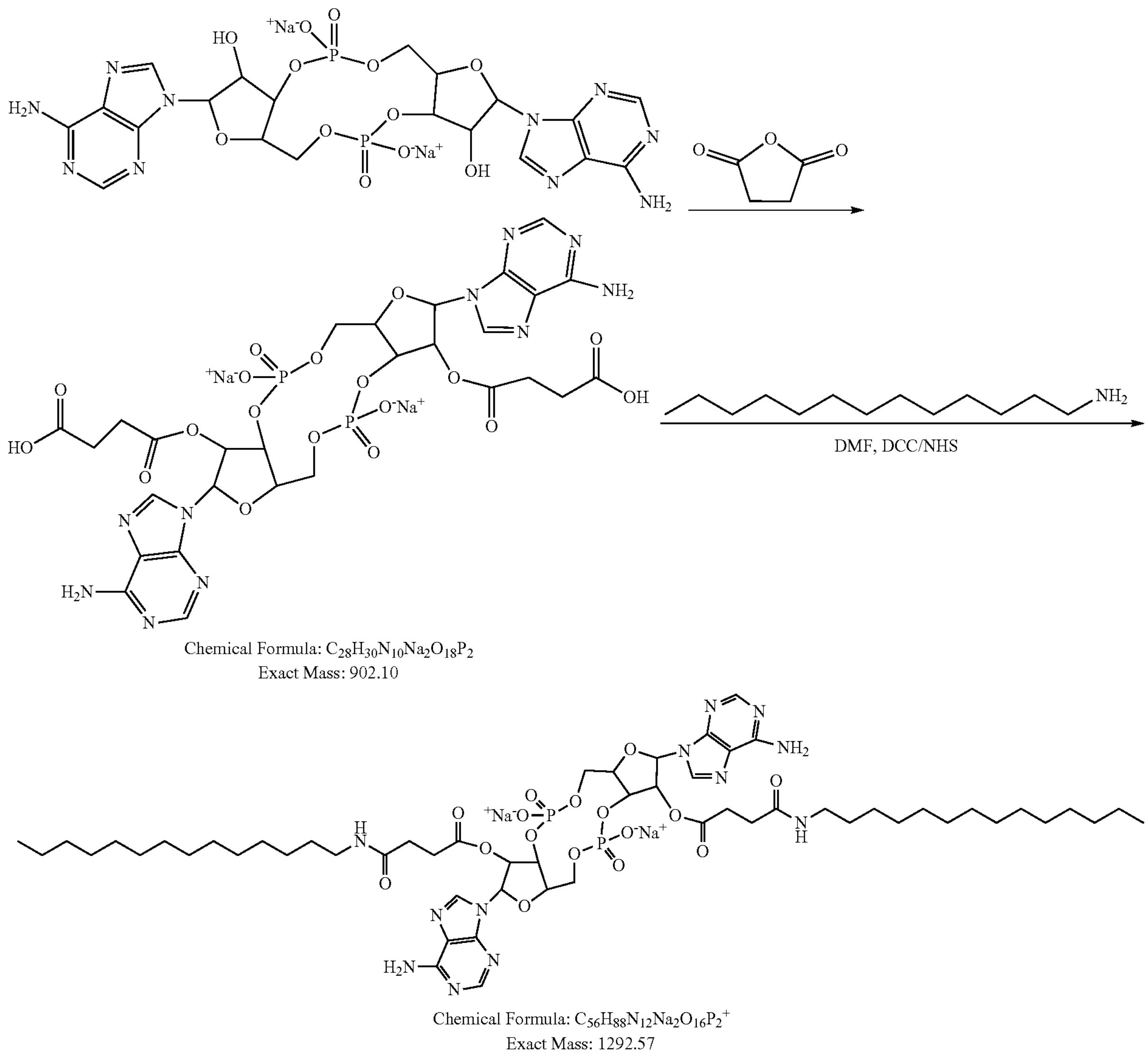
Scheme 2. Synthesis route for lipid-CDN prodrugs.
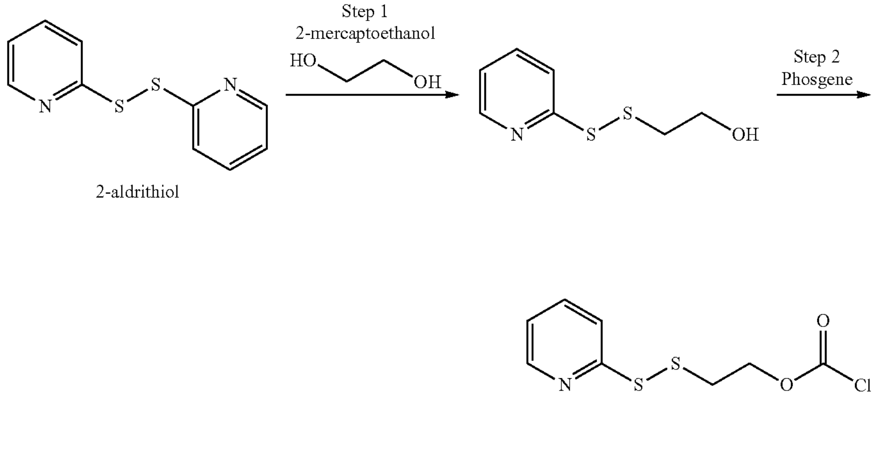

-continued
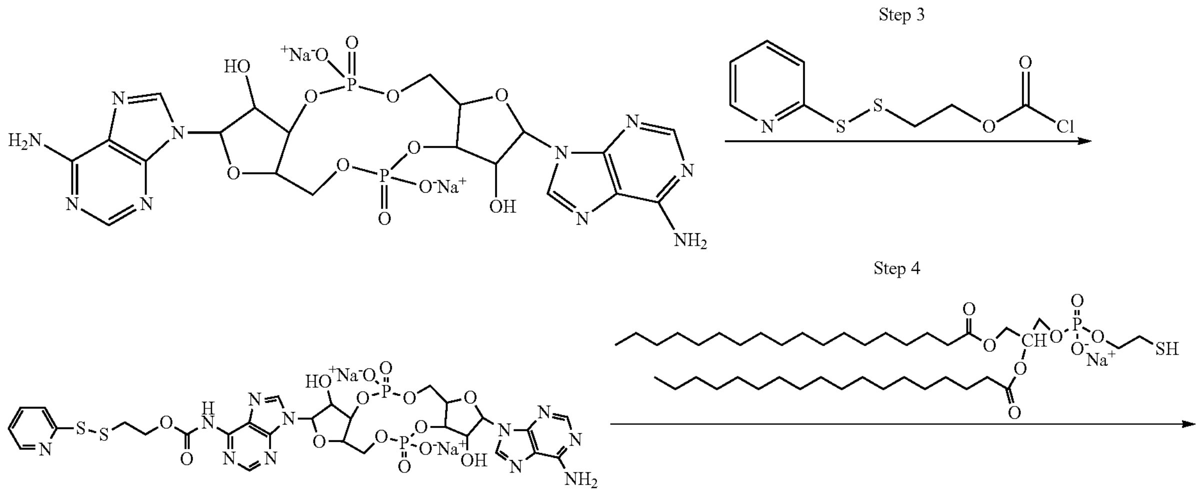
Target compound:
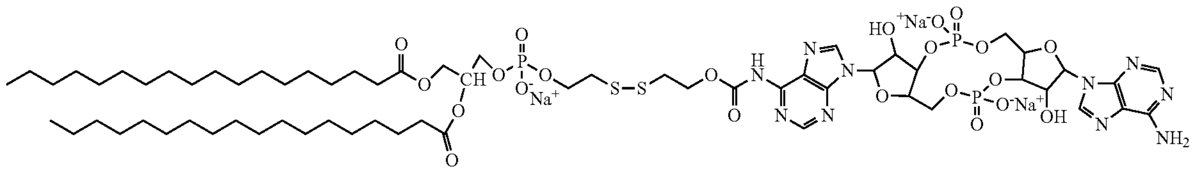
Scheme 3. Synthesis route for lipid-CDN prodrugs.
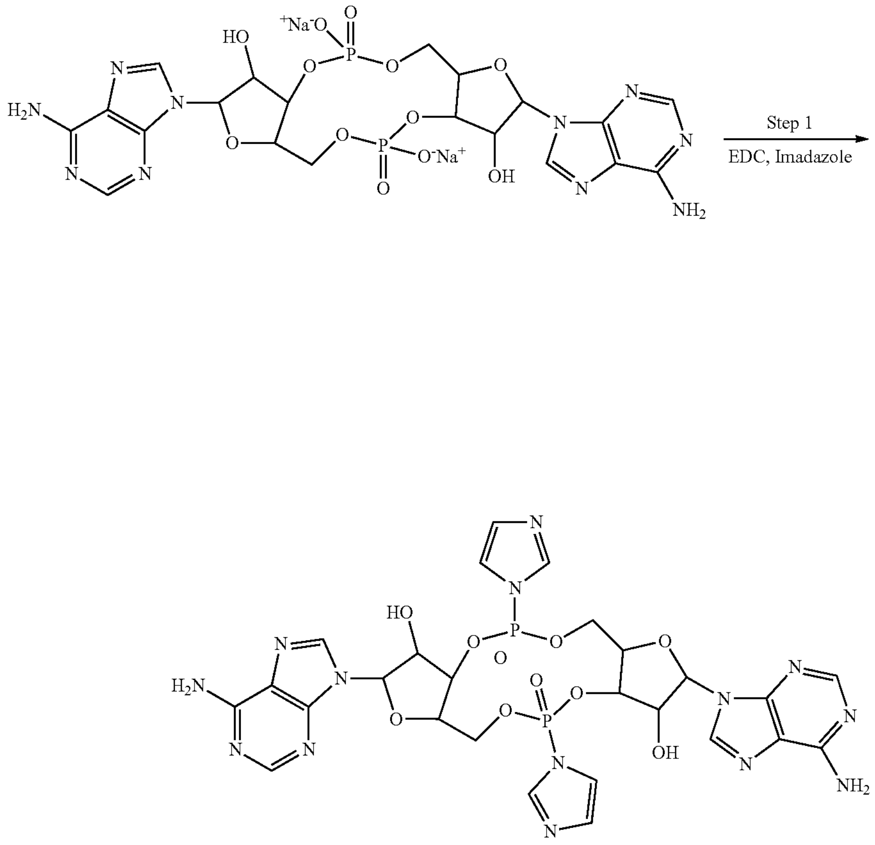

-continued

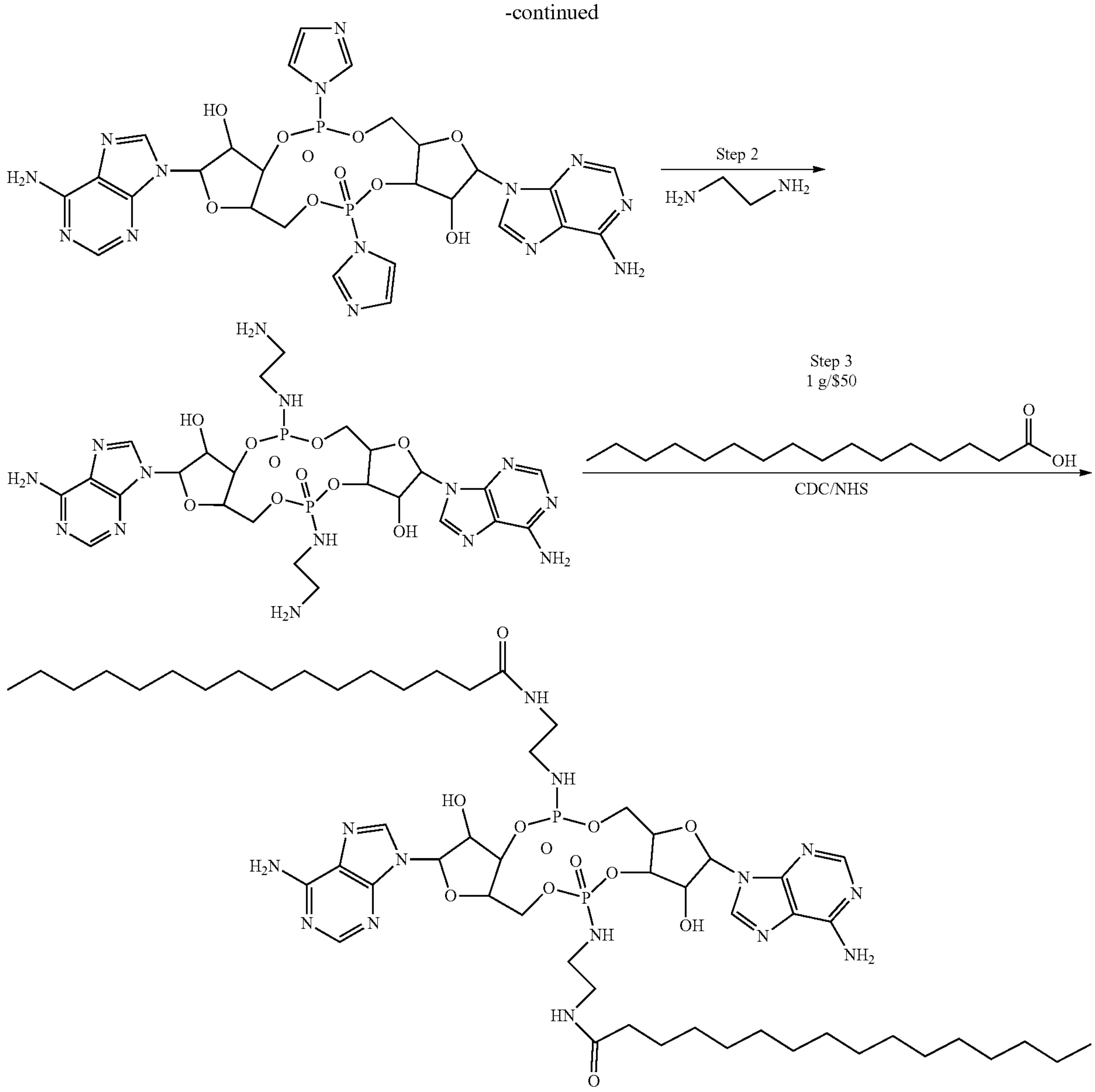

After modification, it is contemplated that the lipid-CDN prodrugs could be administrated either in free form or in liposome-formulated form. Such embodiments would greatly improve the pharmacokinetics and reduce side effects of CDNs. For example, it is contemplated that injected lipid-CDN prodrugs will retain at an injection site and release CDNs slowly in tumor, conferring high bioavailability and reduced side effects to normal tissue. For example, lipid-CDN prodrugs that are formulated into liposome could be administrated either intravenously or locally. Such liposome-formulated lipid-CDNs could greatly extend drug circulation in blood, and increase tumor accumulation and lymph node draining. More importantly, the CDNs are inactive after lipid modification and could be only reactivated when it is cleaved by esterase. In addition, there are previous studies indicating that the metastasis nodes could be distinguished from tumor-free lymph nodes by high esterase level, which would enable selective activation of lipid-CDNs prodrug at tumor sites.

In some embodiments, STING activating compounds are provided (see, e.g., WO2017011920, WO2017027646, WO2017011622, U.S. Patent Application Publication No. 20160287623, WO2016100261, U.S. Patent Application Publication No. 20160074507, and WO2015161762).

In some embodiments, cGAS modulating compounds are provided (see, e.g., WO2014179335).

In some embodiments, STING inhibiting compounds are provided (see, e.g., U.S. Patent Application Publication No. 20170037400).

In some embodiments, compounds capable of killing STING-deficient and/or cGAS-deficient cancer cells are provided (see, e.g., WO2016201450).

In some embodiments, STING pathway agonists combined with pharmaceutically active components are provided (see, e.g., STING activation/chemotherapy (WO2016096577), STING activation/selected vaccine formulation stimulating an immune response (U.S. Patent Application Publication Nos. 20150056224 and 20140205653), and STING activation/cytokines production (WO2013185052)).

In some embodiments, such compositions comprising agents capable of stimulating an innate immune response in a subject upon administration to the subject (e.g., DAMPs/PAMPs) are associated with (e.g., complexed, conjugated, encapsulated, absorbed, adsorbed, admixed) nanoparticles.

In some embodiments, such compositions associated with nanoparticles are further associated (e.g., complexed, conjugated, encapsulated, absorbed, adsorbed, admixed) with calcium phosphate and copolymers of PEI/PEG, PH-PEG, PK-PEG, or PGA-PEG. Indeed, in some embodiments, the associating of the agents capable of stimulating an innate immune response in a subject with the nanoparticle is in the presence of calcium phosphate and copolymers of PEI/PEG, PH-PEG, PK-PEG, or PGA-PEG.

In some embodiments, such compositions associated with nanoparticles are further associated (e.g., complexed, conjugated, encapsulated, absorbed, adsorbed, admixed) with one or more cations selected from the group consisting of $Zn^{2+}$, $Mn^{2+}$, $Ca^{2+}$, $Fe^{2+}$, $Fe^{3+}$, $Cu^{2+}$, $Ni^{2+}$, $Co^{2+}$, $Pb^{2+}$, $Sn^{2+}$, $Ru^{2+}$, $Au^{2+}$, $Mg^{2+}$, $VO^{2+}$, $Al^{3+}$, $Co^{3+}$, $Cr^{3+}$, $Ga^{3+}$, $Tl^{3+}$, $Ln^{3+}$, $MoO^{3+}$, $Cu^{+}$, $Au^{+}$, $Tl^{+}$, $Ag^{+}$, $Hg^{2+}$, $Pt^{2+}$, $Pb^{2+}$, $Hg^{2+}$, $Cd^{2+}$, $Pd^{2+}$, $Pt^{4+}$, $Na^{+}$, $K^{+}$, and relative phosphate or carbonate salt. Indeed, in some embodiments, the associating of the agents capable of stimulating an innate immune response in a subject with the nanoparticle is in the presence of such cations (e.g., $Zn^{2+}$, $Co^{2+}$, or $Mn^{2+}$).

In some embodiments, such compositions associated with nanoparticles and one or more cations (e.g., $Zn^{2+}$, $Co^{2+}$, or $Mn^{2+}$) or calcium phosphate is further associated (e.g., complexed, conjugated, encapsulated, absorbed, adsorbed, admixed) with a hydrophobic molecule.

In some embodiments, the hydrophobic molecule is a lipid molecule. In some embodiments, the lipid molecule is a membrane-forming lipid molecule. In some embodiments, the lipid molecule molecule is a non-membrane-forming lipid molecule.

Examples of lipid molecules applicable with the embodiments of the present invention include, but are not limited to, phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$carbon chains, e.g., lauroyl, myristoyl, palmitoyl, stearoyl, or oleoyl.

Other non-limiting examples of lipid molecules include sterols such as cholesterol and derivatives thereof such as cholestanol, cholestanone, cholestenone, coprostanol, cholesteryl-2'-hydroxyethyl ether, cholesteryl-4'-hydroxy butyl ether, and mixtures thereof.

Other examples of lipid molecules suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

Other examples of lipid molecules suitable for use in the present invention include fatty acids and derivatives or analogs thereof. They include oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_1$-alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Other examples of lipid molecules suitable for use in the present invention include a lipid molecule modified with PEG (PEG-lipid). Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes. Additional PEG-lipids include, without limitation, PEG-C-DOMG, 2 KPEG-DMG, and a mixture thereof.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co, and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxy polyethylene glycol-amine ($MePEG-NH_2$), monomethoxypolyethylene glycol-tresylate (MePEG-TRES), and monomethoxypolyethylene glycol-imidazolyl-carbonyl (MePEG-IM). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycolcolacetic acid (MePEG-$CH_2COOH$) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)$CCH_2CH_2C$(O)—), succinamidyl (—NHC(O)$CH_2CH_2C$(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof. Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

In some embodiments, the nanoparticle associated with such compositions comprising agents capable of stimulating an innate immune response in a subject upon administration to the subject (e.g., DAMPs/PAMPs) are further associated with (e.g., complexed, conjugated, encapsulated, absorbed, adsorbed, admixed) with one or more agents configured to target cancer cells.

In some embodiments, the agent configured to target cancer cells is a tumor antigen selected from the group consisting of alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15 (58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17,1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27,29\BCAA), CA 195, CA 242, CA-50, CAM43, CD68\KP1, CO-029, FGF-5, G250, Ga733 (EpCAM), human EGFR protein or its fragments, such as human EGFR residues 306-325 (SCVRACGADSYEMEEDGVRK (SEQ ID NO:374)) and residues 897-915 (VWSYGVTVWELMTFGSKPY (SEQ ID NO:375)), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, TPS, WT1 (and WT1-derivaed peptide sequences: WT1 126-134 (RMFP NAPYL (SEQ ID NO:376)), WT1 122-140 (SGQARMFPNAPYLPSCLES (SEQ ID NO:377)), and WT1 122-144 30) (SGQARMFPNAPYLPSCLESQPTI (SEQ ID NO:378)), MUC1 (and MUC1-derived peptides and glycopeptides such as RPAPGS (SEQ ID NO:379), PPAHGVT (SEQ ID NO:380), and PDTRP (SEQ ID NO:381)), LMP2, EGFRvIII, Idiotype, GD2, Ras mutant, p53 mutant, Proteinase3 (PRI), Survivin, hTERT, Sarcoma translocation breakpoints, EphA2, EphA4, LMW-PTP, PAP, ML-IAP, AFP, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, sLe (animal), CYP1B1, PLAC1, GM3, BORIS, Tn, GloboH, NY-BR-1, RGS5, SART3, STn, Carbonic anhydrase IX, PAX5, OY-TES1, Sperm protein 17, LCK, HMWMAA, AKAP-4, XAGE 1, B7H3, Legumain, Tie 2, Page4, VEGFR2, MAD-CT-1, FAP, PDGFR-alpha, PDGFR-β, MAD-CT-2, Fos-related antigen 1, ERBB2, Folate receptor 1 (FOLR1 or FBP), IDH1, IDO, LY6K, fms-related tyro-sine kinase 1 (FLT1, best known as VEGFR1), KDR, PADRE, TA-CIN (recombinant HPV16 L2E7E6), SOX2, aldehyde dehydrogenase, and any derivative thereof.

In some embodiments, the one or more agents configured to target cancer cells are conjugated to the outer surface of the nanoparticle. In some embodiments, the one or more agents configured to target cancer cells are encapsulated within the nanoparticle.

In some embodiments, the nanoparticle associated with such compositions comprising agents capable of stimulating an innate immune response in a subject upon administration to the subject (e.g., DAMPs/PAMPs) are further associated with (e.g., complexed, conjugated, encapsulated, absorbed, adsorbed, admixed) with an adjuvant.

In some embodiments, the adjuvant is selected from the group consisting of CPG, polyIC, poly-ICLC, 1018 ISS, aluminum salts (for example, aluminum hydroxide, aluminum phosphate), Amplivax, BCG, CP-870,893, CpG7909, CyaA, dSLIM, Cytokines (such as GM-CSF. IL-2, IFN-α, Flt-3L), IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel.®, vector system, PLGA microparticles, imiquimod, resiquimod, gardiquimod, 3M-052, SRL172, Virosomes and other Virus-like particles, YF-17D, VEGF trap, beta-glucan, Pam3Cys, Aquila's QS21 stimulon, vadimezan, AsA404 (DMXAA), 3M MEDI9197, glucopyranosyl lipid adjuvant (GLA), GLA-SE, CD1d ligands (such as C20:2, OCH, AH04-2, α-galatosylceramide, α-C-galatosylceramide, α-mannosylceramide, α-fructosylceramide, β-galatosylceramide, β-mannosylceramide), STING agonists (e.g. cyclic dinucleotides, including Cyclic [G(3',5")pA(3',5')p], Cyclic [G(2',5')pA(3',5")p], Cyclic [G(2',5')pA(2',5')p], Cyclic diadenylate monophosphate, Cyclic diguanylate monophosphate), CL401, CL413, CL429, Flagellin, RC529, E6020, imidazoquinoline-based small molecule TLR-7/8a (including its lipidated analogues), virosomes, AS01, AS02, AS03, AS04, AS15, IC31, CAF01, ISCOM, Cytokines (such as GM-CSF, IL-2, IFN-α, Flt-3L), and bacterial toxins (such as CT, and LT). In some embodiments, the adjuvant is any derivative of an adjuvant (e.g., cholesterol-modified CpG) or any combinations thereof. In some embodiments, the adjuvant is a dendritic cell targeting molecule.

Such compositions comprising agents capable of stimulating an innate immune response in a subject upon administration to the subject (e.g., DAMPs/PAMPs) associated with nanoparticles are not limited to specific types of nanoparticles.

In some embodiments, the nanoparticle is a sHDL nanoparticle. In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, any nanostructures, microstructures, or their derivatives formed using layer-by-layer processes, self-assembly processes, or polyelectrolytes, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, a modified micelle, metal-polyhistidine-DOPE@liposome, metal-polyhistidine-PEG, 4arm-PEG-polyhistidine-metal hydrogels, and sHDL-polyhistidine, and metal-organic framework (MOF) coordination polymer (CP).

In some embodiments, the average size of the nanoparticle is between 6 to 500 nm.

In some embodiments, the nanoparticle is a sHDL nanoparticle. In some embodiments, the sHDL nanoparticle comprises a mixture of at least one phospholipid and at least one HDL apolipoprotein or apolipoprotein mimetic. In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the phospholipid is selected from the group consisting of dipalmitoylphosphatidylcholine (DPPC), dioleoyl-sn-glycero-3-phosphoethanolamine-N-[3-(2-pyridyldithio)propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof. In some embodiments, the HDL apolipoprotein mimetic is an ApoA-I mimetic.

In some embodiments, the ApoA-I mimetic is described by any of SEQ ID NOs: 1-336 and

```
                                   (SEQ ID NO: 341)
WDRVKDLATVYVDVLKDSGRDYVSQF,

                                   (SEQ ID NO: 342)
LKLLDNWDSVTSTFSKLREOL,

                                   (SEQ ID NO: 343)
PVTOEFWDNLEKETEGLROEMS,

                                   (SEQ ID NO: 344)
KDLEEVKAKVQ,

                                   (SEQ ID NO: 345)
KDLEEVKAKVO,

                                   (SEQ ID NO: 346)
PYLDDFQKKWQEEMELYRQKVE,

                                   (SEQ ID NO: 347)
PLRAELQEGARQKLHELOEKLS,

                                   (SEQ ID NO: 348)
PLGEEMRDRARAHVDALRTHLA,

                                   (SEQ ID NO: 349)
PYSDELRQRLAARLEALKENGG,

                                   (SEQ ID NO: 350)
ARLAEYHAKATEHLSTLSEKAK,

                                   (SEQ ID NO: 351)
PALEDLROGLL,

                                   (SEQ ID NO: 352)
PVLESFKVSFLSALEEYTKKLN,

                                   (SEQ ID NO: 353)
PVLESFVSFLSALEEYTKKLN,

                                   (SEQ ID NO: 352)
PVLESFKVSFLSALEEYTKKLN,

                                   (SEQ ID NO: 354)
TVLLLTICSLEGALVRRQAKEPCV

                                   (SEQ ID NO: 355)
QTVTDYGKDLME,

                                   (SEQ ID NO: 356)
KVKSPELOAEAKSYFEKSKE,

                                   (SEQ ID NO: 357)
VLTLALVAVAGARAEVSADOVATV,

                                   (SEQ ID NO: 358)
NNAKEAVEHLOKSELTOOLNAL,

                                   (SEQ ID NO: 359)
LPVLVWLSIVLEGPAPAOGTPDVSS,

                                   (SEQ ID NO: 360)
LPVLVVVLSIVLEGPAPAQGTPDVSS,

                                   (SEQ ID NO: 361)
ALDKLKEFGNTLEDKARELIS,
```

-continued (SEQ ID NO: 362)
VVALLALLASARASEAEDASLL, (SEQ ID NO: 363)
HLRKLRKRLLRDADDLQKRLAVYOA, (SEQ ID NO: 364)
AQAWGERLRARMEEMGSRTRDR, (SEQ ID NO: 365)
LDEVKEQVAEVRAKLEEQAQ, (SEQ ID NO: 236)
DWLKAFYDKVAEKLKEAF, (SEQ ID NO: 366)
DWLKAFYDKVAEKLKEAFPDWAKAAYDKAAEKAKEAA, (SEQ ID NO: 367)
PVLDLFRELLNELLEALKQKL, (SEQ ID NO: 368)
PVLDLFRELLNELLEALKQKLA, (SEQ ID NO: 4)
PVLDLFRELLNELLEALKQKLK, (SEQ ID NO: 369)
PVLDLFRELLNELLEALKQKLA, (SEQ ID NO: 370)
PVLDLFRELLNELLEALKKLLK, (SEQ ID NO: 371)
PVLDLFRELLNELLEALKKLLA, (SEQ ID NO: 372)
PLLDLFRELLNELLEALKKLLA,
and (SEQ ID NO: 373)
EVRSKLEEWFAAFREFAEEFLARLKS.

In some embodiments, the average particle size of the sHDL nanoparticle is between 6-70 nm.

In some embodiments, the nanoparticles associated with such compositions comprising agents capable of stimulating an innate immune response in a subject upon administration to the subject (e.g., DAMPs/PAMPs) are further associated (e.g., complexed, conjugated, encapsulated, absorbed, adsorbed, admixed) with one or more neo-antigenic peptides, wherein each of the one or more neo-antigenic peptides is specific for a neo-antigenic mutation identified from a neoplasia biological sample obtained from a subject. In some embodiments, the subject is a human being.

In some embodiments, the one or more neo-antigenic peptides range from about 5 to about 50) amino acids in length. In some embodiments, the one or more neo-antigenic peptides range from about 15 to about 35 amino acids in length. In some embodiments, the one or more neo-antigenic peptides range from about 18 to about 30 amino acids in length. In some embodiments, the one or more neo-antigenic peptides range from about 6 to about 15 amino acids in length.

In some embodiments the nanoparticles associated with such compositions comprising agents capable of stimulating an innate immune response in a subject upon administration to the subject (e.g., DAMPs/PAMPs) are further associated (e.g., complexed, conjugated, encapsulated, absorbed, adsorbed, admixed) with one or more biomacromolecule agents.

Such compositions are not limited to a particular biomacromolecule agent.

In some embodiments, the biomacromolecule agent is a nucleic acid. Such embodiments encompass any type of nucleic acid molecule including, but not limited to, RNA, siRNA, microRNA, interference RNA, mRNA, replicon mRNA, RNA-analogues, and DNA.

In some embodiments, the biomacromolecule agent is a peptide.

In some embodiments, the peptide is Adrenocorticotropic Hormone (ACTH), a growth hormone peptide, a Melanocyte Stimulating Hormone (MSH), Oxytocin, Vasopressin, Corticotropin Releasing Factor (CRF), a CRF-related peptide, a Gonadotropin Releasing Hormone Associated Peptide (GAP), Growth Hormone Releasing Factor (GRF), Lutenizing Hormone Release Hormone (LH-RH), an orexin, a Prolactin Releasing Peptide (PRP), a somatostatin, Thyrotropin Releasing Hormone (THR), a THR analog, Calcitonin (CT), a CT-precursor peptide, a Calcitonin Gene Related Peptide (CGRP), a Parathyroid Hormone (PTH), a Parathyroid Hormone Related Protein (PTHrP), Amylin, Glucagon, Insulin, an Insulin-like peptide, NeuroPeptide Y (NPY), a Pancreatic Polypeptide (PP), Peptide YY (PYY), Cholecystokinin (CCK), a CCK-related peptide, Gastrin Releasing Peptide (GRP), Gastrin, a Gastrin-related peptide, a Gastrin inhibitory peptide, Motilin, Secretin, Vasoactive Intestinal Peptide (VIP), a VIP-related peptide, an Atrial-Natriuretic Peptide (ANP), a Brain Natriuretic Peptide (BNP), a C-Type Natriuretic Peptide (CNP), a tachykinin, an angiotensin, a renin substrate, a renin inhibitor, an endothelin, an endothelin-related peptide, an opioid peptide, a thymic peptide, an adrenomedullin peptide, an allostatin peptide, an amyloid beta-protein fragment, an antimicrobial peptide, an antioxidant peptide, an apoptosis related peptide, a Bag Cell Peptide (BCPs), Bombesin, a bone Gla protein peptide, a Cocaine and Amphetamine Related Transcript (CART) peptide, a cell adhesion peptide, a chemotactic peptide, a complement inhibitor, a cortistatin peptide, a fibronectin fragment, a fibrin related peptide, FMRF, a FMRF amide-related peptide (FaRP), Galanin, a Galanin-related peptide, a growth factor, a growth factor-related peptide, a G-Therapeutic Peptide-Binding Protein fragment, Gualylin, Uroguanylin, an Inhibin peptide, Interleukin (IL), an Interleukin Receptor protein, a laminin fragment, a leptin fragment peptide, a leucokinin, Pituitary Adenylate Cyclase Activating Polypeptide (PAPCAP), Pancreastatin, a polypeptide repetitive chain, a signal transducing reagent, a thrombin inhibitor, a toxin, a trypsin inhibitor, a virus-related peptide, an adjuvant peptide analog, Alpha Mating Factor, Antiarrhythmic Peptide, Anorexigenic Peptide, Alpha-1 Antitrypsin, Bovine Pineal Antireproductive Peptide, Bursin, C3 Peptide P16, Cadherin Peptide, Chromogranin A Fragment, Contraceptive Tetrapeptide, Conantokin G, Conantokin T, Crustacean Cardioactive Peptide, C-Telopeptide, Cytochrome b588 Peptide, Decorsin, Delicious Peptide, Delta-Sleep-Inducing Peptide, Diazempam-Binding Inhibitor Fragment, Nitric Oxide Synthase Blocking Peptide, OVA Peptide, Platelet Calpain Inhibitor (PI), Plasminogen Activator Inhibitor 1, Rigin, Schizophrenia Related Peptide, Sodium Potassium Atherapeutic Peptidase Inhibitor-1, Speract, Sperm Activating Peptide, Systemin, a Thrombin receptor agonist, Tuftsin, Adipokinetic Hormone, Uremic Pentapeptide, Antifreeze Polypeptide, Tumor Necrosis Factor (TNF), Leech [Des Asp10]Decorsin, L-Ornithyltaurine Hydrochloride, P-Aminophenylacetyl Tuftsin, Ac-Glu-Glu-Val-Val-Ala-Cys-pNA, Ac-Ser-Asp-Lys-Pro, Ac-rfwink-NH2, Cys-Gly-Tyr-Gly-Pro-Lys-Lys-Lys-Arg-Lys-Val-Gly-Gly, D-Ala-Leu, D-D-D-D-D, D-D-D-D-D-D, N-P-N-A-N-P-N-A, V-A-I-T-V-L-V-K, V-G-V-R-V-R, V-I-

H-S, V-P-D-P-R, Val-Thr-Cys-Gly, R-S-R, Sea Urchin Sperm Activating Peptide, a SHU-9119 antagonist, a MC3-R antagonist, a MC4-R antagonist, Glaspimod, HP-228, Alpha 2-Plasmin Inhibitor, APC Tumor Suppressor, Early Pregnancy Factor, Gamma Interferon, Glandular Kallikrei N-1, Placental Ribonuclease Inhibitor, Sarcolecin Binding Protein, Surfactant Protein D, Wilms' Tumor Suppressor, GABAB 1b Receptor Peptide, Prion Related Peptide (iPRP13), Choline Binding Protein Fragment, Telomerase Inhibitor, Cardiostatin Peptide, Endostatin Derived Peptide, Prion Inhibiting Peptide, N-Methyl D-Aspartate Receptor Antagonist, and C-Peptide Analog.

In some embodiments, the peptide is selected from 177Lu-DOTA0-Tyr3-Octreotate, Abarelix acetate, ADH-1, Afamelanotidec, melanotan-1, CUV1647, Albiglutide, Aprotinin, Argipressin, Atosiban acetate, Bacitracin. Bentiromide, a BH3 domain, Bivalirudin. Bivalirudin trifluoroacetate hydrate, Blisibimod, Bortezomib, Buserelin, Buserelin acetate, Calcitonin, Carbetocin, Carbetocin acetate, Cecropin A and B, Ceruletide, Ceruletide diethylamine, Cetrorelix, Cetrorelix acetate, Ciclosporine, Cilengitidec, EMD121974, Corticorelin acetate injection, hCRF, Corticorelin ovine triflutate, corticorelin trifluoroacetate, Corticotropin, Cosyntropin, ACTH 1-24, tetracosactide hexaacetate, Dalbavancin, Daptomycin, Degarelix acetate. Depreotide trifluoroacetate (plus sodium pertechnetate), Desmopressin acetate, Desmopressin DDAVP, Dulaglutide, Ecallantide, Edotreotide (plus yttrium-90), Elcatonin acetate, Enalapril maleate (or 2-butanedioate), Enfuvirtide, Eptifibatide, Exenatide, Ganirelix acetate, Glatiramer acetate, Glutathion, Gonadorelin, Gonadorelin acetate, GnRH, LHRH, Goserelin, Goserelin acetate, Gramicidin, Histrelin acetate, Human calcitonin, Icatibant, Icatibant acetate, IM862, oglufanide disodium, KLAKLAK, Lanreotide acetate, Lepirudin, Leuprolide. Leuprolide acetate, leuprorelin, Liraglutide, Lisinopril, Lixisenatide, Lypressin, Magainin2, MALP-2Sc, macrophage-activating lipopeptide-2 synthetic, Nafarelin acetate, Nesiritide, NGR-hTNF, Octreotide acetate, Oritavancin, Oxytocin, Pasireotide, Peginesatide, Pentagastrin, Pentetreotide (plus indium-111), Phenypressin, Pleurocidin, Pramlintide, Protirelin, thyroliberin, TRH, TRF, Salmon calcitonin, Saralasin acetate, Secretin (human), Secretin (porcine), Semaglutide, Seractide acetate, ACTH, corticotropin, Sermorelin acetate, GRF 1-29, Sinapultide, KL4 in lucinactant, Sincalide, Somatorelin acetate, GHRH, GHRF, GRF, Somatostatin acetate, Spaglumat magnesium (or sodium) salt, Substance P, Taltirelin hydrate. Teduglutide. Teicoplanin, Telavancin, Teriparatide, Terlipressin acetate, Tetracosactide, Thymalfasin, thymosin a-1. Thymopentin, Trebananib. Triptorelin, Triptorelin pamoate. Tyroserleutide, Ularitide, Vancomycin, Vapreotide acetate, Vasoactive intestinal peptide acetate. Vx-001c, TERT572Y, Ziconotide acetate, $\alpha$5-$\alpha$6 Bax peptide, and $\beta$-defensin.

In some embodiments, the peptide is any peptide which would assist in achieving a desired purpose with the composition. For example, in some embodiments, the peptide is any peptide that will facilitate treatment of any type of disease and/or disorder.

In some embodiments, the peptide is an antigen.

In some embodiments, the antigen is selected from the group consisting of a peptide based antigen, a protein based antigen, a polysaccharide based antigen, a saccharide based antigen, a lipid based antigen, a glycolipid based antigen, a nucleic acid based antigen, an inactivated organism based antigen, an attenuated organism based antigen, a viral antigen, a bacterial antigen, a parasite antigen, an antigen derived from an allergen, and a tumor antigen.

In some embodiments, the antigen is a tumor antigen as described herein.

In some embodiments, the antigen is any type of viral, bacterial or self-antigen including, but not limited to, FimH against urinary tract infection; soluble F protein from respiratory syncytial virus (RSV); NEF, GAG, and ENV protein from HIV; *Streptococcus pneumoniae* proteins; HMGB1 protein; hemagglutinin and neuroamidase protein against influenza; Viral antigens derived from HPV type 16 and 18; gL2, ICP4, 9D2ΔTMR, gD2ΔTMR, or ICP4.2 from HSV-2; antigens from *S. pneumoniae*, such as a pneumolysoid, Choline-binding protein A (CbpA), or Pneumococcal surface protein A (PspA), SP1912, SP1912, SP1912L, SP0148 with or without a signal sequence, SP2108 with or without a signal sequence; Antigens from *Chlamydia trachomatis*, such as a CT209 polypeptide antigen, a CT253 polypeptide antigen, a CT425 polypeptide antigen, a CT497 polypeptide antigen, and a CT843 polypeptide antigen; amyloid-beta peptide.

In some embodiments, the antigen is conjugated to the outer surface of the nanoparticle. In some embodiments, the antigen is encapsulated within the nanoparticle.

In certain embodiments, the present invention provides compositions capable of inhibiting cGAS-STING activation and Type-I IFN response comprising of one or more cellular permeable chelators or their derivative to make intracellular metal ions unavailable for cGAS-STING-Type-I IFN activation.

In certain embodiments, the present invention provides compositions capable of regulating innate immune activation comprising of one or more cellular permeable chelators (e.g., metal ion chelators) to make intracellular metal ions unavailable for the innate immune pathways.

In some embodiments, such cellular permeable chelators (e.g., metal ion chelators) include, but are not limited to, polyphenol-based chelator (-)-Epigallocatechin gallate (EGCG), Punicalagin, (-)-Catechin gallate, (-)-Catechin, Tannic acid, tannin, Punicalin, Vescalagin, Procyanidin C1, Geraniin. Theaflavin 3,3'-digallate, lipid modified NTA, porphyrin, EDTA, NOTA, DOTA, TPEN, Crofelemer, etc.

In some embodiments, such compostions capable of inhibiting cGAS-STING activation and Type-I IFN response are used in treating subjects suffering from or at risk of suffering from autoimmune disorders.

As such, the present invention provides methods for treating autoimmune disorders through administering to a subject (e.g., human subject) compositions capable of regulating innate immune activation comprising of one or more cellular permeable chelators (e.g., metal ion chelators) to make intracellular metal ions unavailable for the innate immune pathways. In such embodiments, such cellular permeable chelators (e.g., metal ion chelators) include, but are not limited to, polyphenol-based chelator (-)-Epigallocatechin gallate (EGCG), Punicalagin, (-)-Catechin gallate, (-)-Catechin, Tannic acid, tannin, Punicalin, Vescalagin, Procyanidin C1, Geraniin, Theaflavin 3,3'-digallate, lipid modified NTA, porphyrin, EDTA, NOTA, DOTA, TPEN, Crofelemer, etc.

Examples of autoimmune disorders include, but are not limited to, Systemic lupus erythematosus, Aicardi-Goutières syndrome, Acute pancreatitis Age-dependent macular degeneration, Alcoholic liver disease, Liver fibrosis, Metastasis, Myocardial infarction, Nonalcoholic steatohepatitis (NASH), Parkinson's disease, Polyarthritis/fetal and neonatal anemia, Sepsis, inflammatory bowel disease, and multiple sclerosis.

In some embodiments, additional therapeutic agents are co-administered with such compositions. Examples of such therapeutic agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-$\alpha$ inhibitors (e.g., adalimumab, certolizumab pegol, etanercept, golimumab, infliximab), IL-1 inhibitors, and metalloprotease inhibitors. In some embodiments, the therapeutic agents include, but are not limited to, infliximab, adalimumab, etanercept, parenteral gold or oral gold.

In certain embodiments, the present invention provides methods for treating cancer in a subject, comprising administering to the subject a composition as described herein (e.g., a composition comprising one or more DAMPs and/or PAMPs) and one or more of an adjuvant (as described herein), a chemotherapeutic agent, an anti-immunosuppressive agent, an immunostimulatory agent, and an antigen (as described herein). In some embodiments, the subject is a human subject.

In some embodiments, the immunostimulatory agent is selected from anti-CTLA-4 antibody, anti-PD-1, anti-PD-L1, anti-TIM-3, anti-BTLA, anti-VISTA, anti-LAG3, anti-CD25, anti-CD27, anti-CD28, anti-CD137, anti-OX40, anti-GITR, anti-ICOS, anti-TIGIT, and inhibitors of IDO.

In some embodiments, the chemotherapeutic agent is selected from aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (TAXOL), pilocarpine, prochloroperazine, rituximab, tamoxifen, taxol, topotecan hydrochloride, trastuzumab, vinblastine, vincristine and vinorelbine tartrate.

In some embodiments, the cancer is one or more selected from bladder cancer, brain cancer, breast cancer, cervical cancer, ovarian cancer, colo-rectal cancer, esophageal cancer, kidney cancer, liver cancer, lung cancer, nasopharangeal cancer, pancreatic cancer, prostate cancer, skin cancer, stomach cancer, gastric cancer, head and neck cancer, testicular cancer, melanoma, acute myelogenous leukemia, chronic myelogenous leukemia, chronic lymphocytic leukemia, T cell lymphocytic leukemia, and B cell lymphomas, and uterine cancer.

Additional embodiments will be apparent to persons skilled in the relevant art based on the teachings contained herein.

DEFINITIONS

Figure 1A:
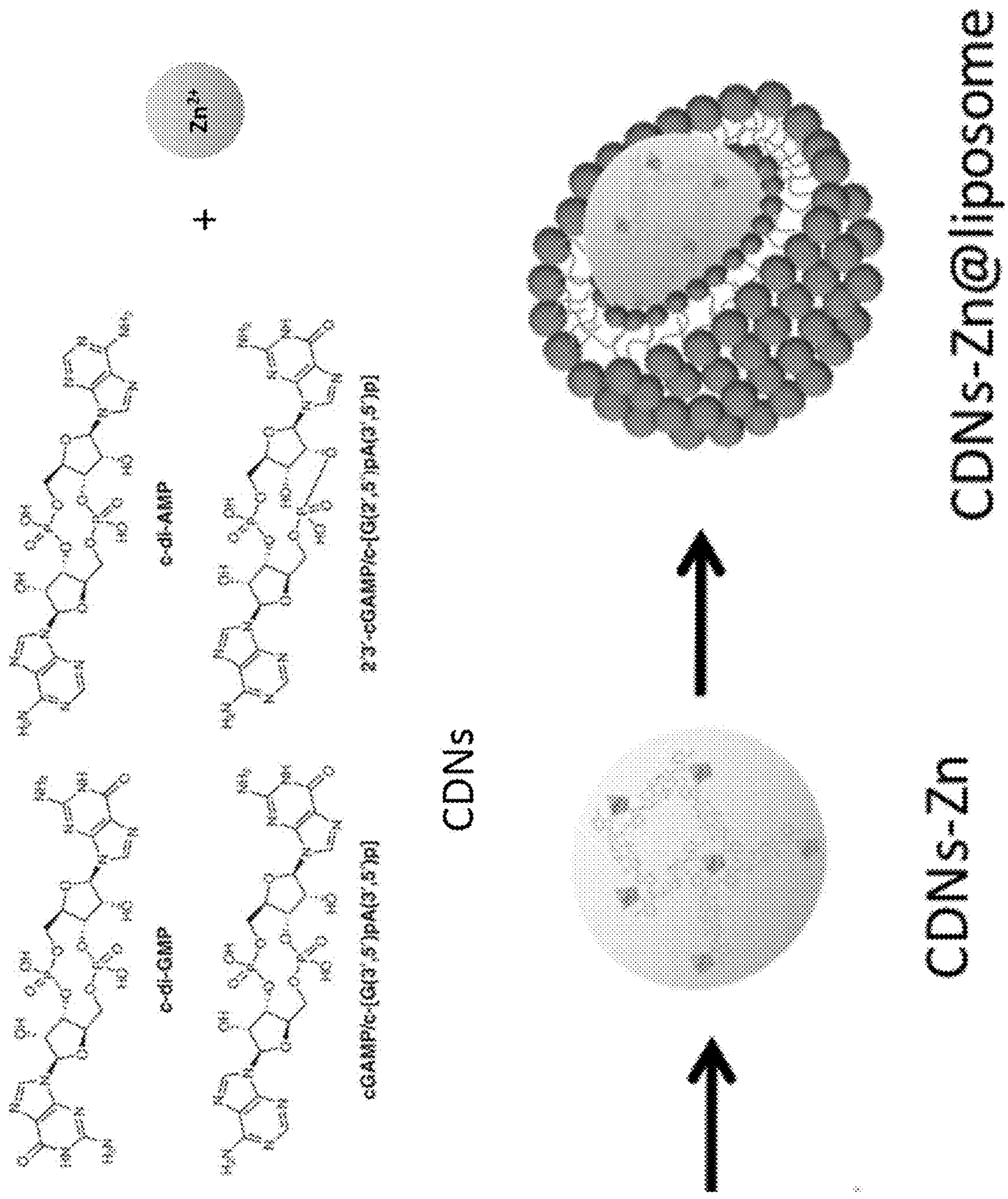
FIG. 1: Schematic illustration of synthesis of CDN-Zn, CDN-Zn@liposomes and CDNs@CaP/PEI-PEG. (A) Coordination crosslinking between $Zn^{2+}$ and CDNs enables assembly of CNDs-Zn NPs, which are then further modified by liposomes. (B) CDNs can be loaded into CaP/PEI-PEG NPs during synthesis by charge interaction between CDNs and backbone of PEI-PEG.

To facilitate an understanding of the present invention, a number of terms and phrases are defined below:

As used here, the term "lipids" or "lipid molecules" refer to fatty substances that are insoluble in water and include fats, oils, waxes, and related compounds. They may be either made in the blood (endogenous) or ingested in the diet (exogenous). Lipids are essential for normal body function and whether produced from an exogenous or endogenous source, they must be transported and then released for use by the cells. The production, transportation and release of lipids for use by the cells is referred to as lipid metabolism. While there are several classes of lipids, two major classes are cholesterol and triglycerides. Cholesterol may be ingested in the diet and manufactured by the cells of most organs and tissues in the body, primarily in the liver. Cholesterol can be found in its free form or, more often, combined with fatty acids as what is called cholesterol esters. As used herein, "lipid" or "lipid molecule" refers to any lipophilic compound. Non-limiting examples of lipid compounds include fatty acids, cholesterol, phospholipids, complex lipids, and derivatives or analogs thereof. They are usually divided into at least three classes: (1) "simple lipids," which include fats and oils as well as waxes: (2) "compound lipids," which include phospholipids and glycolipids; and (3) "derived lipids" such as steroids. Lipids or lipid molecules suitable for use in the present invention include both membrane-forming lipids and non-membrane-forming lipids.

As used herein the term, "lipoproteins" refer to spherical compounds that are structured so that water-insoluble lipids are contained in a partially water-soluble shell. Depending on the type of lipoprotein, the contents include varying amounts of free and esterified cholesterol, triglycerides and apoproteins or apolipoproteins. There are five major types of lipoproteins, which differ in function and in their lipid and apoprotein content and are classified according to increasing density: (i) chylomicrons and chylomicron remnants, (ii) very low density lipoproteins ("VLDL"), (iii) intermediate-density lipoproteins ("IDL"), (iv) low-density lipoproteins ("LDL"), and (v) high-density lipoproteins ("HDL"). Cholesterol circulates in the bloodstream as particles associated with lipoproteins.

As used herein, the term "HDL" or "high density lipoprotein" refers to high-density lipoprotein. HDL comprises a complex of lipids and proteins in approximately equal amounts that functions as a transporter of cholesterol in the blood. HDL is mainly synthesized in and secreted from the liver and epithelial cells of the small intestine. Immediately after secretion, HDL is in a form of a discoidal particle containing apolipoprotein A-I (also called apoA-I) and phospholipid as its major constituents, and also called nascent HDL. This nascent HDL receives, in blood, free cholesterol from cell membranes of peripheral cells or produced in the hydrolysis course of other lipoproteins, and forms mature spherical HDL while holding, at its hydrophobic center, cholesterol ester converted from said cholesterol by the action of LCAT (lecithin cholesterol acyltransferase). HDL plays an extremely important role in a lipid metabolism process called "reverse cholesterol transport", which takes, in blood, cholesterol out of peripheral tissues and transports it to the liver. High levels of HDL are associated with a decreased risk of atherosclerosis and coronary heart disease (CHD) as the reverse cholesterol transport is considered one of the major mechanisms for HDL's prophylactic action on atherosclerosis.

As used herein, the terms "synthetic HDL," "sHDL," "reconstituted HDL", or "rHDL" refer to a particle structurally analogous to native HDL, composed of a lipid or lipids in association with at least one of the proteins of HDL, preferably Apo A-I or a mimetic thereof. Typically, the components of sHDL may be derived from blood, or produced by recombinant technology.

As used herein, the term "complexed" as used herein relates to the non-covalent interaction of a biomacromolecule agent (e.g., antigen, adjuvant, etc) with a nanoparticle and/or microparticle.

As used herein, the term "conjugated" as used herein indicates a covalent bond association between a a biomacromolecule agent (e.g., antigen, adjuvant, etc) and a nanoparticle and/or microparticle.

As used herein, the term "encapsulated" refers to the location of a biomacromolecule agent (e.g., antigen, adjuvant, etc) that is enclosed or completely contained within the inside of a nanoparticle and/or microparticle.

As used herein, the term "absorbed" refers to a biomacromolecule agent (e.g., antigen, adjuvant, etc) that is taken into and stably retained in the interior, that is, internal to the outer surface, of a nanoparticle and/or microparticle.

As used herein, the term "adsorbed" refers to the attachment of a biomacromolecule agent (e.g., antigen, adjuvant, etc) to the external surface of a nanoparticle and/or microparticle. Such adsorption preferably occurs by electrostatic attraction. Electrostatic attraction is the attraction or bonding generated between two or more oppositely charged or ionic chemical groups. Generally, the adsorption is typically reversible.

As used herein, the term "admixed" refers to a biomacromolecule agent (e.g., antigen, adjuvant, etc) that is dissolved, dispersed, or suspended in a nanoparticle and/or microparticle. In some cases, the biomacromolecule agent may be uniformly admixed in the nanoparticle and/or microparticle.

As used herein, the terms "biological biomacromolecule" or "biomacromolecule" or "biomacromolecule agent" as used herein refer to a molecule with a molecular mass exceeding 1 kDa which can be isolated from an organism or from cellular culture, e.g., eukaryotic (e.g., mammalian) cell culture or prokaryotic (e.g., bacterial) cell culture. In some embodiments, the use of the term refers to polymers, e.g., biopolymers such as nucleic acids (including, but not limited to, RNA, siRNA, microRNA, interference RNA, mRNA, replicon mRNA, RNA-analogues, DNA, etc.), polypeptides (such as proteins), carbohydrates, and lipids. In some embodiments, the term "biomacromolecule" refers to a protein. In some embodiments, the term "biomacromolecule" refers to a recombinant protein or a fusion protein. In some embodiments, the protein is soluble. In some embodiments, the biomacromolecule is an antibody, e.g., a monoclonal antibody. In some embodiments, the biomacromolecule is an adjuvant, an antigen, a therapeutic agent, an imaging agent, etc.

As used herein, the term "antigen" is defined herein as a molecule which contains one or more epitopes that will stimulate a hosts immune system to make a cellular antigen-specific immune response, and/or a humoral antibody response. Antigens can be peptides, proteins, polysaccharides, saccharides, lipids, nucleic acids, and combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components. An antigen may be an oligonucleotide or polynucleotide which expresses an antigen. Antigens can be natural or synthetic antigens, for example, haptens, polyepitopes, flanking epitopes, and other recombinant or synthetically derived antigens (see, e.g., Bergmann, et al., Eur. J. Immunol., 23:2777-2781 (1993): Bergmann, et al., J. Immunol., 157:3242-3249 (1996): Suhrbier, Immunol, and Cell Biol., 75:402-408 (1997)).

As used herein, the term "neo-antigen" or "neo-antigenic" means a class of tumor antigens that arises from a tumor-specific mutation(s) which alters the amino acid sequence of genome encoded proteins.

As used herein, the term "tumor-specific antigen" is defined herein as an antigen that is unique to tumor cells and does not occur in or on other cells in the body.

As used herein, the term "tumor-associated antigen" is defined herein as an antigen that is not unique to a tumor cell and is also expressed in or on a normal cell under conditions that fail to induce an immune response to the antigen.

As used herein, the term "adjuvant" is defined herein as a substance increasing the immune response to other antigens when administered with other antigens. Adjuvants are also referred to herein as "immune potentiators" and "immune modulators".

As used herein, the term "antigen-presenting cells" are defined herein as highly specialized cells that can process antigens and display their peptide fragments on the cell surface together with molecules required for lymphocyte activation. The major antigen-presenting cells for T cells are dendritic cells, macrophages and B cells. The major antigen-presenting cells for B cells are follicular dendritic cells.

As used herein, the term "cross-presentation" is defined herein as the ability of antigen-presenting cells to take up, process and present extracellular antigens with MHC class I molecules to CD8 T cells (cytotoxic T cells). This process induces cellular immunity against most tumors and against viruses that do not infect antigen-presenting cells. Cross-presentation is also required for induction of cytotoxic immunity by vaccination with protein antigens, for example in tumor vaccination.

As used herein, the terms "immunologic", "immunological" or "immune" response is the development of a humoral and/or a cellular response directed against an antigen.

As used herein, the term "kit" refers to any delivery system for delivering materials. In the context of the sHDL nanoparticles as described herein (e.g., compositions comprising a sHDL nanoparticle encapsulating siRNA) (e.g., compositions comprising an sHDL nanoparticle configured to activate an immune response), such delivery systems include systems that allow for the storage, transport, or delivery of such compositions and/or supporting materials (e.g., written instructions for using the materials, etc.) from one location to another. For example, kits include one or more enclosures (e.g., boxes) containing the necessary agents and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising an sHDL nanoparticle or the ingredients necessary to synthesize such an sHDL nanoparticle, while a second container contains a second agent (e.g., siRNA, an antigen, an adjuvant) (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components necessary to synthesize and utilize any of the sHDL nanoparticles as described (e.g., in a single box housing each of the desired components). The term "kit" includes both fragmented and combined kits.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "drug" or "therapeutic agent" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "solvent" refers to a medium in which a reaction is conducted. Solvents may be liquid but are not limited to liquid form. Solvent categories include but are not limited to nonpolar, polar, protic, and aprotic.

DETAILED DESCRIPTION OF THE INVENTION

The CDNs cyclic-di-AMP (produced by *Listeria monocytogenes*) and its analog cyclic-di-GMP (produced by *Legionella pneumophila*) are recognized by a host cell as a PAMP (Pathogen Associated Molecular Pattern), which bind to the PRR (Pathogen Recognition Receptor) known as STING. STING is an adaptor protein in the cytoplasm of host mammalian cells which activates the TANK binding kinase (TBK1)-IRF3 signaling axis, resulting in the induction of IFN-β and other IRF-3 dependent gene products that strongly activate innate immunity. It is now recognized that STING is a component of the host cytosolic surveillance pathway, that senses infection with intracellular pathogens and in response induces the production of IFN-β, leading to the development of an adaptive protective pathogen-specific immune response consisting of both antigen-specific CD4 and CD8 T cells as well as pathogen-specific antibodies.

Immunotherapy is advancing cancer treatment in multiple fronts. Recently, it was found that the activation of innate immune system via cyclic GAM-AMP (cGAMP), which activates the stimulator of IFN genes (STING) pathway, could initiate strong anti-tumor immune responses. Besides cGAMP, various other cyclic dinucleotides (CDNs), such as cdiAMP, cdiGMP and cAIMP, can activate STING pathway, which is recognized as an indispensable immune defense mechanism against tumors and exogenous pathogens. However, due to the small molecular weight, poor pharmacokinetic properties and severe off-target cytotoxicity, STING agonists require direct local injection into tumors. Experiments conducted during the course of developing embodiments for the present invention discovered that CDNs can assemble into homogeneous nanoparticles in the presence of either (1) $Zn^{2+}$ or (2) calcium phosphate and PEI-PEG. Based on such results, two categories of drug delivery systems for delivery of CDNs were developed. In a subcutaneous CT26 tumor model, the formulations were shown to significantly inhibit tumor growth and achieved a complete regression ratio of 40% and 60%. Thus, those formulations represent a new class of drug delivery systems for both local and systemic delivery of STING agonists.

Such results have significant clinical importance, as these nanoparticles associated with CDNs can induce immune responses against specific tumors through systemic administration thereby avoiding the need for direct local injection into tumors.

Additional experiments conducted during the course of developing embodiments for the present invention determined that specific metal ions, such as $Mn^{2+}$ and $Co^{2+}$, can enhance STING activation and type-I IFN response of STING agonists. In a murine CT26 colon tumor model, it was shown that the combination of $Mn^{2+}/Co^{2+}$-STING agonists exhibited elevated level of serum type-I IFN, produced higher tumor eradication efficacy, and promote longer survival of tumor-bearing mice, wherein 80% of mice were cured and resistant to second tumor challenging after 80 days. Furthermore, it was found that this phenomenon was general for various other innate immune pathways, including but not limited to the Toll-like receptor (TLR) 3/4/7/8/9 ligands, NOD1/2 ligands, TLR 7/8 ligands, RIG-I & CDS agonist and inflammasome inducers. Based on this discovery, some pharmaceutically acceptable formulations, such as metal salts of DAMP/PAMP, coordination and other metal-loading formulations (hydroxide/carbonate/phosphate minerals, liposome, self-assembly nanoparticles, PLGA, hydrogels, emulsions etc), could be developed to precisely deliver metals-innate immune stimulators combination to desired target and release in ideal manner. Lastly, it was found that some chelators can effectively inhibit DNA-induced cGAS-STING-Type-I IFN/NFkB response and polyIC-induced TLR3-cGAS-STING-Type-I IFN.

Accordingly, such results and embodiments indicate a new class of drug delivery systems for both local and systemic delivery of agents capable of stimulating an innate immune response in a subject upon administration to the subject.

As such, this disclosure provides compositions and methods for stimulating an innate immune response in a subject upon administration to the subject through administration of agents capable of stimulating an innate immune response in the subject. In particular, the present invention is directed to such compositions comprising agents capable of stimulating an innate immune response in a subject upon administration to the subject, methods for synthesizing such compositions, as well as systems and methods utilizing such compositions (e.g., in diagnostic and/or therapeutic settings).

Accordingly, in certain embodiments, the present invention provides compositions comprising one or more DAMPs and/or PAMPs, and either a) calcium phosphate and copolymers of cationic poly (ethylene imine) (PEI) and polyethylene glycol (PEG), poly (histidine)-polyethylene glycol (PH-PEG), lipid-poly-histidine, poly (lysine)-polyethylene glycol PEG (PK-PEG), or anionic poly (glutamic acid)-polyethylene glycol (PGA-PEG): or
b) one or more cations selected from the group consisting of $Zn^{2+}$, $Mn^{2+}$, $Ca^{2+}$, $Fe^{2+}$, $Fe^{3+}$, $Cu^{2+}$, $Ni^{2+}$, $Co^{2+}$, $Pb^{2+}$, $Sn^{2+}$, $Ru^{2+}$, $Au^{2+}$, $Mg^{2+}$, $VO^{2+}$, $Al^{3+}$, $Co^{3+}$, $Cr^{3+}$, $Ga^{3+}$, $Tl^{3+}$, $Ln^{3+}$, $MoO^{3+}$, $Cu^{+}$, $Au^{+}$, $Tl^{+}$, $Ag^{+}$, $Hg^{2+}$, $Pt^{2+}$, $Pb^{2+}$, $Hg^{2+}$, $Cd^{2+}$, $Pd^{2+}$, $Pt^{4+}$, $Na^{+}$, $K^{+}$, and relative phosphate or carbonate salt.

Such compositions are not limited to specific DAMP or PAMP agonists.

In some embodiments, the DAMP and PAMP agonists are selected from STING agonists, purine containing or purine derived agents, Toll-Like receptor (TLR) agonists, NOD-Like receptor (NLRs) agonists, RIG-I-Like receptor (RLR) agonists, cytosolic DNA sensor (CDS) agonists, C-type lectin receptor (CLR) agonists, and inflammasome inducers.

In some embodiments, the DAMP and PAMP agonists are selected from TLR-3 agonists, TLR-4 agonists, TLR-5 agonists, TLR-7 agonists (e.g., Imiquimod), TLR-8 agonists (e.g., Resiquimod), TLR-9 agonists, and NLRP3 agonists.

Such compositions are not limited to specific purine containing or purine derived agents. In some embodiments the purine containing or purine derived agents are selected from 2'3'-cGAMP, 3'3'-cGAMP, c-di-AMP, c-di-GMP, cAIMP, cAIMP Difluor, cAIM(PS)2, Difluor (Rp/Sp), 2'2'-cGAMP, 2'3-cGAM(PS)2 (Rp/Sp), 3'3'-cGAMP Fluorinated, c-di-AMP Fluorinated, 2'3'-c-di-AMP, 2'3-c-di-AM (PS)2 (Rp,Rp), c-di-GMP Fluorinated, 2'3'-c-di-GMP, c-di-IMP, cGAMP, 2'3'-cGAMP, 2'2'-cGAMP, 3'3'-cGAMP, cGAM(PS)2,2'3'-cGAM(PS)2 (Rp/Sp), 2'2"-cGAM(PS)2, 2'3'-cGAM(PS)2, cGAMP Fluorinated, 3'3'-cGAMP Fluorinated, 2'3'-cGAMP Fluorinated, 2'2'-cGAMP Fluorinated, c-di-AMP, 2'3'-cdAMP, 2'2'-cdAMP, 3'3'-cdAMP, c-di-AM (PS)2,2'3'-c-di-AM(PS)2 (Rp,Rp), 2'2'-c-di-AM(PS)2,3'3'-c-di-AM(PS)2, c-di-AMP Fluorinated, 2'3'-cdAMP Fluorinated, 2'2'-cdAMP Fluorinated, 3'3'-cdAMP Fluorinated, cdGMP, 2'3'-cdGMP, 2'2'-cdGMP, 3'3'-cdGMP, c-di-GM (PS)2,2'3"-c-di-GM(PS)2, 2'2'-c-di-GM(PS)2,3'3'-c-di-GM (PS)2, cdGMP Fluorinated, 2'3'-cdGMP Fluorinated, 2'2'-cdGMP Fluorinated, 3'3'-cdGMP Fluorinated, cAIMP, 2'3'-cAIMP, 2'2'-cAIMP, 3'3'-cAIMP, cAIMP Difluor (3'3'-cAIMP Fluorinated, 2'3'-cAIMP Fluorinated, 2'2'-cAIMP Fluorinated, cAIM(PS)2 Difluor, 3'3'-cAIM(PS)2 Difluor (Rp/Sp), 2'3'-cAIM(PS)2 Difluor, 2'2'-cAIM(PS)2 Difluor, c-di-IMP, 2'3'-cdIMP, 2'2'-cdIMP, 3'3'-cdIMP, c-di-IM(PS) 2,2'3'-c-di-IM(PS)2,2'2'-c-di-IM(PS)2, 3'3'-c-di-IM(PS)2, c-di-IMP Fluorinated, 2'3'-cdIMP Fluorinated, 2'2'-cdIMP Fluorinated, 3'3-cdIMP Fluorinated, Imiquimod, Resiquimod, 6-(4-amino-imidazoquinolyl)-norleucines,

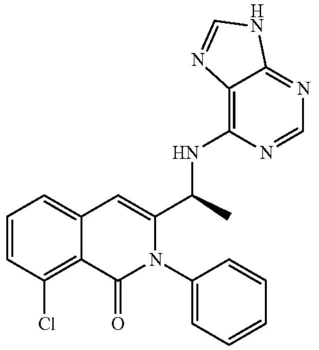

-continued

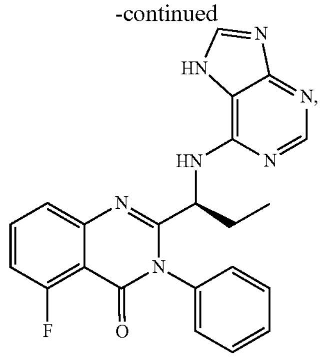

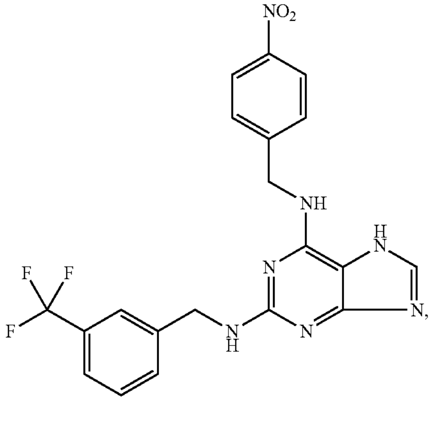

and purine based PI3K inhibitors.

Such compositions are not limited to particular STING agonists. In some embodiments, the STING agonist is a cyclic dinucleotide. For example, in some embodiments, the cyclic dinucleotide is cdi-AMP, cGAMP, or cGMP, or any derivatives thereof. In some embodiments, the small molecular agonists of STING include, but are not limited to, 2'3'-cGAMP, 3'3'-cGAMP, c-di-AMP, c-di-GMP, cAIMP, cAIMP Difluor, cAIM(PS)2, Difluor (Rp/Sp), 2'2'-cGAMP, 2'3'-cGAM(PS)2 (Rp/Sp), 3'3'-cGAMP Fluorinated, c-di-AMP Fluorinated, 2'3'-c-di-AMP, 2'3'-c-di-AM(PS)2 (Rp, Rp), c-di-GMP Fluorinated, 2'3'-c-di-GMP, c-di-IMP, SB11285, STING-agonist-C11, STING agonist-1, STING agonist G10. Gemcitabine, and as additional STING agonists described herein.

Suitable STING agonists for use in the disclosed compositions and methods include, but are not limited to, cyclic dinucleotide molecules. For example, in some embodiments, the small molecule agonists of STING is a cyclic dinucleotide selected from cGAMP, cdiAMP, cdiGMP, and cAIMP. Additional examples of cyclic purine dinucleotides are described in some detail in, e.g., U.S. Pat. Nos. 7,709,458 and 7,592,326; WO2007/054279; and Yan et al., Bioorg. Med. Chem Lett. 18:5631 (2008), each of which is hereby incorporated by reference.

Additional suitable STING agonists for use in the disclosed methods include, but are not limited to, flavonoids. In some embodiments, the STING agonist can comprise a flavonoid. In other embodiments, the STING agonist can consist of a flavonoid. Suitable flavonoids include, but are not limited to, 10-(carboxymethyl)-9 (10H) acridone (CMA), 5,6-Dimethylxanthenone-4-acetic acid (DMXAA), methoxyvone, 6,4'-dimethoxyflavone, 4'-methoxyflavone, 3',6'-dihydroxyflavone, 7,2'-dihydroxyflavone, daidzein, formononetin, retusin 7-methyl ether, xanthone, or any combination thereof. In some aspects, the STING agonist can be 10-(carboxymethyl)-9 (10H) acridone (CMA). In some aspects, the STING agonist can be 5,6-Dimethylxanthenone-4-acetic acid (DMXAA). In some aspects, the STING agonist can be methoxyvone. In some aspects, the STING agonist can be 6,4'-dimethoxyflavone. In some aspects, the STING agonist can be 4'-methoxyflavone. In some aspects, the STING agonist can be 3',6'-dihydroxyflavone. In some aspects, the STING agonist can be 7,2'-dihydroxyflavone. In some aspects, the STING agonist can be daidzein. In some aspects, the STING agonist can be formononetin. In some aspects, the STING agonist can be retusin 7-methyl ether. In some aspects, the STING agonist can be xanthone. In some aspects, the STING agonist can be any combination of the above flavonoids. Thus, for example, in some embodiments the flavonoid comprises DMXAA.

In some embodiments, the small molecular agonists of STING include, but are not limited to, 2'3'-cGAMP, 3'3'-cGAMP, c-di-AMP, c-di-GMP, cAIMP, cAIMP Difluor, CAIM(PS)2, Difluor (Rp/Sp), 2'2'-cGAMP, 2'3'-cGAM (PS)2 (Rp/Sp), 3'3'-cGAMP Fluorinated, c-di-AMP Fluorinated, 2'3'-c-di-AMP, 2'3'-c-di-AM(PS)2 (Rp,Rp), c-di-GMP Fluorinated, 2'3'-c-di-GMP, c-di-IMP, SB11285, STING-agonist-C11, STING agonist-1, STING agonist G10, and Gemcitabine.

In certain embodiments, the present invention provides compositions capable of inhibiting cGAS-STING activation and Type-I IFN response comprising of one or more cellular permeable chelators or their derivative to make intracellular metal ions unavailable for cGAS-STING-Type-I IFN activation.

In certain embodiments, the present invention provides compositions capable of regulating innate immune activation comprising of one or more cellular permeable chelators (e.g., metal ion chelators) to make intracellular metal ions unavailable for the innate immune pathways.

In some embodiments, such cellular permeable chelators (e.g., metal ion chelators) include, but are not limited to, polyphenol-based chelator (-)-Epigallocatechin gallate (EGCG), Punicalagin, (-)-Catechin gallate, (-)-Catechin, Tannic acid, tannin, Punicalin, Vescalagin, Procyanidin C1, Geraniin, Theaflavin 3,3'-digallate, lipid modified NTA, porphyrin, EDTA, NOTA, DOTA, TPEN, Crofelemer, etc.

In some embodiments, such compostions capable of inhibiting cGAS-STING activation and Type-I IFN response are used in treating subjects suffering from or at risk of suffering from autoimmune disorders.

As such, the present invention provides methods for treating autoimmune disorders through administering to a subject (e.g., human subject) compositions capable of regulating innate immune activation comprising of one or more cellular permeable chelators (e.g., metal ion chelators) to make intracellular metal ions unavailable for the innate immune pathways. In such embodiments, such cellular permeable chelators (e.g., metal ion chelators) include, but are not limited to, polyphenol-based chelator (-)-Epigallocatechin gallate (EGCG), Punicalagin, (-)-Catechin gallate, (-)-Catechin, Tannic acid, tannin, Punicalin, Vescalagin, Procyanidin C1, Geraniin, Theaflavin 3,3'-digallate, lipid modified NTA, porphyrin, EDTA, NOTA, DOTA, TPEN, Crofelemer, etc.

Examples of autoimmune disorders include, but are not limited to, Systemic lupus erythematosus, Aicardi-Goutières syndrome, Acute pancreatitis Age-dependent macular degeneration, Alcoholic liver disease, Liver fibrosis, Metastasis, Myocardial infarction, Nonalcoholic steatohepatitis (NASH), Parkinson's disease, Polyarthritis/fetal and neonatal anemia, Sepsis, inflammatory bowel disease, and multiple sclerosis.

In some embodiments, additional therapeutic agents are co-administered with such compositions. Examples of such therapeutic agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-$\alpha$ inhibitors (e.g., adalimumab, certolizumab pegol, etanercept, golimumab, infliximab), IL-1 inhibitors, and metalloprotease inhibitors. In some embodiments, the therapeutic agents include, but are not limited to, infliximab, adalimumab, etanercept, parenteral gold or oral gold.

In certain embodiments, compositions comprising agents capable of stimulating an innate immune response in a subject upon administration to the subject (e.g., DAMPs/PAMPs) are associated with (e.g., complexed, conjugated, encapsulated, absorbed, adsorbed, admixed) nanoparticles.

In some embodiments, such compositions associated with nanoparticles are further associated (e.g., complexed, conjugated, encapsulated, absorbed, adsorbed, admixed) with calcium phosphate and copolymers of PEI/PEG, PH-PEG, PK-PEG, or PGA-PEG. Indeed, in some embodiments, the associating of the agents capable of stimulating an innate immune response in a subject with the nanoparticle is in the presence of calcium phosphate and copolymers of PEI/PEG, PH-PEG, PK-PEG, or PGA-PEG.

In some embodiments, such compositions associated with nanoparticles are further associated (e.g., complexed, conjugated, encapsulated, absorbed, adsorbed, admixed) with one or more cations selected from the group consisting of $Zn^{2+}$, $Mn^{2+}$, $Ca^{2+}$, $Fe^{2+}$, $Fe^{3+}$, $Cu^{2+}$, $Ni^{2+}$, $Co^{2+}$, $Pb^{2+}$, $Sn^{2+}$, $Ru^{2+}$, $Au^{2+}$, $Mg^{2+}$, $VO^{2+}$, $Al^{3+}$, $Co^{3+}$, $Cr^{3+}$, $Ga^{3+}$, $Tl^{3+}$, $Ln^{3+}$, $MoO^{3+}$, $Cu^{+}$, Au×, $Tl^{+}$, $Ag^{+}$, $Hg^{2+}$, $Pt^{2+}$, $Pb^{2+}$, $Hg^{2+}$, $Cd^{2+}$, $Pd^{2+}$, $Pt^{4+}$, $Na^{+}$, $K^{+}$, and relative phosphate or carbonate salt. Indeed, in some embodiments, the associating of the agents capable of stimulating an innate immune response in a subject with the nanoparticle is in the presence of such cations (e.g., $Zn^{2+}$, $Co^{2+}$, or $Mn^{2+}$).

Those skilled in the art know that STING (stimulator of interferon genes) is the adaptor of multiple cytoplasmic DNA receptors and a pattern recognition receptor (PRR) recognizing bacterial second messengers cyclic di-adenosine monophosphate (c-di-AMP) and cyclic di-guanosine monophosphate (c-di-GMP). Cytosolic DNA binds to cyclic guanosine monophosphate-adenosine monophosphate (cGAMP) synthase (cGAS), to produce cyclic guanosine monophosphate-adenosine monophosphate (cyclic GMP-AMP, or cGAMP), which subsequently binds to and activates the adaptor protein STING and induces IFNs. STING comprises five putative transmembrane regions, predominantly resides in the endoplasmic reticulum, and is able to activate both NF-kappaB and IRF3 transcription pathways to induce expression of type I interferon (IFN-alpha and IFN-beta) and exert a potent anti-viral state following expression.

As such, DAMPs and PAMPs (e.g., STING agonists) are capable of stimulating an innate cytokine response in cancer cells. Thus, in some embodiments, the DAMPs and PAMPs (e.g., STING agonists) can stimulate an innate cytokine response in cancer cells.

A DAMP or PAMP stimulated innate cytokine response is mediated through cytokines. In some embodiments, for example, the innate cytokine response can be mediated through type 1 interferon.

As noted, this disclosure provides compositions and methods for stimulating the innate immune response in cancerous cells with agents capable of stimulating an innate immune response in a subject upon administration to the subject (e.g., DAMPs/PAMPs) to suppress and/or inhibit growth of such cancer cells (e.g., tumor cells). In particular, the present invention is directed to compositions comprising nanoparticles associated with (e.g., complexed, conjugated, encapsulated, absorbed, adsorbed, admixed) agents capable of stimulating an innate immune response in a subject upon administration to the subject (e.g., DAMPs/PAMPs), methods for synthesizing such nanoparticles, as well as systems and methods utilizing such nanoparticles (e.g., in diagnostic and/or therapeutic settings).

Indeed, experiments conducted during the course of developing embodiments for the present invention demonstrated that CDNs, including cGAMP, cdiAMP, cdiGMP, and cAIMP, assemble into homogeneous nanoparticles in the presence of $Zn^{2+}$. It was also shown that such CDNs assembled into homogenous nanoparticles in the presence of $Zn^{2+}$ are further stabilized with lipid vesicles. Additional experiments demonstrated that CDNs can be formulated into nanoparticles in the presence of calcium phosphate and copolymers of cationic poly (ethylene imine) (PEI) and polyethylene glycol (PEG). It was further shown that such CDN-nanoparticle assemblies (e.g., CDNs formulated into nanoparticles in the presence of calcium phosphate and copolymers of PEI-PEG) (e.g., CDNs formulated into nanoparticles in the presence of of $Zn^{2+}$, $Co^{2+}$, or $Mn^{2+}$ and liposomes) provide increased cancer cell uptake and more accurate targeting to the tumor microenvironment (e.g., TME), thereby enabling increased STING agonist delivery efficacy and lower toxicity.

The present invention is not limited to specific types or kinds of nanoparticles associated with (e.g., complexed, conjugated, encapsulated, absorbed, adsorbed, admixed) such compostions comprising agents capable of stimulating an innate immune response in a subject upon administration to the subject (e.g., DAMPs/PAMPs).

Examples of nanoparticles include, but are not limited to, metal-polyhistidine-DOPE a liposome, metal-polyhistidine-PEG, 4arm-PEG-polyhistidine-metal hydrogels, and sHDL-polyhistidine, fullerenes (a.k.a. $C_{60}$, $C_{70}$, $C_{76}$, $C_{80}$, $C_{84}$), endohedral metallofullerenes (EMI's) buckyballs, which contain additional atoms, ions, or clusters inside their fullerene cage), trimetallic nitride templated endohedral metallofullerenes (TNT EMEs, high-symmetry four-atom molecular cluster endohedrals, which are formed in a trimetallic nitride template within the carbon cage), single-walled and multi-walled carbon nanotubes, branched and dendritic carbon nanotubes, gold nanorods, silver nanorods, single-walled and multi-walled boron/nitrate nanotubes, carbon nanotube peapods (nanotubes with internal metallo-fullerenes and/or other internal chemical structures), carbon nanohorns, carbon nanohorn peapods, liposomes, nanoshells, dendrimers, quantum dots, superparamagnetic nanoparticles, nanorods, and cellulose nanoparticles. The particle embodiment can also include microparticles with the capability to enhance effectiveness or selectivity. Other non-limiting exemplary nanoparticles include glass and polymer micro- and nano-spheres, biodegradable PLGA micro- and nano-spheres, gold, silver, carbon, and iron nanoparticles.

In some embodiments, the nanoparticle is a modified micelle. In these embodiments, the modified micelle comprises polyol polymers modified to contain a hydrophobic polymer block. The term "hydrophobic polymer block" as used in the present disclosure indicates a segment of the polymer that on its own would be hydrophobic. The term "micelle" as used herein refers to an aggregate of molecules dispersed in a liquid. A typical micelle in aqueous solution forms an aggregate with the hydrophilic "head" regions in contact with surrounding solvent, sequestering the hydrophobic single tail regions in the micelle centre. In some embodiments the head region may be, for example, a surface region of the polyol polymer while the tail region may be, for example, the hydrophobic polymer block region of the polyol polymer.

The invention further encompasses use of particles on the micrometer scale in addition to the nanometer scale. Where microparticles are used, it is preferred that they are relatively small, on the order of 1-50 micrometers. For ease of discussion, the use herein of "nanoparticles" encompasses true nanoparticles (sizes of from about 1 nm to about 1000 nm), microparticles (e.g., from about 1 micrometer to about 50) micrometers), or both.

Examples of nanoparticles include, by way of example and without limitation, paramagnetic nanoparticles, superparamagnetic nanoparticles, metal nanoparticles, fullerene-like materials, inorganic nanotubes, dendrimers, dendrimers with covalently attached metal chelates, nanofibers, nanohorns, nano-onions, nanorods, nanoropes and quantum dots. In some embodiments, a nanoparticle is a metal nanoparticle (for example, a nanoparticle of gold, palladium, platinum, silver, copper, nickel, cobalt, iridium, or an alloy of two or more thereof). Nanoparticles can include a core or a core and a shell, as in core-shell nanoparticles.

In some embodiments, the nanoparticles are sHDL nanoparticles. Generally, sHDL nanoparticles are composed of a mixture of HDL apolipoprotein and an amphipathic lipid.

The present invention is not limited to use of a particular type or kind of HDL apolipoprotein. HDL apolipoproteins include, for example apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, preproApoA-IV, proApoA-IV, ApoA-IV, ApoA-V, preproApoE, proApoE, ApoE, preproApoA-1Milano, proApoA-1Milano ApoA-1Milano preproApoA-IParis, proApoA-IParis, and ApoA-IParis and peptide mimetics of these proteins mixtures thereof, Preferably, the carrier particles are composed of Apo A-I or Apo A-II, however the use of other lipoproteins including apolipoprotein A4, apolipoprotein Cs or apolipoprotein E may be used alone or in combination to formulate carrier particle mixtures for delivery of therapeutic agents. In some embodiments, mimetics of such HDL apolipoproteins are used.

ApoA-I is synthesized by the liver and small intestine as preproapolipoprotein which is secreted as a proprotein that is rapidly cleaved to generate a mature polypeptide having 243 amino acid residues. ApoA-I consists mainly of 6 to 8 different 22 amino acid repeats spaced by a linker moiety which is often proline, and in some cases consists of a stretch made up of several residues. ApoA-I forms three types of stable complexes with lipids; small, lipid-poor complexes referred to as pre-beta-1 HDL; flattened discoidal particles containing polar lipids (phospholipid and cholesterol) referred to as pre-beta-2 HDL; and spherical particles containing both polar and nonpolar lipids, referred to as spherical or mature HDL ($HDL_3$ and $HDL_2$). Most HDL in the circulating population contain both ApoA-I and ApoA-II (the second major HDL protein).

In some embodiments, ApoA-I agonists or mimetics are provided. In some embodiments, such ApoA-I mimetics are capable of forming amphipathic a-helices that mimic the activity of ApoA-I, and have specific activities approaching or exceeding that of the native molecule. In some, the ApoA-I mimetics are peptides or peptide analogues that: form amphipathic helices (in the presence of lipids), bind lipids, form pre-β-like or HDL-like complexes, activate lecithin:cholesterol acyltransferase (LCAT), increase serum levels of HDL fractions, and promote cholesterol efflux.

The present invention is not limited to use of a particular ApoA-I mimetic. In some embodiments, any of the ApoA-I mimetics described in Srinivasa, et al., 2014 Curr. Opinion Lipidology Vol. 25 (4): 304-308 are utilized. In some embodiments, any of the ApoA-I mimetics described in U.S. Patent Application Publication Nos. 20110046056 and 20130231459 are utilized.

In some embodiments, the "22A" ApoA-I mimetic is used (PVLDLFRELLNELLEALKQKLK) (SEQ ID NO: 4) (see, e.g., U.S. Pat. No. 7,566,695). In some embodiments, any of the following ApoA-I mimetics shown in Table 1 as described in U.S. Pat. No. 7,566,695 are utilized:

TABLE 1

ApoA-I mimetics

| SEQ ID NO | AMINO ACID SEQUENCE |
|---|---|
| (SEQ ID NO: 1) | PVLDLFRELLNELLEZLKQKLK |
| (SEQ ID NO: 2) | GVLDLFRELLNELLEALKQKLKK |
| (SEQ ID NO: 3) | PVLDLFRELLNELLEWLKQKLK |
| (SEQ ID NO: 4) | PVLDLFRELLNELLEALKQKLK |
| (SEQ ID NO: 5) | pVLDLFRELLNELLEALKQKLKK |
| (SEQ ID NO: 6) | PVLDLFRELLNEXLEALKQKLK |
| (SEQ ID NO: 7) | PVLDLFKELLNELLEALKQKLK |
| (SEQ ID NO: 8) | PVLDLFRELLNEGLEALKQKLK |
| (SEQ ID NO: 9) | PVLDLFRELGNELLEALKQKLK |
| (SEQ ID NO: 10) | PVLDLFRELLNELLEAZKQKLK |
| (SEQ ID NO: 11) | PVLDLFKELLQELLEALKQKLK |
| (SEQ ID NO: 12) | PVLDLFRELLNELLEAGKQKLK |
| (SEQ ID NO: 13) | GVLDLFRELLNEGLEALKQKLK |
| (SEQ ID NO: 14) | PVLDLFRELLNELLEALOQOLO |
| (SEQ ID NO: 15) | PVLDLFRELWNELLEALKQKLK |
| (SEQ ID NO: 16) | PVLDLLRELLNELLEALKQKLK |
| (SEQ ID NO: 17) | PVLELFKELLQELLEALKQKLK |
| (SEQ ID NO: 18) | GVLDLFRELLNELLEALKQKLK |
| (SEQ ID NO: 19) | pVLDLFRELLNEGLEALKQKLK |
| (SEQ ID NO: 20) | PVLDLFREGLNELLEALKQKLK |
| (SEQ ID NO: 21) | pVLDLFRELLNELLEALKQKLK |

TABLE 1-continued

ApoA-I mimetics

| SEQ ID NO | AMINO ACID SEQUENCE |
|---|---|
| (SEQ ID NO: 22) | PVLDLFRELLNELLEGLKQKLK |
| (SEQ ID NO: 23) | PLLELFKELLQELLEALKQKLK |
| (SEQ ID NO: 24) | PVLDLFRELLNELLEALQKKLK |
| (SEQ ID NO: 25) | PVLDFFRELLNEXLEALKQKLK |
| (SEQ ID NO: 26) | PVLDLFRELLNELLELLKQKLK |
| (SEQ ID NO: 27) | PVLDLFRELLNELZEALKQKLK |
| (SEQ ID NO: 28) | PVLDLFRELLNELWEALKQKLK |
| (SEQ ID NO: 29) | AVLDLFRELLNELLEALKQKLK |
| (SEQ ID NO: 30) | PVLDLPRELLNELLEALKQKLK[1] |
| (SEQ ID NO: 31) | PVLDLFLELLNEXLEALKQKLK |
| (SEQ ID NO: 32) | XVLDLFRELLNELLEALKQKLK |
| (SEQ ID NO: 33) | PVLDLFREKLNELLEALKQKLK |
| (SEQ ID NO: 34) | PVLDZFRELLNELLEALKQKLK |
| (SEQ ID NO: 35) | PVLDWFRELLNELLEALKQKLK |
| (SEQ ID NO: 36) | PLLELLKELLQELLEALKQKLK |
| (SEQ ID NO: 37) | PVLDLFREWLNELLEALKQKLK |
| (SEQ ID NO: 38) | PVLDLFRELLNEXLEAWKQKLK |
| (SEQ ID NO: 39) | PVLDLFRELLEELLKALKKKLK |
| (SEQ ID NO: 40) | PVLDLFNELLRELLEALQKKLK |
| (SEQ ID NO: 41) | PVLDLWRELLNEXLEALKQKLK |
| (SEQ ID NO: 42) | PVLDEFREKLNEXWEALKQKLK |
| (SEQ ID NO: 43) | PVLDEFREKLWEXLEALKQKLK |
| (SEQ ID NO: 44) | pvldefreklneXlealkqklk |
| (SEQ ID NO: 45) | PVLDEFREKLNEXLEALKQKLK |
| (SEQ ID NO: 46) | PVLDLFREKLNEXLEALKQKLK |
| (SEQ ID NO: 47) | ~VLDLFRELLNEGLEALKQKLK |
| (SEQ ID NO: 48) | pvLDLFRELLNELLEALKQKLK |
| (SEQ ID NO: 49) | PVLDLFRNLLEKLLEALEQKLK |
| (SEQ ID NO: 50) | PVLDLFRELLWEXLEALKQKLK |
| (SEQ ID NO: 51) | PVLDLFWELLNEXLEALKQKLK |
| (SEQ ID NO: 52) | PVWDEFREKLNEXLEALKQKLK |
| (SEQ ID NO: 53) | VVLDLFRELLNELLEALKQKLK |
| (SEQ ID NO: 54) | PVLDLFRELLNEWLEALKQKLK |
| (SEQ ID NO: 55) | P~~~LFRELLNELLEALKQKLK |
| (SEQ ID NO: 56) | PVLDLFRELLNELLEALKQKKK |
| (SEQ ID NO: 57) | PVLDLFRNLLEELLKALEQKLK |
| (SEQ ID NO: 58) | PVLDEFREKLNEXLEALKQKL~ |
| (SEQ ID NO: 59) | LVLDLFRELLNELLEALKQKLK |

TABLE 1-continued

ApoA-I mimetics

| SEQ ID NO | AMINO ACID SEQUENCE |
|---|---|
| (SEQ ID NO: 60) | PVLDLFRELLNELLEALKQ~~~ |
| (SEQ ID NO: 61) | PVLDEFRWKLNEXLEALKQKLK |
| (SEQ ID NO: 62) | PVLDEWREKLNEXLEALKQKLK |
| (SEQ ID NO: 63) | PVLDFFREKLNEXLEALKQKLK |
| (SEQ ID NO: 64) | PWLDEFREKLNEXLEALKQKLK |
| (SEQ ID NO: 65) | ~VLDEFREKLNEXLEALKQKLK |
| (SEQ ID NO: 66) | PVLDLFRNLLEELLEALQKKLK |
| (SEQ ID NO: 67) | ~VLDLFRELLNELLEALKQKLK |
| (SEQ ID NO: 68) | PVLDEFRELLKEXLEALKQKLK |
| (SEQ ID NO: 69) | PVLDEFRKKLNEXLEALKQKLK |
| (SEQ ID NO: 70) | PVLDEFRELLYEXLEALKQKLK |
| (SEQ ID NO: 71) | PVLDEFREKLNELXEALKQKLK |
| (SEQ ID NO: 72) | PVLDLFRELLNEXLWALKQKLK |
| (SEQ ID NO: 73) | PVLDEFWEKLNEXLEALKQKLK |
| (SEQ ID NO: 74) | PVLDKFREKLNEXLEALKQKLK |
| (SEQ ID NO: 75) | PVLDEFREKLNEELEALKQKLK |
| (SEQ ID NO: 76) | PVLDEFRELLFEXLEALKQKLK |
| (SEQ ID NO: 77) | PVLDEFREKLNKXLEALKQKLK |
| (SEQ ID NO: 78) | PVLDEFRDKLNEXLEALKQKLK |
| (SEQ ID NO: 79) | PVLDEFRELLNELLEALKQKLK |
| (SEQ ID NO: 80) | PVLDLFERLLNELLEALQKKLK |
| (SEQ ID NO: 81) | PVLDEFREKLNWXLEALKQKLK |
| (SEQ ID NO: 82) | ~~LDEFREKLNEXLEALKQKLK |
| (SEQ ID NO: 83) | PVLDEFREKLNEXLEALWQKLK |
| (SEQ ID NO: 84) | PVLDEFREKLNELLEALKQKLK |
| (SEQ ID NO: 85) | P~LDLFRELLNELLEALKQKLK |
| (SEQ ID NO: 86) | PVLELFERLLDELLNALQKKLK |
| (SEQ ID NO: 87) | pllellkellqellealkqklk |
| (SEQ ID NO: 88) | PVLDKFRELLNEXLEALKQKLK |
| (SEQ ID NO: 89) | PVLDEFREKLNEXLWALKQKLK |
| (SEQ ID NO: 90) | ~~~DEFREKLNEXLEALKQKLK |
| (SEQ ID NO: 91) | PVLDEFRELLNEXLEALKQKLK |
| (SEQ ID NO: 92) | PVLDEFRELYNEXLEALKQKLK |
| (SEQ ID NO: 93) | PVLDEFREKLNEXLKALKQKLK |
| (SEQ ID NO: 94) | PVLDEFREKLNEALEALKQKLK |
| (SEQ ID NO: 95) | PVLDLFRELLNLXLEALKQKLK |
| (SEQ ID NO: 96) | pvldlfrellneXlealkqklk |
| (SEQ ID NO: 97) | PVLDLFRELLNELLE~~~~~~~ |

TABLE 1-continued

| ApoA-I mimetics | |
|---|---|
| SEQ ID NO | AMINO ACID SEQUENCE |
| (SEQ ID NO: 98) | PVLDLFRELLNEELEALKQKLK |
| (SEQ ID NO: 99) | KLKQKLAELLENLLERFLDLVP |
| (SEQ ID NO: 100) | pvldlfrellnellealkqklk |
| (SEQ ID NO: 101) | PVLDLFRELLNWXLEALKQKLK |
| (SEQ ID NO: 102) | PVLDLFRELLNLXLEALKEKLK |
| (SEQ ID NO: 103) | PVLDEFRELLNEELEALKQKLK |
| (SEQ ID NO: 104) | P~~~~~~~LLNELLEALKQKLK |
| (SEQ ID NO: 105) | PAADAFREAANEAAEAAKQKAK |
| (SEQ ID NO: 106) | PVLDLFREKLNEELEALKQKLK |
| (SEQ ID NO: 107) | klkqklaellenllerfldlvp |
| (SEQ ID NO: 108) | PVLDLFRWLLNEXLEALKQKLK |
| (SEQ ID NO: 109) | PVLDEFREKLNERLEALKQKLK |
| (SEQ ID NO: 110) | PVLDEFREKLNEXXEALKQKLK |
| (SEQ ID NO: 111) | PVLDEFREKLWEXWEALKQKLK |
| (SEQ ID NO: 112) | PVLDEFREKLNEXSEALKQKLK |
| (SEQ ID NO: 113) | PVLDEFREKLNEPLEALKQKLK |
| (SEQ ID NO: 114) | PVLDEFREKLNEXMEALKQKLK |
| (SEQ ID NO: 115) | PKLDEFREKLNEXLEALKQKLK |
| (SEQ ID NO: 116) | PHLDEFREKLNEXLEALKQKLK |
| (SEQ ID NO: 117) | PELDEFREKLNEXLEALKQKLK |
| (SEQ ID NO: 118) | PVLDEFREKLNEXLEALEQKLK |
| (SEQ ID NO: 119) | PVLDEFREKLNEELEAXKQKLK |
| (SEQ ID NO: 120) | PVLDEFREKLNEELEXLKQKLK |
| (SEQ ID NO: 121) | PVLDEFREKLNEELEALWQKLK |
| (SEQ ID NO: 122) | PVLDEFREKLNEELEWLKQKLK |
| (SEQ ID NO: 123) | QVLDLFRELLNELLEALKQKLK |
| (SEQ ID NO: 124) | PVLDLFQELLNELLEALOQOLO |
| (SEQ ID NO: 125) | NVLDLFRELLNELLEALKQKLK |
| (SEQ ID NO: 126) | PVLDLFRELLNELGEALKQKLK |
| (SEQ ID NO: 127) | PVLDLFRELLNELLELLKQKLK |
| (SEQ ID NO: 128) | PVLDLFRELLNELLEFLKQKLK |
| (SEQ ID NO: 129) | PVLELFNDLLRELLEALQKKLK |
| (SEQ ID NO: 130) | PVLELFNDLLRELLEALKQKLK |
| (SEQ ID NO: 131) | PVLELFKELLNELLDALRQKLK |
| (SEQ ID NO: 132) | PVLDLFRELLENLLEALQKKLK |
| (SEQ ID NO: 133) | PVLELFERLLEDLLQALNKKLK |
| (SEQ ID NO: 134) | PVLELFERLLEDLLKALNOKLK |
| (SEQ ID NO: 135) | DVLDLFRELLNELLEALKQKLK |

TABLE 1-continued

| ApoA-I mimetics | |
|---|---|
| SEQ ID NO | AMINO ACID SEQUENCE |
| (SEQ ID NO: 136) | PALELFKDLLQELLEALKQKLK |
| (SEQ ID NO: 137) | PVLDLFRELLNEGLEAZKQKLK |
| (SEQ ID NO: 138) | PVLDLFRELLNEGLEWLKQKLK |
| (SEQ ID NO: 139) | PVLDLFRELWNEGLEALKQKLK |
| (SEQ ID NO: 140) | PVLDLFRELLNEGLEALOQOLO |
| (SEQ ID NO: 141) | PVLDFFRELLNEGLEALKQKLK |
| (SEQ ID NO: 142) | PVLELFRELLNEGLEALKQKLK |
| (SEQ ID NO: 143) | PVLDLFRELLNEGLEALKQKLK* |
| (SEQ ID NO: 144) | pVLELFENLLERLLDALQKKLK |
| (SEQ ID NO: 145) | GVLELFENLLERLLDALQKKLK |
| (SEQ ID NO: 146) | PVLELFENLLERLLDALQKKLK |
| (SEQ ID NO: 147) | PVLELFENLLERLFDALQKKLK |
| (SEQ ID NO: 148) | PVLELFENLLERLGDALQKKLK |
| (SEQ ID NO: 149) | PVLELFENLWERLLDALQKKLK |
| (SEQ ID NO: 150) | PLLELFENLLERLLDALQKKLK |
| (SEQ ID NO: 151) | PVLELFENLGERLLDALQKKLK |
| (SEQ ID NO: 152) | PVFELFENLLERLLDALQKKLK |
| (SEQ ID NO: 153) | AVLELFENLLERLLDALQKKLK |
| (SEQ ID NO: 154) | PVLELFENLLERGLDALQKKLK |
| (SEQ ID NO: 155) | PVLELFLNLWERLLDALQKKLK |
| (SEQ ID NO: 156) | PVLELFLNLLERLLDALQKKLK |
| (SEQ ID NO: 157) | PVLEFFENLLERLLDALQKKLK |
| (SEQ ID NO: 158) | PVLELFLNLLERLLDWLQKKLK |
| (SEQ ID NO: 159) | PVLDLFENLLERLLDALQKKLK |
| (SEQ ID NO: 160) | PVLELFENLLERLLDWLQKKLK |
| (SEQ ID NO: 161) | PVLELFENLLERLLEALQKKLK |
| (SEQ ID NO: 162) | PVLELFENWLERLLDALQKKLK |
| (SEQ ID NO: 163) | PVLELFENLLERLWDALQKKLK |
| (SEQ ID NO: 164) | PVLELFENLLERLLDAWQKKLK |
| (SEQ ID NO: 165) | PVLELFENLLERLLDLLQKKLK |
| (SEQ ID NO: 166) | PVLELFLNLLEKLLDALQKKLK |
| (SEQ ID NO: 167) | PVLELFENGLERLLDALQKKLK |
| (SEQ ID NO: 168) | PVLELFEQLLEKLLDALQKKLK |
| (SEQ ID NO: 169) | PVLELFENLLEKLLDALQKKLK |
| (SEQ ID NO: 170) | PVLELFENLLEOLLDALQOOLO |
| (SEQ ID NO: 171) | PVLELFENLLEKLLDLLQKKLK |
| (SEQ ID NO: 172) | PVLELFLNLLERLGDALQKKLK |
| (SEQ ID NO: 173) | PVLDLFDNLLDRLLDLLNKKLK |

TABLE 1-continued

ApoA-I mimetics

| SEQ ID NO | AMINO ACID SEQUENCE |
|---|---|
| (SEQ ID NO: 174) | pvlelfenllerlldalqkklk |
| (SEQ ID NO: 175) | PVLELFENLLERLLELLNKKLK |
| (SEQ ID NO: 176) | PVLELWENLLERLLDALQKKLK |
| (SEQ ID NO: 177) | GVLELFLNLLERLLDALQKKLK |
| (SEQ ID NO: 178) | PVLELFDNLLEKLLEALQKKLR |
| (SEQ ID NO: 179) | PVLELFDNLLERLLDALQKKLK |
| (SEQ ID NO: 180) | PVLELFDNLLDKLLDALQKKLR |
| (SEQ ID NO: 181) | PVLELFENLLERWLDALQKKLK |
| (SEQ ID NO: 182) | PVLELFENLLEKLLEALQKKLK |
| (SEQ ID NO: 183) | PLLELFENLLEKLLDALQKKLK |
| (SEQ ID NO: 184) | PVLELFLNLLERLLDAWQKKLK |
| (SEQ ID NO: 185) | PVLELFENLLERLLDALQOOLO |
| (SEQ ID NO: 186) | PVLELFEQLLERLLDALQKKLK |
| (SEQ ID NO: 187) | PVLELFENLLERLLDALNKKLK |
| (SEQ ID NO: 188) | PVLELFENLLDRLLDALQKKLK |
| (SEQ ID NO: 189) | DVLELFENLLERLLDALQKKLK |
| (SEQ ID NO: 190) | PVLEFWDNLLDKLLDALQKKLR |
| (SEQ ID NO: 191) | PVLDLLRELLEELKQKLK* |
| (SEQ ID NO: 192) | PVLDLFKELLEELKQKLK* |
| (SEQ ID NO: 193) | PVLDLFRELLEELKQKLK* |
| (SEQ ID NO: 194) | PVLELFRELLEELKQKLK* |
| (SEQ ID NO: 195) | PVLELFKELLEELKQKLK* |
| (SEQ ID NO: 196) | PVLDLFRELLEELKNKLK* |
| (SEQ ID NO: 197) | PLLDLFRELLEELKQKLK* |
| (SEQ ID NO: 198) | GVLDLFRELLEELKQKLK* |
| (SEQ ID NO: 199) | PVLDLFRELWEELKQKLK* |
| (SEQ ID NO: 200) | NVLDLFRELLEELKQKLK* |
| (SEQ ID NO: 201) | PLLDLFKELLEELKQKLK* |
| (SEQ ID NO: 202) | PALELFKDLLEELRQKLR* |
| (SEQ ID NO: 203) | AVLDLFRELLEELKQKLK* |
| (SEQ ID NO: 204) | PVLDFFRELLEELKQKLK* |
| (SEQ ID NO: 205) | PVLDLFREWLEELKQKLK* |
| (SEQ ID NO: 206) | PLLELLKELLEELKQKLK* |
| (SEQ ID NO: 207) | PVLELLKELLEELKQKLK* |
| (SEQ ID NO: 208) | PALELFKDLLEELRQRLK* |
| (SEQ ID NO: 209) | PVLDLFRELLNELLQKLK |
| (SEQ ID NO: 210) | PVLDLFRELLEELKQKLK |
| (SEQ ID NO: 211) | PVLDLFRELLEELOQOLO* |

TABLE 1-continued

ApoA-I mimetics

| SEQ ID NO | AMINO ACID SEQUENCE |
|---|---|
| (SEQ ID NO: 212) | PVLDLFQELLEELOQOLK* |
| (SEQ ID NO: 213) | PALELFKDLLEEFRQRLK* |
| (SEQ ID NO: 214) | pVLDLFRELLEELKQKLK* |
| (SEQ ID NO: 215) | PVLDLFRELLEEWKQKLK* |
| (SEQ ID NO: 216) | PVLELFKELLEELKQKLK |
| (SEQ ID NO: 217) | PVLDLFRELLELLKQKLK |
| (SEQ ID NO: 218) | PVLDLFRELLNELLQKLK* |
| (SEQ ID NO: 219) | PVLDLFRELLNELWQKLK |
| (SEQ ID NO: 220) | PVLDLFRELLEELQKKLK |
| (SEQ ID NO: 221) | DVLDLFRELLEELKQKLK* |
| (SEQ ID NO: 222) | PVLDAFRELLEALLQLKK |
| (SEQ ID NO: 223) | PVLDAFRELLEALAQLKK |
| (SEQ ID NO: 224) | PVLDLFREGWEELKQKLK |
| (SEQ ID NO: 225) | PVLDAFRELAEALAQLKK |
| (SEQ ID NO: 226) | PVLDAFRELGEALLQLKK |
| (SEQ ID NO: 227) | PVLDLFRELGEELKQKLK* |
| (SEQ ID NO: 228) | PVLDLFREGLEELKQKLK* |
| (SEQ ID NO: 229) | PVLDLFRELLEEGKQKLK* |
| (SEQ ID NO: 230) | PVLELFERLLEDLQKKLK |
| (SEQ ID NO: 231) | PVLDLFRELLEKLEQKLK |
| (SEQ ID NO: 232) | PLLELFKELLEELKQKLK* |
| (SEQ ID NO: 233) | LDDLLQKWAEAFNQLLKK |
| (SEQ ID NO: 234) | EWLKAFYEKVLEKLKELF* |
| (SEQ ID NO: 235) | EWLEAFYKKVLEKLKELF* |
| (SEQ ID NO: 236) | DWLKAFYDKVAEKLKEAF* |
| (SEQ ID NO: 237) | DWFKAFYDKVFEKFKEFF |
| (SEQ ID NO: 238) | GIKKFLGSIWKFIKAFVG |
| (SEQ ID NO: 239) | DWFKAFYDKVAEKFKEAF |
| (SEQ ID NO: 240) | DWLKAFYDKVAEKLKEAF |
| (SEQ ID NO: 241) | DWLKAFYDKVFEKFKEFF |
| (SEQ ID NO: 242) | EWLEAFYKKVLEKLKELP |

TABLE 1-continued

| ApoA-I mimetics | |
|---|---|
| SEQ ID NO | AMINO ACID SEQUENCE |
| (SEQ ID NO: 243) | DWFKAFYDKFFEKFKEFF |
| (SEQ ID NO: 244) | EWLKAFYEKVLEKLKELF |
| (SEQ ID NO: 245) | EWLKAEYEKVEEKLKELF* |
| (SEQ ID NO: 246) | EWLKAEYEKVLEKLKELF* |
| (SEQ ID NO: 247) | EWLKAFYKKVLEKLKELF* |
| (SEQ ID NO: 248) | PVLDLFRELLEQKLK* |
| (SEQ ID NO: 249) | PVLDLFRELLEELKQK* |
| (SEQ ID NO: 250) | PVLDLFRELLEKLKQK* |
| (SEQ ID NO: 251) | PVLDLFRELLEKLQK* |
| (SEQ ID NO: 252) | PVLDLFRELLEALKQK* |
| (SEQ ID NO: 253) | PVLDLFENLLERLKQK* |
| (SEQ ID NO: 254) | PVLDLFRELLNELKQK* |

*indicates peptides that are N-terminal acetylated and C-terminal amidated; indicates peptides that are N-terminal dansylated; sp indicates peptides that exhibited solubility problems under the experimental conditions; X is Aib; Z is Nal; O is Orn; He (%) designates percent helicity; mics designates micelles; and ~ indicates deleted amino acids.

In some embodiments, an ApoA-I mimetic having the following sequence as described in U.S. Pat. No. 6,743,778 is utilized: Asp Trp Leu Lys Ala Phe Tyr Asp Lys Val Ala Glu Lys Leu Lys Glu Ala Phe (SEQ ID NO:255).

In some embodiments, any of the following ApoA-I mimetics shown in Table 2 as described in U.S. Patent Application Publication No. 2003/0171277 are utilized:

TABLE 2

| SEQ ID NO | AMINO ACID SEQUENCE |
|---|---|
| (SEQ ID NO: 256) | D-W-L-K-A-F-Y-D-K-V-A-E-K-L-K-E-A-F |
| (SEQ ID NO: 257) | Ac-D-W-L-K-A-F-Y-D-K-V-A-E-K-L-K-E-A-F-$NH_2$ |
| (SEQ ID NO: 258) | Ac-D-W-F-K-A-F-Y-D-K-V-A-E-K-L-K-E-A-F-$NH_2$ |
| (SEQ ID NO: 259) | Ac-D-W-L-K-A-F-Y-D-K-V-A-E-K-F-K-E-A-F-$NH_2$ |
| (SEQ ID NO: 260) | Ac-D-W-F-K-A-F-Y-D-K-V-A-E-K-F-K-E-A-F-$NH_2$ |
| (SEQ ID NO: 261) | Ac-D-W-L-K-A-F-Y-D-K-V-F-E-K-F-K-E-F-F-$NH_2$ |
| (SEQ ID NO: 262) | Ac-D-W-L-K-A-F-Y-D-K-F-F-E-K-F-K-E-F-F-$NH_2$ |
| (SEQ ID NO: 263) | Ac-D-W-F-K-A-F-Y-D-K-F-F-E-K-F-K-E-F-F-$NH_2$ |
| (SEQ ID NO: 264) | Ac-D-W-L-K-A-F-Y-D-K-V-A-E-K-L-K-E-F-F-$NH_2$ |
| (SEQ ID NO: 265) | Ac-D-W-L-K-A-F-Y-D-K-V-F-E-K-F-K-E-A-F-$NH_2$ |
| (SEQ ID NO: 266) | Ac-D-W-L-K-A-F-Y-D-K-V-F-E-K-L-K-E-F-F-$NH_2$ |
| (SEQ ID NO: 267) | Ac-D-W-L-K-A-F-Y-D-K-V-A-E-K-F-K-E-F-F-$NH_2$ |
| (SEQ ID NO: 268) | Ac-D-W-L-K-A-F-Y-D-K-V-F-E-K-F-K-E-F-F-$NH_2$ |
| (SEQ ID NO: 269) | Ac-E-W-L-K-L-F-Y-E-K-V-L-E-K-F-K-E-A-F-$NH_2$ |
| (SEQ ID NO: 270) | Ac-E-W-L-K-A-F-Y-D-K-V-A-E-K-F-K-E-A-F-$NH_2$ |
| (SEQ ID NO: 271) | Ac-E-W-L-K-A-F-Y-D-K-V-A-E-K-L-K-E-F-F-$NH_2$ |
| (SEQ ID NO: 272) | Ac-E-W-L-K-A-F-Y-D-K-V-F-E-K-F-K-E-A-F-$NH_2$ |
| (SEQ ID NO: 273) | Ac-E-W-L-K-A-F-Y-D-K-V-F-E-K-L-K-E-F-F-$NH_2$ |
| (SEQ ID NO: 274) | Ac-E-W-L-K-A-F-Y-D-K-V-A-E-K-F-K-E-F-F-$NH_2$ |
| (SEQ ID NO: 275) | Ac-E-W-L-K-A-F-Y-D-K-V-F-E-K-F-K-E-F-F-$NH_2$ |
| (SEQ ID NO: 276) | AC-A-F-Y-D-K-V-A-E-K-L-K-E-A-F-$NH_2$ |
| (SEQ ID NO: 277) | Ac-A-F-Y-D-K-V-A-E-K-F-K-E-A-F-$NH_2$ |
| (SEQ ID NO: 278) | Ac-A-F-Y-D-K-V-A-E-K-F-K-E-A-F-$NH_2$ |
| (SEQ ID NO: 279) | Ac-A-F-Y-D-K-F-F-E-K-F-K-E-F-F-$NH_2$ |
| (SEQ ID NO: 280) | Ac-A-F-Y-D-K-F-F-E-K-F-K-E-F-F-$NH_2$ |

TABLE 2-continued

| SEQ ID NO | AMINO ACID SEQUENCE |
|---|---|
| (SEQ ID NO: 281) | Ac-A-F-Y-D-K-V-A-E-K-F-K-E-A-F-$NH_2$ |
| (SEQ ID NO: 282) | Ac-A-F-Y-D-K-V-A-E-K-L-K-E-F-F-$NH_2$ |
| (SEQ ID NO: 283) | Ac-A-F-Y-D-K-V-F-E-K-F-K-E-A-F-$NH_2$ |
| (SEQ ID NO: 284) | Ac-A-F-Y-D-K-V-F-E-K-L-K-E-F-F-$NH_2$ |
| (SEQ ID NO: 285) | Ac-A-F-Y-D-K-V-A-E-K-F-K-E-F-F-$NH_2$ |
| (SEQ ID NO: 286) | Ac-K-A-F-Y-D-K-V-F-E-K-F-K-E-F-$NH_2$ |
| (SEQ ID NO: 287) | Ac-L-F-Y-E-K-V-L-E-K-F-K-E-A-F-$NH_2$ |
| (SEQ ID NO: 288) | Ac-A-F-Y-D-K-V-A-E-K-F-K-E-A-F-$NH_2$ |
| (SEQ ID NO: 289) | Ac-A-F-Y-D-K-V-A-E-K-L-K-E-F-F-$NH_2$ |
| (SEQ ID NO: 290) | Ac-A-F-Y-D-K-V-F-E-K-F-K-E-A-F-$NH_2$ |
| (SEQ ID NO: 291) | Ac-A-F-Y-D-K-V-F-E-K-L-K-E-F-F-$NH_2$ |
| (SEQ ID NO: 292) | Ac-A-F-Y-D-K-V-A-E-K-F-K-E-F-F-$NH_2$ |
| (SEQ ID NO: 293) | Ac-A-F-Y-D-K-V-F-E-K-F-K-E-F-F-$NH_2$ |
| (SEQ ID NO: 294) | Ac-D-W-L-K-A-L-Y-D-K-V-A-E-K-L-K-E-A-L-$NH_2$ |
| (SEQ ID NO: 295) | Ac-D-W-F-K-A-F-Y-E-K-V-A-E-K-L-K-E-F-F-$NH_2$ |
| (SEQ ID NO: 296) | Ac-D-W-F-K-A-F-Y-E-K-F-F-E-K-F-K-E-F-F-$NH_2$ |
| (SEQ ID NO: 297) | Ac-E-W-L-K-A-L-Y-E-K-V-A-E-K-L-K-E-A-L-$NH_2$ |
| (SEQ ID NO: 298) | Ac-E-W-L-K-A-F-Y-E-K-V-A-E-K-L-K-E-A-F-$NH_2$ |
| (SEQ ID NO: 299) | Ac-E-W-F-K-A-F-Y-E-K-V-A-E-K-L-K-E-F-F-$NH_2$ |
| (SEQ ID NO: 300) | Ac-E-W-L-K-A-F-Y-E-K-V-F-E-K-F-K-E-F-F-$NH_2$ |
| (SEQ ID NO: 301) | Ac-E-W-L-K-A-F-Y-E-K-F-F-E-K-F-K-E-F-F-$NH_2$ |
| (SEQ ID NO: 302) | Ac-E-W-F-K-A-F-Y-E-K-F-F-E-K-F-K-E-F-F-$NH_2$ |
| (SEQ ID NO: 303) | Ac-D-F-L-K-A-W-Y-D-K-V-A-E-K-L-K-E-A-W-$NH_2$ |
| (SEQ ID NO: 304) | Ac-E-F-L-K-A-W-Y-E-K-V-A-E-K-L-K-E-A-W-$NH_2$ |
| (SEQ ID NO: 305) | Ac-D-F-W-K-A-W-Y-D-K-V-A-E-K-L-K-E-W-W-$NH_2$ |
| (SEQ ID NO: 306) | Ac-E-F-W-K-A-W-Y-E-K-V-A-E-K-L-K-E-W-W-$NH_2$ |
| (SEQ ID NO: 307) | Ac-D-K-L-K-A-F-Y-D-K-V-F-E-W-A-K-E-A-F-$NH_2$ |
| (SEQ ID NO: 308) | Ac-D-K-W-K-A-V-Y-D-K-F-A-E-A-F-K-E-F-L-$NH_2$ |
| (SEQ ID NO: 309) | Ac-E-K-L-K-A-F-Y-E-K-V-F-E-W-A-K-E-A-F-$NH_2$ |
| (SEQ ID NO: 310) | Ac-E-K-W-K-A-V-Y-E-K-F-A-E-A-F-K-E-F-L-$NH_2$ |
| (SEQ ID NO: 311) | Ac-D-W-L-K-A-F-V-D-K-F-A-E-K-F-K-E-A-Y-$NH_2$ |
| (SEQ ID NO: 312) | Ac-E-K-W-K-A-V-Y-E-K-F-A-E-A-F-K-E-F-L-$NH_2$ |
| (SEQ ID NO: 313) | Ac-D-W-L-K-A-F-V-Y-D-K-V-F-K-L-K-E-F-F-$NH_2$ |
| (SEQ ID NO: 314) | Ac-E-W-L-K-A-F-V-Y-E-K-V-F-K-L-K-E-F-F-$NH_2$ |
| (SEQ ID NO: 315) | Ac-D-W-L-R-A-F-Y-D-K-V-A-E-K-L-K-E-A-F-$NH_2$ |
| (SEQ ID NO: 316) | Ac-E-W-L-R-A-F-Y-E-K-V-A-E-K-L-K-E-A-F-$NH_2$ |
| (SEQ ID NO: 317) | Ac-D-W-L-K-A-F-Y-D-R-V-A-E-K-L-K-E-A-F-$NH_2$ |
| (SEQ ID NO: 318) | Ac-E-W-L-K-A-F-Y-E-R-V-A-E-K-L-K-E-A-F-$NH_2$ |
| (SEQ ID NO: 319) | Ac-D-W-L-K-A-F-Y-D-K-V-A-E-R-L-K-E-A-F-$NH_2$ |

TABLE 2-continued

| SEQ ID NO | AMINO ACID SEQUENCE |
|---|---|
| (SEQ ID NO: 320) | Ac-E-W-L-K-A-F-Y-E-K-V-A-E-R-L-K-E-A-F-$NH_2$ |
| (SEQ ID NO: 321) | Ac-D-W-L-K-A-F-Y-D-K-V-A-E-K-L-R-E-A-F-$NH_2$ |
| (SEQ ID NO: 322) | Ac-E-W-L-K-A-F-Y-E-K-V-A-E-K-L-R-E-A-F-$NH_2$ |
| (SEQ ID NO: 323) | Ac-D-W-L-K-A-F-Y-D-R-V-A-E-R-L-K-E-A-F-$NH_2$ |
| (SEQ ID NO: 324) | Ac-E-W-L-K-A-F-Y-E-R-V-A-E-R-L-K-E-A-F-$NH_2$ |
| (SEQ ID NO: 325) | Ac-D-W-L-R-A-F-Y-D-K-V-A-E-K-L-R-E-A-F-$NH_2$ |
| (SEQ ID NO: 326) | Ac-E-W-L-R-A-F-Y-E-K-V-A-E-K-L-R-E-A-F-$NH_2$ |
| (SEQ ID NO: 327) | Ac-D-W-L-R-A-F-Y-D-R-V-A-E-K-L-K-E-A-F-$NH_2$ |
| (SEQ ID NO: 328) | Ac-E-W-L-R-A-F-Y-E-R-V-A-E-K-L-K-E-A-F-$NH_2$ |
| (SEQ ID NO: 329) | Ac-D-W-L-K-A-F-Y-D-K-V-A-E-R-L-R-E-A-F-$NH_2$ |
| (SEQ ID NO: 330) | Ac-E-W-L-K-A-F-Y-E-K-V-A-E-R-L-R-E-A-F-$NH_2$ |
| (SEQ ID NO: 331) | Ac-D-W-L-R-A-F-Y-D-K-V-A-E-R-L-K-E-A-F-$NH_2$ |
| (SEQ ID NO: 332) | Ac-E-W-L-R-A-F-Y-E-K-V-A-E-R-L-K-E-A-F-$NH_2$ |

In some embodiments, an ApoA-I mimetic having the following sequence as described in U.S. Patent Application Publication No. 2006/0069030 is utilized: F-A-E-K-F-K-E-A-V-K-D-Y-F-A-K-F-W-D (SEQ ID NO:333).

In some embodiments, an ApoA-I mimetic having the following sequence as described in U.S. Patent Application Publication No. 2009/0081293 is utilized: DWFKAFYDKVAEKFKEAF (SEQ ID NO: 334); DWLKAFYDKVAEKLKEAF (SEQ ID NO: 335); PALEDLRQGLLPVLESFKVFLSALEEYTKKLNTQ (SEQ ID NO: 336).

In some embodiments, an ApoA-I mimetic having one of the following sequences is utilized:

(SEQ ID NO: 341)
WDRVKDLATVYVDVLKDSGRDYVSQF, (SEQ ID NO: 342)
LKLLDNWDSVTSTFSKLREOL, (SEQ ID NO: 343)
PVTOEFWDNLEKETEGLROEMS, (SEQ ID NO: 344)
KDLEEVKAKVQ, (SEQ ID NO: 345)
KDLEEVKAKVO, (SEQ ID NO: 346)
PYLDDFQKKWQEEMELYRQKVE, (SEQ ID NO: 347)
PLRAELQEGARQKLHELOEKLS, (SEQ ID NO: 348)
PLGEEMRDRARAHVDALRTHLA, (SEQ ID NO: 349)
PYSDELRQRLAARLEALKENGG, (SEQ ID NO: 350)
ARLAEYHAKATEHLSTLSEKAK,

-continued (SEQ ID NO: 351)
PALEDLROGLL, (SEQ ID NO: 352)
PVLESFKVSFLSALEEYTKKLN, (SEQ ID NO: 353)
PVLESFVSFLSALEEYTKKLN, (SEQ ID NO: 352)
PVLESFKVSFLSALEEYTKKLN, (SEQ ID NO: 354)
TVLLLTICSLEGALVRRQAKEPCV (SEQ ID NO: 355)
QTVTDYGKDLME, (SEQ ID NO: 356)
KVKSPELOAEAKSYFEKSKE, (SEQ ID NO: 357)
VLTLALVAVAGARAEVSADOVATV, (SEQ ID NO: 358)
NNAKEAVEHLOKSELTOOLNAL, (SEQ ID NO: 359)
LPVLVWLSIVLEGPAPAOGTPDVSS, (SEQ ID NO: 360)
LPVLVVVLSIVLEGPAPAQGTPDVSS, (SEQ ID NO: 361)
ALDKLKEFGNTLEDKARELIS, (SEQ ID NO: 362)
VVALLALLASARASEAEDASLL, (SEQ ID NO: 363)
HLRKLRKRLLRDADDLQKRLAVYOA, (SEQ ID NO: 364)
AQAWGERLRARMEEMGSRTRDR, (SEQ ID NO: 365)
LDEVKEQVAEVRAKLEEQAQ, -continued (SEQ ID NO: 236)
DWLKAFYDKVAEKLKEAF, (SEQ ID NO: 366)
DWLKAFYDKVAEKLKEAFPDWAKAAYDKAAEKAKEAA, (SEQ ID NO: 367)
PVLDLFRELLNELLEALKQKL, (SEQ ID NO: 368)
PVLDLFRELLNELLEALKQKLA, (SEQ ID NO: 4)
PVLDLFRELLNELLEALKQKLK, (SEQ ID NO: 369)
PVLDLFRELLNELLEALKQKLA, (SEQ ID NO: 370)
PVLDLFRELLNELLEALKKLLK, (SEQ ID NO: 371)
PVLDLFRELLNELLEALKKLLA, (SEQ ID NO: 372)
PLLDLFRELLNELLEALKKLLA,
and (SEQ ID NO: 373)
EVRSKLEEWFAAFREFAEEFLARLKS.

Amphipathic lipids include, for example, any lipid molecule which has both a hydrophobic and a hydrophilic moiety. Examples include phospholipids or glycolipids. Examples of phospholipids which may be used in the sHDL-TA nanoparticles include but are not limited to dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl) butyramide], 1,2-dihexadecanoyl-sn-glycero-3-phosphoethanolamine-N-[4-(p-maleimidophenyl) butyramide], 1,2-dihexadecanoyl-sn-glycero-3-phosphoethanolamine-N-[4-(p-maleimidomethyl) cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof. In some embodiments, the phospholipid is complexed with an imaging agent (e.g., rhodamine (Rhod)-labeled DOPE (DOPE-Rhod)). In some embodiments, the phospholipids are thiol reactive phospholipids such as, for example, Dioleoyl-sn-glycero-3-phosphoethanolamine-N-[3-(2-pyridyldithio) propionate] (DOPE-PDP), 1,2-dihexadecanoyl-sn-glycero-3-phosphothioethanol, or N-4-(p-maleimidophenyl) butyryl) dipalmitoylphosphatidylethanolamine (MPB-DPPE)).

In some embodiments, exemplary phospholipids include, but are not limited to, small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, phosphatidylglycerols, diphosphatidylglycerols such as dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, egg sphingomyelin, milk sphingomyelin, palmitoyl sphingomyelin, phytosphingomyelin, dipalmitoylsphingomyelin, distearoylsphingomyelin, dipalmitoylphosphatidylglycerol salt, phosphatidic acid, galactocerebroside, gangliosides, cerebrosides, dilaurylphosphatidylcholine, (1,3)-D-mannosyl-(1,3) diglyceride, aminophenylglycoside, 3-cholesteryl-6'-(glycosylthio) hexyl ether glycolipids, and cholesterol and its derivatives. Phospholipid fractions including SM and palmitoylsphingomyelin can optionally include small quantities of any type of lipid, including but not limited to lysophospholipids, sphingomyelins other than palmitoylsphingomyelin, galactocerebroside, gangliosides, cerebrosides, glycerides, triglycerides, and cholesterol and its derivatives.

In some embodiments, the sHDL nanoparticles have a molar ratio of phospholipid/HDL apolipoprotein from 2 to 250 (e.g., 10 to 200, 20 to 100, 20 to 50, 30 to 40).

Generally, the sHDL nanoparticles so formed are spherical and have a diameter of from about 5 nm to about 20 nm (e.g., 4-75 nm, 4-60) nm, 4-50 nm, 4-22 nm, 6-18 nm, 8-15 nm, 8-10 nm, etc.). In some embodiments, the sHDL nanoparticles are subjected to size exclusion chromatography to yield a more homogeneous preparation.

Compared to other strategies, including conventional nanoparticle vehicles, sHDL nanoparticles have impressive biocompatibility and capacity for cargo loading. For example, the ultrasmall but tunable size (e.g., 10-20 nm) enables the sHDL nanoparticles to effectively drain to lymph nodes and deliver cargo peptide antigens and nucleic acid-based adjuvants to lymph node-resident dendritic cells, thus positioning them as an efficient platform for co-delivery of a STING agonist and adjuvant for tumor immunotherapy.

In certain embodiments, the present invention provides compositions comprising a nanoparticle associated with such compositions comprising one or more agents capable of stimulating an innate immune response in a subject upon administration to the subject (e.g., DAMPs/PAMPs), wherein any kind of biomacromolecule agent (e.g., nucleic acid, peptides, glycolipids, etc.) is associated with the nanoparticle.

In some embodiments, the biomacromolecule agent is a peptide.

For example, in some embodiments, the peptide is an antigen.

In some embodiments, the antigen is a tumor antigen. The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triose-phosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100) (Pmel 17), tyrosinase, TRP-1, TRP-2, MAGE-1, MAGE-3, BAGE, GAGE-1, GAGE-2, p15 (58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17,1, NuMa, K-ras, β-Catenin, CDK4, Mum-1, p16, TAGE, PSMA, PSCA, CT7, telomerase, 43-9F, 5T4, 791Tgp72, a-fetoprotein, 13HCG, BCA225, BTAA, CA 125, CA 15-3 (CA 27,29\BCAA), CA 195, CA 242, CA-50, CAM43, CD68\KP1, CO-029, FGF-5, G250, Ga733 (EpCAM), human EGFR protein or its fragments, such as human EGFR residues 306-325 (SCVRACGADSYEMEEDGVRK (SEQ ID NO: 374)) and residues 897-915 (VWSYGVTVWELMTFGSKPY (SEQ ID NO:375)), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, TPS, WT1 (and WT1-derived peptide sequences: WT1 126-134 (RMFP NAPYL (SEQ ID NO:376)), WT1 122-140 (SGQARMFPNAPYLPSCLES (SEQ ID NO:377)), and WT1 122-144 (SGQARMFPNAPYLPSCLESQPTI (SEQ ID NO:378)), MUC1 (and MUC1-derived peptides and glycopeptides such as RPAPGS (SEQ ID NO:379), PPAHGVT (SEQ ID NO:380), and PDTRP (SEQ ID NO:381))), LMP2, EGFRvIII, Idiotype, GD2, Ras mutant, p53 mutant, Proteinase3 (PRI), Survivin, hTERT, Sarcoma translocation breakpoints, EphA2, EphA4, LMW-PTP, PAP, ML-IAP, AFP, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, sLe (animal), CYP1B1, PLAC1, GM3, BORIS, Tn, GloboH, NY-BR-1, RGS5, SART3, STn, Carbonic anhydrase IX, PAX5, OY-TES1, Sperm protein 17, LCK, HMWMAA, AKAP-4, XAGE 1, B7H3, Legumain, Tie 2, Page4, VEGFR2, MAD-CT-1, FAP, PDGFR-alpha, PDGFR-β, MAD-CT-2, Fos-related antigen 1, ERBB2, Folate receptor 1 (FOLR1 or FBP), IDH1, IDO, LY6K, fms-related tyro-sine kinase 1 (FLT1, best known as VEGFR1), KDR, PADRE, TA-CIN (recombinant HPV16 L2E7E6), SOX2, and aldehyde dehydrogenase.

In some embodiments wherein the biomacromolecule is an antigen, the composition further comprises an adjuvant (as described herein).

In some embodiments, the peptide is Adrenocorticotropic Hormone (ACTH), a growth hormone peptide, a Melanocyte Stimulating Hormone (MSH), Oxytocin, Vasopressin, Corticotropin Releasing Factor (CRF), a CRF-related peptide, a Gonadotropin Releasing Hormone Associated Peptide (GAP), Growth Hormone Releasing Factor (GRF), Lutenizing Hormone Release Hormone (LH-RH), an orexin, a Prolactin Releasing Peptide (PRP), a somatostatin, Thyrotropin Releasing Hormone (THR), a THR analog, Calcitonin (CT), a CT-precursor peptide, a Calcitonin Gene Related Peptide (CGRP), a Parathyroid Hormone (PTH), a Parathyroid Hormone Related Protein (PTHrP), Amylin, Glucagon, Insulin, an Insulin-like peptide, NeuroPeptide Y (NPY), a Pancreatic Polypeptide (PP), Peptide YY (PYY), Cholecystokinin (CCK), a CCK-related peptide, Gastrin Releasing Peptide (GRP), Gastrin, a Gastrin-related peptide, a Gastrin inhibitory peptide, Motilin, Secretin, Vasoactive Intestinal Peptide (VIP), a VIP-related peptide, an Atrial-Natriuretic Peptide (ANP), a Brain Natriuretic Peptide (BNP), a C-Type Natriuretic Peptide (CNP), a tachykinin, an angiotensin, a renin substrate, a renin inhibitor, an endothelin, an endothelin-related peptide, an opioid peptide, a thymic peptide, an adrenomedullin peptide, an allostatin peptide, an amyloid beta-protein fragment, an antimicrobial peptide, an antioxidant peptide, an apoptosis related peptide, a Bag Cell Peptide (BCPs), Bombesin, a bone Gla protein peptide, a Cocaine and Amphetamine Related Transcript (CART) peptide, a cell adhesion peptide, a chemotactic peptide, a complement inhibitor, a cortistatin peptide, a fibronectin fragment, a fibrin related peptide, FMRF, a FMRF amide-related peptide (FaRP), Galanin, a Galanin-related peptide, a growth factor, a growth factor-related peptide, a G-Therapeutic Peptide-Binding Protein fragment, Gualylin, Uroguanylin, an Inhibin peptide, Interleukin (IL), an Interleukin Receptor protein, a laminin fragment, a leptin fragment peptide, a leucokinin, Pituitary Adenylate Cyclase Activating Polypeptide (PAPCAP), Pancreastatin, a polypeptide repetitive chain, a signal transducing reagent, a thrombin inhibitor, a toxin, a trypsin inhibitor, a virus-related peptide, an adjuvant peptide analog, Alpha Mating Factor, Antiarrhythmic Peptide, Anorexigenic Peptide, Alpha-1 Antitrypsin, Bovine Pineal Antireproductive Peptide, Bursin, C3 Peptide P16, Cadherin Peptide, Chromogranin A Fragment, Contraceptive Tetrapeptide, Conantokin G, Conantokin T, Crustacean Cardioactive Peptide, C-Telopeptide, Cytochrome b588 Peptide, Decorsin, Delicious Peptide, Delta-Sleep-Inducing Peptide, Diazempam-Binding Inhibitor Fragment, Nitric Oxide Synthase Blocking Peptide, OVA Peptide, Platelet Calpain Inhibitor (P1), Plasminogen Activator Inhibitor 1, Rigin, Schizophrenia Related Peptide, Sodium Potassium Atherapeutic Peptidase Inhibitor-1, Speract, Sperm Activating Peptide, Systemin, a Thrombin receptor agonist, Tuftsin, Adipokinetic Hormone, Uremic Pentapeptide, Antifreeze Polypeptide, Tumor Necrosis Factor (TNF), Leech [Des Asp10]Decorsin, L-Ornithyltaurine Hydrochloride, P-Aminophenylacetyl Tuftsin, Ac-Glu-Glu-Val-Val-Ala-Cys-pNA, Ac-Ser-Asp-Lys-Pro, Ac-rfwink-NH2, Cys-Gly-Tyr-Gly-Pro-Lys-Lys-Lys-Arg-Lys-Val-Gly-Gly, D-Ala-Leu, D-D-D-D-D, D-D-D-D-D-D, N-P-N-A-N-P-N-A, V-A-I-T-V-L-V-K, V-G-V-R-V-R, V-I-H-S, V-P-D-P-R, Val-Thr-Cys-Gly, R-S-R, Sea Urchin Sperm Activating Peptide, a SHU-9119 antagonist, a MC3-R antagonist, a MC4-R antagonist, Glaspimod, HP-228, Alpha 2-Plasmin Inhibitor, APC Tumor Suppressor, Early Pregnancy Factor, Gamma Interferon, Glandular Kallikrei N-1, Placental Ribonuclease Inhibitor, Sarcolecin Binding Protein, Surfactant Protein D, Wilms' Tumor Suppressor, GABAB 1b Receptor Peptide, Prion Related Peptide (iPRP13), Choline Binding Protein Fragment, Telomerase Inhibitor, Cardiostatin Peptide, Endostatin Derived Peptide, Prion Inhibiting Peptide, N-Methyl D-Aspartate Receptor Antagonist, and C-PeptideAnalog.

In some embodiments, the peptide is selected from 177Lu-DOTA0-Tyr3-Octreotate, Abarelix acetate, ADH-1, Afamelanotidec, melanotan-1, CUV1647, Albiglutide, Aprotinin, Argipressin, Atosiban acetate, Bacitracin, Bentiromide, a BH3 domain, Bivalirudin, Bivalirudin trifluoroacetate hydrate, Blisibimod, Bortezomib, Buserelin, Buserelin acetate, Calcitonin, Carbetocin, Carbetocin acetate, Cecropin A and B, Ceruletide, Ceruletide diethylamine, Cetrorelix, Cetrorelix acetate, Ciclosporine, Cilengitidec, EMD121974, Corticorelin acetate injection, hCRF, Corticorelin ovine triflutate, corticorelin trifluoroacetate, Corticotropin, Cosyntropin, ACTH 1-24, tetracosactide hexaacetate, Dalbavancin, Daptomycin, Degarelix acetate, Depreotide trifluoroacetate (plus sodium pertechnetate), Desmopressin acetate, Desmopressin DDAVP, Dulaglutide, Ecallantide, Edotreotide (plus yttrium-90), Elcatonin acetate, Enalapril maleate (or 2-butanedioate), Enfuvirtide, Eptifibatide, Exenatide, Ganirelix acetate, Glatiramer acetate, Glutathion, Gonadorelin, Gonadorelin acetate, GnRH, LHRH, Goserelin, Goserelin acetate, Gramicidin, Histrelin acetate, Human calcitonin, Icatibant, Icatibant acetate, IM862, oglufanide disodium, KLAKLAK, Lanreotide acetate, Lepirudin, Leuprolide, Leuprolide acetate, leuprorelin, Liraglutide, Lisinopril, Lixisenatide, Lypressin, Magainin2, MALP-2Sc, macrophage-activating lipopeptide-2 synthetic, Nafarelin acetate, Nesiritide, NGR-hTNF, Octreotide acetate, Oritavancin, Oxytocin, Pasireotide, Peginesatide, Pentagastrin, Pentetreotide (plus indium-111), Phenypressin, Pleurocidin, Pramlintide, Protirelin, thyroliberin, TRH, TRF, Salmon calcitonin, Saralasin acetate, Secretin (human), Secretin (porcine), Semaglutide, Seractide acetate, ACTH, corticotropin, Sermorelin acetate, GRF 1-29, Sinapultide, KL4 in lucinactant, Sincalide, Somatorelin acetate, GHRH, GHRF, GRF, Somatostatin acetate, Spaglumat magnesium (or sodium) salt, Substance P, Taltirelin hydrate, Teduglutide, Teicoplanin, Telavancin, Teriparatide, Terlipressin acetate, Tetracosactide, Thymalfasin, thymosin a-1, Thymopentin, Trebananib, Triptorelin, Triptorelin pamoate, Tyroserleutide, Ularitide, Vancomycin, Vapreotide acetate, Vasoactive intestinal peptide acetate, Vx-001c, TERT572Y, Ziconotide acetate, α5-α6 Bax peptide, and β-defensin.

In some embodiments, the peptide is any peptide which would assist in achieving a desired purpose with the composition. For example, in some embodiments, the peptide is any peptide that will facilitate treatment of any type of disease and/or disorder.

In some embodiments, the biomacromolecule agent is a nucleic acid. Such embodiments encompass any type of nucleic acid molecule including, but not limited to, RNA, siRNA, microRNA, interference RNA, mRNA, replicon mRNA, RNA-analogues, and DNA.

In certain embodiments, nanoparticles associated with such compositions comprising agents capable of stimulating an innate immune response in a subject upon administration to the subject (e.g., DAMPs/PAMPs) and an antigen are used for inducing an immune response. In some embodiments, such nanoparticles are further associated with (e.g., complexed, conjugated, encapsulated, absorbed, adsorbed, admixed) an adjuvant (e.g., dendritic cell targeting molecule (DC)). In some embodiments, the nanoparticles are co-administered with an adjuvant. In some embodiments, the antigen is associated with (e.g., complexed, conjugated, encapsulated, absorbed, adsorbed, admixed) the adjuvant. In some embodiments, the antigen is not associated with (e.g., complexed, conjugated, encapsulated, absorbed, adsorbed, admixed) the adjuvant. In some embodiments, the antigen is conjugated with a hydrophobic molecule. In some embodiments, the adjuvant is conjugated with a hydrophobic molecule. In some embodiments, the average size of the nanoparticle is between 6 to 500 nm.

In some embodiments, the hydrophobic molecule is a lipid molecule. In some embodiments, the lipid molecule is a membrane-forming lipid molecule. In some embodiments, the lipid molecule molecule is a non-membrane-forming lipid molecule.

Examples of lipid molecules applicable with the embodiments of the present invention include, but are not limited to, phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$carbon chains, e.g., lauroyl, myristoyl, palmitoyl, stearoyl, or oleoyl.

Other non-limiting examples of lipid molecules include sterols such as cholesterol and derivatives thereof such as cholestanol, cholestanone, cholestenone, coprostanol, cholesteryl-2'-hydroxyethyl ether, cholesteryl-4'-hydroxy butyl ether, and mixtures thereof.

Other examples of lipid molecules suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

Other examples of lipid molecules suitable for use in the present invention include fatty acids and derivatives or analogs thereof. They include oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems. 1991, p. 92; Muranishi, Critical Review's in Therapeutic Drug Carrier Systems, 1990, 7, 1-33; El Hariri et al, J. Pharm Pharmacol, 1992, 44, 651-654).

Other examples of lipid molecules suitable for use in the present invention include a lipid molecule modified with PEG (PEG-lipid). Examples of PEG-lipids include, but are not limited to, PEG coupled to dialkyloxypropyls (PEG-DAA) as described in, e.g., PCT Publication No. WO 05/026372. PEG coupled to diacylglycerol (PEG-DAG) as described in, e.g., U.S. Patent Publication Nos. 20030077829 and 2005008689. PEG coupled to phospholipids such as phosphatidylethanolamine (PEG-PE). PEG conjugated to ceramides as described in, e.g., U.S. Pat. No. 5,885,613. PEG conjugated to cholesterol or a derivative thereof, and mixtures thereof. The disclosures of these patent documents are herein incorporated by reference in their entirety for all purposes. Additional PEG-lipids include, without limitation, PEG-C-DOMG, 2 KPEG-DMG, and a mixture thereof.

PEG is a linear, water-soluble polymer of ethylene PEG repeating units with two terminal hydroxyl groups. PEGs are classified by their molecular weights: for example, PEG 2000 has an average molecular weight of about 2,000 daltons, and PEG 5000 has an average molecular weight of about 5,000 daltons. PEGs are commercially available from Sigma Chemical Co, and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), and monomethoxypolyethylene glycol-imidazolyl-carbonyl (MePEG-IM). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycolacetic acid (MePEG-$CH_2COOH$) is particularly useful for preparing PEG-lipid conjugates including, e.g., PEG-DAA conjugates.

The PEG moiety of the PEG-lipid conjugates described herein may comprise an average molecular weight ranging from about 550) daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750) daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety, Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)C$CH_2CH_2$C(O)—), succinamidyl (—NHC(O)$CH_2CH_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art.

Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

Such embodiments are not limited to particular antigen. Indeed, antigens can be peptides, proteins, polysaccharides, saccharides, lipids, glycolipids, nucleic acids, or combinations thereof. The antigen can be derived from any source, including, but not limited to, a virus, bacterium, parasite, plant, protozoan, fungus, tissue or transformed cell such as a cancer or leukemic cell and can be a whole cell or immunogenic component thereof, e.g., cell wall components or molecular components thereof.

In some embodiments, the antigens are known in the art and are available from commercial government and scientific sources. In some embodiments, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. Criteria for identifying and selecting effective antigenic peptides (e.g., minimal peptide sequences capable of eliciting an immune response) can be found in the art. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids.

In some embodiments, the antigen is a self antigen. As used herein, the term "self-antigen" refers to an immunogenic antigen or epitope which is native to a mammal and which may be involved in the pathogenesis of an autoimmune disease.

In some embodiments, the antigen is a viral antigen. Viral antigens can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3. Viral antigens may be derived from a particular strain such as a papilloma virus, a herpes virus, i.e. herpes simplex 1 and 2: a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

In some embodiments, the antigen is a bacterial antigen. Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus*, Hemophilus influenza type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia.*

In some embodiments, the antigen is a parasite antigen. Parasite antigens can be obtained from parasites such as, but not limited to, an antigen derived from *Cryptococcus neoformans. Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

In some embodiments, the antigen is an allergen and environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia. Artemisia*, and *Parietaria*. Other allergen antigens that may be used include allergens from house dust mites of the genus *Dermatophagoides* and Euroglyphus, storage mite e.g *Lepidoglyphys, Glycyphagus* and Tyrophagus, those from cockroaches, midges and fleas e.g. *Blatella, Periplaneta, Chironomus* and *Ctenoceppha-lides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium.*

In some embodiments, the antigen is a tumor antigen (described herein).

One of the critical barriers to developing curative and tumor-specific immunotherapy is the identification and selection of highly specific and restricted tumor antigens to avoid autoimmunity. Tumor neo-antigens, which arise as a result of genetic change (e.g., inversions, translocations, deletions, missense mutations, splice site mutations, etc.) within malignant cells, represent the most tumor-specific class of antigens.

In some embodiments, the antigen is a neo-antigen. The term neoantigen is used herein to define any newly expressed antigenic determinant. Neoantigens may arise upon conformational change in a protein, as newly expressed determinants (especially on the surfaces of transformed or infected cells), as the result of complex formation of one or more molecules or as the result of cleavage of a molecule with a resultant display of new antigenic determinants. Thus, as used herein, the term neoantigen covers antigens expressed upon infection (e.g. viral infection, protozoal infection or bacterial infection), in prion-mediated diseases, an on cell transformation (cancer), in which latter case the neoantigen may be termed a tumour-associated antigen.

The present invention is not limited to a particular manner of identifying neo-antigens. In some embodiments, identification of neo-antigens involves identifying all, or nearly all, mutations in the neoplasia/tumor at the DNA level using whole genome sequencing, whole exome (e.g., only captured exons) sequencing, or RNA sequencing of tumor versus matched germline samples from each patient. In some embodiments, identification of neo-antigens involves analyzing the identified mutations with one or more peptide-MHC binding prediction algorithms to generate a plurality of candidate neo-antigen T cell epitopes that are expressed within the neoplasia/tumor and may bind patient HLA alleles. In some embodiments, identification of neo-antigens involves synthesizing the plurality of candidate neo-antigen peptides selected from the sets of all neo open reading frame peptides and predicted binding peptides for use in a cancer vaccine.

As such, the present invention is based, at least in part, on the ability to identify all, or nearly all, of the mutations within a neoplasia/tumor (e.g., translocations, inversions, large and small deletions and insertions, missense mutations, splice site mutations, etc.). In particular, these mutations are present in the genome of neoplasia/tumor cells of a subject, but not in normal tissue from the subject. Such mutations are of particular interest if they lead to changes that result in a protein with an altered amino acid sequence that is unique to the patient's neoplasia/tumor (e.g., a neo-antigen). For example, useful mutations may include: (1) non-synonymous mutations leading to different amino acids in the protein: (2) read-through mutations in which a stop codon is modified or deleted, leading to translation of a longer protein with a novel tumor-specific sequence at the C-terminus: (3) splice site mutations that lead to the inclusion of an intron in the mature mRNA and thus a unique tumor-specific protein sequence: (4) chromosomal rearrangements that give rise to a chimeric protein with tumor-specific sequences at the junction of 2 proteins (i.e., gene fusion): (5) frameshift mutations or deletions that lead to a new open reading frame with a novel tumor-specific protein sequence; and the like. Peptides with mutations or mutated polypeptides arising from, for example, splice-site, frameshift, read-through, or gene fusion mutations in tumor cells may be identified by sequencing DNA, RNA or protein in tumor versus normal cells.

Also within the scope of the present invention is personal neo-antigen peptides derived from common tumor driver genes and may further include previously identified tumor specific mutations.

Preferably, any suitable sequencing-by-synthesis platform can be used to identify mutations. Four major sequencing-by-synthesis platforms are currently available: the Genome Sequencers from Roche/454 Life Sciences, the HiSeq Analyzer from Illumina/Solexa, the SOLID system from Applied BioSystems, and the Heliscope system from Helicos Biosciences. Sequencing-by-synthesis platforms have also been described by Pacific Biosciences and VisiGen Biotechnologies. Each of these platforms can be used in the methods of the invention. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids may be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair. Subsequent to the capture, the sequence may be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or in a step-and-repeat mode. For real-time analysis, different optical labels to each nucleotide may be incorporated and multiple lasers may be utilized for stimulation of incorporated nucleotides.

Any cell type or tissue may be utilized to obtain nucleic acid samples for use in the sequencing methods described herein. In some embodiments, the DNA or RNA sample is obtained from a neoplasia/tumor or a bodily fluid, e.g., blood, obtained by known techniques (e.g. venipuncture) or saliva. Alternatively, nucleic acid tests can be performed on dry samples (e.g. hair or skin).

A variety of methods are available for detecting the presence of a particular mutation or allele in an individual's DNA or RNA. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

PCR based detection means may include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. In one embodiment, the single base polymorphism can be detected by using a specialized exonuclease-resistant nucleotide, as disclosed, e.g., U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site (see, e.g. French Patent No. 2,650,840; PCT Application No. WO1991/02087). As in the method of U.S. Pat. No. 4,656,127, a primer may be employed that is complementary to allelic sequences immediately 3' to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis or GBAR is described in PCT Application No. WO 1992/15712). GBA® uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Application No. W01991/02087) the GBAR: method is preferably a heterogeneous phase assay, in which the primer or the target molecule is immobilized to a solid phase. Recently, several primer-guided nucleotide incorporation procedures for assaying polymorphic sites in DN A have been described (see, e.g., Komher, J. S. et al., Nucl. Acids. Res. 17:7779-7784 (1989): Sokolov, B. P., Nucl. Acids Res. 18:3671 (1990): Syvanen, A.-C, et al., Genomics 8:684-692 (1990): Kuppuswamy, M. N. et al., Proc. Natl. Acad. Sci. (U.S.A.) 88:1143-1147 (1991); Prezant, T. R. et al., Hum. Mutat. 1:159-164 (1992): Ugozzoli, L. et al., GATA 9:107-112 (1992): Nyren, P. et al., Anal. Biochem. 208: 171-175 (1993)). These methods differ from GBAR; in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (see, e.g., Syvanen, A.-C, et al., Amer. J. Hum. Genet. 52:46-59 (1993)).

An alternative method for identifying tumor specific neo-antigens is direct protein sequencing. Protein sequencing of enzymatic digests using multidimensional MS techniques (MSn) including tandem mass spectrometry (MS/MS)) can also be used to identify neo-antigens of the invention. Such proteomic approaches permit rapid. highly automated analysis (see, e.g., K. Gevaert and J. Vandekerckhove. Electrophoresis 21:1145-1154 (2000)). It is further contemplated within the scope of the invention that high-throughput methods for de novo sequencing of unknown proteins may be used to analyze the proteome of a patient's tumor to identify expressed neo-antigens. For example, meta shotgun protein sequencing may be used to identify expressed neo-antigens (see, e.g., Guthals et al. (2012) Shotgun Protein Sequencing with Meta-contig Assembly. Molecular and Cellular Proteomics 11 (10): 1084-96).

Tumor specific neo-antigens may also be identified using MHC multimers to identify neo-antigen-specific T-cell responses. For example, highthroughput analysis of neo-antigen-specific T-cell responses in patient samples may be performed using MHC tetramer-based screening techniques (see, e.g., Hombrink et al. (2011) High-Throughput Identification of Potential Minor Histocompatibility Antigens by MHC Tetramer-Based Screening: Feasibility and Limitations 6 (8): 1-11; Hadrup et al. (2009) Parallel detection of antigen-specific T-cell responses by multidimensional encoding of MHC multimers. Nature Methods. 6 (7): 520-26; van Rooij et al. (2013) Tumor exome analysis reveals neoantigen-specific T-cell reactivity in an Ipilimumab-responsive melanoma. Journal of Clinical Oncology. 31: 1-4; and Heemskerk et al. (2013) The cancer antigenome. EMBO Journal, 32 (2): 194-203). It is contemplated within the scope of the invention that such tetramer-based screening techniques may be used for the initial identification of tumor specific neo-antigens, or alternatively as a secondary screening protocol to assess what neo-antigens a patient may have already been exposed to, thereby facilitating the selection of candidate neo-antigens for the vaccines of the invention.

The invention further includes isolated peptides (e.g., neo-antigenic peptides containing the tumor specific mutations identified by the described methods. peptides that comprise known tumor specific mutations, and mutant polypeptides or fragments thereof identified by the described methods). These peptides and polypeptides are referred to herein as "neo-antigenic peptides" or "neo-antigenic polypeptides." The polypeptides or peptides can be of a variety of lengths and will minimally include the small region predicted to bind to the HLA molecule of the patient (the "epitope") as well as additional adjacent amino acids extending in both the N- and C-terminal directions. The polypeptides or peptides can be either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

In certain embodiments the size of the at least one neo-antigenic peptide molecule may comprise, but is not limited to, about 8, about 9), about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40), about 41, about 42, about 43, about 44, about 45, about 46, about 47, about 48, about 49, about 50, about 60, about 70), about 80, about 90, about 100, about 110, about 120 or greater amino molecule residues, and any range derivable therein. In specific embodiments the neo-antigenic peptide molecules are equal to or less than 50 amino acids. In a preferred embodiment, the neo-antigenic peptide molecules are equal to about 20 to about 30 amino acids.

As such, the present invention provides nanoparticles associated with such compositions comprising agents capable of stimulating an innate immune response in a subject upon administration to the subject (e.g., DAMPs/PAMPs) and one or more neo-antigenic peptides. In some embodiments, the nanoparticle is associated with two neo-antigenic peptides. In some embodiments, the nanoparticle is associated with at least 5 or more neo-antigenic peptides. In some embodiments, the nanoparticle is associated with at least about 6, about 8, about 10, about 12, about 14, about 16, about 18, or about 20 distinct peptides. In some embodiments, the nanoparticle is associated with at least 20 distinct peptides.

The neo-antigenic peptides, polypeptides, and analogs can be further modified to contain additional chemical moieties not normally part of the protein. Those derivatized moieties can improve the solubility, the biological half-life, absorption of the protein, or binding affinity. The moieties can also reduce or eliminate any desirable side effects of the proteins and the like. An overview for those moieties can be found in Remington's Pharmaceutical Sciences, $20^{th}$ ed., Mack Publishing Co., Easton, PA (2000). For example, neo-antigenic peptides and polypeptides having the desired activity may be modified as necessary to provide certain desired attributes. e.g. improved pharmacological characteristics, while increasing or at least retaining substantially all of the biological activity of the unmodified peptide to bind the desired MHC molecule and activate the appropriate T cell. For instance, the neo-antigenic peptide and polypeptides may be subject to various changes, such as substitutions, either conservative or non-conservative, where such changes might provide for certain advantages in their use, such as improved MHC binding. Such conservative substitutions may encompass replacing an amino acid residue with another amino acid residue that is biologically and/or chemically similar, e.g., one hydrophobic residue for another, or one polar residue for another. The effect of single amino acid substitutions may also be probed using D-amino acids. Such modifications may be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, III., Pierce), 2d Ed. (1984).

In some embodiments, the neo-antigenic peptides and polypeptides may be modified with linking agents for purposes of facilitating association with the nanoparticle (e.g., sHDL nanoparticle). The invention is not limited to a particular type or kind of linking agent. In some embodiments, the linking agent is a cysteine-serine-serine (CSS) molecule.

In some embodiments wherein the nanoparticle is sHDL and the neo-antigenic peptide or polypeptide is modified with CSS, the sHDL is further modified with dioleoyl-sn-glycero-3-phosphoethanolamine-N-[3-(2-pyridyldithio) propionate] (DOPE-PDP) wherein upon mixing, the DOPE-PDP and CSS engage thereby resulting in a complexing (linking) of the CSS-Ag with the sHDL.

The neo-antigenic peptide and polypeptides may also be modified by extending or decreasing the compound's amino acid sequence, e.g., by the addition or deletion of amino acids. The neo-antigenic peptides, polypeptides, or analogs can also be modified by altering the order or composition of certain residues. It will be appreciated by the skilled artisan that certain amino acid residues essential for biological activity, e.g., those at critical contact sites or conserved residues, may generally not be altered without an adverse effect on biological activity. The non-critical amino acids need not be limited to those naturally occurring in proteins, such as L-a-amino acids, or their D-isomers, but may include non-natural amino acids as well, such as B-y-8-amino acids, as well as many derivatives of L-a-amino acids.

Typically, a neo-antigen polypeptide or peptide may be optimized by using a series of peptides with single amino acid substitutions to determine the effect of electrostatic charge, hydrophobicity, etc. on MHC binding. For instance, a series of positively charged (e.g., Lys or Arg) or negatively charged (e.g., Glu) amino acid substitutions may be made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding. Amino acid substitutions are typically of single residues. Substitutions, deletions, insertions or any combination thereof may be combined to arrive at a final peptide.

One of skill in the art will appreciate that there are a variety of ways in which to produce such tumor specific neo-antigens. In general, such tumor specific neo-antigens may be produced either in vitro or in vivo. Tumor specific neo-antigens may be produced in vitro as peptides or polypeptides, which may then be formulated into a personalized neoplasia vaccine and administered to a subject. Such in vitro production may occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide.

Alternatively, tumor specific neo-antigens may be produced in vivo by introducing molecules (e.g., DNA, RNA, viral expression systems, and the like) that encode tumor specific neo-antigens into a subject, whereupon the encoded tumor specific neo-antigens are expressed.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Peptides can be readily synthesized chemically utilizing reagents that are free of contaminating bacterial or animal substances (Merrifield RB: Solid phase peptide synthesis. I. The synthesis of a tetrapeptide. J. Am. Chem. Soc. 85:2149-54, 1963).

A further aspect of the invention provides a nucleic acid (e.g., a polynucleotide) encoding a neo-antigenic peptide of the invention, which may be used to produce the neo-antigenic peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. A still further aspect of the invention provides an expression vector capable of expressing a polypeptide according to the invention. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

The invention further embraces variants and equivalents which are substantially homologous to the identified tumor specific neo-antigens described herein. These can contain. for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art.

The invention also includes expression vectors comprising the isolated polynucleotides, as well as host cells containing the expression vectors. It is also contemplated within the scope of the invention that the neo-antigenic peptides may be provided in the form of RNA or cDNA molecules encoding the desired neo-antigenic peptides. The invention also provides that the one or more neo-antigenic peptides of the invention may be encoded by a single expression vector. The invention also provides that the one or more neoantigenic peptides of the invention may be encoded and expressed in vivo using a viral based system (e.g., an adenovirus system).

The term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides may comprise the coding sequence for the tumor specific neo-antigenic peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In some embodiments, the polynucleotides can comprise the coding sequence for the tumor specific neo-antigenic peptide fused in the same reading frame to a marker sequence that allows, for example, for purification of the encoded polypeptide, which may then be incorporated into the personalized neoplasia vaccine. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags. FLAG tags, Myc tags, S tags, SBP tags, Softag 1, Softag 3, V5 tag, Xpress tag, Isopeptag, Spy Tag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like. In embodiments, the polynucleotides may comprise the coding sequence for one or more of the tumor specific neo-antigenic peptides fused in the same reading frame to create a single concatemerized neo-antigenic peptide construct capable of producing multiple neo-antigenic peptides.

In embodiments, the present invention provides isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a tumor specific neo-antigenic peptide of the present invention.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman. Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The isolated tumor specific neo-antigenic peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest will be inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host. Recombinant expression vectors may be used to amplify and express DNA encoding the tumor specific neo-antigenic peptides. Recombinant expression vectors are replicable DNA constructs which have synthetic or cDNA-derived DNA fragments encoding a tumor specific neo-antigenic peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers. (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9) and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23: 175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine, maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein. Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

As such, in certain embodiments, the present invention relates to personalized strategies for the treatment of disorders (e.g., neoplasia), and more particularly tumors, by administering a therapeutically effective amount of a composition comprising agents capable of stimulating an innate immune response in a subject upon administration to the subject (e.g., DAMPs/PAMPs) (as described herein) and one or more neoplasia/tumor specific neo-antigens to a subject (e.g., a mammal such as a human) (e.g., a vaccine composition capable of raising a specific T-cell response). In some embodiments, such a composition is further associated with a nanoparticle. Indeed, in certain embodiments, whole genome/exome sequencing may be used to identify all, or nearly all, mutated neo-antigens that are uniquely present in a neoplasia/tumor of an individual patient, and that this collection of mutated neo-antigens may be analyzed to identify a specific, optimized subset of neo-antigens for use as a personalized cancer vaccine for treatment of the patient's neoplasia/tumor. For example, in some embodiments, a population of neoplasia/tumor specific neo-antigens may be identified by sequencing the neoplasia/tumor and normal DNA of each patient to identify tumor-specific mutations, and determining the patient's HLA allotype. The population of neoplasia/tumor specific neo-antigens and their cognate native antigens may then be subject to bioinformatic analysis using validated algorithms to predict which tumor-specific mutations create epitopes that could bind to the patient's HLA allotype, and in particular which tumor-specific mutations create epitopes that could bind to the patient's HLA allotype more effectively than the cognate native antigen. Based on this analysis, one or more peptides corresponding to a subset of these mutations may be designed and synthesized for each patient, and pooled together for use as a cancer vaccine in immunizing the patient. The neo-antigens peptides may be combined another anti-neoplastic agent. In some embodiments, such neo-antigens are expected to bypass central thymic tolerance (thus allowing stronger antitumor T cell response), while reducing the potential for autoimmunity (e.g., by avoiding targeting of normal self-antigens).

The invention further provides a method of inducing a neoplasia/tumor specific immune response in a subject, vaccinating against a neoplasia/tumor, treating and or alleviating a symptom of cancer in a subject by administering the subject a neo-antigenic peptide or vaccine composition of the invention.

According to the invention, the above-described cancer vaccine may be used for a patient that has been diagnosed as having cancer, or at risk of developing cancer. In one embodiment, the patient may have a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

The peptide or composition of the invention is administered in an amount sufficient to induce a CTL response. The neo-antigenic peptide, polypeptide or vaccine composition of the invention can be administered alone or in combination with other therapeutic agents. The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate. For prostate cancer treatment, a preferred chemotherapeutic agent with which anti-CTLA-4 can be combined is paclitaxel (Taxol®).

In addition, the subject may be further administered an anti-immunosuppressive or immuno stimulatory agent. For example, the subject is further administered an anti-CTLA-4 antibody, anti-PD-1, anti-PD-L1, anti-TIM-3, anti-BTLA, anti-VISTA, anti-LAG3, anti-CD25, anti-CD27, anti-CD28, anti-CD137, anti-OX40, anti-GITR, anti-ICOS, anti-TIGIT, and inhibitors of IDO. Blockade of CTLA-4 or PD-1/PD-L1 by antibodies can enhance the immune response to cancerous cells in the patient. In particular, CTLA-4 blockade has been shown effective when following a vaccination protocol.

The optimum amount of each peptide to be included in the vaccine composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c. i.d., i.p., i.m., and i.v. Preferred methods of DNA injection include i.d., i.m., s.c, i.p, and i.v. For example, doses of between 1 and 500 mg 50 μg and 1.5 mg, preferably 10 μg to 500 μg, of peptide or DNA may be given and will depend from the respective peptide or DNA. Doses of this range were successfully used in previous trials (Brunsvig P F, et al., Cancer Immunol Immunother. 2006; 55 (12): 1553-1564; M. Staehler, et al., ASCO meeting 2007: Abstract No 3017). Other methods of administration of the vaccine composition are known to those skilled in the art.

The inventive vaccine may be compiled so that the selection, number and/or amount of peptides present in the composition is/are tissue, cancer, and/or patient-specific. For instance, the exact selection of peptides can be guided by expression patterns of the parent proteins in a given tissue to avoid side effects. The selection may be dependent on the specific type of cancer, the status of the disease, earlier treatment regimens, the immune status of the patient, and, of course, the HLA-haplotype of the patient. Furthermore, the vaccine according to the invention can contain individualized components, according to personal needs of the particular patient. Examples include varying the amounts of peptides according to the expression of the related neoantigen in the particular patient, unwanted side-effects due to personal allergies or other treatments, and adjustments for secondary treatments following a first round or scheme of treatment.

Such vaccines may be administered to an individual already suffering from cancer. In therapeutic applications, such vaccines are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg to about 50,000 μg of peptide for a 70 kg patient, followed by boosting dosages or from about 1.0 μg to about 10,000 μg of peptide pursuant to a boosting regimen over weeks to months depending upon the patient's response and condition and possibly by measuring specific CTL activity in the patient's blood. It should be kept in mind that the peptide and compositions of the present invention may generally be employed in serious disease states, that is, life-threatening or potentially life threatening situations, especially when the cancer has metastasized. For therapeutic use, administration should begin as soon as possible after the detection or surgical removal of tumors. This is followed by boosting doses until at least symptoms are substantially abated and for a period thereafter. The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor.

Such embodiments are not limited to a particular type of adjuvant. Generally, adjuvants are any substance whose admixture into the vaccine composition increases or otherwise modifies the immune response to the mutant peptide. Carriers are scaffold structures, for example a polypeptide or a polysaccharide, to which the antigenic peptide (e.g., neoantigenic peptide) is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Suitable adjuvants include, but are not limited to 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel.®, vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox, Quil or Superfos. Several immunological adjuvants (e.g., MF59) specific for dendritic cells and their preparation have been described previously (Dupuis M. et al., Cell Immunol. 1998; 186 (1): 18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I. et al., J Immunother Emphasis Tumor Immunol. 1996 (6): 414-418). Toll like receptors (TLRs) may also be used as adjuvants, and are important members of the family of pattern recognition receptors (PRRs) which recognize conserved motifs shared by many micro-organisms, termed "pathogen-associated molecular patterns" (PAMPS).

Recognition of these "danger signals" activates multiple elements of the innate and adaptive immune system. TLRs are expressed by cells of the innate and adaptive immune systems such as dendritic cells (DCs), macrophages, T and B cells, mast cells, and granulocytes and are localized in different cellular compartments, such as the plasma membrane, lysosomes, endosomes, and endolysosomes. Different TLRs recognize distinct PAMPS. For example, TLR4 is activated by LPS contained in bacterial cell walls. TLR9 is activated by unmethylated bacterial or viral CpG DNA, and TLR3 is activated by double stranded RNA. TLR ligand binding leads to the activation of one or more intracellular signaling pathways, ultimately resulting in the production of many key molecules associated with inflammation and immunity (particularly the transcription factor NF-κB and the Type-I interferons). TLR mediated DC activation leads to enhanced DC activation, phagocytosis, upregulation of activation and co-stimulation markers such as CD80, CD83, and CD86, expression of CCR7 allowing migration of DC to draining lymph nodes and facilitating antigen presentation to T cells, as well as increased secretion of cytokines such as type I interferons, IL-12, and IL-6. All of these downstream events are critical for the induction of an adaptive immune response.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly (inosinic-cytidylic) acid (bacterial), lipoteichoic acid (bacterial) or imidazoquinolines (synthetic).

Among the most promising cancer vaccine adjuvants currently in clinical development are the TLR9 agonist CpG and the synthetic double-stranded RNA (dsRNA) TLR3 ligand poly-ICLC. In preclinical studies poly-ICLC appears to be the most potent TLR adjuvant when compared to LPS and CpG due to its induction of pro-inflammatory cytokines and lack of stimulation of IL-10, as well as maintenance of high levels of co-stimulatory molecules in DCs. Furthermore, poly-ICLC was recently directly compared to CpG in non-human primates (rhesus macaques) as adjuvant for a protein vaccine consisting of human papillomavirus (HPV) 16 capsomers (Stahl-Hennig C, Eisenblatter M, Jasny E, et al. Synthetic double-stranded RNAs are adjuvants for the induction of T helper 1 and humoral immune responses to human papillomavirus in rhesus macaques. PLOS pathogens. April 2009; 5 (4)).

In some embodiments, the adjuvant is a dendritic cell targeting molecule (DC). DC is potent and is responsible for initiating antigen-specific immune responses. One biological feature of DCs is their ability to sense conditions under which antigen is encountered, initiating a process of "DC maturation". Using receptors for various microbial and inflammatory products, DCs respond to antigen exposure in different ways depending on the nature of the pathogen (virus, bacteria, protozoan) encountered. This information is transmitted to T cells by altered patterns of cytokine release at the time of antigen presentation in lymph nodes, altering the type of T cell response elicited. Thus, targeting DCs provides the opportunity not only to quantitatively enhance the delivery of antigen and antigen responses in general, but to qualitatively control the nature of the immune response depending on the desired vaccination outcome.

Dendritic cells express a number of cell surface receptors that can mediate the endocytosis of bound antigen. Targeting exogenous antigens to internalizing surface molecules on systemically-distributed antigen presenting cells facilitates uptake of antigens and thus overcomes a major rate-limiting step in immunization and thus in vaccination.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (see, e.g., Hawiger, et al., J. Exp. Med., 194 (6): 769-79 (2001); Bonifaz, et al., J. Exp. Med., 196 (12): 1627-38 (2002); Bonifaz, et al., J. Exp. Med., 199 (6): 815-24 (2004)).

A variety of other endocytic receptors, including a mannose-specific lectin (mannose receptor) and IgG Fc receptors, have also been targeted in this way with similar enhancement of antigen presentation efficiency. Other suitable receptors which may be targeted include, but are not limited to, DC-SIGN, 33D1, SIGLEC-H, DC1R, CD11c, heat shock protein receptors and scavenger receptors.

In some embodiments, the adjuvant is CpG. CpG immuno stimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9, CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly. it enhances dendritic cell maturation and differentiation, resulting in enhanced activation of Th1 cells and strong cytotoxic T-lymphocyte (CTL) generation, even in the absence of CD4 T-cell help. The Th1 bias induced by TLR9 stimulation is maintained even in the presence of vaccine adjuvants such as alum or incomplete Freund's adjuvant (IFA) that normally promote a Th2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg. Nature Reviews, Drug Discovery, 5, June 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin. GERMANY), which is a preferred component of the pharmaceutical composition of the present invention. Other TLR binding molecules such as RNA binding TLR 7, TLR 8 and/or TLR 9 may also be used.

Xanthenone derivatives such as, for example, Vadimezan or AsA404 (also known as 5,6-dimethylaxanthenone-4-acetic acid (DMXAA)), may also be used as adjuvants according to embodiments of the invention. Alternatively, such derivatives may also be administered in parallel to the vaccine of the invention, for example via systemic or intratumoral delivery, to stimulate immunity at the tumor site. Without being bound by theory, it is believed that such vanthenone derivatives act by stimulating interferon (IFN) production via the stimulator of IFN gene ISTING) receptor (see e.g., Conlon et al. (2013) Mouse, but not Human STING. Binds and Signals in Response to the Vascular Disrupting Agent 5, 6-Dimethylxanthenone-4-Acetic Acid. Journal of Immunology. 190:5216-25 and Kim et al. (2013) Anticancer Flavonoids are Mouse-Selective STING Agonists. 8:1396-1401). Other examples of useful adjuvants include, but are not limited to, chemically modified CpGs (e.g. CpR, Idera), Poly (I:C) (e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

Poly-ICLC is a synthetically prepared double-stranded RNA consisting of polyl and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2'5'-OAS and the P1/eIF2a kinase, also known as the PKR (4-6), as well as RIG-I helicase and MDA5.

Such methods are not limited to generating sHDL nanoparticles associated with compositions comprising agents capable of stimulating an innate immune response in a subject upon administration to the subject (e.g., DAMPs/PAMPs), an antigen and an adjuvant (e.g., dendritic cell targeting molecule). In some embodiments, the antigen and adjust are conjugated to outer surface of the sHDL nanoparticle.

In some embodiments, the sHDL nanoparticle is synthesized with thiol-reactive phospholipids that permit reduction-sensitive linkage of the antigen and/or adjuvant. In some embodiments, loading of the DC within the sHDL nanoparticle is facilitated through cholesterol modification of the DC molecule. In some embodiments, lyophilization methods are used for the preparation of homogenous sHDL. In some embodiments, phospholipids and ApoA mimetic peptides are dissolved in glacial acetic acid and lyophilized. In some embodiments, antigen peptides are incubated with sHDL in a buffer (e.g., a sodium phosphate buffer (pH 7.4)) (e.g., at room temperature for 3 hours) to allow for the conjugation of antigen peptides. In some embodiments, the unconjugated antigen peptides are removed using a desalting column (MWCO=7000 Da). In some embodiments, incorporation of the cholesterol modified DC (Cho-DC) to sHDL involves incubation with sHDL at room temperature for approximately 30 min.

Such embodiments are not limited to a particular manner of characterizing the sHDL conjugated with antigen and DC. In some embodiments, the morphology of sHDL is observed by TEM. In some embodiments, the size distribution of sHDL is analyzed by dynamic light scattering (DLS) using a Malven Nanosizer instrument and GPC assay.

The sHDL nanoparticles configured to activate an immune response (e.g., sHDL-αGalCer) (e.g., Ag/DC-sHDL) are useful for activating T cells in subjects for prophylactic and therapeutic applications. Activation of T cells by nanoparticle vaccine compositions increases their proliferation, cytokine production, differentiation, effector functions and/or survival. Methods for measuring these are well known to those in the art. The T cells activated by the nanoparticle vaccine compositions can be any cell which express the T cell receptor, including α/B and γ/δ T cell receptors. T-cells include all cells which express CD3, including T-cell subsets which also express CD4 and CD8. T-cells include both naive and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage. In some embodiments, the T cells that are activated are CD8+ T cells.

In general, compositions comprising the sHDL nanoparticles configured to activate an immune response (e.g., sHDL-STING agonist-αGalCer) (e.g., Ag/DC-STING agonist-sHDL) are useful for treating a subject having or being predisposed to any disease or disorder to which the subject's immune system mounts an immune response. The compositions are useful as prophylactic vaccines, which confer resistance in a subject to subsequent exposure to infectious agents. The compositions are also useful as therapeutic vaccines, which can be used to initiate or enhance a subject's immune response to a pre-existing antigen, such as a tumor antigen in a subject with cancer, or a viral antigen in a subject infected with a virus. The compositions are also useful as desensitizing vaccines, which function to "tolerize" an individual to an environmental antigen, such as an allergen.

The ability to target these compositions to professional antigen-presenting cells such as dendritic cells, and the ability of these compositions to elicit T-cell mediated immune responses by causing cross-presentation of antigens makes these compositions especially useful for eliciting a cell-mediated response to a disease-related antigen in order to attack the disease. Thus, in some embodiments, the type of disease to be treated or prevented is a malignant tumor or a chronic infectious disease caused by a bacterium, virus, protozoan, helminth, or other microbial pathogen that enters intracellularly and is attacked, i.e., by the cytotoxic T lymphocytes.

The desired outcome of a prophylactic, therapeutic or de-sensitized immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms: if it reduces the number of individuals in a population with symptoms: or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

Subjects with or exposed to infectious agents can be treated therapeutically or prophylactically the sHDL nanoparticles configured to activate an immune response (e.g., SHDL-STING agonist-αGalCer) (e.g., Ag/DC-STING agonist-sHDL) as disclosed herein. Infectious agents include bacteria, viruses and parasites. In some instances, the subject can be treated prophylactically, such as when there may be a risk of developing disease from an infectious agent. An individual traveling to or living in an area of endemic infectious disease may be considered to be at risk and a candidate for prophylactic vaccination against the particular infectious agent. Preventative treatment can be applied to any number of diseases where there is a known relationship between the particular disease and a particular risk factor, such as geographical location or work environment.

Subjects with or at risk for developing malignant tumors can be treated therapeutically or prophylactically the sHDL nanoparticles configured to activate an immune response (e.g., sHDL-STING agonist-αGalCer) (e.g., Ag/DC-STING agonist-sHDL) as disclosed herein. In a mature animal, a balance usually is maintained between cell renewal and cell death in most organs and tissues. The various types of mature cells in the body have a given life span: as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site. The sHDL nanoparticles configured to activate an immune response (e.g., sHDL-STING agonist-αGalCer) (e.g., Ag/DC-STING agonist-sHDL) as disclosed herein are useful for treating subjects having malignant tumors.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this invention is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided sHDL nanoparticles configured to activate an immune response (e.g., sHDL-STING agonist-αGalCer) (e.g., Ag/DC-STING agonist-sHDL) include, but are not limited to, the following: bladder, brain, breast, cervical, colo-rectal, esophageal, kidney, liver, lung, nasopharangeal, pancreatic, prostate, skin, stomach, uterine, and the like. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

Subjects with or at risk for exposure to allergens can be treated therapeutically or prophylactically the sHDL nanoparticles configured to activate an immune response (e.g., sHDL-STING agonist-αGalCer) (e.g., Ag/DC-STING agonist-sHDL) as disclosed herein. Such sHDL nanoparticles may be administered to subjects for the purpose of preventing and/or attenuating allergic reactions, such as allergic reactions which lead to anaphylaxis. Allergic reactions may be characterized by the $T_H2$ responses against an antigen leading to the presence of IgE antibodies. Stimulation of $T_H1$ immune responses and the production of IgG antibodies may alleviate allergic disease. Thus, the sHDL nanoparticles configured to activate an immune response (e.g., sHDL-STING agonist-αGalCer) (e.g., Ag/DC-STING agonist-sHDL) as disclosed herein are useful for producing antibodies that prevent and/or attenuate allergic reactions in subjects exposed to allergens.

Subjects with or at risk for immunosuppressed conditions can be treated therapeutically or prophylactically the sHDL nanoparticles configured to activate an immune response (e.g., sHDL-STING agonist-αGalCer) (e.g., Ag/DC-STING agonist-sHDL) as disclosed herein. The sHDL nanoparticle vaccines disclosed herein can be used for treatment of disease conditions characterized by immunosuppression, including, but not limited to, AIDS or AIDS-related complex, idiopathic immuno suppression, drug induced immunosuppression, other virally or environmentally-induced conditions, and certain congenital immune deficiencies. Such sHDL nanoparticle vaccine compositions can also be employed to increase immune function that has been impaired by the use of radiotherapy of immunosuppressive drugs (e.g., certain chemotherapeutic agents), and therefore can be particularly useful when used in conjunction with such drugs or radiotherapy.

In general, methods of administering vaccines as disclosed herein (e.g., sHDL nanoparticles configured to activate an immune response (e.g., sHDL-STING agonist-αGalCer) (e.g., Ag/DC-STING agonist-sHDL)) are well known in the art. Any acceptable method known to one of ordinary skill in the art may be used to administer a formulation to the subject. The administration may be localized (i.e., to a particular region, physiological system, tissue, organ, or cell type) or systemic. Vaccines can be administered by a number of routes including, but not limited to: oral, inhalation (nasal or pulmonary), intravenous, intraperitoneal, intramuscular, transdermal, subcutaneous, topical, sublingual, or rectal means. Injections can be e.g., intravenous, intradermal, subcutaneous, intramuscular, or intraperitoneal. In some embodiments, the injections can be given at multiple locations.

Administration of the formulations may be accomplished by any acceptable method which allows an effective amount of the vaccine to reach its target. The particular mode selected will depend upon factors such as the particular formulation, the severity of the state of the subject being treated, and the dosage required to induce an effective immune response. As generally used herein, an "effective amount" is that amount which is able to induce an immune response in the treated subject. The actual effective amounts of vaccine can vary according to the specific antigen or combination thereof being utilized, the particular composition formulated, the mode of administration, and the age, weight, condition of the individual being vaccinated, as well as the route of administration and the disease or disorder.

In certain embodiments, glycolipids encapsulated within sHDL nanoparticles are used as stimulators of natural killer T cell-mediated immune responses.

Natural killer T (NKT) cells are a heterogeneous group of T cells that share properties of both T cells and natural killer cells. Many of these cells recognize the non-polymorphic CD1d molecule, an antigen-presenting molecule that binds self and foreign lipids and glycolipids. NKT cells constitute only approximately 0.1% of all peripheral blood T cells. NKT cells are a subset of T cells that coexpress an αβ T-cell receptor, but also express a variety of molecular markers that are typically associated with NK cells, such as NK1.1. The best-known NKT cells differ from conventional αβ T cells in that their T-cell receptors are far more limited in diversity ('invariant' or 'type 1' NKT). They and other CD1d-restricted T cells ('type 2' NKT) recognize lipids and glycolipids presented by CD1d molecules, a member of the CD1 family of antigen-presenting molecules, rather than peptide-major histocompatibility complexes (MHCs). NKT cells include both $NK1.1^+$ and $NK1.1^-$, as well as $CD4^+$, $CD4^-$, $CD8^+$ and $CD8^-$ cells.

In certain embodiments, the compositions comprising agents capable of stimulating an innate immune response in a subject upon administration to the subject (e.g., DAMPs/PAMPs) are further associated with (e.g., complexed, conjugated, encapsulated, absorbed, adsorbed, admixed) one or more therapeutic agents. Such embodiments are not limited to particular type or kind of therapeutic agent.

In some embodiments, the therapeutic agent configured for treating and/or preventing cancer. Examples of such therapeutic agents include, but are not limited to, chemotherapeutic agents, anti-oncogenic agents, anti-angiogenic agents, tumor suppressor agents, anti-microbial agents, etc.

In some embodiments, the therapeutic agent is configured for treating and/or preventing autoimmune disorders and/or inflammatory disorders. Examples of such therapeutic agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-α inhibitors (e.g., adalimumab, certolizumab pegol, etanercept, golimumab, infliximab), IL-1 inhibitors, and metalloprotease inhibitors. In some embodiments, the therapeutic agents include, but are not limited to, infliximab, adalimumab, etanercept, parenteral gold or oral gold.

In some embodiments, the therapeutic agent is configured for treating and/or preventing cardiovascular related disorders (e.g., atherosclerosis, heart failure, arrhythmia, atrial fibrillation, hypertension, coronary artery disease, angina pectoris, etc.). Examples of therapeutic agents known to be useful in treating and/or preventing cardiovascular related disorders include, angiotensin-converting enzyme (ACE) inhibitors (e.g., benazepril, enalapril, Lisinopril, perindopril. Ramipril), adenosine, alpha blockers (alpha adrenergic antagonist medications) (e.g., clonidine, guanabenz, labetalol, phenoxy benzamine, terazosin, doxazosin, guanfacine, methyldopa, prazosin), angtiotensin II receptor blockers (ARBs) (e.g., candesartan, irbesartan, olmesartan medoxomil, telmisartan, eprosartan, losartan, tasosartan, valsartan), antiocoagulants (e.g., heparin fondaparinux, warfarin, ardeparin, enoxaparin, reviparin, dalteparin, nadroparin, tinzaparin), antiplatelet agents (e.g., abciximab, clopidogrel, eptifibatide, ticlopidine, cilostazol, dipyridamole, sulfinpyrazone, tirofiban), beta blockers (e.g., acebutolol, betaxolol, carteolol, metoprolol, penbutolol, propranolol, atenolol, bisoprolol, esmolol, nadolol, pindolol, timolol), calcium channel blockers (e.g., amlopidine, felodipine, isradipine, nifedipine, verapamil, diltiazem, nicardipine, nimodipine, nisoldipine), diuretics, aldosterone blockers, loop diuretics (e.g., bumetanide, furosemide, ethacrynic acid, torsemide), potassium-sparing diuretics, thiazide diuretics (e.g., chlorothiazide, chlorthalidone, hydrochlorothiazide, hydroflumethiazide, methyclothiazide, metolazone, polythiazide, quinethazone, trichlormethiazide), inoptropics, bile acid sequestrants (e.g., cholestyramine, coletipol, colesevelam), fibrates (e.g., clofibrate, gemfibrozil, fenofibrate), statins (e.g., atorvastatinm, lovastatin, simvastatin, fluvastatin, pravastatin), selective cholesterol absorption inhibitors (e.g., ezetimibe), potassium channel blockers (e.g., amidarone, ibutilide, dofetilide), sodium channel blockers (e.g., disopyramide, mexiletine, procainamide, quinidine, flecainide, moricizine, propafenone), thrombolytic agents (e.g., alteplase, reteplase, tenecteplase, anistreplase, streptokinase, urokinase), vasoconstrictors, vasodilators (e.g., hydralazine, minoxidil, mecamylamine, isorbide dintrate, isorbide mononitrate, nitroglycerin).

Generally, the nanoparticles so formed are spherical and have a diameter of from about 5 nm to about 20 nm (e.g., 4-75 nm, 4-60 nm, 4-50) nm, 4-22 nm, 6-18 nm, 8-15 nm, 8-10 nm, etc.). In some embodiments, the sHDL nanoparticles are subjected to size exclusion chromatography to yield a more homogeneous preparation.

In some embodiments, the nanoparticles associated with such compositions as described herein are further associated with (e.g., complexed, conjugated, encapsulated, absorbed, adsorbed, admixed) agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DIA, DID, Dil, DIO, DIR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue, POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3. In some embodiments, ceramides are provided as imaging agents. In some embodiments, SIP agonists are provided as imaging agents.

Additionally radionuclides can be used as imaging agents. Suitable radionuclides include, but are not limited to radioactive species of Fe(III), Fe(II), Cu(II), Mg(II), Ca(II), and Zn(I1) Indium, Gallium and Technetium, Other suitable contrast agents include metal ions generally used for chelation in paramagnetic Tl-type MIR contrast agents, and include di- and tri-valent cations such as copper, chromium, iron, gadolinium, manganese, erbium, europium, dysprosium and holmium, Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium, Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

In some embodiments, the nanoparticles associated with such compositions as described herein are further associated with (e.g., complexed, conjugated, encapsulated, absorbed, adsorbed, admixed) a targeting agent. In some embodiments, targeting agents are used to assist in delivery of the nanoparticles associated with such compositions as described herein to desired body regions (e.g., bodily regions affected by a cardiovascular related disorder). Examples of targeting agents include, but are not limited to, an antibody, receptor ligand, hormone, vitamin, and antigen, however, the present invention is not limited by the nature of the targeting agent. In some embodiments, the antibody is specific for a disease-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

In some embodiments, the nanoparticles associated with such compositions as described herein may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered: needle injection devices such as hypodermic needles and needle injection catheters: needleless injection devices such as jet injectors: coated stents, bifurcated stents, vascular grafts, stent grafts, etc.; and coated vaso-occlusive devices such as wire coils.

Exemplary devices are described in U.S. Pat. Nos. 5,935,114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS (SCIMED LIFE SYSTEMS, Inc.), the SYMPHONY (Boston Scientific Corporation), the Wallstent (Schneider Inc.), the PRECEDENT II (Boston Scientific Corporation) and the NIR (Medinol Inc.). Such devices are delivered to and/or implanted at target locations within the body by known techniques.

In some embodiments, the present invention also provides kits comprising compositions as described herein. In some embodiments, the kits comprise one or more of the reagents and tools necessary to generate such compositions, and methods of using such compositions.

The nanoparticles associated with such compositions as described herein may be characterized for size and uniformity by any suitable analytical techniques. These include, but are not limited to, atomic force microscopy (AFM), electrospray-ionization mass spectroscopy, MALDI-TOF mass spectroscopy. $^{13}C$ nuclear magnetic resonance spectroscopy, high performance liquid chromatography (HPLC) size exclusion chromatography (SEC) (equipped with multi-angle laser light scattering, dual UV and refractive index detectors), capillary electrophoresis and get electrophoresis. These analytical methods assure the uniformity of the sHDL nanoparticle population and are important in the production quality control for eventual use in in vivo applications.

In some embodiments, gel permeation chromatography (GPC), which can separate sHDL nanoparticles from liposomes and free ApoA-I mimetic peptide, is used to analyze the sHDL-TA nanoparticles. In some embodiments, the size distribution and zeta-potential is determined by dynamic light scattering (DLS) using, for example, a Malven Nanosizer instrument.

Where clinical applications are contemplated, in some embodiments of the present invention, the sHDL nanoparticles are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight sHDL nanoparticle formulation may be administered using one or more of the routes described herein.

In preferred embodiments, the nanoparticles associated with such compositions as described herein are used in conjunction with appropriate salts and buffers to render delivery of the compositions in a stable manner to allow for uptake by target cells. Buffers also are employed when the sHDL nanoparticles are introduced into a patient. Aqueous compositions comprise an effective amount of the sHDL nanoparticles to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active nanoparticles associated with such compositions as described herein may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active nanoparticles associated with such compositions as described herein in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, nanoparticles associated with such compositions as described herein are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides: such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. The sHDL nanoparticles also may be formulated as inhalants.

The present invention also includes methods involving co-administration of the nanoparticles associated with such compositions as described herein with one or more additional active agents. Indeed, it is a further aspect of this invention to provide methods for enhancing prior art therapies and/or pharmaceutical compositions by co-administering the sHDL nanoparticles of this invention. In co-administration procedures, the agents may be administered concurrently or sequentially. In some embodiments, the sHDL nanoparticles described herein are administered prior to the other active agent(s). The agent or agents to be co-administered depends on the type of condition being treated.

The present disclosure further provides kits comprising compositions comprising nanoparticles associated with such compositions as described herein or the ingredients necessary to synthesize the nanoparticles as described herein. In some embodiments, the kit includes all of the components necessary, sufficient or useful for administering such nanoparticles associated with such compositions as described herein.

EXPERIMENTAL

The following examples are provided in order to demonstrate and further illustrate certain preferred embodiments and aspects of the present invention and are not to be construed as limiting the scope thereof.

Example 1

This example describes the synthesis and characterization of CDN/Zn, CDN/Zn@liposome NPs and CDN@CaP/PEI-PEG.

As shown in FIG. 1A, CDN-Zn NPs were prepared by a simple coordination assembly. It is assumed that the Zn with a pyramidal coordination geometry could coordinate with both adenine and phosphate. To further increase the stability of the resulted particles, CDNs/Zn nanoparticles were modified with liposomes. There are several different approaches for MOF surface modification, such as coordination modulation during the MOF synthesis and post-synthesis modification by ligand exchange and silica or polymer shell coating. As DOPA has been widely used to capping $Zn^{2+}$-based MOF during the synthesis, coordination modulation was applied here for synthesis of CDN/Zn@DOPA with the lipid tail on the surface, which allows for another lipid layer coating.

Figure 2:
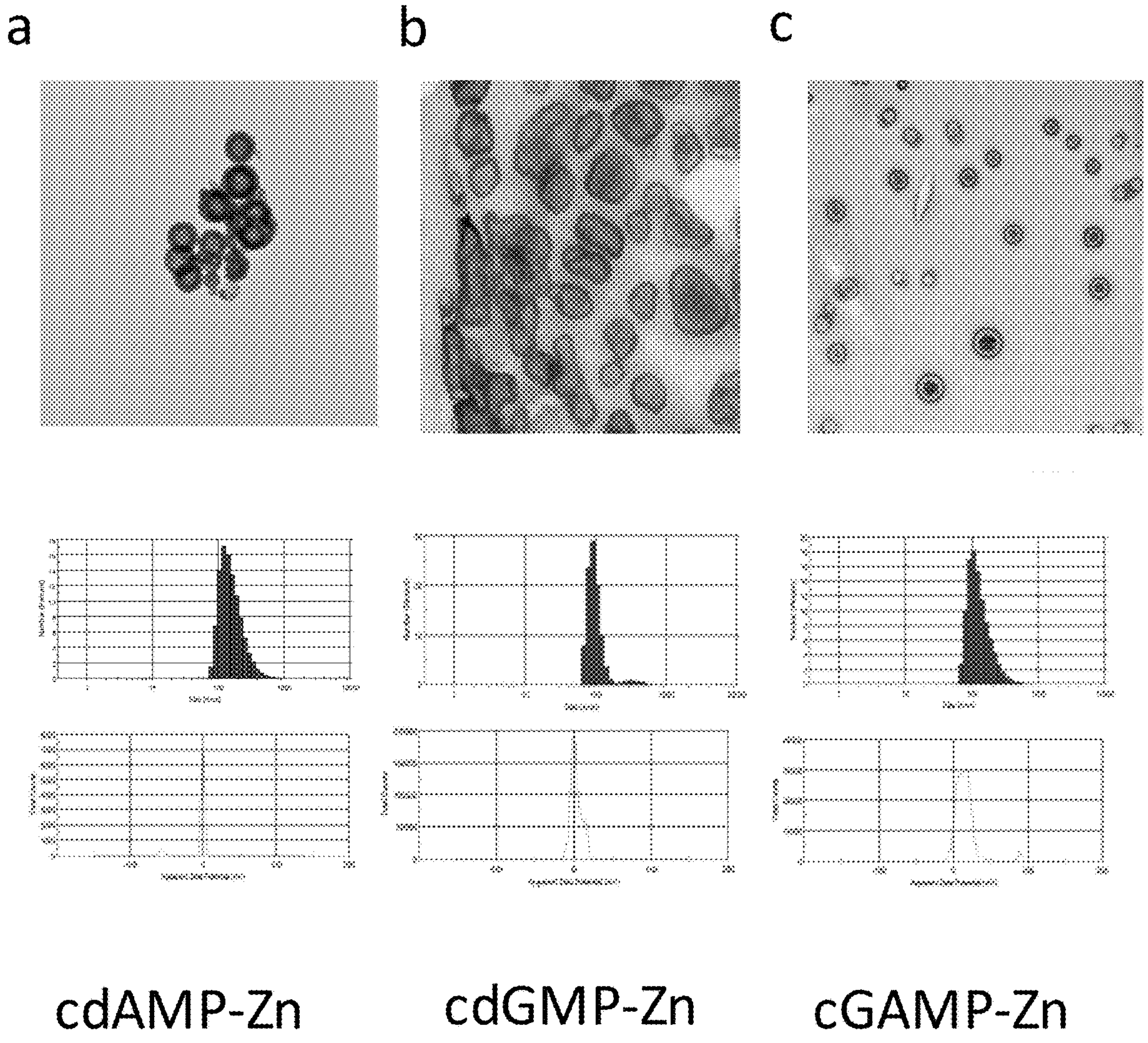
FIG. 2: Characterization of CDN-Zn, CDN-Zn a liposomes and CDN@CaP/PEI-PEG. The TEM images (up panel), size (middle panel) and zeta potential (bottom panel) of cdAMP-Zn (a), cdGMP-Zn (b), cGAMP-Zn (c), CDN-Zn@liposome (d) and CDN'@CaP/PEI-PEG (e).
Figure 2:
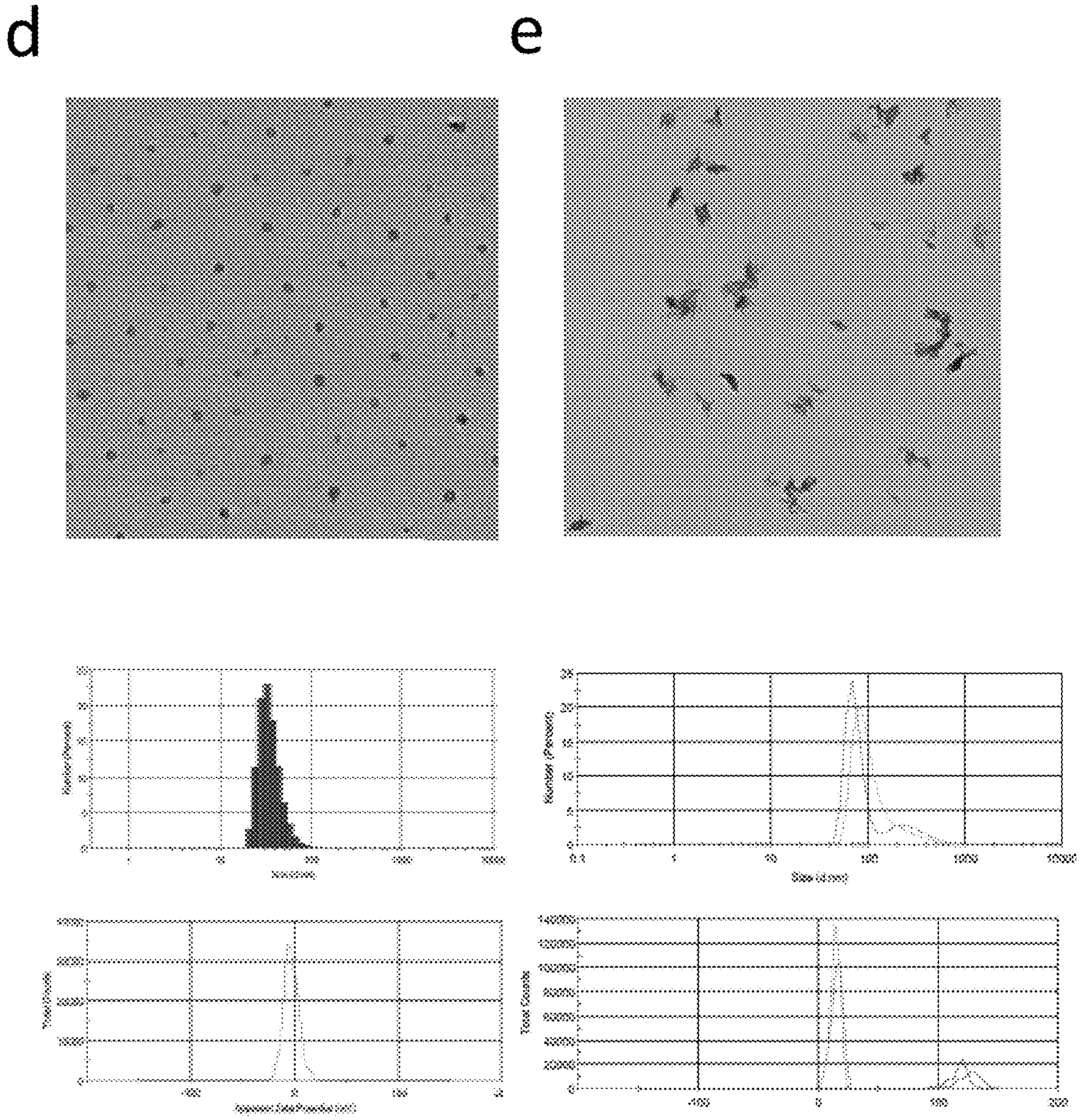

The morphology of the resulting CDNs-Zn and CDN-Zn@liposome NPs are shown in the TEM images (FIG. 2). As shown in FIG. 2*a*, cdAMP-Zn NPs exhibited sphere shape with higher TEM contrast on the surface. It is suspected that the fast nucleation of cdAMP-Zn in methanol caused $Zn^{2+}$ coordination deficiency in the core while the particle surface had saturated coordination of $Zn^{2+}$ to increase the surface contrast, resulting in "core-shell"-like structure. It was also found that homogeneous sphere structure was obtained when the synthesis was conducted in aquatic media because slower nucleation happens in water (not shown). Consistent with the TEM image, the DLS and zeta potential data indicated that the size of cdAMP-Zn was around 150 nm and the surface charge was neutral. As shown in FIG. 2*b*, in the same synthesis condition, cd-GMP NPs showed homogeneous irregular sphere structure of a size around 100 nm and neutral surface charge. In contract to cdAMP-Zn and cdGMP-Zn, the morphology and charge of cGAMP-Zn were different (FIG. 2*c*). The sphere-shaped nanoparticles were composed of several accumulated smaller clusters, and the surface had slight positive charge. To increase the stability of CDN-Zn NPs, we modified CDN-Zn with liposomes. As shown in FIG. 2*d*, cdAMP-Zn@liposomes were shown as a representative CDN-Zn@liposome structure. The TEM image indicated that CDN-Zn@liposomes showed more homogenous and smaller size due to the DOPA capping effect. And their surface also exhibited slightly negative charge after modification of liposome-PEG.

Figure 1B:
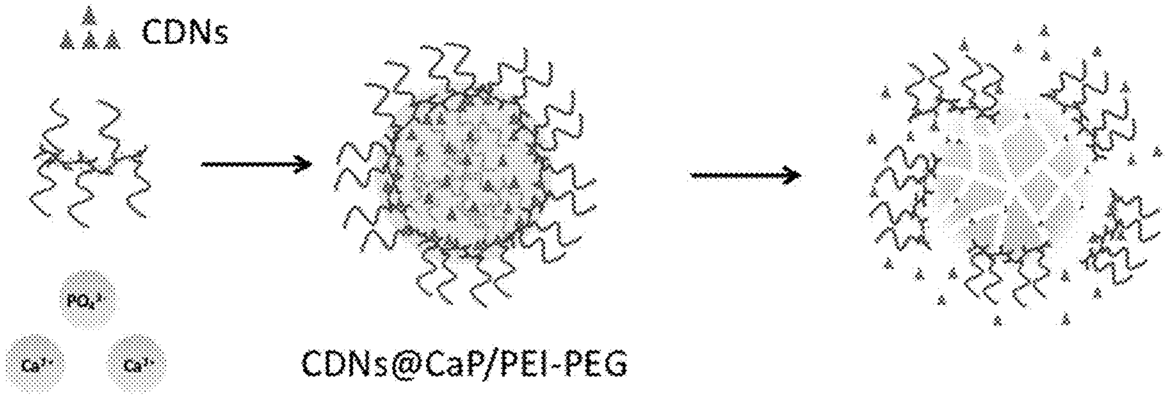

For the CaP/PEI-PEG formulation, experiments started from the clinically-used adjuvant CaP hydrogel. Generally, CaP hydrogel was prepared by fast mixing of $Ca^{2+}$ and $PO4^{3-}$ and a needle-like nanostructure was formed. To increase the loading of CDN to CaP hydrogel, PEI-PEG were added to increase the charge attraction to CDN, which could simultaneously increase the colloid stability (FIG. 1B). Different from traditional CaP hydrogel, which tended to aggregate into gel, the CaP/PEI-PEG were dispersed well in water. As shown in FIG. 2*e*, the CDN@CaP/PEI-PEG NPs showed homogeneous needle cluster structure of a size around 70 nm and a surface charge around +15 mV. Based on the morphology, size and surface properties, all the formulations here may have great potential for drug delivery applications.

Example II

This example demonstrates release profile and In vitro STING activation of CDN-Zn and CDNs@CaP/PEI-PEG.

Figure 3:
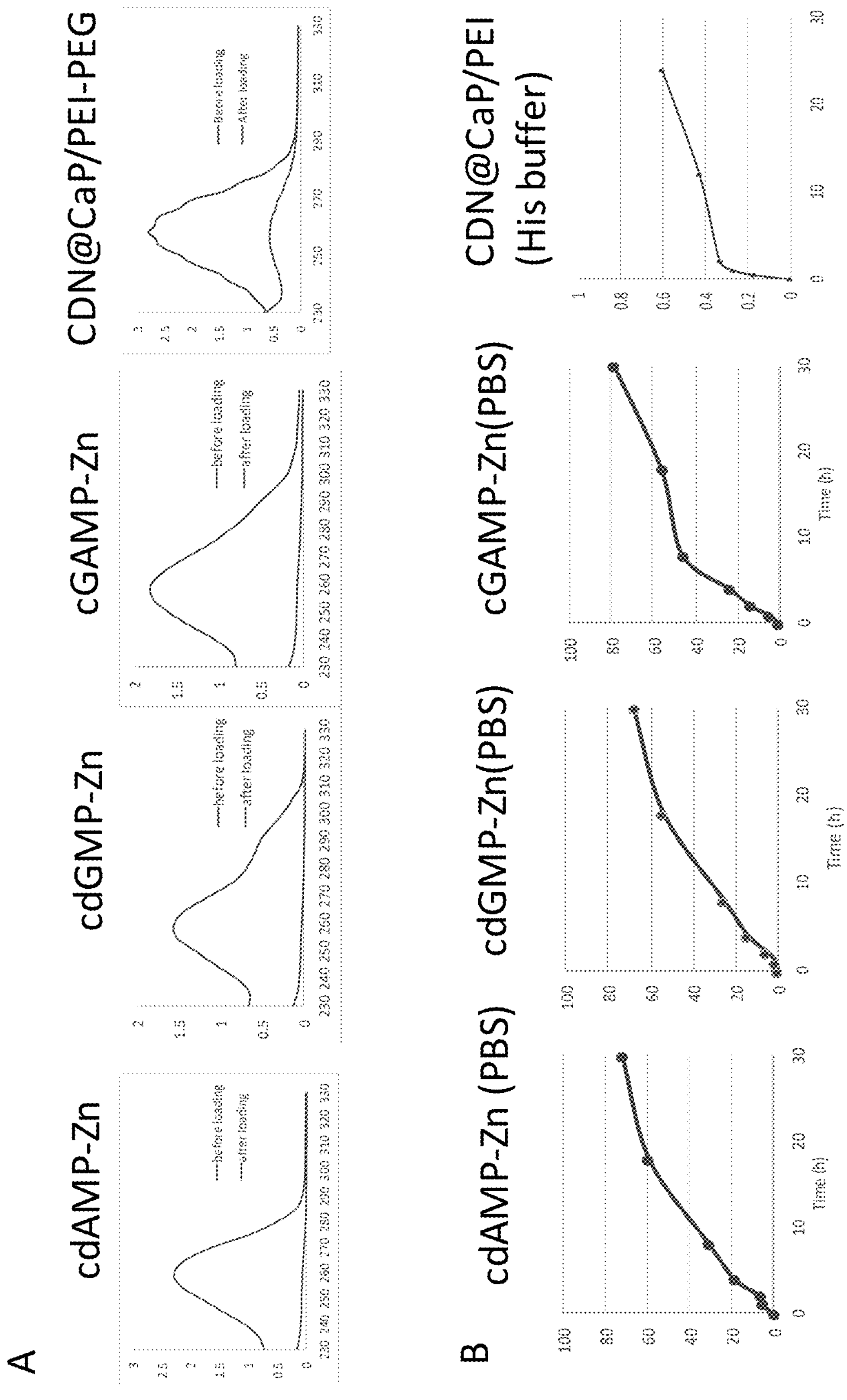
FIG. 3: Release profile and in vitro STING activation of different CDN formulations. (A) Loading efficacy of CDNs to relative formulation. The red line indicates CDN absorbance before loading, while the blue line indicates the absorbance of unloaded free CDNs in the supernatant after loading. (B) Release kinetics of CDNs from nano-formulations. (C) Representative THP1 activation assessment by free CDN and CDN-Zn in different concentration. The CDN used here is cdAMP. (D) Representative THP1 activation by free CDN and CDN@CaP/PEI-PEG in different concentration. The CDN used here is cdAMP$(ps)_2$.
Figure 3:
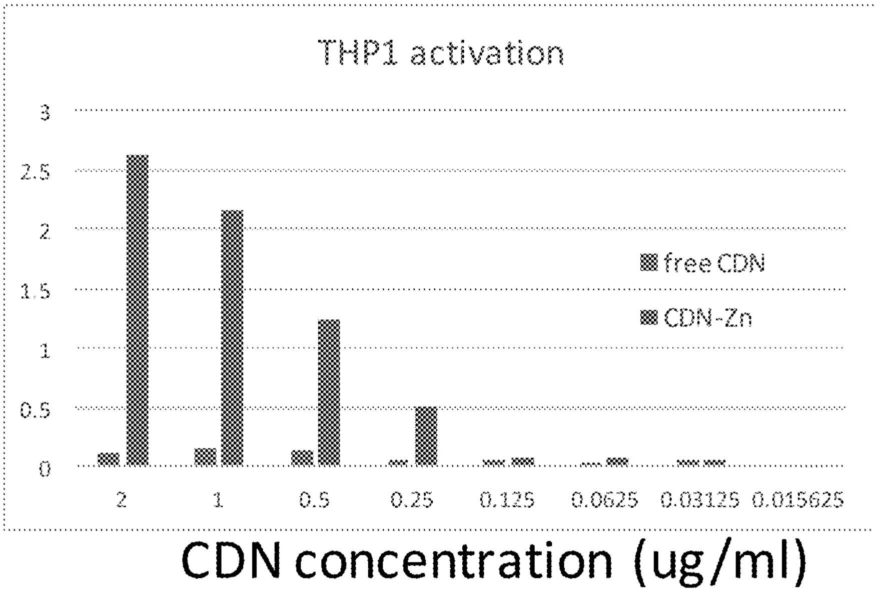
Figure 3:
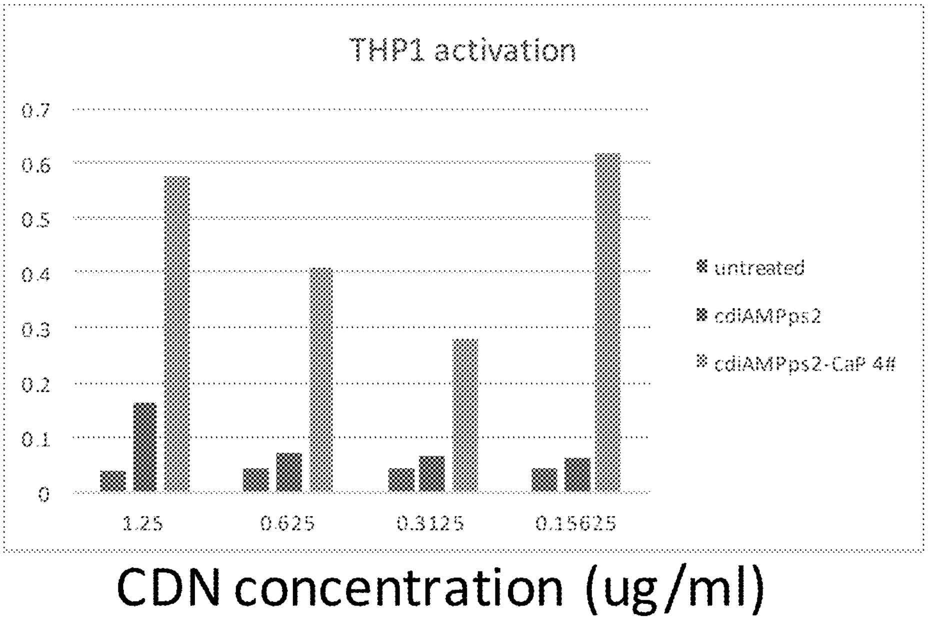

As two key parameters of drug delivery systems, experiments further determined the drug loading and release properties of the CDN nano-formulations. The CDN loading efficacies in the nano-formulations were over 90% for CDN-Zn formulations and more than 80% for CDN/CaP-PEI-PEG (FIG. 3A). As for drug release, cdAMP/Zn and cdGMP/Zn showed quite similar release profiles (FIG. 3B). In the first 18 h, the release was close to zero-order release, after which a slightly slower release phase was observed. It is supposed that the zero-order drug release from cdAMP/Zn and cdGMP/Zn may have resulted from the stable constant dissociation of the framework. But further study in a physiological condition with different biomolecular interaction is needed. As for cGAMP/Zn NPs, there was a fast-release phase in the first 8 hours of incubation, followed by a phase of slower release (FIG. 3B). The overall release of cGAMP/Zn was faster than that of cdAMP/Zn and cdGMP/Zn, which may be related to its unique nanoparticle structure. For CDN@CAP/PEI-PEG, there was a significant burst drug release followed by another phase of constant release (FIG.

3B). This profile may be attributed to that part of the CDN was attached to the surface of CAP/PEI-PEG by charge interaction and easily released in high ion intensity and high pH condition. The release profile of CDN-Zn@liposome was not shown here because we are yet to develop a reliable method to quantify the drug loading after liposome coating on CDN-Zn. It is anticipated that the liposomes on the CDN-Zn surface would greatly increase particle stability and delay drug release. The extended drug release would be helpful to increase in-situ drug exposure and degree of immune stimulation.

Experiments tested whether the CDNs delivery systems can effectively activate STING pathway in vitro and trigger immune responses. THP1-Blue™ ISG (interferon-stimulated genes) cells with an IFN regulatory factor (IRF)-inducible SEAP reporter construct were used in the experiments to monitor the activation of STING by CDN formulations. As shown in FIG. 3C, in 0.25-2 μg/ml cdAMP, the activation of IFN signaling pathway was much higher for cdAMP/Zn formulation than the free cdAMP in a soluble form. Similar stimulation improvement was also observed for CDN@CaP/PEI-PEG formulation, compared with the free form (FIG. 3D). These in vitro assessment results demonstrate that CDN-Zn and CDN@CaP/PEI-PEG have favorable properties for in vivo therapeutic applications.

Example III

This example describes therapeutic effects of CDN-Zn and CDNs@CaP/PEI-PEG.

Figure 4:
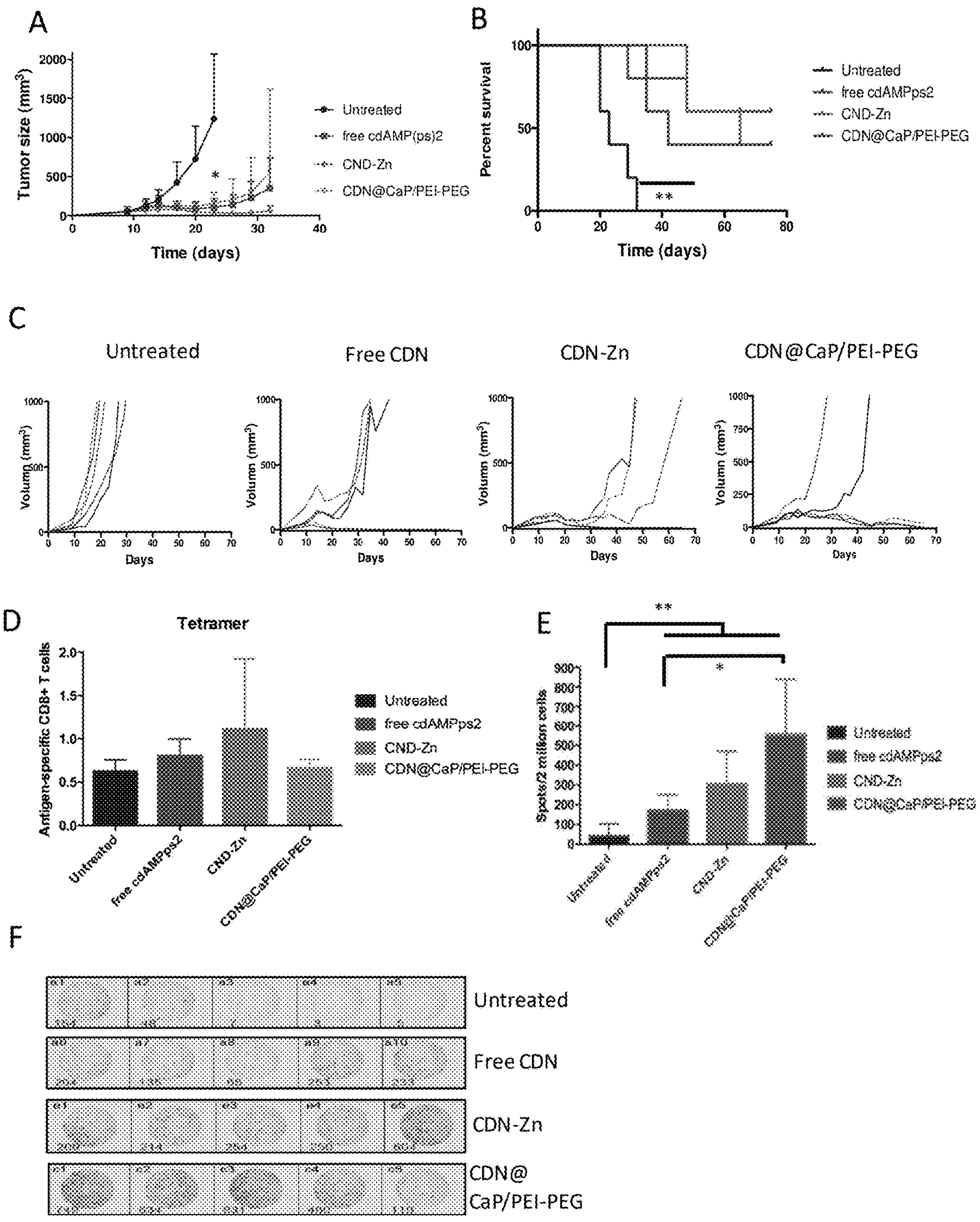
FIG. 4: Therapeutic effect of CDN formulation in CT26 tumor model. (A-C) Balb/c mice of 6-7 weeks were inoculated with $1.5\times10^5$ CT26 tumor cells on day 0. On days 10, 15, tumor-bearing mice were treated with indicated formulations containing 25 μg/dose of adAMP$(ps)_2$ intratumorally. Shown are (A) the average tumor growth curve of tumor-bearing mice; (B) survival of mice after different treatments; (C) tumor growth curve of individual mouse in different groups. (D-E) Seven days after the 2nd dose of CDN treatment. PBMCs were collected for (D) tetramer staining and (E) ELISPOT analysis with AH1 peptides. (F) Seven days after the first dose of CDN treatment. PBMCs were collected for ELISPOT analysis with AH1 peptides.

Finally, the therapeutic effect of CDN formulation was studied on tumor-bearing mice. cdAMP$(ps)_2$ was used here as a representative CDN for demonstration. When tumor size reach ~60 $mm^3$, 2 doses of 25 μg/dose cdAMP$(ps)_2$ were administrated intra-tumorally on days 10 and 15. To evaluate antigen-specific immune responses, PBMCs were collected for tetramer staining on day 17 and ELISPOT analysis with AH1 antigen peptides on day 22. As shown in FIG. 4A, the average tumor growth of mice treated with free CDN, CDN-Zn and CDNs@CaP/PEI-PEG was greatly delayed, compared with the untreated group. Although CDN-Zn seemed to better inhibit tumor growth, compared with CDN and CDNs@CaP/PEI-PEG, there was no statistical difference among them. For the survival of mice after treatment, median survival time for untreated. CDN, CDN-Zn and CDNs@CaP/PEI-PEG group was 23 days, 42 days, 64 days and unreached, respectively (FIG. 4B). From the individual tumor growth curve (FIG. 4C), complete tumor regression was observed in 0 out of 5 mice in untreated group: 2 out of 5 mice in free CDN group and CDN-Zn group; and 3 out of 5 in CDN@CaP/PEI-PEG group.

For PBMC tetramer staining assay, no significant difference was observed among the groups (FIG. 4D). PBMC tetramer staining may not be sensitive enough to show antigen-specific T cell response after non-specific intra-tumoral CDN stimulation or the time point may not have been optimal. In contrast, ELISPOT assessment on day 22 showed significant antigen-specific immune responses (FIG. 4E-F). Seven days after the 2nd dose of CDN treatment, significant AH1 antigen-specific T cell response was observed in the groups of free CDN, CDN-Zn, and CDNs@CaP/PEI-PEG. The response of CDN-Zn and CDNs@CaP/PEI-PEG also higher than the free CDN and statistical difference was observed between free CDN and CDNs@CaP/PEI-PEG. Overall, such results demonstrated that the therapeutic activities of both CDN-Zn and CDN@CaP/PEI-PEG are as high as or even better than that of free CDNs. The therapy benefits of the formulations may come from the combined effect of the slow release and increase cellular uptake. Base on this, the CDN-Zn@liposome exerts improved therapeutic efficacy due to the more sustained release and improved in vivo stability.

Example IV

This example describes the materials and methods for Examples I, II and III.

Synthesis of CDN-Zn Nanoparticles (NPs)

cGAMP, cdAMP and cdGMP were obtained from Invivogen and cdAMP$(ps)_2$ was obtained from MedchemExpress. The CDNs were dissolved in methanol before use. Meanwhile, $ZnCl_2$ (Sigma-Aldrich) was dissolved in methanol to prepare 100 mM storage solution. In a typical synthesis reaction, 10:1 (n/n) $Zn^{2+}$ solution was added to 1 mg/ml CDN work solution with vigorous stirring. The solution was stirred for another 24 h at room temperature. The resulting CDN-Zn NPs were centrifuged 20000×g, 15 min to remove free CDN and $Zn^{2+}$, followed by another washing with methanol.

Synthesis of CDN-Zn@Liposomes

Two steps were used to synthesize CDN-Zn@liposomes. Firstly, CDN-Zn@DOPA NPs were synthesized by the coordination-modulation approach. Briefly, 10-molar ratio of $Zn^{2+}$ solution was added to the mixture of CDN/DOPA (Avanti Lipids) in chloroform with vigorous stirring. After 24 h incubation, CDN-Zn@DOPA NPs were separated by centrifugation at 20000×g, 15 min. Then, CDN-Zn@DOPA NPs were re-suspended in a THF solution of DOPC, cholesterol, DSPE-PEG2k (2:2:1, Avanti Lipids) and added into a solution of 30% (v/v) ethanol/$H_2O$ at 60° C. Finally, CDN-Zn@liposomes were obtained by evaporating THE under reduced pressure, cooling the final solution to room temperature and removing empty liposomes at 20000×g, 20 min centrifugation. The resulting CDN-Zn (@liposomes were then re-suspended in PBS for further use.

Synthesis of CDNs@CaP/PEI-PEG NPs

CDN@CaP/PEI-PEG NPs was prepared by a 1-step precipitation method. Briefly, a solution of $CaCl_2$) (Sigma-Aldrich) and a solution of $Na_2HPO_4$ (Sigma-Aldrich) were simultaneously injected to a mixed solution of PEI-PEG and CDN with continuous stirring. After overnight incubation, CDN (@CaP/PEI-PEG NPs were separated with centrifugation 18000×g, 15 min. The resulting NPs were washing twice with histidine buffer (pH 7.4).

In Vitro Release Analysis

The release profiles of CDN-Zn and CDN-Zn@liposomes were studied by a Slide-A-Lyzer™ MINI Dialysis Device, 3.5K MWCO (Thermo Scientific). Briefly, 0.5 ml CDN-Zn or CDN-Zn@liposome solution was filled in the cup with regenerated cellulose membrane and 14 ml release buffer (PBS) was put in the tube. After dialysis cup was inserted into the conical tube and capped, the device was incubated at 37° C. under continuous shaking (200 rpm). At the indicated time points, 300 ul of release media were collected and equal amount of fresh PBS was refilled. The concentration of CDN in the release medium was analyzed by HPLC (GPC). Finally, the release percentage was calculated based on the CDN concentration in the release buffer, volume of buffer, and the total CDN loading amount.

Assessing Activation of Interferon-Stimulated Genes

THP1-Blue™ ISG (interferon-stimulated genes) cells purchased from Invivogen was handled and cultured according to instruction of the manufacturer. Briefly, the cell was thawed immediately after receiving and transferred to a 25

$cm^2$ flask of 5 ml growth medium. After one-generation passage, the cells were maintained in the growth medium, passaged every 3 days with a starting cell concentration $7\times10^5$ cells/ml with the addition of selection antibiotics every other passage. To assess the bioactivity of CDN formulations, 20 ul of pre-warmed solution of indicated formulation was added into a 96-well flat-bottom plate. Then 180 ul of cell suspension (~100,000 cells/per well) were mixed with CDN samples. After 18 h incubation at 37° C., 5% $CO_2$, 20 ul of the supernatant was collected and incubated with 180 ul QUANTI-Blue solution (Invivogen) for colorimetric reaction. The THP1 activation was quantified by measuring absorbance at 620-655 nm.

Animal Studies

All animals were cared for following federal, state, and local guidelines. All work performed on animals was in accordance with and approved by the University Committee on Use and Care of Animals (UCUCA) at University of Michigan, Ann Arbor. Female Balb/c mice of age 6-8 weeks (Jackson Laboratories) were inoculated with $1\times10^5$ CT26 colon cancer cells. When tumor size achieved ~100 $mm^3$, 2 doses of 25 μg cdAMP$(ps)_2$ in different formulations were administrated via intra-tumoral route on day 10 and day 15. Tumor size and survival were monitored every 2 or 3 days. Tumor size was calculated based on equation: volume=length×width$^2$×0.5. Animals were euthanized when the tumor reached 1.5 cm in diameter or when animals became moribund with severe weight loss or ulceration. At day 17, the percentages of tumor antigen-specific CD8α+ T cells among PBMC were analyzed using the tetramer staining assay as described previously with peptide-MHC tetramer (H-2Kb-restricted AH1) (the NIH Tetramer Core Facility, Atlanta, GA). On day 22, ELISPOT assay was performed with PBMC from the treated mice as described previously.

Example V

This example provides the materials and methods utilized in Examples VI-XI.

Screening for Metal Ion to Modulate Innate Immune Stimulator In Vitro

Mouse Bone Marrow-derived Dendritic Cells (BMDCs) were isolated and cultured. Briefly, bone marrow stem cells were harvested and plated in bacteriological petri dishes with GM-CSF containing culture media. The cell culture media were refreshed at day 3, 6 and 8. After 10 days of differentiation, the immature DC were harvested for use. To screen for metal ions that could modulate cytokine profiles of innate immune stimulators, we first seeded 0.1 million BMDCs/100 ul each well in 96-well plate. Then different concentrations of various metal ions were added with various concentrations of various innate immune stimulators. Simultaneously, the same concentrations of free metal ions alone or free innate immune stimulators alone were used as controls. After 24 h incubation at 37° C., 5% CO2, the supernatants were collected for ELISA assay of various cytokines.

Formulation of Cyclic Innate Immune Stimulators-Metal Ions Combinations

CDNs-metal ion coordination polymers: cGAMP, cdAMP and cdGMP were obtained from Invivogen, and cdAMP $(ps)_2$ was obtained from MedchemExpress. The CDNs were dissolved in methanol or endotoxin-free water before use. Meanwhile, metal ions were dissolved in methanol or water to prepare 100 mM stock solution. In a typical synthesis reaction, 10:1 (n/n) metal ions solution was added to 1 mg/ml CDN working solution with vigorous stirring. The solution was stirred for another 24 h at room temperature. The resulting CDN-metal combinations were centrifuged 20000×g. 15 min to remove free CDN and metal ions, followed by another washing with methanol.

CDNs-metal ions @ liposome: Two steps were used to synthesize CDN-metal@liposomes. Here, we take CDN-Zn@liposomes for example, First, Zn-CDN/H11-DOPE NPs were synthesized by a coordination-modulation approach. Briefly, 10-molar ratio of $Zn^{2+}$ solution was added to the mixture of CDN/H11-DOPE (Avanti Lipids) in chloroform with vigorous stirring. After 24 h incubation, Zn-CDN/H11-DOPE NPs were separated by centrifugation at 20000×g. 15 min. Then, Zn-CDN/H11-DOPE NPs were re-suspended in a THE solution of DPPC, cholesterol, DSPE-PEG5k (2:2:1, Avanti Lipids) and added into a solution of 50% (v/v) ethanol/$H_2O$. Finally, CDN-Zn@liposomes were obtained by evaporating THF under reduced pressure, cooling the final solution to room temperature and removing empty liposomes by 20000 xg, 20 min centrifugation. The resulting CDN-Zn@liposomes were then re-suspended in PBS for further use.

Metal ions-CDN/polyhistidine-PEG nano coordination polymer (NCP); Metal ions-CDN/polyhistidine-PEG NCP was prepared by a 1-step precipitation method. Here, we take $Co^{2+}$-CDN/polyhistidine-PEG for example, Briefly, solution of $CoCl_2$ (Sigma-Aldrich), CDN, polyhistidine-PEG and HEPES buffer in fixed ratio were added dropwise to a mixed solution with continuous stirring. After 24 h incubation, $Co^{2+}$-CDN/polyhistidine-PEG nanoparticles (NPs) were separated with 10 kD centrifugal ultrafiltration filter to remove free metal ions and CDNs.

CDNs@CaP/PEI-PEG NPs: CDN@CaP/PEI-PEG NPs was prepared by a 1-step precipitation method. Briefly, a solution of $CaCl_2$) (Sigma-Aldrich) and a solution of $Na_2HPO_4$ (Sigma-Aldrich) were simultaneously injected to a mixed solution of PEI-PEG and CDN with continuous stirring. After overnight incubation, CDN@CaP/PEI-PEG NPs were separated with centrifugation 18000×g. 15 min. The resulting NPs were washing twice with histidine buffer (pH 7.4).

Innate immune stimulator-metal minerals a anionic polypeptide-PEG: Innate immune stimulator-metal minerals@anionic polypeptide-PEG was prepared by a 1-step precipitation method. Take MnP@PGA-PEG NPs for example: a solution of $MnCl_2$ (Sigma-Aldrich) and a solution of $Na_2HPO_4$ (Sigma-Aldrich) were simultaneously injected to a mixed solution of PGA-PEG and innate immune stimulators with continuous stirring. After overnight incubation, innate immune stimulators-MnP@PGA-PEG NPs were separated with centrifugation 18000×g, 15 min. The resulting NPs were washed twice with histidine buffer (pH 7.4).

In Vitro Release Analysis

The release profiles of formulations were studied by a Slide-A-Lyzer™ MINI Dialysis Device, 3.5K MWCO (Thermo Scientific). Briefly, 0.5 ml formulation solution was filled in the cup with regenerated cellulose membrane and 14 ml release buffer (PBS) was put in the tube. After dialysis cup was inserted into the conical tube and capped, the device was incubated at 37° C. under continuous shaking (200 rpm). At the indicated time points, 300 μl of release media were collected and equal amount of fresh PBS was refilled. The concentration of CDN in the release medium was analyzed by HPLC (GPC). Finally, the release percentage was calculated based on the CDN concentration in the release buffer, volume of buffer, and the total CDN loading amount.

Animal Studies

All animals were cared for following federal, state, and local guidelines. All work performed on animals was in accordance with and approved by the University Committee on Use and Care of Animals (UCUCA) at University of Michigan, Ann Arbor. Female Balb/c mice of age 6-8 weeks (Jackson Laboratories) were inoculated with $1\times10^5$ CT26 colon cancer cells. When tumor size achieved ~50 $mm^3$, indicated drugs or formulations were administrated via the indicated route. Tumor size and survival were monitored every 2 or 3 days. Tumor size was calculated based on equation: volume=length×$width^2$×0.5. Animals were euthanized when the tumor reached 1.5 cm in diameter or when animals became moribund with severe weight loss or un-healing ulceration. At day 17, the percentages of tumor antigen-specific CD8α+ T cells among PBMC were analyzed using the tetramer staining assay as described previously with peptide-MHC tetramer (H-2Kb-restricted AH1) (the NIH Tetramer Core Facility, Atlanta, GA). On day 22, ELISPOT assay was performed with PBMC from the treated mice as described previously.

Example VI

This example describes the identification of metal ions that can enhance STING activation of STING agonists.

Figure 5:
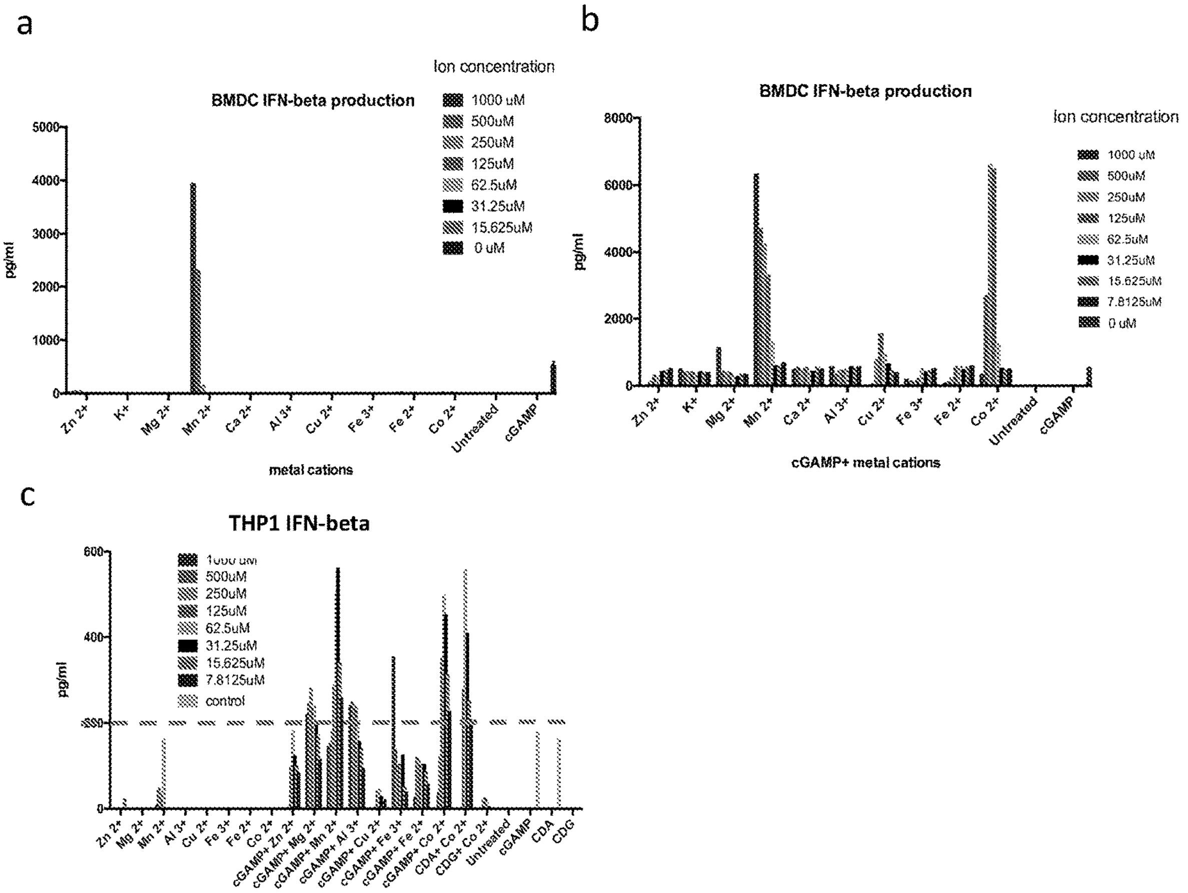
FIG. 5: Enhance cGAS-STING-Type-I IFN activation by metal ions in vitro. a-c) Bone marrow derived dendritic cells (BMDCs) (a-b) and human monocytes cell line THP1 (c) were incubated with different concentration of metal ions with or without STING agonist. STING activation was quantified by interferon-beta (IFN-b) release in the cell culture media.

As shown in FIGS. 5A and 5B, mouse bone marrow-derived dendritic cells (BMDCs) were treated with different metal ions or co-treated with different metal ions and STING agonist. We selected metal ions from essential minerals and trace mineral elements of biological systems. $Mn^{2+}$ alone was able to activate BMDCs at high toxic dose. But when $Mn^{2+}$ was combined with STING agonist, this led to significantly enhanced STING activation at much lower concentration. Similarly, $Co^{2+}$ itself did not exhibit STING activation. However, when $Co^{2+}$ at 125 uM or 250 uM was combined with 5 uM cGAMP, the combination greatly enhanced the activation of STING pathway. Both concentrations are well-tolerated. To further confirm whether this phenomenon still works in human cells, we repeated the same experiment using THP 1, a human monocytes cell line (FIG. 5C). A similar trend was observed in human THP1 cells, and we validated that this phenomenon was independent of the types of STING agonists.

Example VII

This example demonstrates $Co^{2+}$ and $Mn^{2+}$ enhanced STING activation and anti-cancer therapeutic efficacy.

Figure 6:
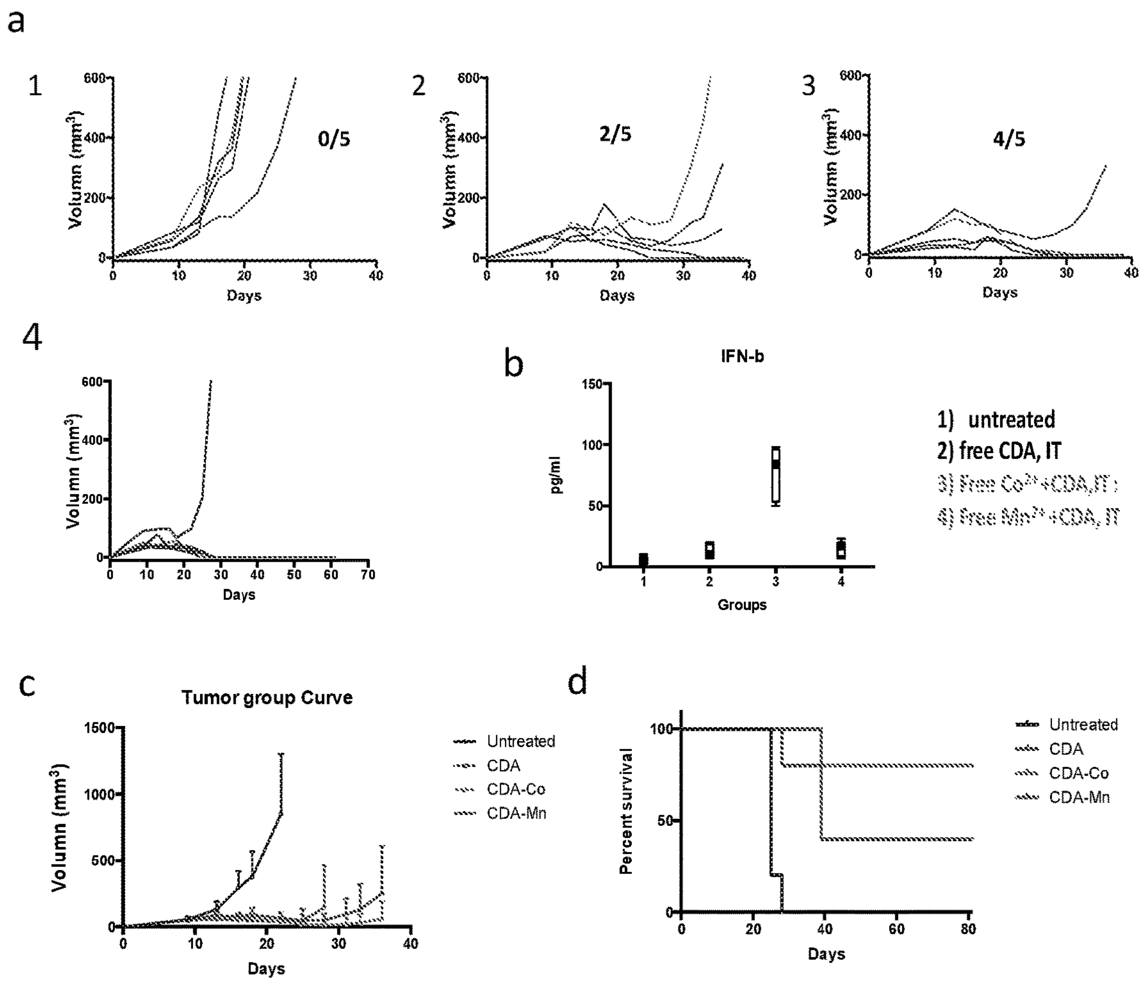
FIG. 6: Enhanced STING activation and cancer therapy efficacy by $Co^{2+}$ and $Mn^{2+}$ in vivo. a) individual tumor growth curve after three dose of intratumor injection of the indicated formulation at day 9, 12, 15 after tumor inoculation. b) Serum IFN-beta concentration 8 h after the 1st dose of the indicated formulation. c-d) individual tumor growth (c) and survival (d) of the tumor bearing mice after treated with the indicated formulations.

We examined whether the enhanced type-I IFN response in vitro could benefit cancer treatment in vivo. We evaluated the combination of metal ions and STING agonist in a murine tumor model. As shown in FIGS. 6*a* and 6*c*, $Co^{2+}$-CDA and $Mn^{2+}$-CDA delayed tumor growth. Especially, there were significantly more tumor-free mice in the metal-CDA groups than free CDA group, as demonstrated by 80% survival rate in metal-CDA groups vs. 20% survival rate in free CDA group (FIG. 6*d*). Furthermore, $Co^{2+}$-CDA treatment led to significantly higher serum IFNbeta levels at 8 hr after injection, compared with free CDA treatment (FIG. 6*b*). However, we did not observe the same phenomenon for the $Mn^{2+}$-CDA combination.

Example VIII

This example demonstrates improved in-vivo immune response for STING agonists-metal combination.

Figure 7:
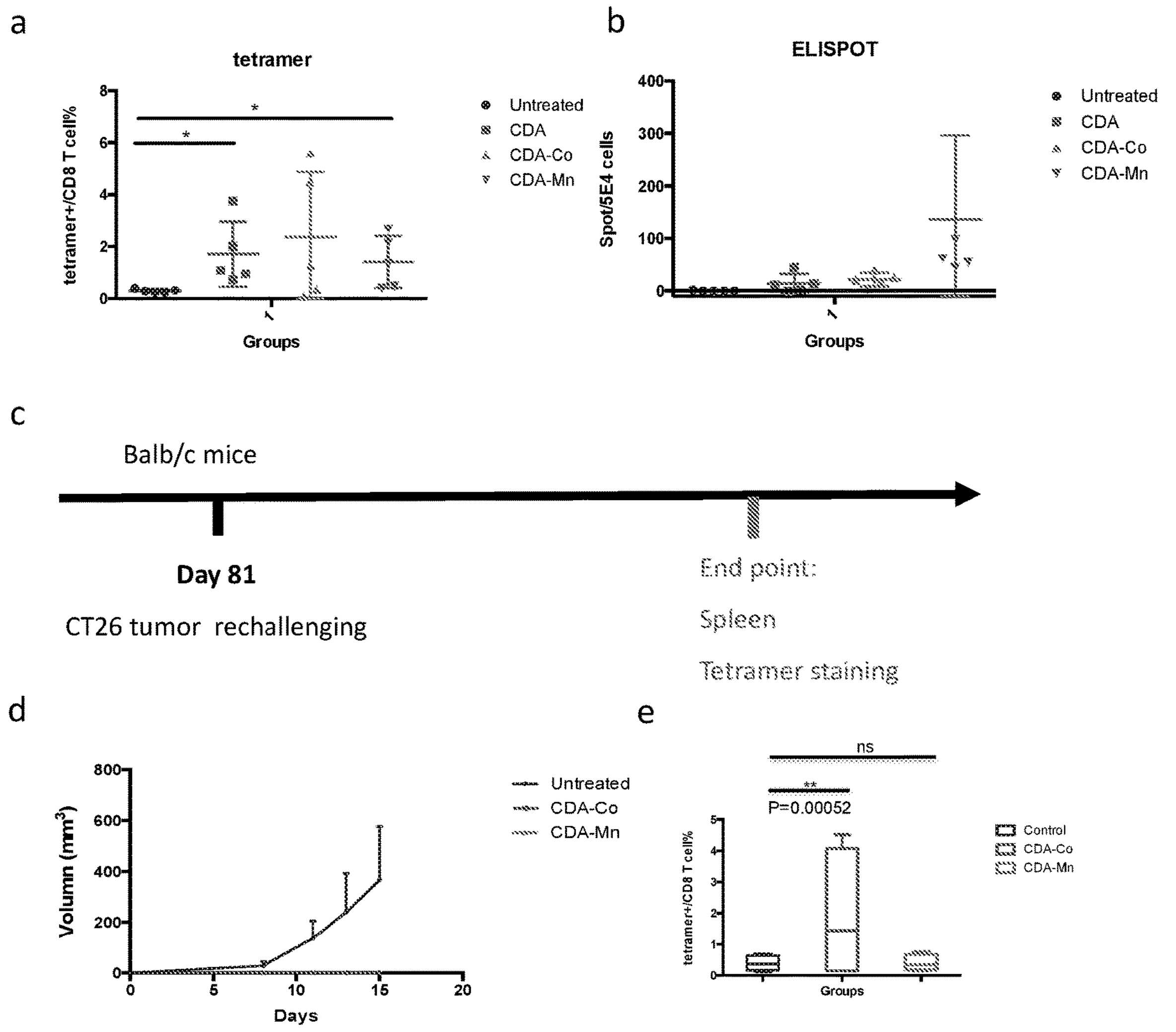
FIG. 7: Enhanced STING activation by $Co^{2+}$ and $Mn^{2+}$ led to improved antigen specific immune response after in vivo. a) the percentage of AH1-specific CD8+ T cells among PBMC on day 16. b) IFN-$\gamma$ secreting cells counts per 5E4 PBMCs after stimulation with AH1 peptides at day 22. c-e) timeline (c). tumor growth curve (d) and AH1-specific CD8+ T cells percentage in spleen CD8+ T cells (e) in tumor re-challenging study starting from day 81.

To study the mechanisms of action for the improved cancer therapy efficacy, we evaluated the treated animals for antigen-specific T cell responses and performed tumor re-challenging study after 81 days of the initial treatment. CDA-$Mn^{2+}$ showed better T cell-specific response as shown in ELISPOT result at day 22 of the experiment, while T cell ELISPOT results were similar between CDA-$Co^{2+}$ and free CDA groups (FIG. 7*b*). For tumor re-challenging study, survivors from the CDA-$Co^{2+}$ and CDA-$Mn^{2+}$ treatment group completely prevented the growth of the second CT26 tumor. The CDA-$Co^{2+}$ treatment group showed significantly increased antigen-specific T cell responses.

Example IX

This example demonstrates identification of metal ions that could modulate other innate immune stimulators.

Figure 8A:
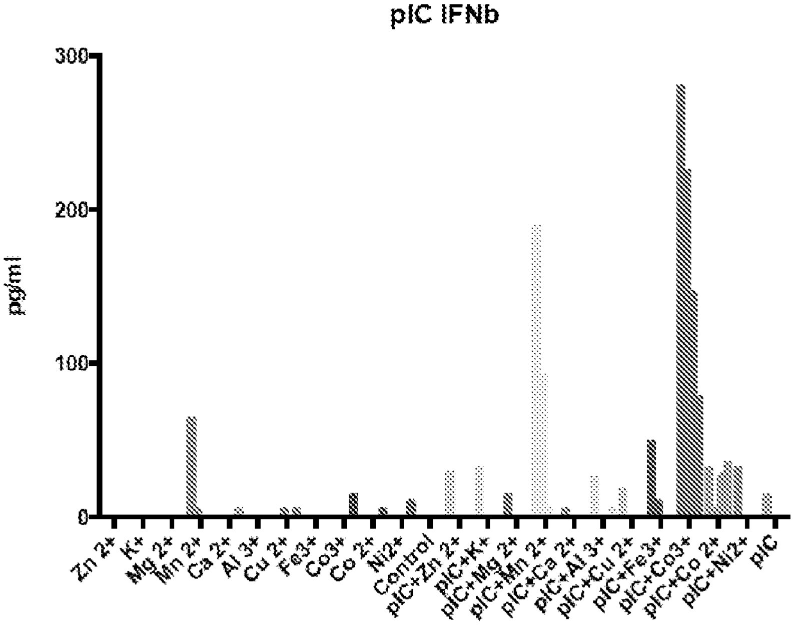
FIG. 8: Modulation of cytokine profiles of representative PAMPs by metal ions in vitro. a-d) Bone marrow derived dendritic cells (BMDCs) were incubated with different concentration of metal ions with or without TLR3 agonist polyIC. (e-f) BMDCs were incubated with different concentration of metal ions with or without TLR4 agonist MPLA. (g-h) BMDCs were incubated with different concentration of metal ions with or without TLR7/8 agonist R848. (i-j) BMDCs were incubated with different concentration of metal ions with or without TLR9 agonist CpG. The cytokines levels of cell culture media were quantify by ELISA assay.
Figure 8B:
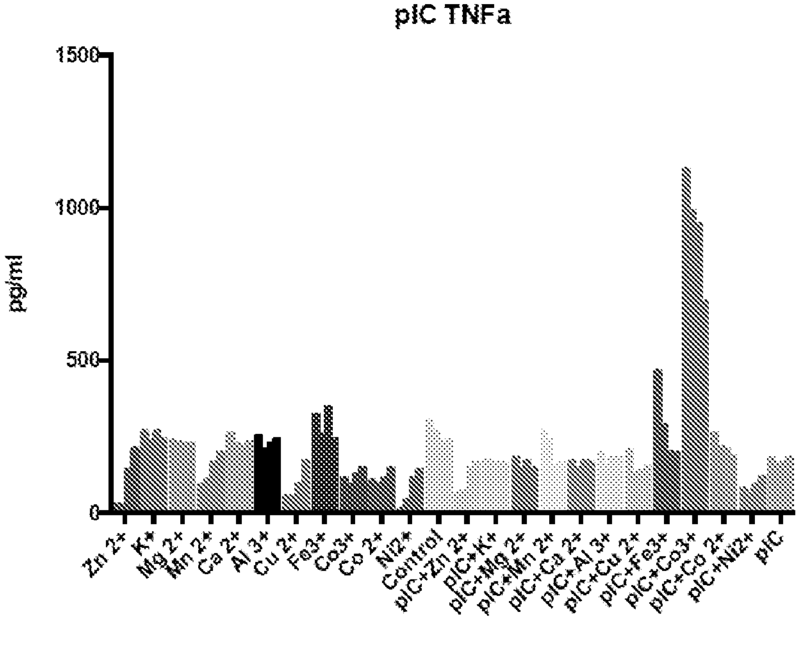
Figure 8C:
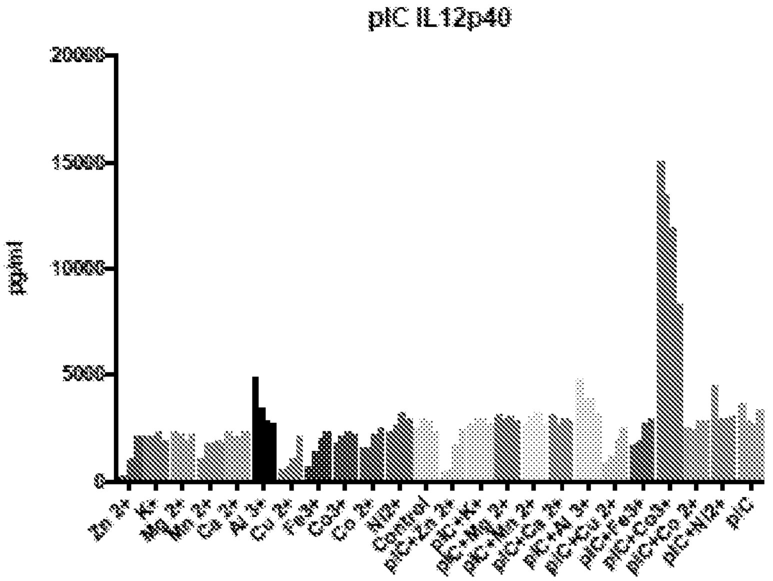
Figure 8D:
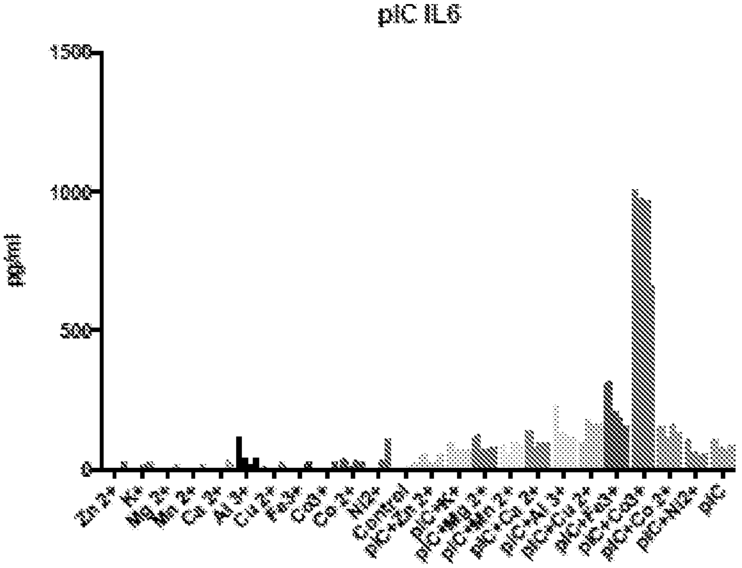
Figure 8E:
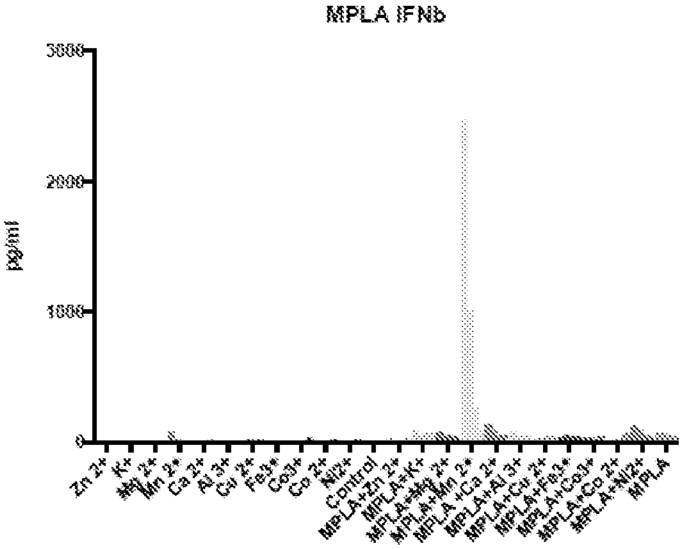
Figure 8F:
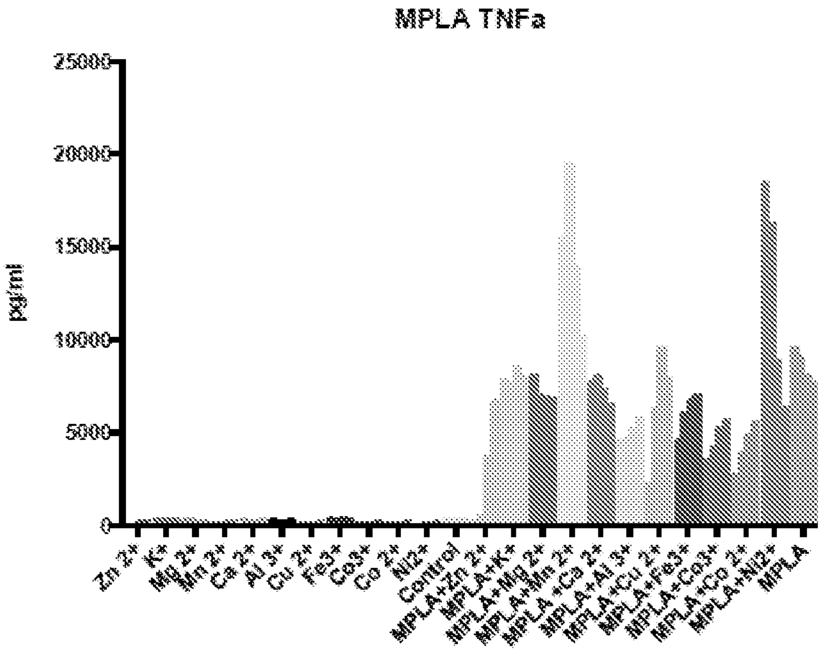
Figure 8G:
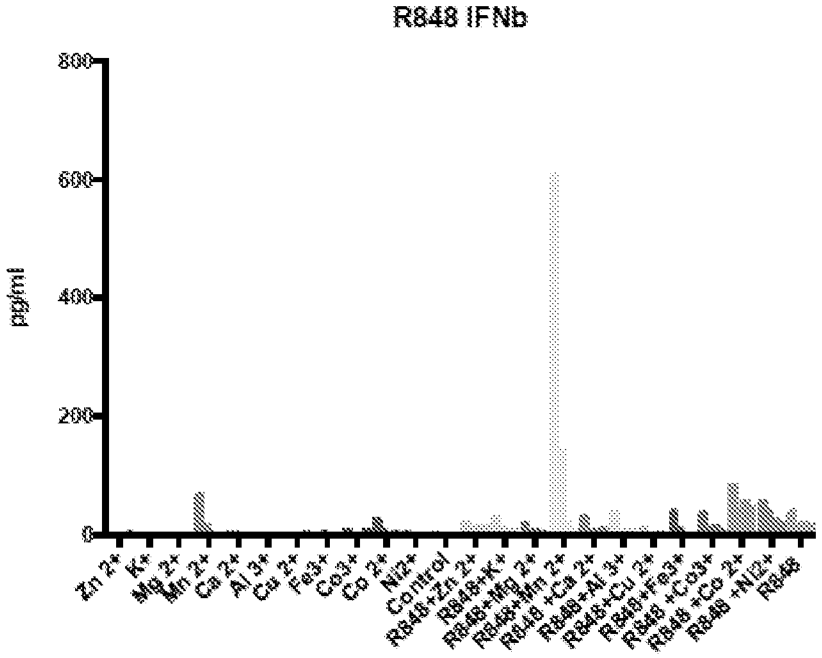
Figure 8H:
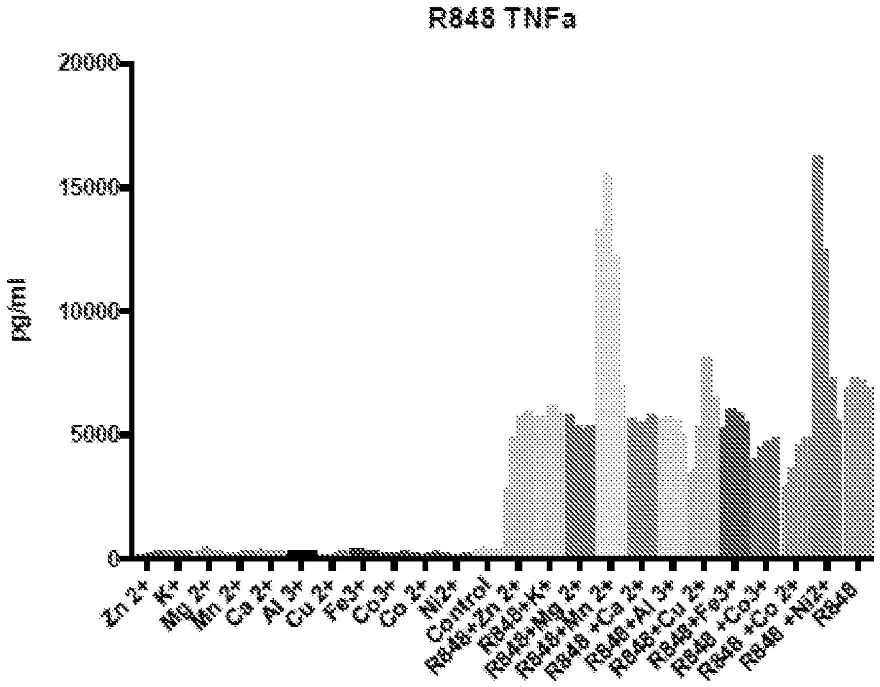
Figure 8I:
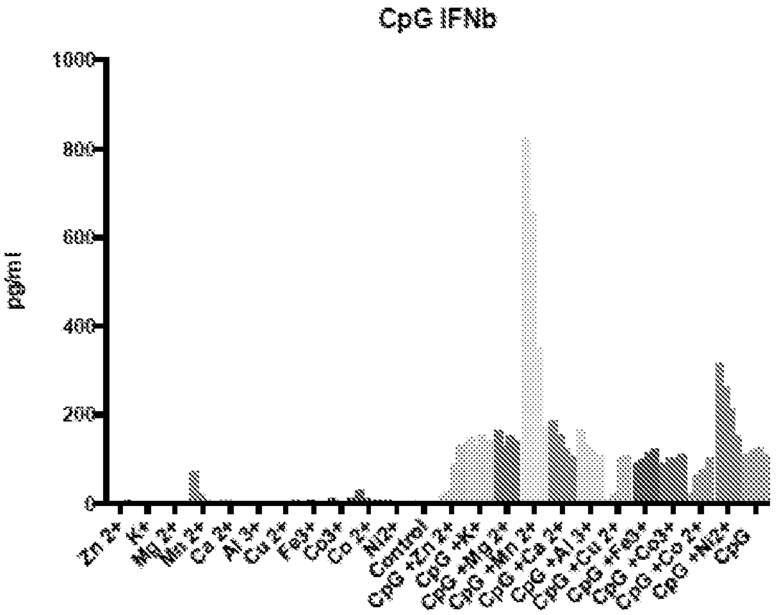
Figure 8J:
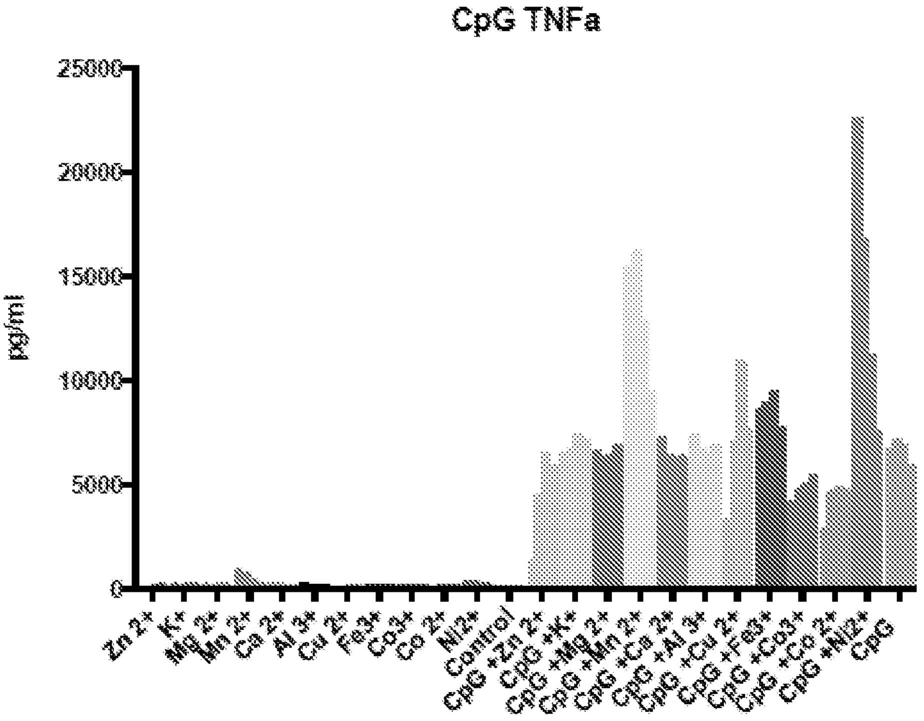
Figure 9:
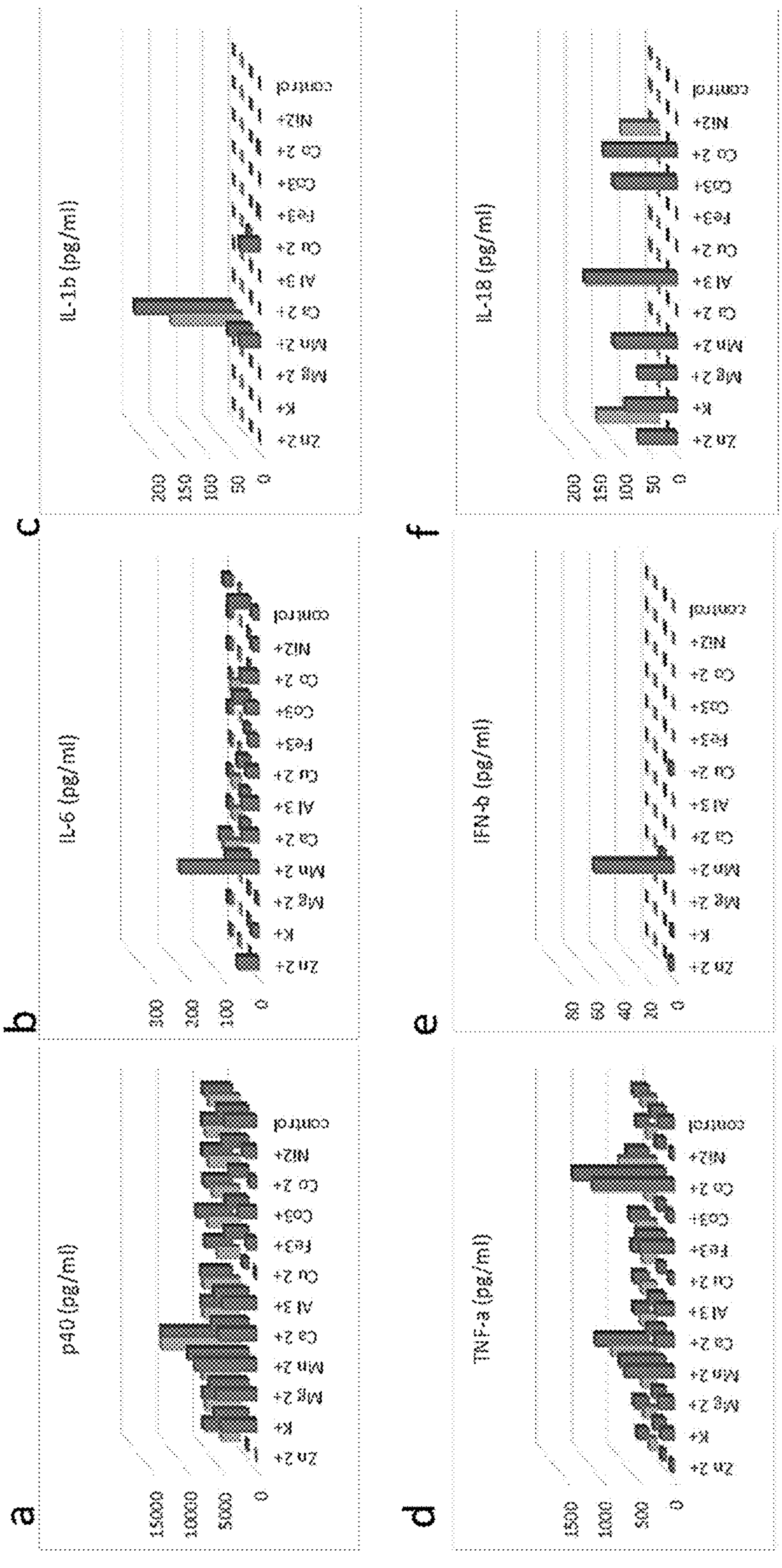
FIG. 9: Modulate immune response of representative NOD-Like Receptors (NLRs) ligands by metal ions in vitro. a-f) Bone marrow derived dendritic cells (BMDCs) were incubated with different concentration of metal ions with or without NOD1 agonist C12-iE-DAP. (g-1) BMDCs were incubated with different concentration of metal ions with or without NOD2 agonist C18-MDP. The cytokines level of cell culture media were quantify by ELISA assay. Control: relative PAMPs in saline.
Figure 9:
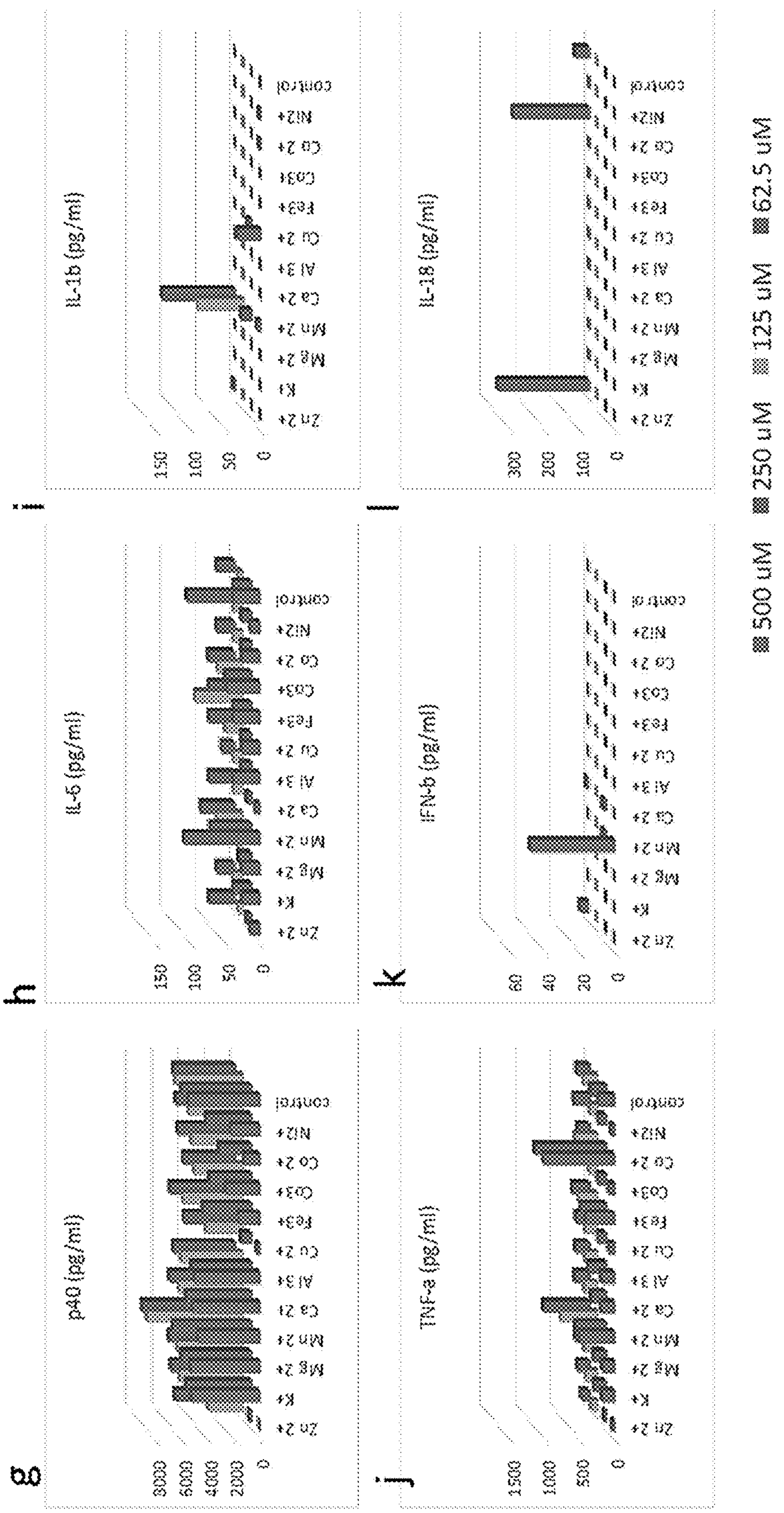
Figure 10:
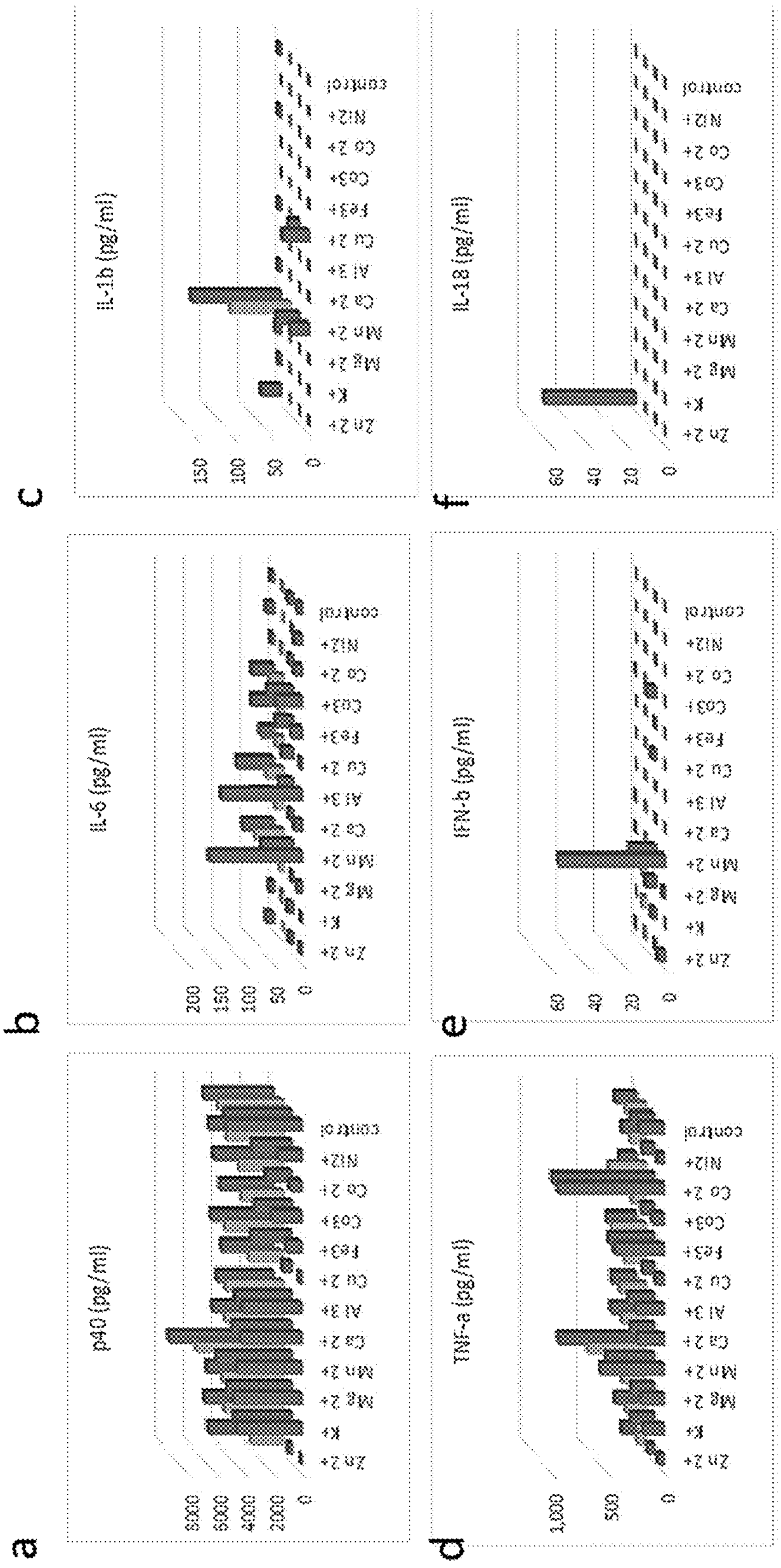
FIG. 10: Modulate immune response of representative RIG-I-Like Receptors-(RLRs) ligands by metal ions in vitro. a-f) Bone marrow derived dendritic cells (BMDCs) were incubated with different concentration of metal ions with or without RLR ligand Poly (dA:dT)/LyoVec™ (Invivogen). The cytokines level of cell culture media were quantify by ELISA assay. Control: relative PAMPs in saline.
Figure 11:
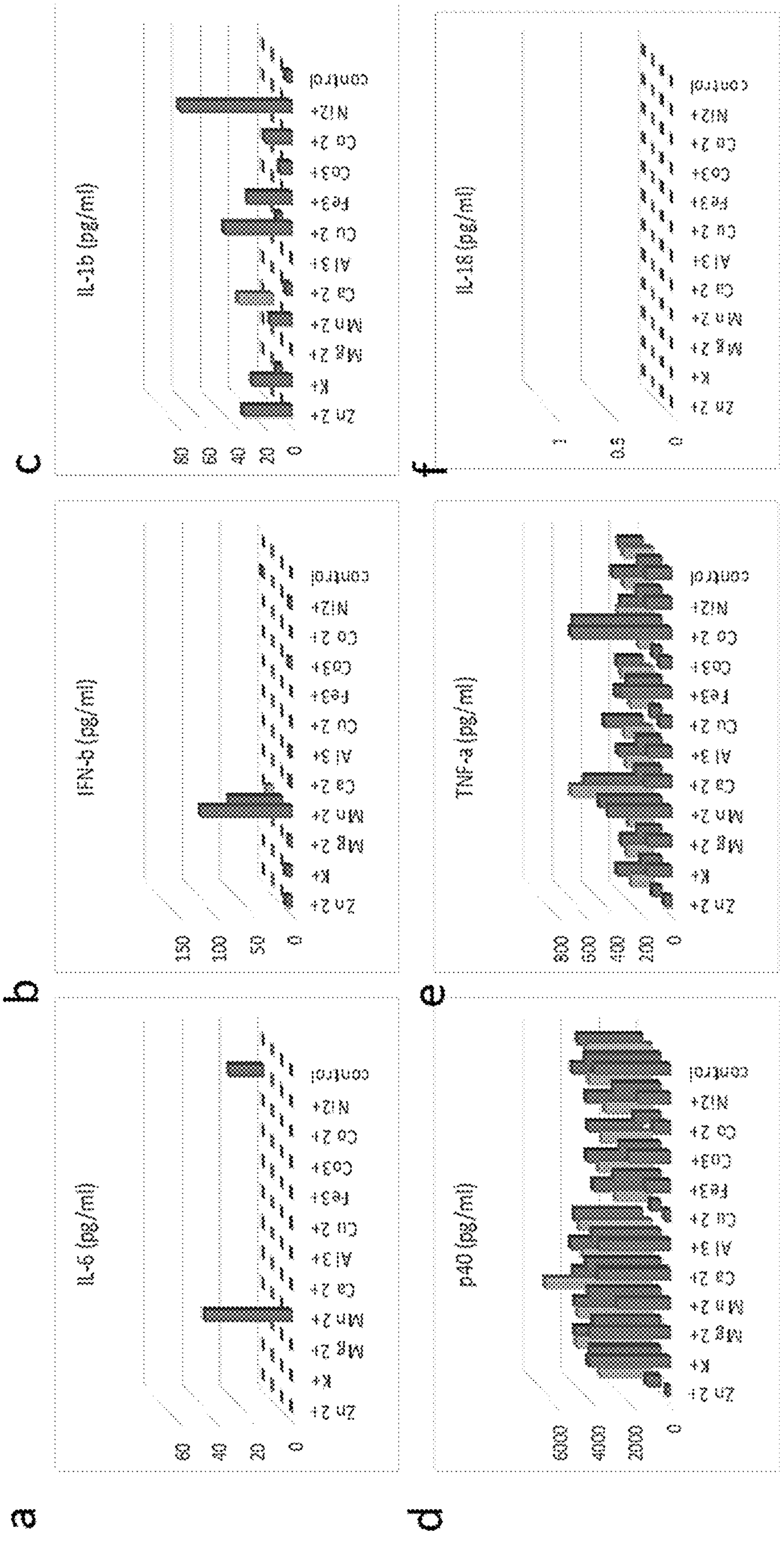
FIG. 11: Modulate immune response of representative inflammasome inducers by metal ions in vitro. a-f) Bone marrow derived dendritic cells (BMDCs) were pre-treated for 3 h with 300 ng/ml phorbol 12-myristate 13-acetate (PMA), followed with 10-200 mg/ml alum Crystal treatment after twice washing. Formation of NLRP3 inflammasome could be characterized by IL-1b secretion. (g-k) BMDCs were incubated with Non-canonical inflammasome inducer *E. coli* outer membrane vesicles and different concentration of various metal ions. The cytokines level of cell culture media were quantify by ELISA assay. Control: relative PAMPs in saline.
Figure 11:
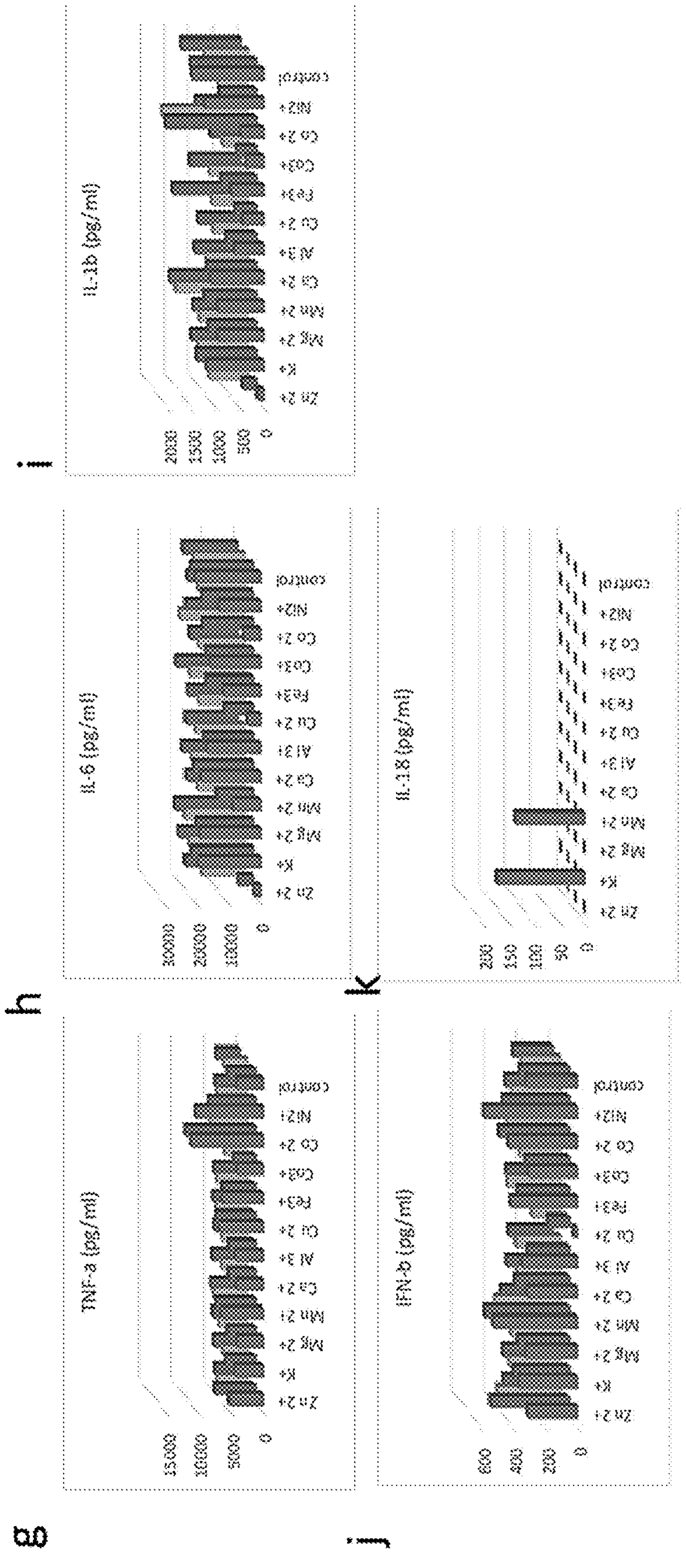
Figure 12:
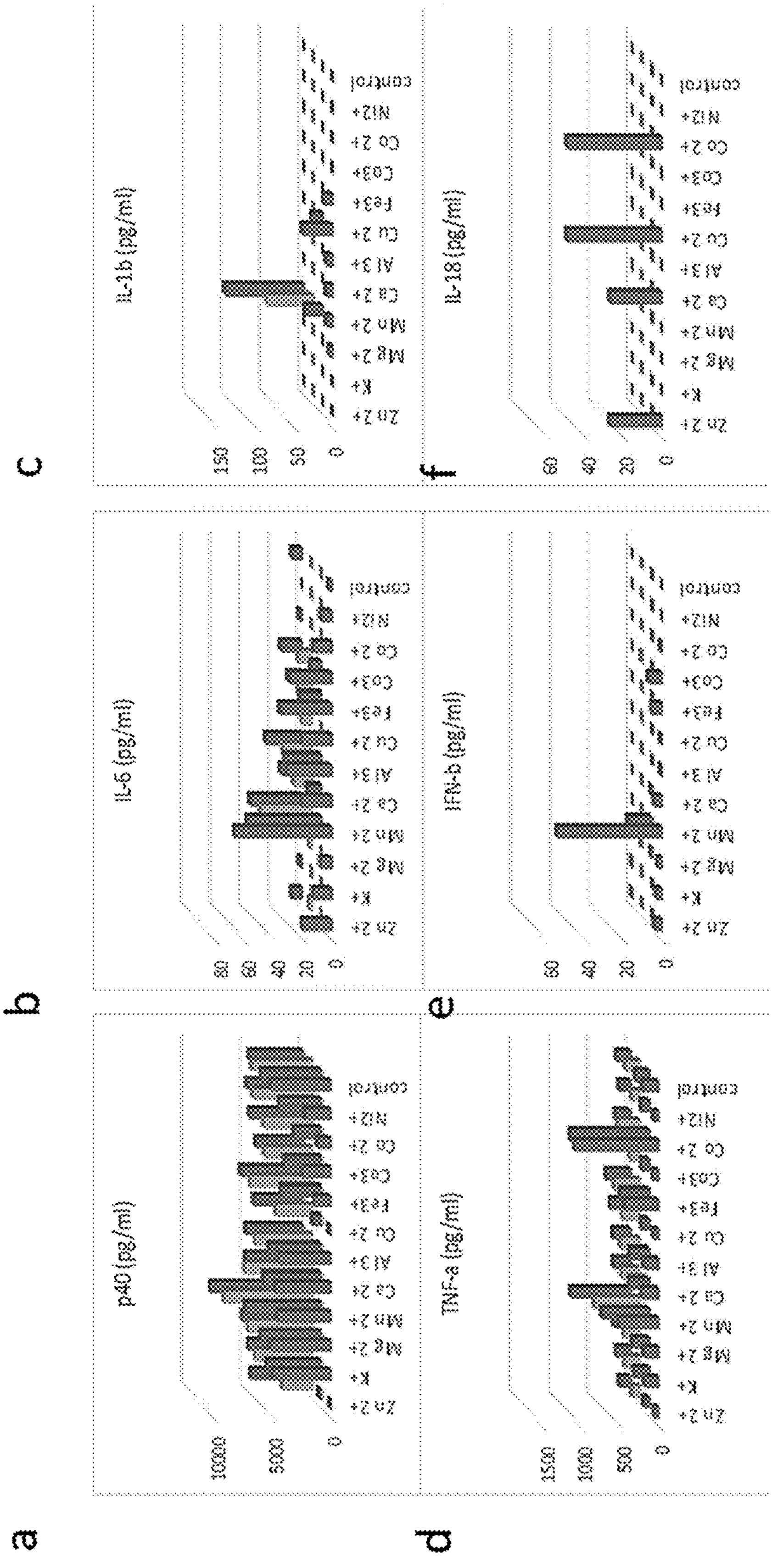
FIG. 12: Immune effect of metal ions alone in vitro. a-f) Bone marrow derived dendritic cells (BMDCs) were different concentration of metal ions. The cytokines level of cell culture media were quantify by ELISA assay. Control: Saline.

Based on our results on the STING pathway, we also examined whether metal ions could modulate other innate immune stimulators. We treated mouse BMDCs with different metal ions or combinations of different metal ions and innate immune stimulators. We observed similar metal ion-innate immune stimulators synergy: however, different metal ions synergized with different DAMP or PAMP, including TLR 3/4/7/8/9 ligands, NOD 1/2 ligands, TLR 7/8 ligands, RIG-I & CDS agonist and inflammasome inducers. For example, $Co^{3+}$ dramatically increased IFNb, TNFa, IL6 and IL2 production by polyIC, whereas $Mn^{2+}$ only increased IFNb production by polyIC (FIG. 8*a-d*). $Mn^{2+}$ increased IFNb and TNFa production of MPLA, whereas $Ni^{2+}$ increased TNFa production of MPLA (FIG. 8*e-f*). $Mn^{2+}$ increased IFNb and TNFa production of R848, whereas $Ni^{2+}$ increased TNFa production of R848 (FIG. 7*g-h*). $Ni^{2+}$ and $Mn^{2+}$ increased IFN beta and TNFa production by CpG (FIG. 8*i-j*). The cytokine profile of NOD1/2 ligands, TLR 7/8 ligands, RIG-I & CDS agonist and inflammasome inducers could also be modulated by Mn2+, Co2+. Al3+, Cu2+, Fe3+, Ni2+ (FIG. 9-12). These results indicate that our metal ion-based approach is a simple but effective way to modulate cytokine profiles of a wide range of immune stimulators. Based on this discovery, we anticipate that pharmaceutically acceptable formulations can be developed to make better and stronger vaccine adjuvants or cancer immune therapy agents. For example, specific metal salts of DAMP/PAMP may perform better than the original form. Coordination polymer composed of selected metal ions and DAMPs/PAMPs with or without pharmaceutically acceptable coordination molecules may lead to optimized metal ions-DAMPs/PAMPs combinations. Other pharmaceutically acceptable formulations, including but not limited to metal-hydroxide/carbonate/phosphate minerals, liposomes, lipid nanoparticles, PLGA particles, hydrogels, emulsions, and etc., for co-delivery of metal ions and DAMPs/PAMPs may also be possible.

Example X

Figure 13:
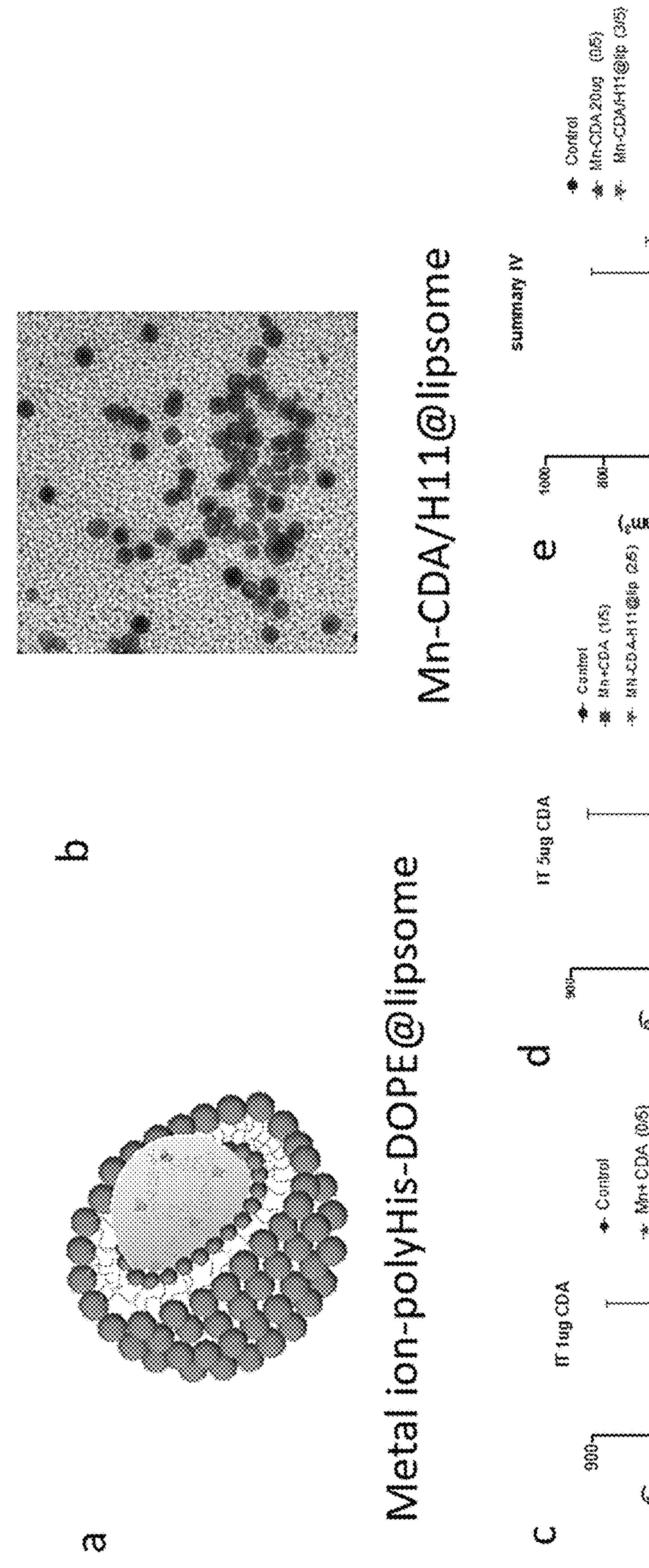
FIG. 13: Representative formulation 1 composed of innate immune stimulator and metal ions. a) scheme of metal ion-poly His-DOPE@liposome nanoparticle composition. b) TEM image of manganese-CDA-H11-DOPE@liposome nanoparticles (Mn-CDA/H11@liposome). c-e) Tumor growth curves of CT26 colon tumor model treated with the indicated formulations and the number of cured tumor-free mice out of 5 mice: c) 3 doses of 5 μg free CDA/$Mn^{2+}$ or Mn-CDA/H11@liposome containing 5 μg CDA and d) 3 doses of 1 μg free CDA/$Mn^{2+}$ or Mn-CDA/H11@liposome containing 1 ug CDA were injected intratumorally (IT) at day 9, 12 and 15 after tumor inoculation: e) 3 doses of 20 μg free CDA/$Mn^{2+}$ or Mn-CDA/H11@liposome containing 20 μg CDA were injected intravenously (IV) at day 9, 12 and 15 after tumor inoculation. f) AH-1 antigen-specific T cell ratio in PBMC 7 days after the first dose. g) ELISPOT counting per 0.1 million PBMCs 14 days after the first dose. h-j) serum IFN-beta, IP10 and TNF-α level four hours after injection of the indicated formulations.
Figure 13:
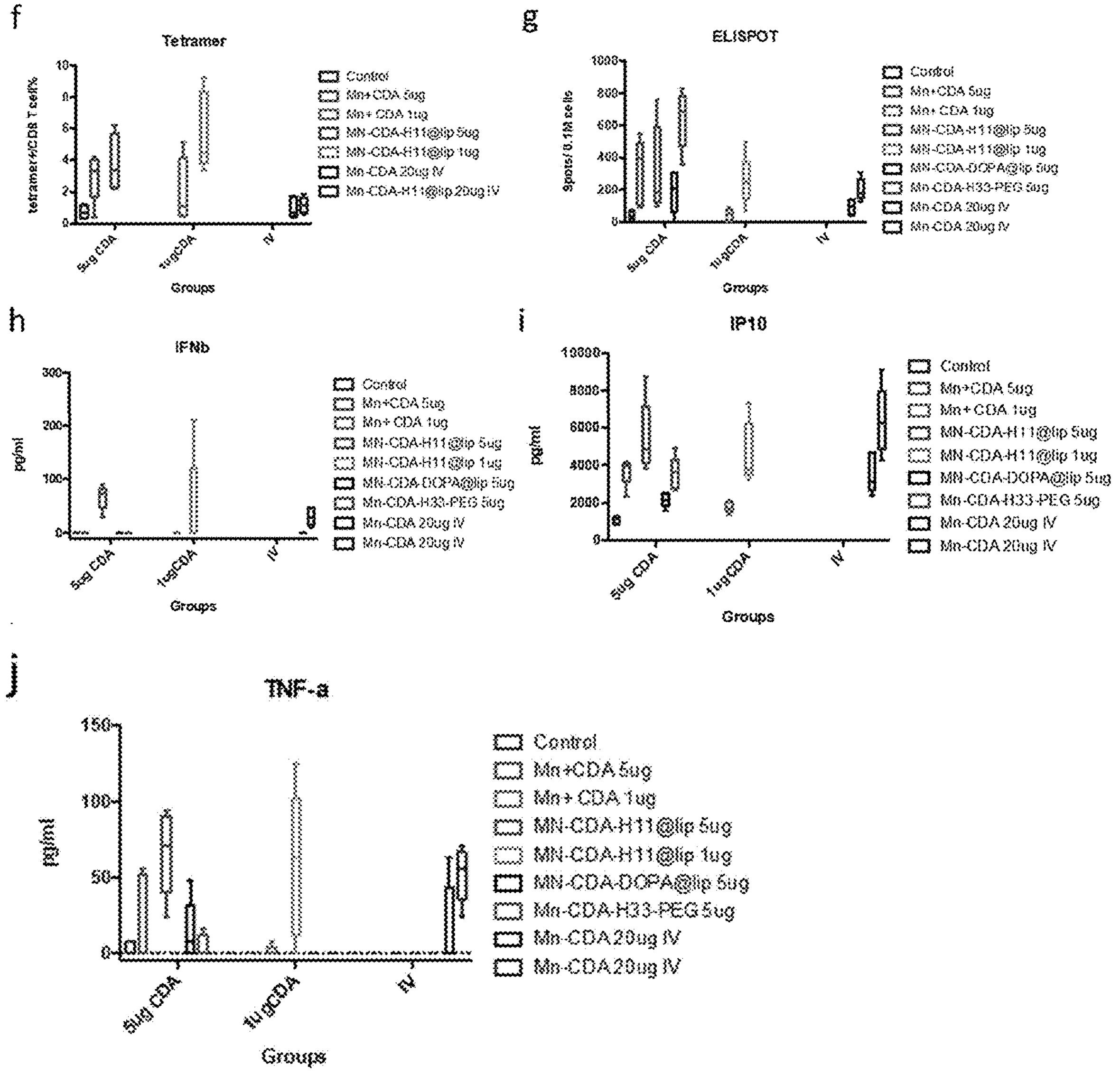
Figure 14:
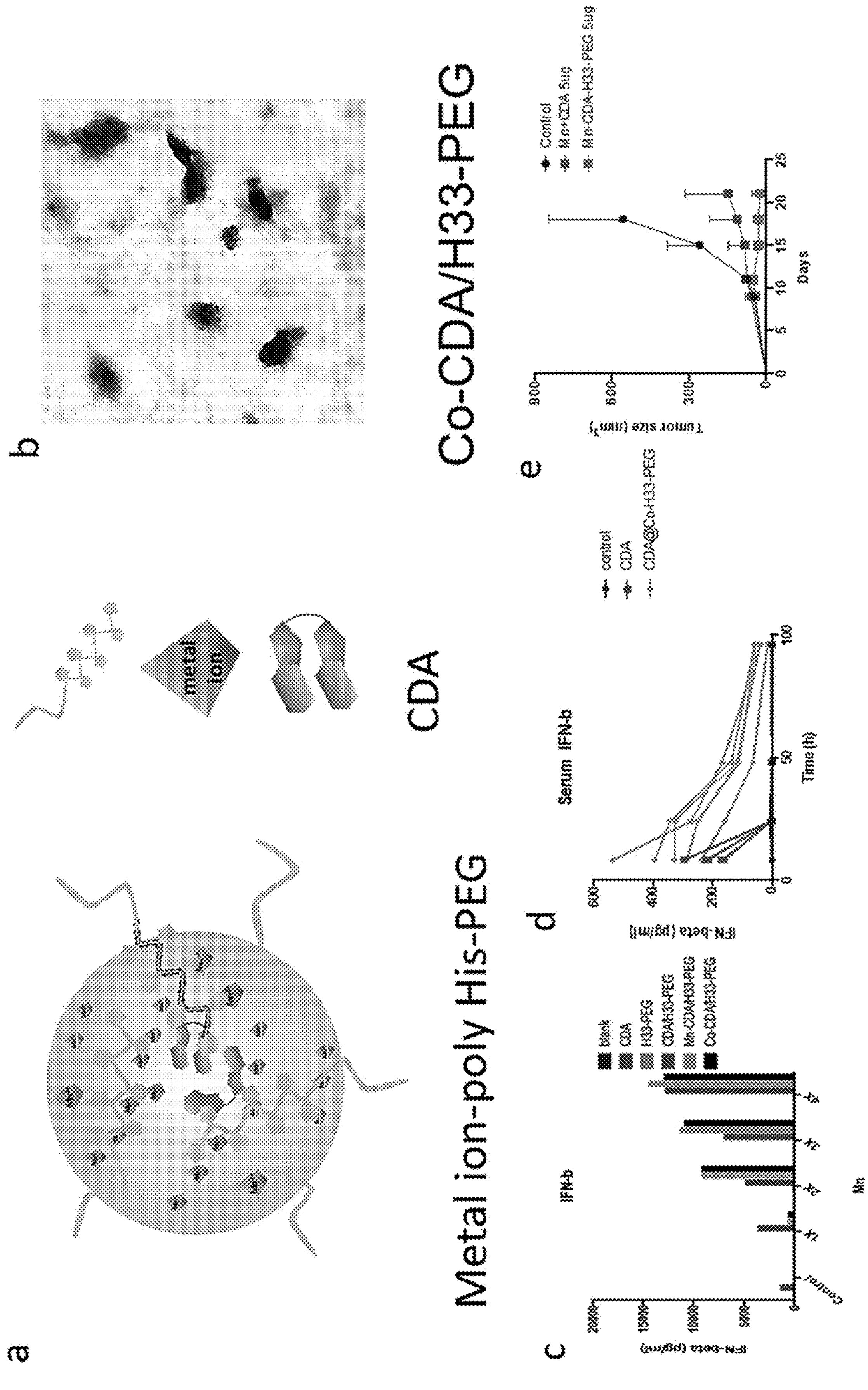
FIG. 14: Representative formulation 2 composed of innate immune stimulators and metal ions. a) scheme of metal ion-poly His-PEG nanoparticle composition. b) TEM image of Co-CDA/H33-PEG nanoparticle. c) In vitro STING activation of BMDC treated with the indicated formulations. d) serum IFN-beta after single injection of the indicated formulations intratumorally in B16F10 melanoma model. e-f) tumor growth (e) and individual tumor growth(f) of the mice treated with the indicated formulations. 3 doses of 5 μg free CDA/$Mn^{2+}$ or Mn-CDA-H33-PEG containing 5 μg CDA were injected into CT16 tumor, IT, at day 9, 12 and 15 after tumor inoculation. g-h) AH-1 antigen-specific T cell ratio in PBMC 7 days after the first dose (g) and ELISPOT counting per 0.1 million PBMCs 14 days after the first dose.
Figure 14:
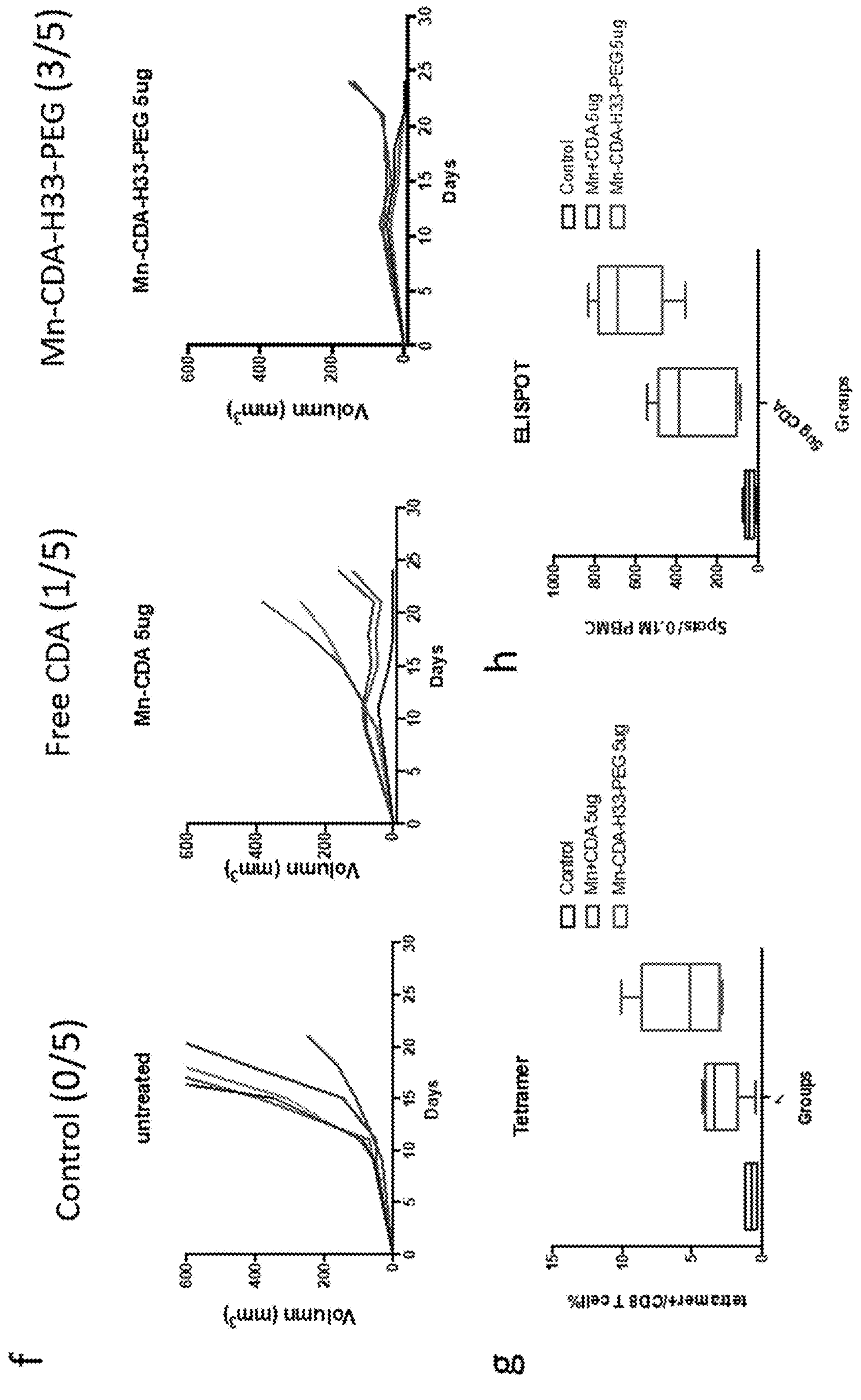
Figure 15:
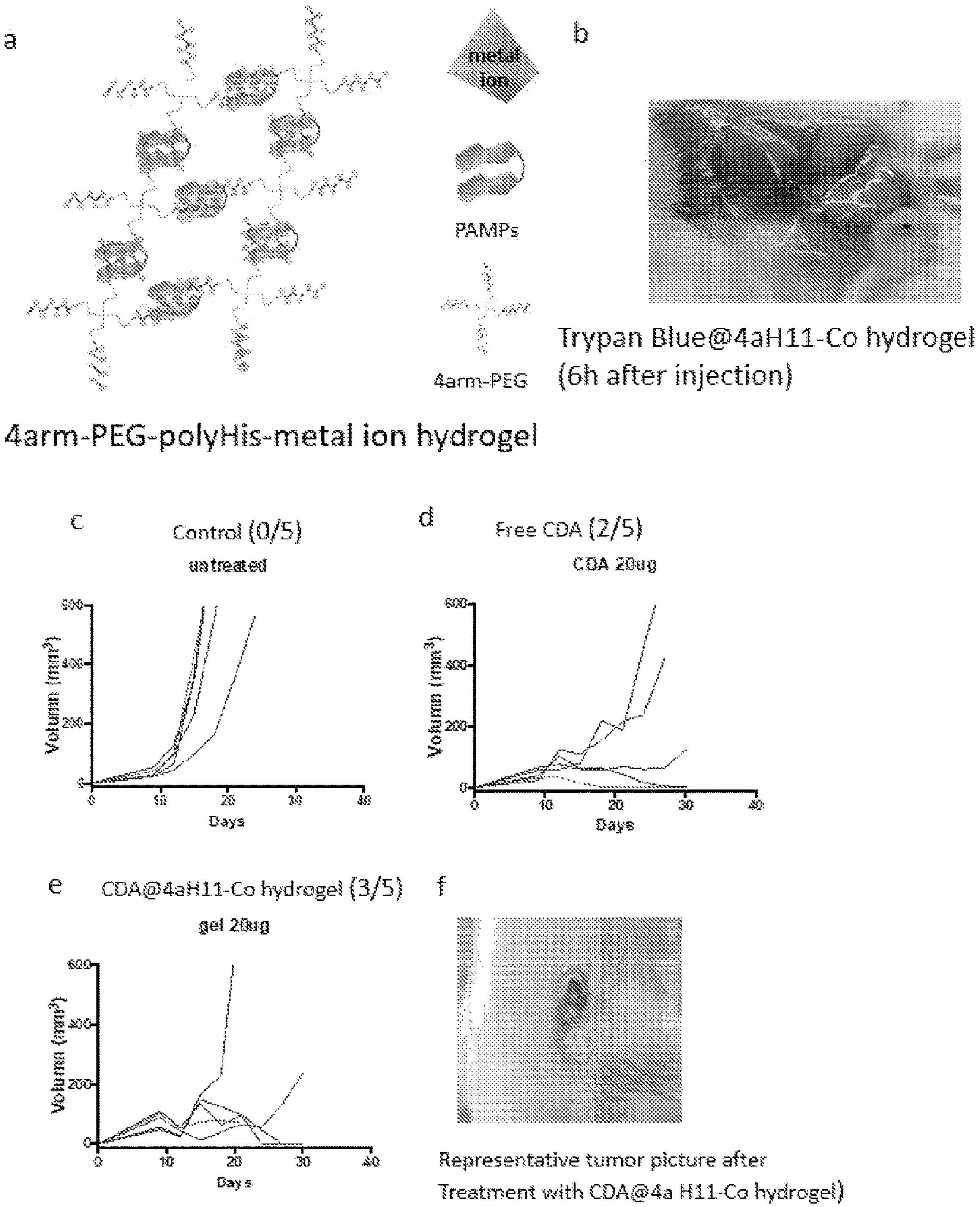
FIG. 15: Representative formulation 3 composed of innate immune stimulators and metal ions. a) schematic composition of metal ion-4arm-PEG-polyHis coordination hydrogel. Shown is CDA@$Co^{2+}$-4arm-PEG-His11 hydrogel (CDA@4aH11-Co hydrogel). b) Retention of injectable Trypan Blue@4aH11-Co hydrogel at the injected site 6 h after injection. c-e) individual tumor growth of the mice treated with the indicated formulations. 3 doses of 20 μg free CDA/$Mn^{2+}$ or hydrogel containing 20 μg CDA were injected intratumorally (IT) at day 9, 12 and 15 after tumor inoculation. f) Representative tumor picture after treatment with CDA@4a H11-Co hydrogel.
Figure 15A:
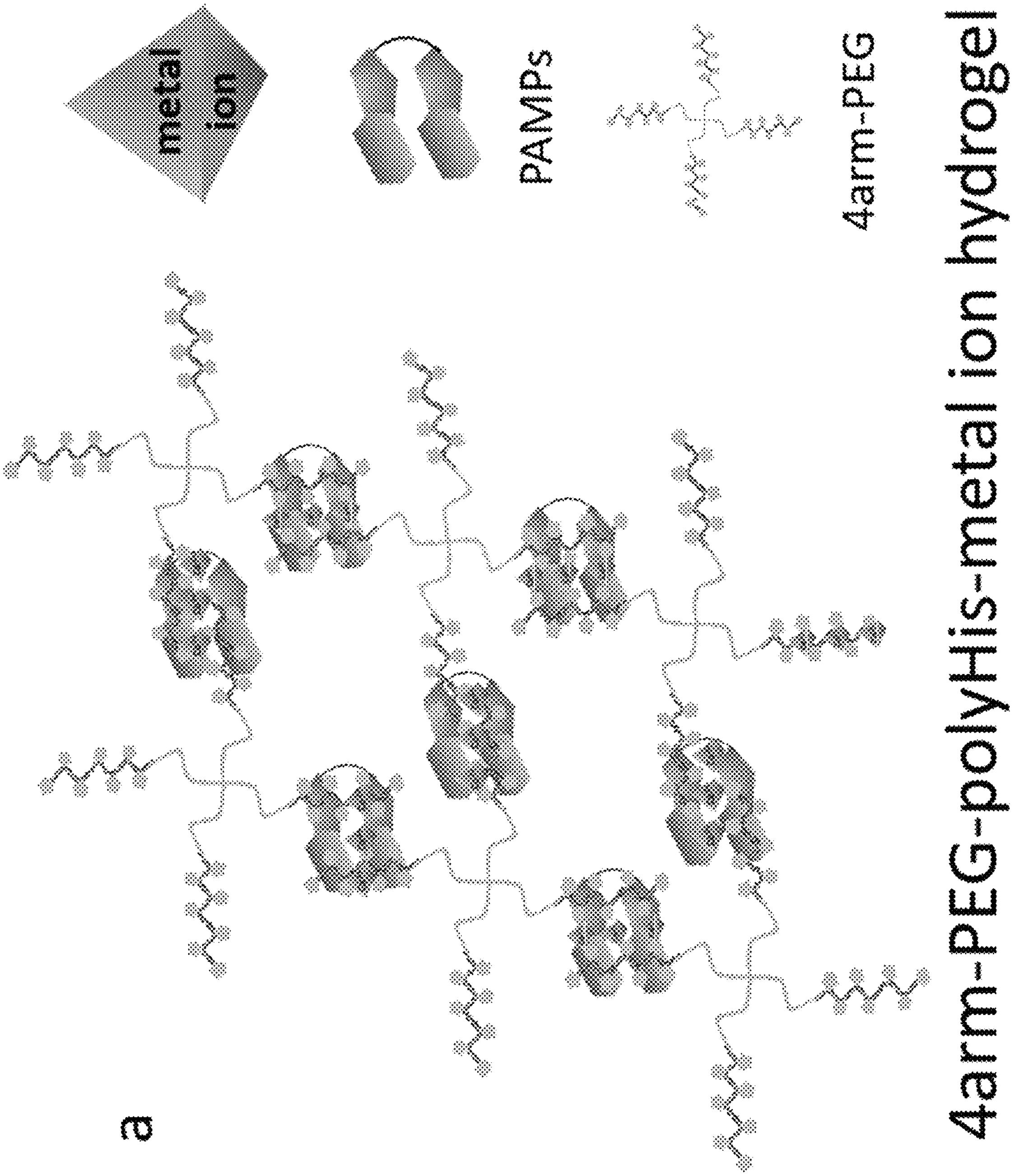

This example describes a representative formulation of metal-innate immune stimulators. To co-deliver metal ions and innate immune stimulators to the right target tissues with ideal release profile, appropriate formulations based on the physical and chemical properties could be designed, such as specific metal salts of DAMP/PAMP, coordination and other pharmaceutically acceptable formulations (hydroxide/carbonate/phosphate minerals, liposome, lipid nanoparticles. PLGA, hydrogels, emulsions etc). Here we provide several representative example of coordination formulations, manganese-CDA-H11-DOPE a liposome nanoparticles (Mn-CDA/H11@liposome, FIG. 13), Co-CDA/H33-PEG coordination nanoparticle (Co-CDA/H33-PEG, FIG. 14) and CDA@Co2+-4arm-PEG-His11 hydrogel (CDA@4aH11-Co hydrogel. FIG. 15). CDA itself could coordinate with $Co^{2+}$ and $Mn^{2+}$ via the N of the purine ring, which could be further stabilized by poly-Histidine. A nanoparticle structure (FIG. 13-14) or hydrogel (FIG. 15) were generated by different building module design and could be adjusted by optimizing the ratio and concentration of $Co^{2+}$/$Mn^{2+}$:CDA: poly-histidine-PEG, reaction time, and pH. The loading efficacy was around 30% for $Co^{2+}$/$Mn^{2+}$ and over 70% for CDA. We further tested those coordination formulations in a murine CT26 colon tumor model. As shown in Figure FIG. 13-15. those nanoparticle structure or hydrogel formulation could greatly enhanced STING activation in vivo compared with free CDA or free CDA+ metal ions. Especially. liposome-coated nanoparticle. CDA-Mn-His11-DOPE@liposome (Mn-CDA/H11@lip) could be used for systemic delivery of STING agonist and eradicated 60% established CT26 colon tumor (FIG. 13); Co-CDA/His33-PEG could greatly prolong the production of IFNb production, which was detectable even 4 days after injection (FIG. 14); and injectable CDA@4aH11-Co hydrogel induced very strong local ablative immune response and notable ulcer formed after $1^{st}$ dose (FIG. 15*f*). These improved therapeutic effect were also characterized by elevated antigen specific T cell response. Type-I IFN response and pro-inflammation cytokine release.

Figure 16:
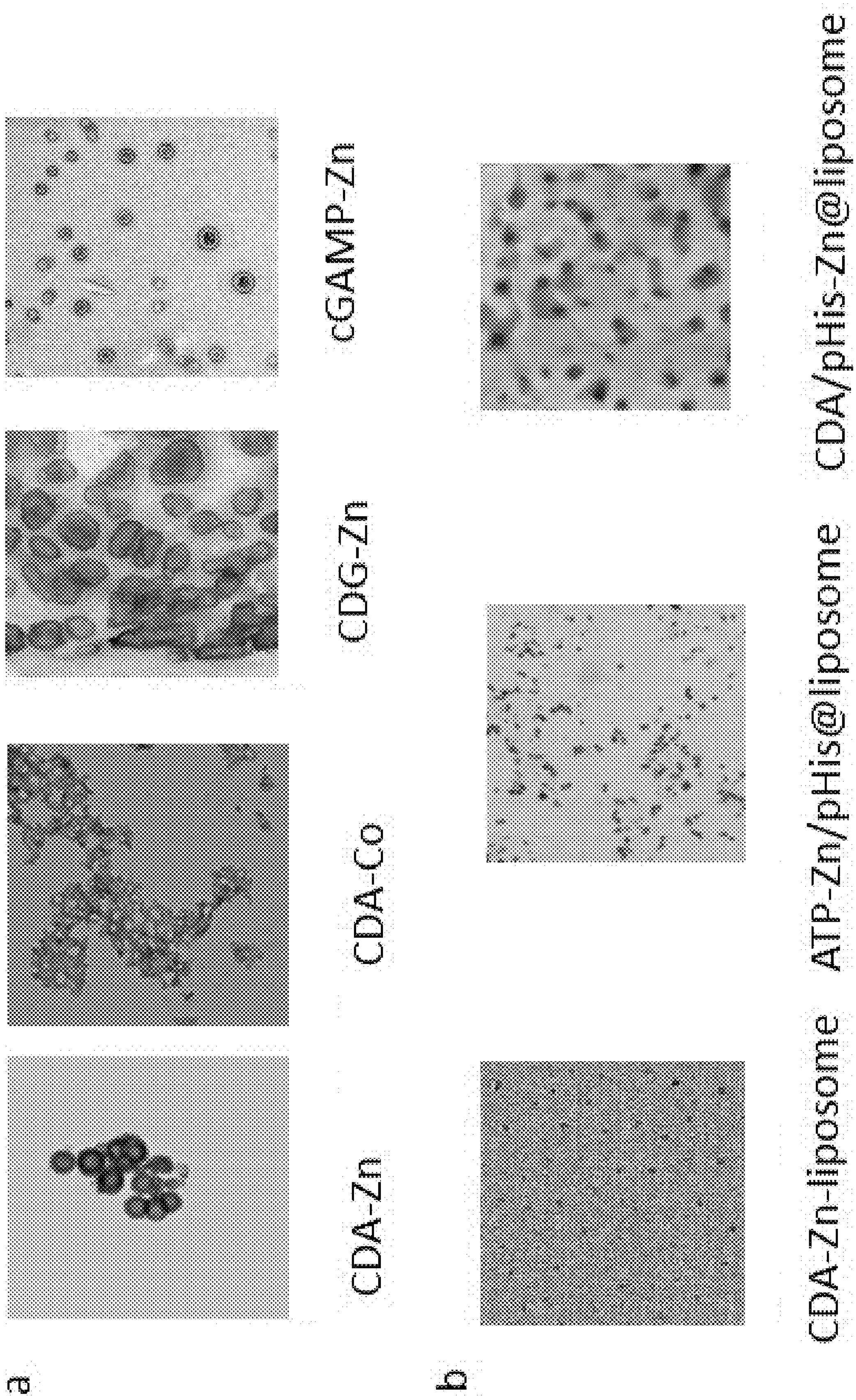
FIG. 16: Some other representative formulations may be used to deliver metal ions and PAMPs. a) metal ions and CDNs self assembly. b) liposome coated CDN-metal ion coordination nanoparticles. c) polyhistidine coated nanoparticles. d-e) polymer stabilized metal-CDN coordination nanoparticles or metal mineral nanoparticles. Copolymers of poly (histidine)-polyethylene glycol: PH-PEG or pHis-PEG, poly (ethylene imine)-polyethylene glycol: PEI-PEG, poly (lysine)-polyethylene glycol PEG: PK-PEG, anionic poly (glutamic acid)-polyethylene glycol: PGA-PEG.
Figure 16:
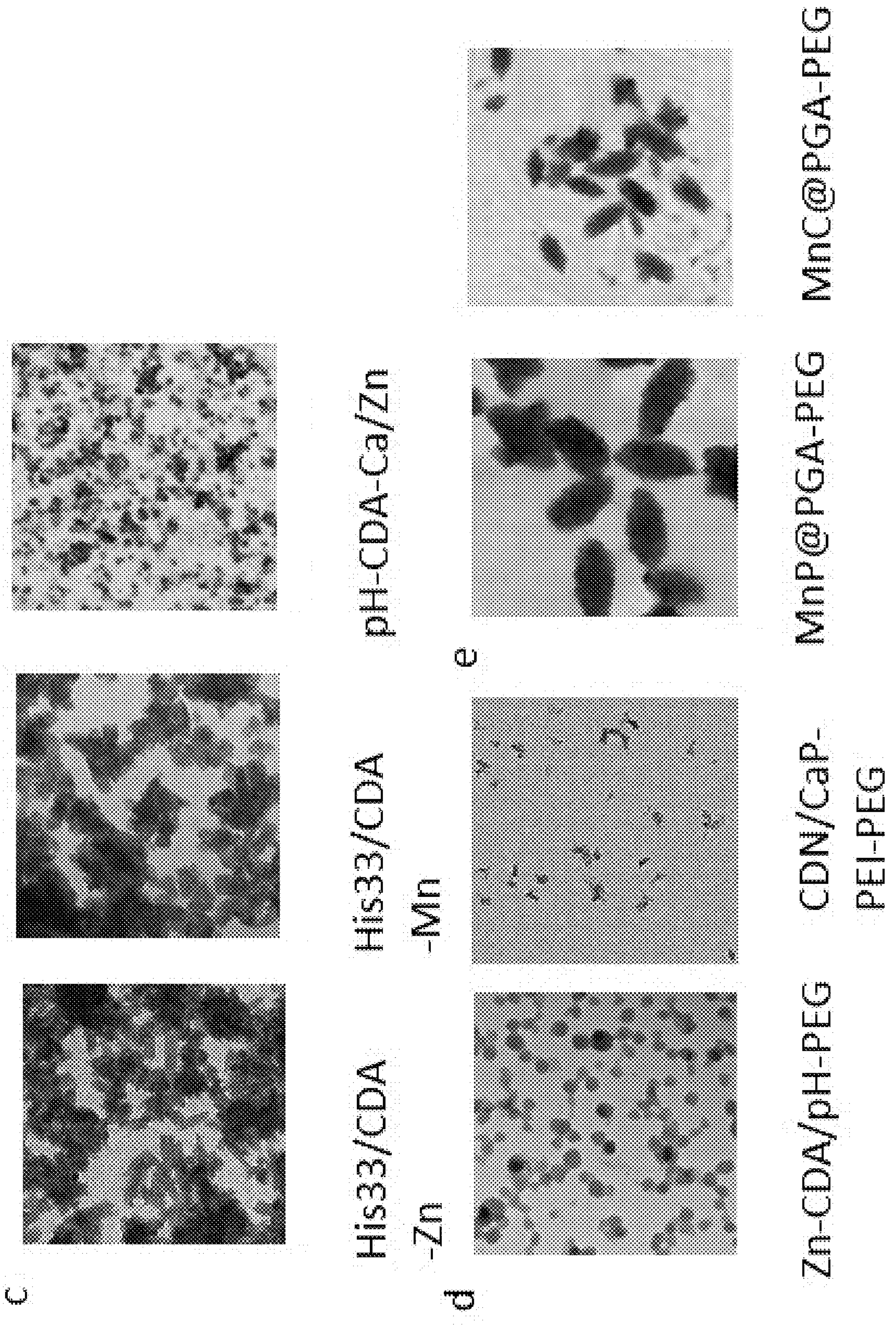

In addition to the formulations mentioned above, there are many other formulations that can be synthesized to deliver metal-innate immune stimulators. Here we have provided some examples with their morphologies shown in the TEM images (FIG. 16). As shown in FIG. 16*a*. CDA-Zn NPs exhibited sphere shape with higher TEM contrast on the surface, resulting in "core-shell"-like structure. We also found that homogeneous sphere structure was obtained when the synthesis was conducted in aqueous media because nucleation occurs more slowly in water. Consistent with the TEM images, the DLS and zeta potential data indicated that the size of cdAMP-Zn was around 150 nm and the surface charge was neutral. Under the same synthesis condition. CDA-$Co^{2+}$ NPs showed crosslinked nanoparticle cluster: CDG-$Zn^{2+}$ showed homogeneous irregular sphere structure of a size around 100 nm and neutral surface charge: cGAMP-$Zn^{2+}$ showed sphere-shaped nanoparticles composed of accumulated smaller clusters and the surface had slight positive charge. To increase the stability of CDN-$Zn^{2+}$ NPs, we also added other multi-valent coordination agents, such as liposomes (FIG. 16*b*), polyhistidine (FIG. 16*c*) and polyhistidine-PEG (FIG. 16*d*). In addition, innate immune stimulators loaded in nanoscale metal minerals could also be prepared for delivery of metal ion-innate immune stimulator combinations (FIG. 16*d-e*). To increase the stability of the nanoparticles, surface modification with PEI-PEG. PGA-PEG and other anionic polypeptide-PEG could be applied.

Figure 17A:
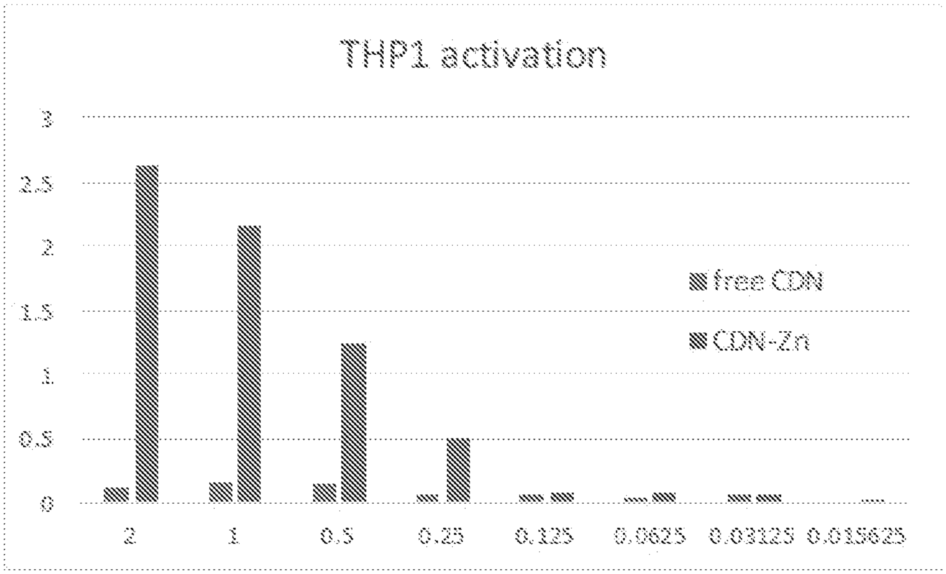
FIG. 17: Therapeutic effect of selected formulations from FIG. 12 in CT26 colon tumor model. a) Representative THP1 activation assessment by free CDN and CDN-Zn in different concentration. The CDN used here is cdAMP. b) Representative THP1 activation by free CDN and CDN@CaP/PEI-PEG in different concentration. The CDN used here is $cdAMP(ps)_2$. b-e) Balb/c mice of 6-7 weeks were inoculated with $1.5\times10^5$ CT26 tumor cells on day 0. On days 10, 15, tumor-bearing mice were treated with indicated formulations containing 25 μg/dose of adAMP (ps) 2 intratumorally. Shown are c) the average tumor growth curve of tumor-bearing mice: d) survival of mice after different treatments: e) tumor growth curve of individual mouse in different groups. (f-g) tetramer staining (f) seven days after the first dose of treatments and ELISPOT analysis (g) seven days after the second dose of treatment.
Figure 17B:
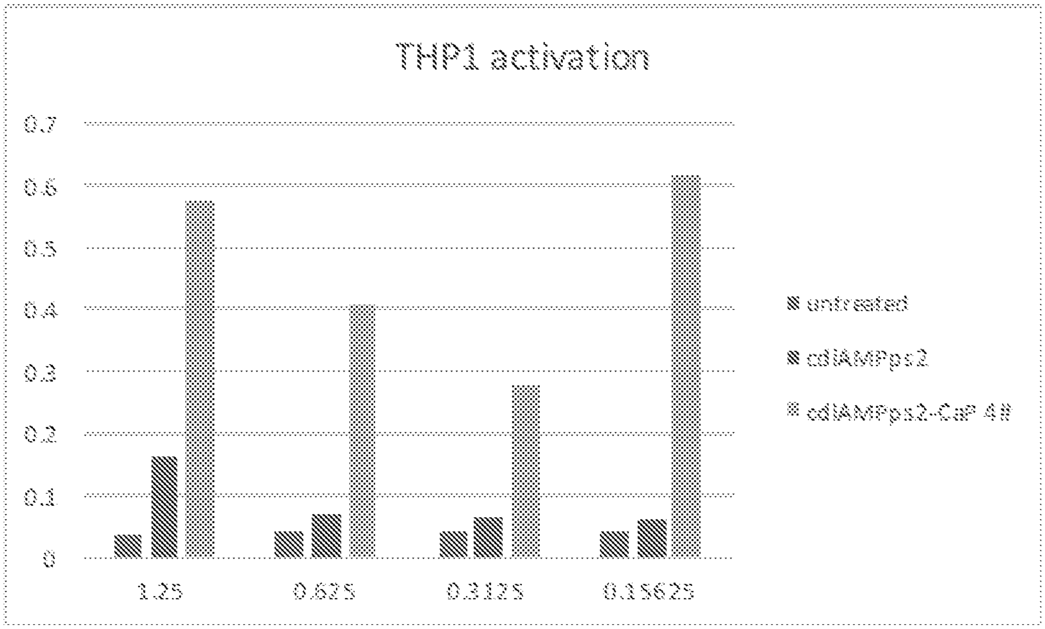
Figure 17C:
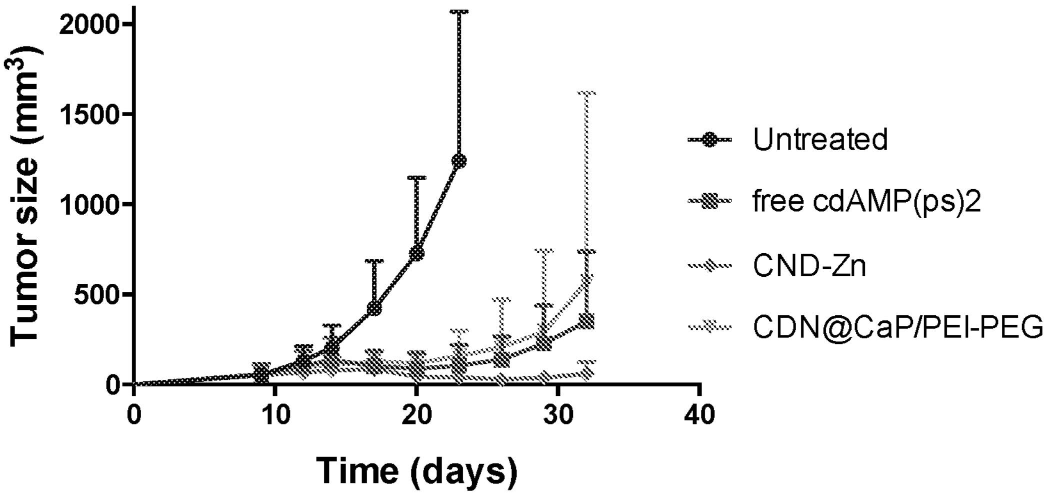
Figure 17D:
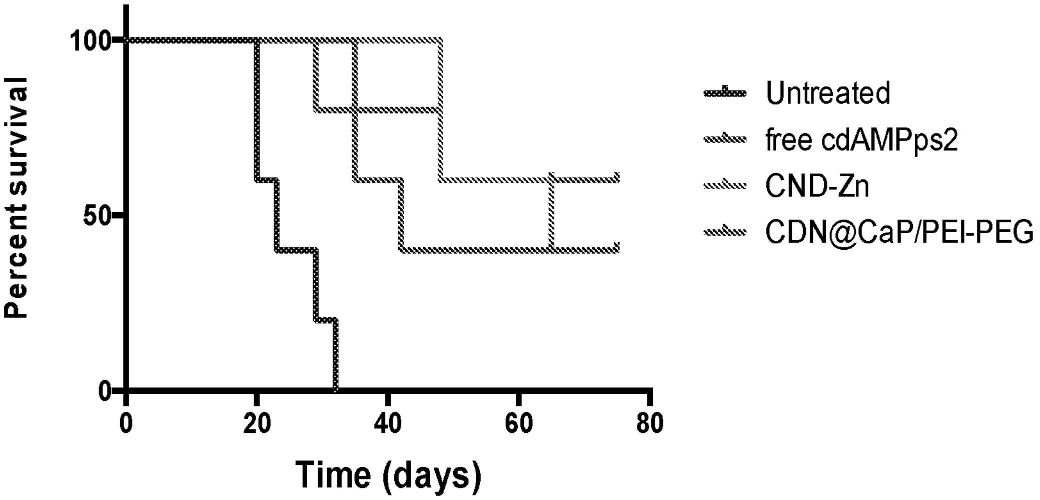
Figure 17E:
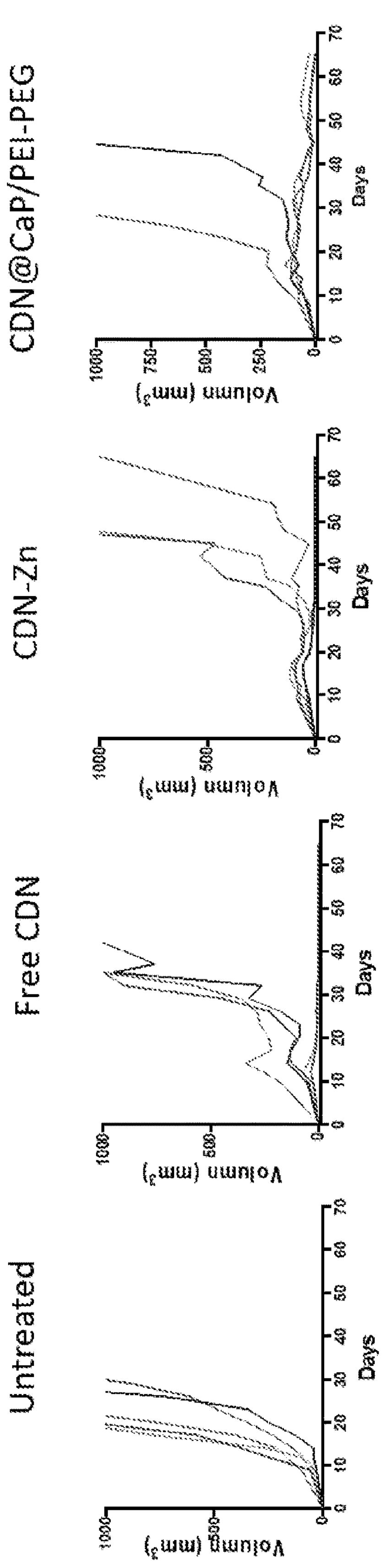
Figure 17F:
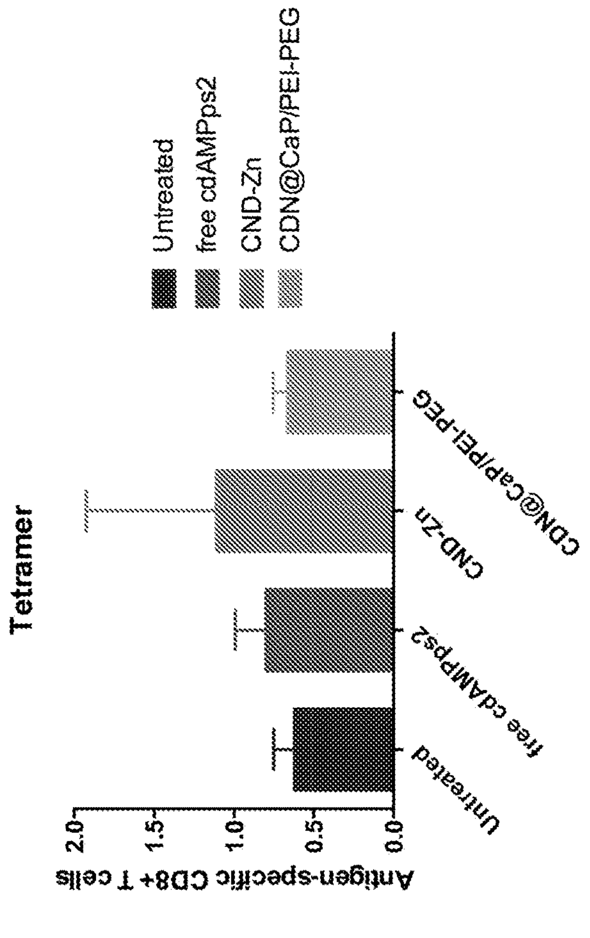
Figure 17G:
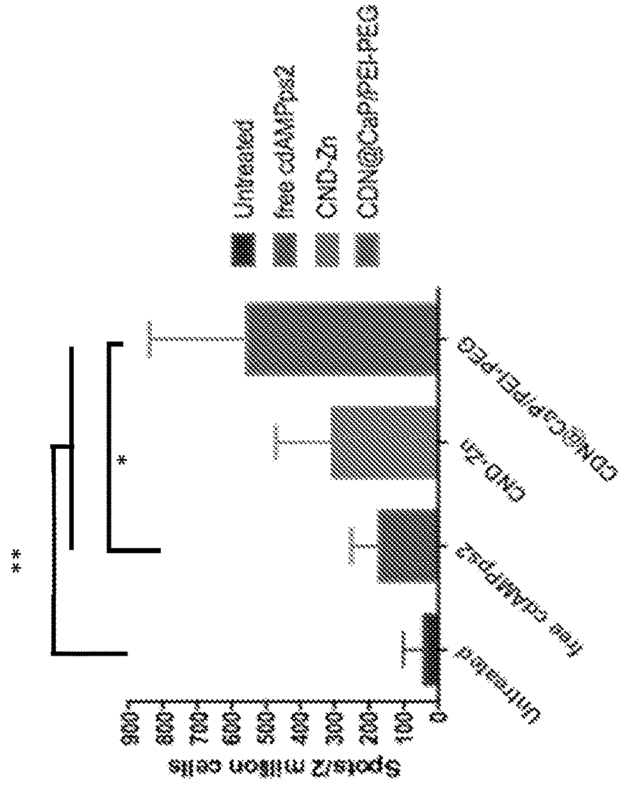

We also evaluated a subset of the formulations mentioned above in tumor-bearing mice. When tumor size reached ~60 $mm^3$, 2 doses of indicated formulation with 25 μg/dose adAMP(ps)2 were administrated intratumorally on days 10 and 15. As shown in FIG. 17, the tumor growth of mice treated with free CDN, CDN-$Zn^{2+}$ and CDNs@CaP/PEI-PEG was greatly delayed, compared with the untreated group. CDN-$Zn^{2+}$ inhibited tumor growth more efficiently, compared with CDN and CDNs a CaP/PEI-PEG even though there was no statistical difference among them. For the survival of mice after treatment, median survival times for the untreated, CDN, CDN-$Zn^{2+}$ and CDNs@CaP/PEI-PEG groups were 23 days, 42 days, 64 days and unreached, respectively (FIG. 17*d*). From the individual tumor growth curve (FIG. 17*e*), we observed complete tumor regression in 0 out of 5 mice in untreated group: 2 out of 5 mice in free CDN group and CDN-$Zn^{2+}$ group; and 3 out of 5 in CDN@CaP/PEI-PEG group. For PBMC tetramer staining assay, no significant difference was observed among the groups (FIG. 17*f*). PBMC tetramer staining may not be sensitive enough to show antigen-specific T cell response after non-specific intra-tumoral CDN stimulation or the time point may not have been optimal. In contrast, ELISPOT assessment on day 22 showed significant antigen-specific immune responses (FIG. 17*f-g*). Seven days after the 2nd dose of CDN treatment, significant AH1 antigen-specific T cell response was observed in the groups of free CDN, CDN-$Zn^{2+}$, and CDNs@CaP/PEI-PEG. The response of CDN-$Zn^{2+}$ and CDNs@CaP/PEI-PEG are also higher than the free CDN, and statistical difference was observed between free CDN and CDNs@CaP/PEI-PEG.

Example XI

This example describes chelating metal ions to inhibit innate immune response.

Figure 18A:
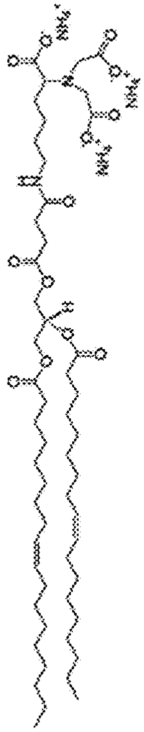
FIG. 18: Chelating metal ions to inhibit cGAS-STING-Type I IFN pathway. a) Molecular structure of representative chelators that could inhibit cGAS-STING-Type I IFN pathway. b-c) Dose-inhibition curves of the IFN-I response (b) and NF-kB inflammation response (c) by the indicated compounds in DNA/lipofectamine 2000 (ThermoFisher, 11668027) treated THP 1 dual-KI-$hSTING^{WT(R232)}$ reporter cells (Invivogen, thpd-r232). d) Cellular viability of b-c. e) Dose-inhibition curves of the IFN-I response by the indicated compounds in DNA/lipofectamine 2000 (ThermoFisher, 11668027) treated THP 1-ISG $hSTING^{HAQ}$ reporter cells (Invivogen, thp-isg). (f) Dose-inhibition curves of the IFN-I response by the indicated compounds in cGAMP treated THP 1 dual-KI-$hSTING^{WT(R232)}$ reporter cells (Invivogen, thpd-r232).
Figure 18A:
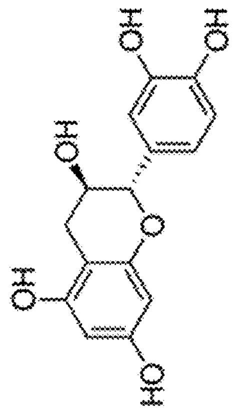
Figure 18A:
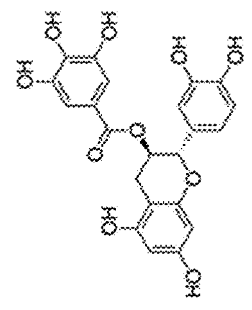
Figure 18A:
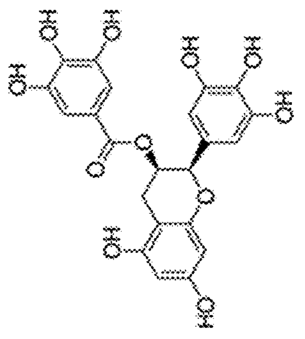
Figure 18A:
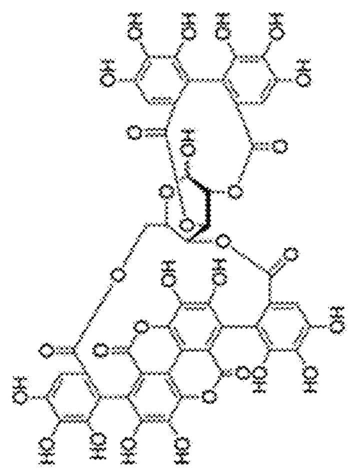
Figure 18A:
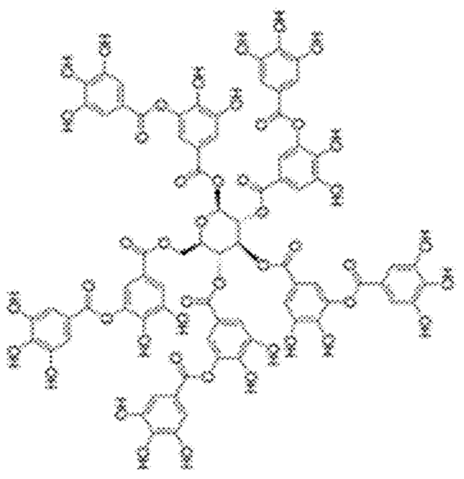
Figure 18B:
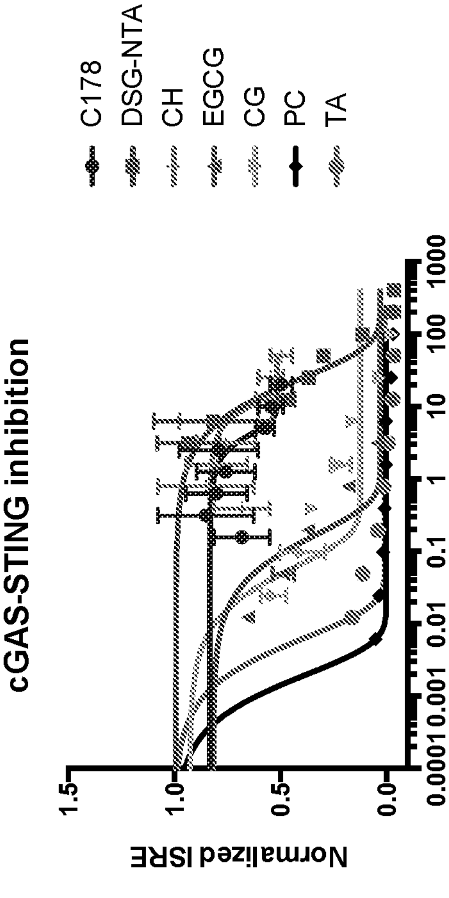
Figure 18C:
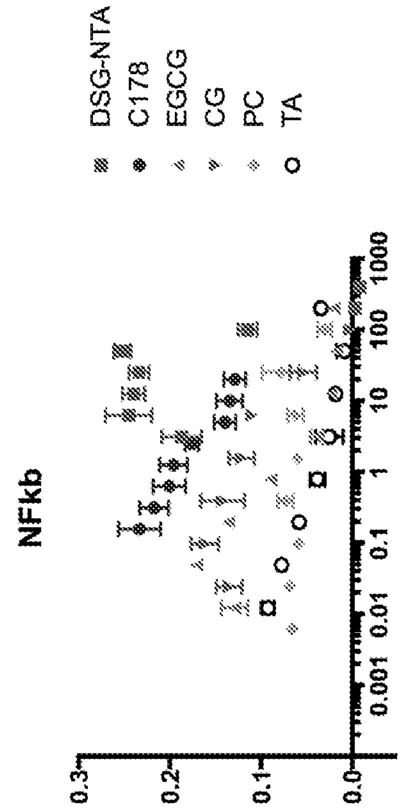
Figure 18D:
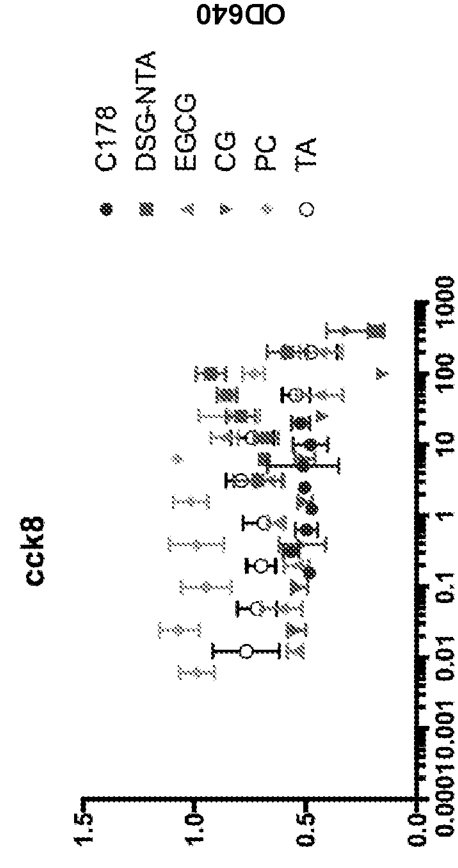
Figure 18E:
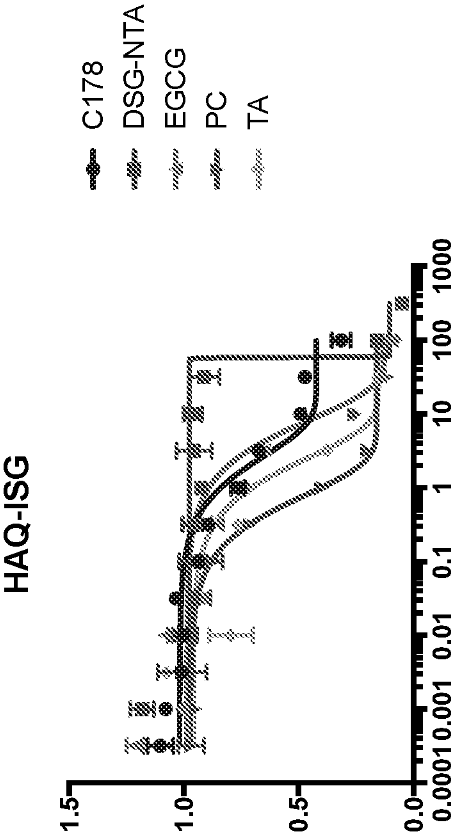
Figure 18F:
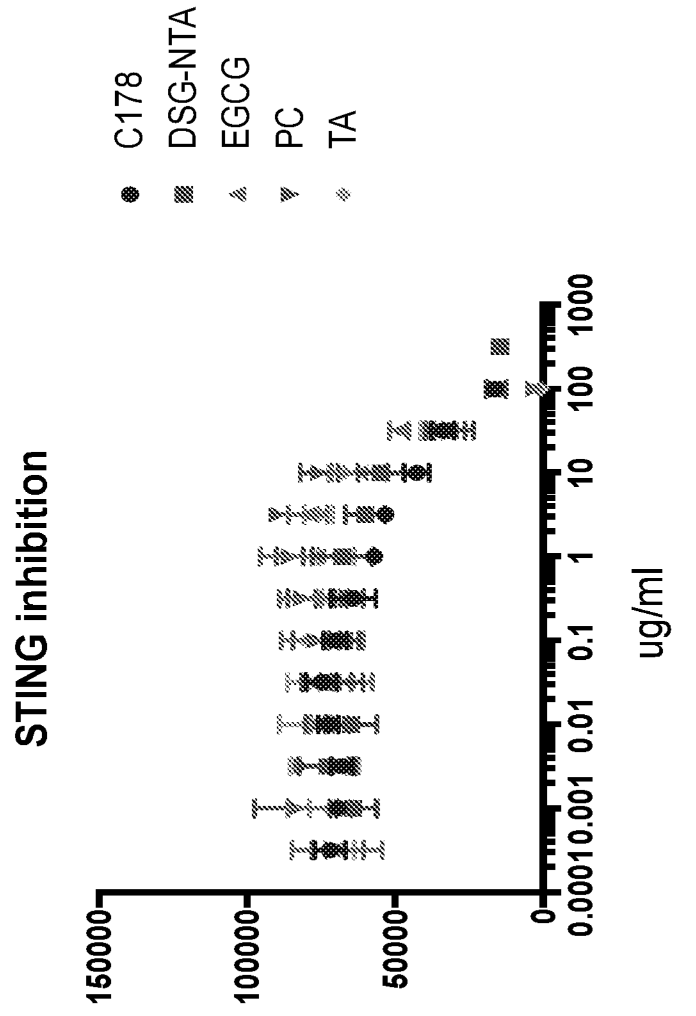
Figure 19:
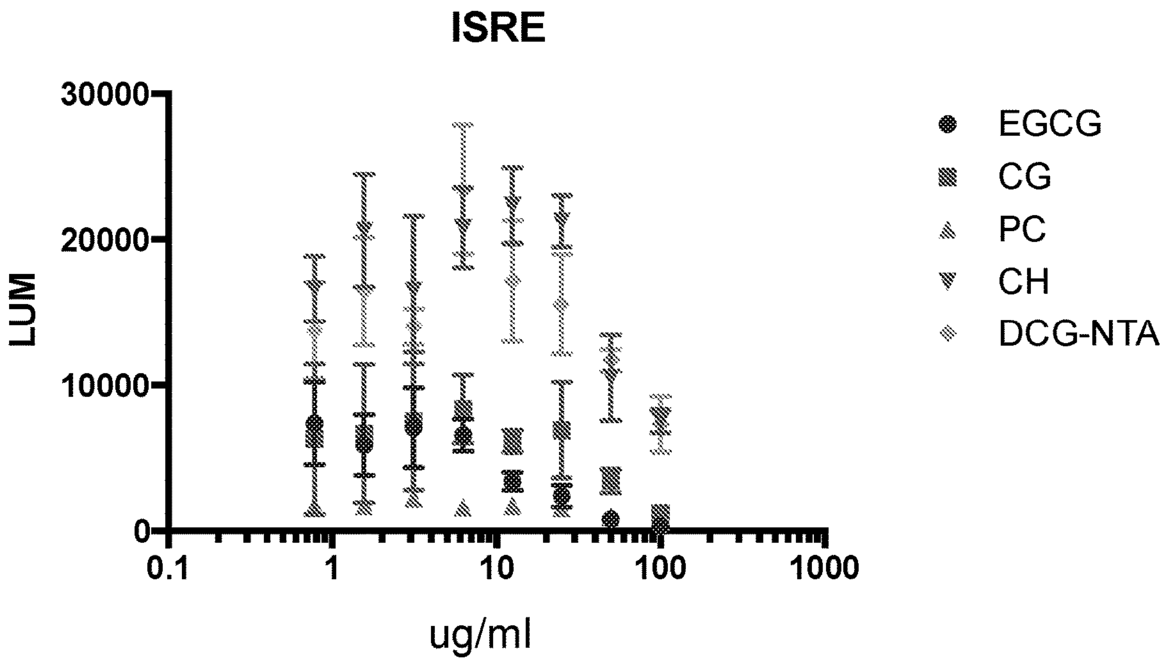
FIG. 19: Chelating metal ions to inhibit TLR3-Type I IFN pathway. Dose-inhibition curves of the IFN-I response by the indicated compounds in polyIC/lipofectamine 2000 (ThermoFisher) treated THP 1 dual-STING KO reporter cells (Invivogen).
Figure 20:
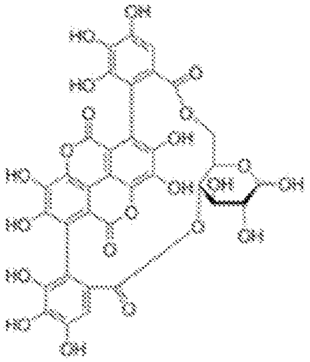
FIG. 20: Molecular structure of other representative potent polyphenol chelators.
Figure 20:
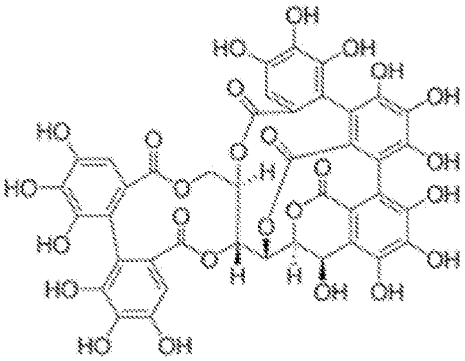
Figure 20:
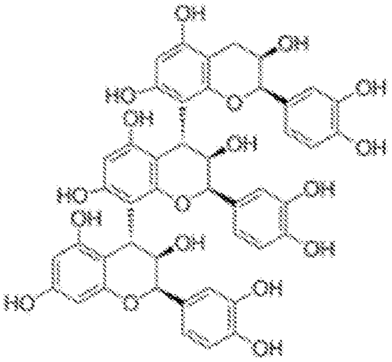
Figure 20:
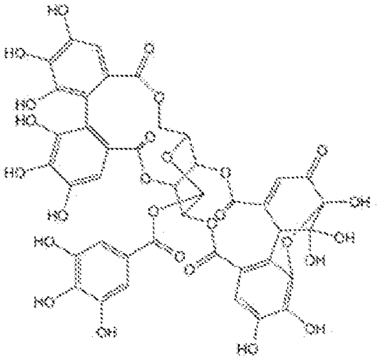
Figure 20:
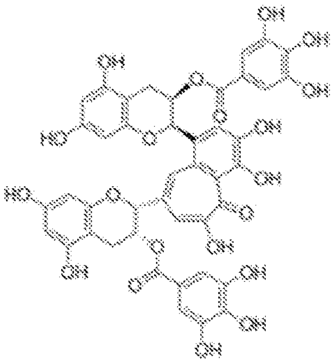

Given the interesting function of metal ions on modulating innate immune response in our finding, we further evaluated whether chelating metal ions could inhibit the according innate immune pathways, which may be used to treat autoimmune diseases, such as Systemic lupus erythematosus, Aicardi-Goutières syndrome, Acute pancreatitis Age-dependent macular degeneration, Alcoholic liver disease, Liver fibrosis, Metastasis, Myocardial infarction, Non-alcoholic steatohepatitis (NASH), Parkinson's disease, Polyarthritis/fetal and neonatal anemia, Sepsis, inflammatory bowel disease, multiple sclerosis, etc. By unbiased screening, we identify several chelators showing notable function to inhibit innate immune response (FIG. 18-19). As shown in FIG. 18*a-b*, with increase of the structure complexity, the chelators performed higher inhibition function. This is consistent with our hypothesis as the higher chelator structure complexity the better chelating ability they are supposed to have. Using a THP 1 dual-KI-$hSTING^{WT(R232)}$ reporter cell line, we co-incubated those chelators with DNA/lipofectamine complex challenging, which is supposed to have very high activity to activate cGAS-STING-Type I IFN pathway. By a ISRE induced luminescence, we could read the degree of inhibition. We found the IC50 of DNA-induced Type I IFN response for Punicalagin (PC) and tannin acid (TA) is as low as nanomolar level and they are well-tolerated in in-vitro assay (FIG. 18*b-d*). We also confirmed the inhibition effect in another human STING allele HAQ and similar results were gotten (FIG. 18*e*). To look into which step of the cGAS-STING-Type I IFN the chelators were affecting, we study whether they could inhibit cGAMP induced Type I IFN ((FIG. 18*f*). We found the inhibition effect were eliminated, which indicate these chelators may mainly work on cGAS inhibition. Note that the chelators we show here are mostly natural polyphenol. The polyphenols were widely reported to delete ROS and anti-inflammation. But few recognize their potent inhibition effect on DNA induced inflammation. By the same token, we also found these chelators could be used to inhibit poly IC-induced inflammation response in a STING-knockout THP1 reporter cell line (FIG. 19). We anticipate many other chelators, especially those in polyphenol structure (shown in FIG. 20), could be used as innate immune inhibitors for DNA and RNA induced inflammation.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A composition comprising a nanoparticle comprising one or more stimulator of interferon genes (STING) agonists and/or Toll-Like receptor (TLR) agonists, and one or more cations selected from the group consisting of $Zn^{2+}$, $Mn^{2+}$, $Fe^{2+}$, $Fe^{3+}$, $Cu^{2+}$, $Ni^{2+}$, $Co^{2+}$, $Pb^{2+}$, $Sn^{2+}$, $Ru^{2+}$, $Au^{2+}$, $Mg^{2+}$, $VO^{2+}$, $Al^{3+}$, $Co^{3+}$, $Cr^{3+}$, $Ga^{3+}$, $Tl^{3+}$, $Ln^{3+}$, $MoO^{3+}$, $Cu^{+}$, $Au^{+}$, $Tl^{+}$, $Ag^{+}$, $Hg^{2+}$, $Pt^{2+}$, $Pb^{2+}$, $Hg^{2+}$, $Cd^{2+}$, $Pd^{2+}$, $Pt^{4+}$, $Na^{+}$, and $K^{+}$, wherein the nanoparticle further comprises poly (histidine)-polyethylene glycol (PH-PEG) or lipid-poly-histidine.

2. The composition of claim 1, wherein the one or more STING agonists, is selected from the group consisting of cGAMP, cdiAMP, cdiGMP, cAIMP, 2'3'-cGAMP, 3'3'-cGAMP, c-di-AMP, c-di-GMP, cAIMP Difluor, cAIM(PS)2, Difluor (Rp/Sp), 2'2'-cGAMP, 2'3'-cGAM(PS)2 (Rp/Sp), 3'3'-cGAMP Fluorinated, c-di-AMP Fluorinated, 2'3'-c-di-AMP, 2'3'-c-di-AM(PS)2 (Rp,Rp), c-di-GMP Fluorinated, 2'3'-c-di-GMP, c-di-IMP,

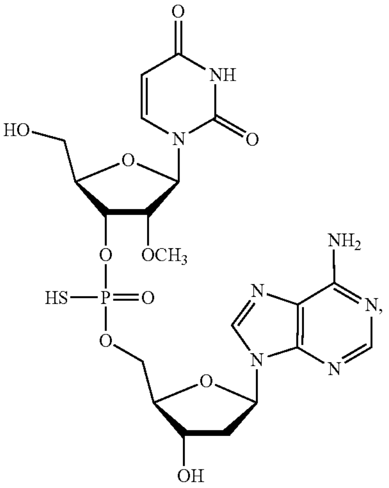

-continued

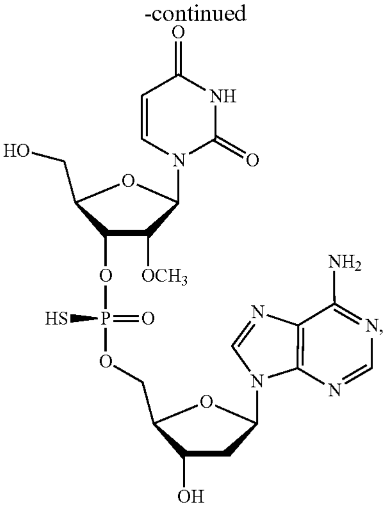

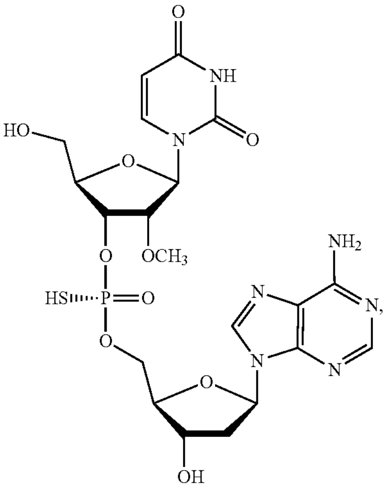

-continued

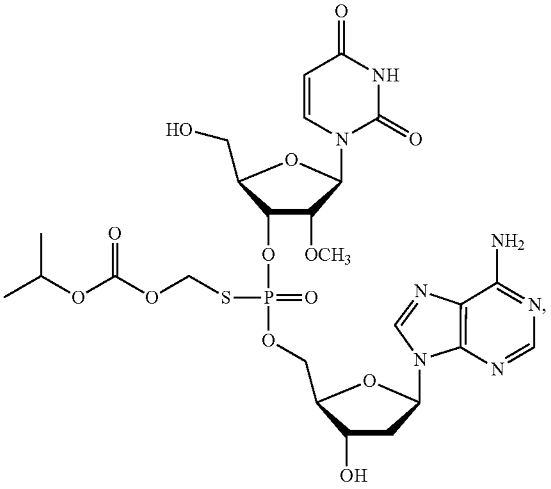

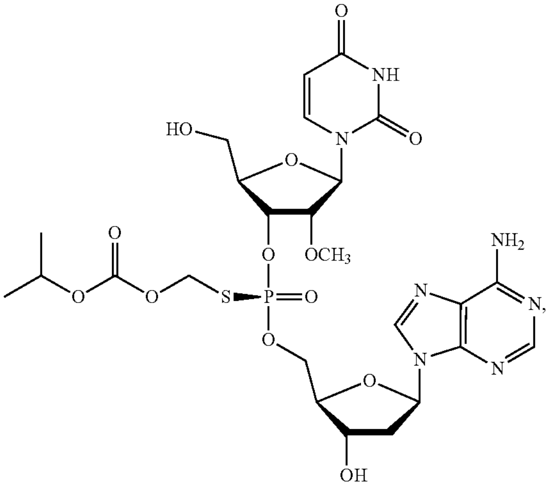

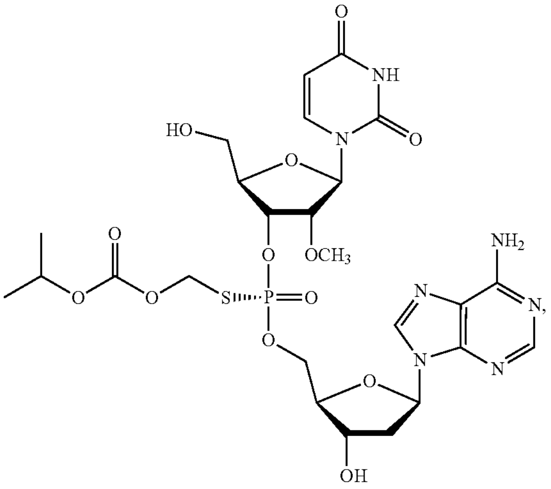

Gemcitabine

-continued ( 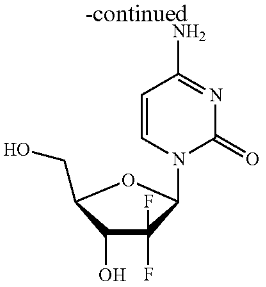 ),

STING-agonist-C11

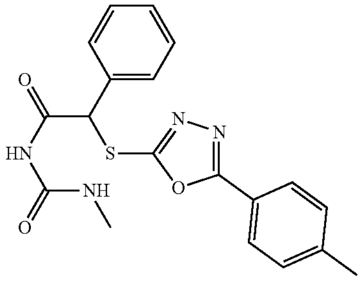

( $C_{19}H_{18}N_4O_3S$ Mol. Wt: 382.44 ),

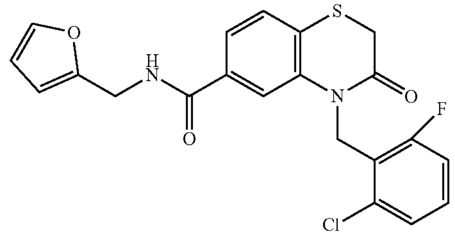

( STING agonist G10 ),

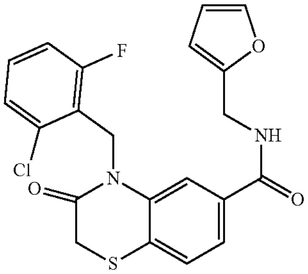

( $C_{21}H_{16}ClFN_2O_3S$ Mol. Wt: 430.88 ), eGAM(PS)2, 2'2'-cGAM(PS)2,2'3'-cGAM(PS)2, cGAMP Fluorinated, 2'3'-cGAMP Fluorinated, 2'2'-cGAMP Fluorinated, 2'3'-cdAMP, 2'2'-cdAMP, 3'3'-cdAMP, c-di-AM(PS) 2, 2'2'-c-di-AM(PS)2,3'3'-c-di-AM(PS)2, 2'3'-cdAMP Fluorinated, 2'2'-cdAMP Fluorinated, 3'3'-cdAMP Fluorinated, cdGMP, 2'3'-cdGMP, 2'2'-cdGMP, 3'3'-cdGMP, c-di-GM (PS)2,2'3'-c-di-GM(PS)2,2'2'-c-di-GM(PS)2,3'3'-c-di-GM (PS)2, cdGMP Fluorinated, 2'3'-cdGMP Fluorinated, 2'2'-cdGMP Fluorinated, 3'3'-cdGMP Fluorinated, 2'3'-cAIMP, 2'2'-cAIMP, 3'3'-cAIMP, cAIMP Difluor (3'3'-cAIMP Fluorinated, 2'3'-cAIMP Fluorinated, 2'2'-cAIMP Fluorinated, cAIM(PS)2 Difluor, 3'3'-cAIM(PS)2 Difluor (Rp/Sp), 2'3'-cAIM(PS)2 Difluor, 2'2'-cAIM(PS)2 Difluor, 2'3'-cdIMP, 2'2'-cdIMP, 3'3'-cdIMP, c-di-IM(PS)2,2'3'-c-di-IM(PS)2, 2'2'-c-di-IM(PS)2,3'3'-c-di-IM(PS)2, c-di-IMP Fluorinated, 2'3'-cdIMP Fluorinated, 2'2'-cdIMP Fluorinated, 3'3'-cdIMP Fluorinated, and amidobenzimidazole (ABZI)-based compounds;

wherein the one or more TLR agonists are selected from TLR-3 agonists, TLR-4 agonists, TLR-5 agonists, TLR-7 agonists, TLR-8 agonists, TLR-9 agonists.

3. The composition of claim 1, wherein the nanoparticle is encapsulated within a liposome.

4. The composition of claim 3, wherein the nanoparticle is further associated with an antigen, wherein associated is selected from complexed, conjugated, encapsulated, absorbed, adsorbed, and admixed;

wherein the antigen is derived from a self-antigen and/or is selected from the group consisting of alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomerase, Bage-1, Gage 3,4,5,6,7, GnTV, Herv-K-mel, Lage-1, Mage-A1,2,3,4, 6, 10,12, Mage-C2, NA-88, NY-Eso-1/Lage-2, SP17, SSX-2, and TRP2-Int2, MelanA, gp100, tyrosinase, TRP-1, TRP-2, MAGE-1, MAGE-3, BAGE, GAGE-1, GAGE-2, p15 (58), CEA, RAGE, NY-ESO, SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3, CA 195, CA 242, CA-50, CAM43, CD68\KP1, CO-029, FGF-5, G250, Ga733, human EGFR protein or its fragments, HTgp-175, M344, MA-50, MG7-Ag, MOV18, NB\70K, NY-CO-1, RCAS1, SDCCAG16, TA-90, TAAL6, TAG72, TLP, TPS, WT1 (and WT1-derived peptide sequences: WT1 126-134 (RMFP NAPYL (SEQ ID NO:376)), WT1 122-140 (SGQARMFPNAPYLPSCLES (SEQ ID NO:377)), and WT1 122-144 (SGQARMFPNAPYLPSCLESQPTI (SEQ ID NO:378)), MUC1, LMP2, EGFRVIII, Idiotype, GD2, Ras mutant, p53 mutant, Proteinase3, Survivin, hTERT, Sarcoma translocation breakpoints, EphA2, EphA4, LMW-PTP, PAP, ML-IAP, AFP, ERG, NA17, PAX3, ALK, Androgen receptor, Cyclin B1, Polysialic acid, MYCN, RhoC, TRP-2, GD3, Fucosyl GM1, Mesothelin, sLe, CYP1B1, PLAC1, GM3, BORIS, Tn, GloboH, NY-BR-1, RGS5, SART3, STn, Carbonic anhydrase IX, PAX5, OY-TES1, Sperm protein 17, LCK, HMWMAA, AKAP-4, XAGE 1, B7H3, Legumain, Tie 2, Page4, VEGFR2, MAD-CT-1, FAP, PDGFR-alpha, PDGFR-β, MAD-CT-2, Fos-related antigen 1, ERBB2, Folate receptor 1, IDH1, IDO, LY6K, fms-related tyro-sine kinase 1, KDR, PADRE, TA-CIN, SOX2, neoantigens, and aldehyde dehydrogenase.

5. The composition of claim 4, wherein the antigen is conjugated to the outer surface of the nanoparticle.

6. The composition of claim 1, wherein the nanoparticle is further associated with an adjuvant, wherein associated is selected from complexed, conjugated, encapsulated, absorbed, adsorbed, and admixed, wherein the adjuvant is selected from the group consisting of CPG, polyIC, poly-ICLC, 1018 ISS, aluminum salts, BCG, CP-870,893, CpG7909, CyaA, dSLIM, Cytokines, IC30, IC31, Imiquimod, IS Patch, ISS, MF59, monophosphoryl lipid A, OK-432, OM-174, OM-197-MP-EC, vector system, PLGA microparticles, imiquimod, resiquimod, gardiquimod, 3M-052, SRL172, Virosomes, YF-17D, VEGF trap, beta-glucan, Pam3Cys, vadimezan, AsA404, glucopyranosyl lipid adjuvant, GLA-SE, CD1d ligands, STING agonists, CL401, CL413, CL429, Flagellin, RC529, E6020, imidazoquinoline-based small molecule TLR-7/8a, AS01, AS02, AS03, AS04, AS15, IC31, CAF01, ISCOM, Cytokines, bacterial toxins, and any combination of adjuvant.

7. The composition of claim 3, wherein the average particle size of the nanoparticle is between 6 to 500 nm.

8. The composition of claim 1, wherein the nanoparticle comprises (i) one or more STING agonists and/or TLR agonists, (ii) $Zn^{2+}$, and (iii) PH-PEG or lipid-poly-histidine.

9. The composition of claim 8, wherein the nanoparticle comprises (i) c-di-AMP, $Zn^{2+}$, and PH-PEG or lipid-poly-histidine.

10. The composition of claim 9, wherein the nanoparticle comprises PH-PEG.

11. The composition of claim 9, wherein the nanoparticle comprises lipid-poly-histidine.

12. The composition of claim 11, wherein the lipid-poly-histidine comprises 11 histidine residues.

13. The composition of claim 11, wherein the lipid of the lipid-poly-histidine is dioleoylphosphatidylethanolamine (DOPE).

14. The composition of claim 1, wherein the nanoparticle comprises (i) one or more STING agonists and/or TLR agonists, (ii) $Mn^{2+}$, and (iii) PH-PEG or lipid-poly-histidine.

15. The composition of claim 14, wherein the nanoparticle comprises (i) c-di-AMP, (ii) $Mn^{2+}$, and (iii) PH-PEG or lipid-poly-histidine.

16. The composition of claim 15, wherein the nanoparticle comprises PH-PEG.

17. The composition of claim 15, wherein the nanoparticle comprises lipid-poly-histidine.

18. The composition of claim 17, wherein the lipid-poly-histidine comprises 11 histidine residues.

19. The composition of claim 17, wherein the lipid of the lipid-poly-histidine is dioleoylphosphatidylethanolamine.

* * * * *

SEQUENCE LISTING

```
<160> NUMBER OF SEQ ID NOS: 386

<210> SEQ ID NO 1
<211> LENGTH: 22
<212> TYPE: PRT
<213> ORGANISM: Artificial sequence
<220> FEATURE:
<223> OTHER INFORMATION: synthetic

<400> SEQUENCE: 1

Pro Val Leu Asp Leu Phe Arg Glu Leu Leu Asn Glu Leu Leu Glu Glx
1               5                   10                  15

Leu Lys Gln Lys Leu Lys
            20


<210> SEQ ID NO 2
<211> LENGTH: 23
<212> TYPE: PRT
<213> ORGANISM: Artificial sequence
<220> FEATURE:
<223> OTHER INFORMATION: synthetic

<400> SEQUENCE: 2

Gly Val Leu Asp Leu Phe Arg Glu Leu Leu Asn Glu Leu Leu Glu Ala
1               5                   10                  15

Leu Lys Gln Lys Leu Lys Lys
            20


<210> SEQ ID NO 3
<211> LENGTH: 22
<212> TYPE: PRT
<213> ORGANISM: Artificial sequence
<220> FEATURE:
<223> OTHER INFORMATION: synthetic

<400> SEQUENCE: 3

Pro Val Leu Asp Leu Phe Arg Glu Leu Leu Asn Glu Leu Leu Glu Trp
1               5                   10                  15

Leu Lys Gln Lys Leu Lys
            20


<210> SEQ ID NO 4
<211> LENGTH: 22
<212> TYPE: PRT
<213> ORGANISM: Artificial sequence
<220> FEATURE:
<223> OTHER INFORMATION: synthetic

<400> SEQUENCE: 4

Pro Val Leu Asp Leu Phe Arg Glu Leu Leu Asn Glu Leu Leu Glu Ala
1               5                   10                  15

Leu Lys Gln Lys Leu Lys
            20
```

<210> SEQ ID NO 5
<211> LENGTH: 23
<212> TYPE: PRT
<213> ORGANISM: Artificial sequence
<220> FEATURE:
<223> OTHER INFORMATION: synthetic

<400> SEQUENCE: 5

Pro Val Leu Asp Leu Phe Arg Glu Leu Leu Asn Glu Leu Leu Glu Ala
1 5 10 15

Leu Lys Gln Lys Leu Lys Lys
20

<210> SEQ ID NO 6
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: Xaa = Hydroxyproline

<400> SEQUENCE: 6

Pro Val Leu Asp Leu Phe Arg Glu Leu Leu Asn Glu Xaa Leu Glu Ala
1 5 10 15

Leu Lys Gln Lys Leu Lys
20

<210> SEQ ID NO 7
<211> LENGTH: 22
<212> TYPE: PRT
<213> ORGANISM: Artificial sequence
<220> FEATURE:
<223> OTHER INFORMATION: synthetic

<400> SEQUENCE: 7

Pro Val Leu Asp Leu Phe Lys Glu Leu Leu Asn Glu Leu Leu Glu Ala
1 5 10 15

Leu Lys Gln Lys Leu Lys
20

<210> SEQ ID NO 8
<211> LENGTH: 22
<212> TYPE: PRT
<213> ORGANISM: Artificial sequence
<220> FEATURE:
<223> OTHER INFORMATION: synthetic

<400> SEQUENCE: 8

Pro Val Leu Asp Leu Phe Arg Glu Leu Leu Asn Glu Gly Leu Glu Ala
1 5 10 15

Leu Lys Gln Lys Leu Lys
20

<210> SEQ ID NO 9
<211> LENGTH: 22
<212> TYPE: PRT
<213> ORGANISM: Artificial sequence
<220> FEATURE:
<223> OTHER INFORMATION: synthetic

<400> SEQUENCE: 9

-continued

Pro Val Leu Asp Leu Phe Arg Glu Leu Gly Asn Glu Leu Leu Glu Ala
1 5 10 15

Leu Lys Gln Lys Leu Lys
20

<210> SEQ ID NO 10
<211> LENGTH: 22
<212> TYPE: PRT
<213> ORGANISM: Artificial sequence
<220> FEATURE:
<223> OTHER INFORMATION: synthetic

<400> SEQUENCE: 10

Pro Val Leu Asp Leu Phe Arg Glu Leu Leu Asn Glu Leu Leu Glu Ala
1 5 10 15

Glx Lys Gln Lys Leu Lys
20

<210> SEQ ID NO 11
<211> LENGTH: 22
<212> TYPE: PRT
<213> ORGANISM: Artificial sequence
<220> FEATURE:
<223> OTHER INFORMATION: synthetic

<400> SEQUENCE: 11

Pro Val Leu Asp Leu Phe Lys Glu Leu Leu Gln Glu Leu Leu Glu Ala
1 5 10 15

Leu Lys Gln Lys Leu Lys
20

<210> SEQ ID NO 12
<211> LENGTH: 22
<212> TYPE: PRT
<213> ORGANISM: Artificial sequence
<220> FEATURE:
<223> OTHER INFORMATION: synthetic

<400> SEQUENCE: 12

Pro Val Leu Asp Leu Phe Arg Glu Leu Leu Asn Glu Leu Leu Glu Ala
1 5 10 15

Gly Lys Gln Lys Leu Lys
20

<210> SEQ ID NO 13
<211> LENGTH: 22
<212> TYPE: PRT
<213> ORGANISM: Artificial sequence
<220> FEATURE:
<223> OTHER INFORMATION: synthetic

<400> SEQUENCE: 13

Gly Val Leu Asp Leu Phe Arg Glu Leu Leu Asn Glu Gly Leu Glu Ala
1 5 10 15

Leu Lys Gln Lys Leu Lys
20

<210> SEQ ID NO 14
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature

```
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 14

Pro Val Leu Asp Leu Phe Arg Glu Leu Leu Asn Glu Leu Leu Glu Ala
1               5                   10                  15

Leu Xaa Gln Xaa Leu Xaa
            20


<210> SEQ ID NO 15
<211> LENGTH: 22
<212> TYPE: PRT
<213> ORGANISM: Artificial sequence
<220> FEATURE:
<223> OTHER INFORMATION: synthetic

<400> SEQUENCE: 15

Pro Val Leu Asp Leu Phe Arg Glu Leu Trp Asn Glu Leu Leu Glu Ala
1               5                   10                  15

Leu Lys Gln Lys Leu Lys
            20


<210> SEQ ID NO 16
<211> LENGTH: 22
<212> TYPE: PRT
<213> ORGANISM: Artificial sequence
<220> FEATURE:
<223> OTHER INFORMATION: synthetic

<400> SEQUENCE: 16

Pro Val Leu Asp Leu Leu Arg Glu Leu Leu Asn Glu Leu Leu Glu Ala
1               5                   10                  15

Leu Lys Gln Lys Leu Lys
            20


<210> SEQ ID NO 17
<211> LENGTH: 22
<212> TYPE: PRT
<213> ORGANISM: Artificial sequence
<220> FEATURE:
<223> OTHER INFORMATION: synthetic

<400> SEQUENCE: 17

Pro Val Leu Glu Leu Phe Lys Glu Leu Leu Gln Glu Leu Leu Glu Ala
1               5                   10                  15

Leu Lys Gln Lys Leu Lys
            20


<210> SEQ ID NO 18
<211> LENGTH: 22
<212> TYPE: PRT
<213> ORGANISM: Artificial sequence
<220> FEATURE:
<223> OTHER INFORMATION: synthetic

<400> SEQUENCE: 18
```

-continued

```
Gly Val Leu Asp Leu Phe Arg Glu Leu Leu Asn Glu Leu Leu Glu Ala
1               5                   10                  15

Leu Lys Gln Lys Leu Lys
            20


<210> SEQ ID NO 19
<211> LENGTH: 22
<212> TYPE: PRT
<213> ORGANISM: Artificial sequence
<220> FEATURE:
<223> OTHER INFORMATION: synthetic

<400> SEQUENCE: 19

Pro Val Leu Asp Leu Phe Arg Glu Leu Leu Asn Glu Gly Leu Glu Ala
1               5                   10                  15

Leu Lys Gln Lys Leu Lys
            20


<210> SEQ ID NO 20
<211> LENGTH: 22
<212> TYPE: PRT
<213> ORGANISM: Artificial sequence
<220> FEATURE:
<223> OTHER INFORMATION: synthetic

<400> SEQUENCE: 20

Pro Val Leu Asp Leu Phe Arg Glu Gly Leu Asn Glu Leu Leu Glu Ala
1               5                   10                  15

Leu Lys Gln Lys Leu Lys
            20


<210> SEQ ID NO 21
<211> LENGTH: 22
<212> TYPE: PRT
<213> ORGANISM: Artificial sequence
<220> FEATURE:
<223> OTHER INFORMATION: synthetic

<400> SEQUENCE: 21

Pro Val Leu Asp Leu Phe Arg Glu Leu Leu Asn Glu Leu Leu Glu Ala
1               5                   10                  15

Leu Lys Gln Lys Leu Lys
            20


<210> SEQ ID NO 22
<211> LENGTH: 22
<212> TYPE: PRT
<213> ORGANISM: Artificial sequence
<220> FEATURE:
<223> OTHER INFORMATION: synthetic

<400> SEQUENCE: 22

Pro Val Leu Asp Leu Phe Arg Glu Leu Leu Asn Glu Leu Leu Glu Gly
1               5                   10                  15

Leu Lys Gln Lys Leu Lys
            20


<210> SEQ ID NO 23
<211> LENGTH: 22
<212> TYPE: PRT
<213> ORGANISM: Artificial sequence
<220> FEATURE:
<223> OTHER INFORMATION: synthetic
```

<400> SEQUENCE: 23

Pro Leu Leu Glu Leu Phe Lys Glu Leu Leu Gln Glu Leu Leu Glu Ala
1               5                   10                  15

Leu Lys Gln Lys Leu Lys
            20

<210> SEQ ID NO 24
<211> LENGTH: 22
<212> TYPE: PRT
<213> ORGANISM: Artificial sequence
<220> FEATURE:
<223> OTHER INFORMATION: synthetic

<400> SEQUENCE: 24

Pro Val Leu Asp Leu Phe Arg Glu Leu Leu Asn Glu Leu Leu Glu Ala
1               5                   10                  15

Leu Gln Lys Lys Leu Lys
            20

<210> SEQ ID NO 25
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 25

Pro Val Leu Asp Phe Phe Arg Glu Leu Leu Asn Glu Xaa Leu Glu Ala
1               5                   10                  15

Leu Lys Gln Lys Leu Lys
            20

<210> SEQ ID NO 26
<211> LENGTH: 22
<212> TYPE: PRT
<213> ORGANISM: Artificial sequence
<220> FEATURE:
<223> OTHER INFORMATION: synthetic

<400> SEQUENCE: 26

Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 27
<211> LENGTH: 22
<212> TYPE: PRT
<213> ORGANISM: Artificial sequence
<220> FEATURE:
<223> OTHER INFORMATION: synthetic

<400> SEQUENCE: 27

Pro Val Leu Asp Leu Phe Arg Glu Leu Leu Asn Glu Leu Glx Glu Ala
1               5                   10                  15

Leu Lys Gln Lys Leu Lys
            20

<210> SEQ ID NO 28
<211> LENGTH: 22
<212> TYPE: PRT
<213> ORGANISM: Artificial sequence
<220> FEATURE:
<223> OTHER INFORMATION: synthetic

<400> SEQUENCE: 28

Pro Val Leu Asp Leu Phe Arg Glu Leu Leu Asn Glu Leu Trp Glu Ala
1 5 10 15

Leu Lys Gln Lys Leu Lys
20

<210> SEQ ID NO 29
<211> LENGTH: 22
<212> TYPE: PRT
<213> ORGANISM: Artificial sequence
<220> FEATURE:
<223> OTHER INFORMATION: synthetic

<400> SEQUENCE: 29

Ala Val Leu Asp Leu Phe Arg Glu Leu Leu Asn Glu Leu Leu Glu Ala
1 5 10 15

Leu Lys Gln Lys Leu Lys
20

<210> SEQ ID NO 30
<211> LENGTH: 22
<212> TYPE: PRT
<213> ORGANISM: Artificial sequence
<220> FEATURE:
<223> OTHER INFORMATION: synthetic

<400> SEQUENCE: 30

Pro Val Leu Asp Leu Pro Arg Glu Leu Leu Asn Glu Leu Leu Glu Ala
1 5 10 15

Leu Lys Gln Lys Leu Lys
20

<210> SEQ ID NO 31
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 31

Pro Val Leu Asp Leu Phe Leu Glu Leu Leu Asn Glu Xaa Leu Glu Ala
1 5 10 15

Leu Lys Gln Lys Leu Lys
20

<210> SEQ ID NO 32
<211> LENGTH: 22
<212> TYPE: PRT
<213> ORGANISM: Artificial sequence
<220> FEATURE:
<223> OTHER INFORMATION: synthetic
<220> FEATURE:

<221> NAME/KEY: misc_feature
<223> OTHER INFORMATION: Xaa can be any naturally occurring amino acid
<220> FEATURE:
<221> NAME/KEY: misc_feature
<222> LOCATION: (1)..(1)
<223> OTHER INFORMATION: Xaa can be any naturally occurring amino acid

<400> SEQUENCE: 32

Xaa Val Leu Asp Leu Phe Arg Glu Leu Leu Asn Glu Leu Leu Glu Ala
1 5 10 15

Leu Lys Gln Lys Leu Lys
20

<210> SEQ ID NO 33
<211> LENGTH: 22
<212> TYPE: PRT
<213> ORGANISM: Artificial sequence
<220> FEATURE:
<223> OTHER INFORMATION: synthetic

<400> SEQUENCE: 33

Pro Val Leu Asp Leu Phe Arg Glu Lys Leu Asn Glu Leu Leu Glu Ala
1 5 10 15

Leu Lys Gln Lys Leu Lys
20

<210> SEQ ID NO 34
<211> LENGTH: 22
<212> TYPE: PRT
<213> ORGANISM: Artificial sequence
<220> FEATURE:
<223> OTHER INFORMATION: synthetic

<400> SEQUENCE: 34

Pro Val Leu Asp Glx Phe Arg Glu Leu Leu Asn Glu Leu Leu Glu Ala
1 5 10 15

Leu Lys Gln Lys Leu Lys
20

<210> SEQ ID NO 35
<211> LENGTH: 22
<212> TYPE: PRT
<213> ORGANISM: Artificial sequence
<220> FEATURE:
<223> OTHER INFORMATION: synthetic

<400> SEQUENCE: 35

Pro Val Leu Asp Trp Phe Arg Glu Leu Leu Asn Glu Leu Leu Glu Ala
1 5 10 15

Leu Lys Gln Lys Leu Lys
20

<210> SEQ ID NO 36
<211> LENGTH: 22
<212> TYPE: PRT
<213> ORGANISM: Artificial sequence
<220> FEATURE:
<223> OTHER INFORMATION: synthetic

<400> SEQUENCE: 36

Pro Leu Leu Glu Leu Leu Lys Glu Leu Leu Gln Glu Leu Leu Glu Ala
1 5 10 15

Leu Lys Gln Lys Leu Lys
20

-continued

```
<210> SEQ ID NO 37
<211> LENGTH: 22
<212> TYPE: PRT
<213> ORGANISM: Artificial sequence
<220> FEATURE:
<223> OTHER INFORMATION: synthetic

<400> SEQUENCE: 37

Pro Val Leu Asp Leu Phe Arg Glu Trp Leu Asn Glu Leu Leu Glu Ala
1               5                   10                  15

Leu Lys Gln Lys Leu Lys
            20


<210> SEQ ID NO 38
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 38

Pro Val Leu Asp Leu Phe Arg Glu Leu Leu Asn Glu Xaa Leu Glu Ala
1               5                   10                  15

Trp Lys Gln Lys Leu Lys
            20


<210> SEQ ID NO 39
<211> LENGTH: 22
<212> TYPE: PRT
<213> ORGANISM: Artificial sequence
<220> FEATURE:
<223> OTHER INFORMATION: synthetic

<400> SEQUENCE: 39

Pro Val Leu Asp Leu Phe Arg Glu Leu Leu Glu Glu Leu Leu Lys Ala
1               5                   10                  15

Leu Lys Lys Lys Leu Lys
            20


<210> SEQ ID NO 40
<211> LENGTH: 22
<212> TYPE: PRT
<213> ORGANISM: Artificial sequence
<220> FEATURE:
<223> OTHER INFORMATION: synthetic

<400> SEQUENCE: 40

Pro Val Leu Asp Leu Phe Asn Glu Leu Leu Arg Glu Leu Leu Glu Ala
1               5                   10                  15

Leu Gln Lys Lys Leu Lys
            20


<210> SEQ ID NO 41
<211> LENGTH: 22
<212> TYPE: PRT
<213> ORGANISM: Artificial sequence
<220> FEATURE:
<223> OTHER INFORMATION: synthetic
<220> FEATURE:
```

<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 41

Pro Val Leu Asp Leu Trp Arg Glu Leu Leu Asn Glu Xaa Leu Glu Ala
1               5                   10                  15

Leu Lys Gln Lys Leu Lys
            20

<210> SEQ ID NO 42
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 42

Pro Val Leu Asp Glu Phe Arg Glu Lys Leu Asn Glu Xaa Trp Glu Ala
1               5                   10                  15

Leu Lys Gln Lys Leu Lys
            20

<210> SEQ ID NO 43
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 43

Pro Val Leu Asp Glu Phe Arg Glu Lys Leu Trp Glu Xaa Leu Glu Ala
1               5                   10                  15

Leu Lys Gln Lys Leu Lys
            20

<210> SEQ ID NO 44
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 44

Pro Val Leu Asp Glu Phe Arg Glu Lys Leu Asn Glu Xaa Leu Glu Ala

-continued 1 5 10 15

Leu Lys Gln Lys Leu Lys
20

<210> SEQ ID NO 45
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 45

Pro Val Leu Asp Glu Phe Arg Glu Lys Leu Asn Glu Xaa Leu Glu Ala
1 5 10 15

Leu Lys Gln Lys Leu Lys
20

<210> SEQ ID NO 46
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 46

Pro Val Leu Asp Leu Phe Arg Glu Lys Leu Asn Glu Xaa Leu Glu Ala
1 5 10 15

Leu Lys Gln Lys Leu Lys
20

<210> SEQ ID NO 47
<211> LENGTH: 21
<212> TYPE: PRT
<213> ORGANISM: Artificial sequence
<220> FEATURE:
<223> OTHER INFORMATION: synthetic

<400> SEQUENCE: 47

Val Leu Asp Leu Phe Arg Glu Leu Leu Asn Glu Gly Leu Glu Ala Leu
1 5 10 15

Lys Gln Lys Leu Lys
20

<210> SEQ ID NO 48
<211> LENGTH: 22
<212> TYPE: PRT
<213> ORGANISM: Artificial sequence
<220> FEATURE:
<223> OTHER INFORMATION: synthetic

<400> SEQUENCE: 48

Pro Val Leu Asp Leu Phe Arg Glu Leu Leu Asn Glu Leu Leu Glu Ala
1 5 10 15

Leu Lys Gln Lys Leu Lys
20

<210> SEQ ID NO 49
<211> LENGTH: 22
<212> TYPE: PRT
<213> ORGANISM: Artificial sequence
<220> FEATURE:
<223> OTHER INFORMATION: synthetic

<400> SEQUENCE: 49

Pro Val Leu Asp Leu Phe Arg Asn Leu Leu Glu Lys Leu Leu Glu Ala
1 5 10 15

Leu Glu Gln Lys Leu Lys
20

<210> SEQ ID NO 50
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 50

Pro Val Leu Asp Leu Phe Arg Glu Leu Leu Trp Glu Xaa Leu Glu Ala
1 5 10 15

Leu Lys Gln Lys Leu Lys
20

<210> SEQ ID NO 51
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 51

Pro Val Leu Asp Leu Phe Trp Glu Leu Leu Asn Glu Xaa Leu Glu Ala
1 5 10 15

Leu Lys Gln Lys Leu Lys
20

<210> SEQ ID NO 52
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)

<223> OTHER INFORMATION: Xaa can be any naturally occurring amino acid

<400> SEQUENCE: 52

Pro Val Trp Asp Glu Phe Arg Glu Lys Leu Asn Glu Xaa Leu Glu Ala
1 5 10 15

Leu Lys Gln Lys Leu Lys
20

<210> SEQ ID NO 53
<211> LENGTH: 22
<212> TYPE: PRT
<213> ORGANISM: Artificial sequence
<220> FEATURE:
<223> OTHER INFORMATION: synthetic

<400> SEQUENCE: 53

Val Val Leu Asp Leu Phe Arg Glu Leu Leu Asn Glu Leu Leu Glu Ala
1 5 10 15

Leu Lys Gln Lys Leu Lys
20

<210> SEQ ID NO 54
<211> LENGTH: 22
<212> TYPE: PRT
<213> ORGANISM: Artificial sequence
<220> FEATURE:
<223> OTHER INFORMATION: synthetic

<400> SEQUENCE: 54

Pro Val Leu Asp Leu Phe Arg Glu Leu Leu Asn Glu Trp Leu Glu Ala
1 5 10 15

Leu Lys Gln Lys Leu Lys
20

<210> SEQ ID NO 55
<211> LENGTH: 19
<212> TYPE: PRT
<213> ORGANISM: Artificial sequence
<220> FEATURE:
<223> OTHER INFORMATION: synthetic

<400> SEQUENCE: 55

Pro Leu Phe Arg Glu Leu Leu Asn Glu Leu Leu Glu Ala Leu Lys Gln
1 5 10 15

Lys Leu Lys

<210> SEQ ID NO 56
<211> LENGTH: 22
<212> TYPE: PRT
<213> ORGANISM: Artificial sequence
<220> FEATURE:
<223> OTHER INFORMATION: synthetic

<400> SEQUENCE: 56

Pro Val Leu Asp Leu Phe Arg Glu Leu Leu Asn Glu Leu Leu Glu Ala
1 5 10 15

Leu Lys Gln Lys Lys Lys
20

<210> SEQ ID NO 57
<211> LENGTH: 22
<212> TYPE: PRT
<213> ORGANISM: Artificial sequence
<220> FEATURE:

-continued

<223> OTHER INFORMATION: synthetic

<400> SEQUENCE: 57

Pro Val Leu Asp Leu Phe Arg Asn Leu Leu Glu Glu Leu Leu Lys Ala
1 5 10 15

Leu Glu Gln Lys Leu Lys
20

<210> SEQ ID NO 58
<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 58

Pro Val Leu Asp Glu Phe Arg Glu Lys Leu Asn Glu Xaa Leu Glu Ala
1 5 10 15

Leu Lys Gln Lys Leu
20

<210> SEQ ID NO 59
<211> LENGTH: 22
<212> TYPE: PRT
<213> ORGANISM: Artificial sequence
<220> FEATURE:
<223> OTHER INFORMATION: synthetic

<400> SEQUENCE: 59

Leu Val Leu Asp Leu Phe Arg Glu Leu Leu Asn Glu Leu Leu Glu Ala
1 5 10 15

Leu Lys Gln Lys Leu Lys
20

<210> SEQ ID NO 60
<211> LENGTH: 19
<212> TYPE: PRT
<213> ORGANISM: Artificial sequence
<220> FEATURE:
<223> OTHER INFORMATION: synthetic

<400> SEQUENCE: 60

Pro Val Leu Asp Leu Phe Arg Glu Leu Leu Asn Glu Leu Leu Glu Ala
1 5 10 15

Leu Lys Gln

<210> SEQ ID NO 61
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 61

Pro Val Leu Asp Glu Phe Arg Trp Lys Leu Asn Glu Xaa Leu Glu Ala
1               5                   10                  15

Leu Lys Gln Lys Leu Lys
            20

<210> SEQ ID NO 62
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 62

Pro Val Leu Asp Glu Trp Arg Glu Lys Leu Asn Glu Xaa Leu Glu Ala
1               5                   10                  15

Leu Lys Gln Lys Leu Lys
            20

<210> SEQ ID NO 63
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 63

Pro Val Leu Asp Phe Phe Arg Glu Lys Leu Asn Glu Xaa Leu Glu Ala
1               5                   10                  15

Leu Lys Gln Lys Leu Lys
            20

<210> SEQ ID NO 64
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 64

Pro Trp Leu Asp Glu Phe Arg Glu Lys Leu Asn Glu Xaa Leu Glu Ala
1               5                   10                  15

Leu Lys Gln Lys Leu Lys
            20

<210> SEQ ID NO 65

<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 65

Val Leu Asp Glu Phe Arg Glu Lys Leu Asn Glu Xaa Leu Glu Ala Leu
1 5 10 15

Lys Gln Lys Leu Lys
20

<210> SEQ ID NO 66
<211> LENGTH: 22
<212> TYPE: PRT
<213> ORGANISM: Artificial sequence
<220> FEATURE:
<223> OTHER INFORMATION: synthetic

<400> SEQUENCE: 66

Pro Val Leu Asp Leu Phe Arg Asn Leu Leu Glu Glu Leu Leu Glu Ala
1 5 10 15

Leu Gln Lys Lys Leu Lys
20

<210> SEQ ID NO 67
<211> LENGTH: 21
<212> TYPE: PRT
<213> ORGANISM: Artificial sequence
<220> FEATURE:
<223> OTHER INFORMATION: synthetic

<400> SEQUENCE: 67

Val Leu Asp Leu Phe Arg Glu Leu Leu Asn Glu Leu Leu Glu Ala Leu
1 5 10 15

Lys Gln Lys Leu Lys
20

<210> SEQ ID NO 68
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 68

Pro Val Leu Asp Glu Phe Arg Glu Leu Leu Lys Glu Xaa Leu Glu Ala
1 5 10 15

Leu Lys Gln Lys Leu Lys
20

<210> SEQ ID NO 69
<211> LENGTH: 22

<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 69

```
Pro Val Leu Asp Glu Phe Arg Lys Lys Leu Asn Glu Xaa Leu Glu Ala
1               5                   10                  15

Leu Lys Gln Lys Leu Lys
            20
```

<210> SEQ ID NO 70
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 70

```
Pro Val Leu Asp Glu Phe Arg Glu Leu Leu Tyr Glu Xaa Leu Glu Ala
1               5                   10                  15

Leu Lys Gln Lys Leu Lys
            20
```

<210> SEQ ID NO 71
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 71

```
Pro Val Leu Asp Glu Phe Arg Glu Lys Leu Asn Glu Leu Xaa Glu Ala
1               5                   10                  15

Leu Lys Gln Lys Leu Lys
            20
```

<210> SEQ ID NO 72
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)

-continued

```
<223> OTHER INFORMATION: Xaa can be any naturally occurring amino acid

<400> SEQUENCE: 72

Pro Val Leu Asp Leu Phe Arg Glu Leu Leu Asn Glu Xaa Leu Trp Ala
1               5                   10                  15

Leu Lys Gln Lys Leu Lys
            20


<210> SEQ ID NO 73
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 73

Pro Val Leu Asp Glu Phe Trp Glu Lys Leu Asn Glu Xaa Leu Glu Ala
1               5                   10                  15

Leu Lys Gln Lys Leu Lys
            20


<210> SEQ ID NO 74
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 74

Pro Val Leu Asp Lys Phe Arg Glu Lys Leu Asn Glu Xaa Leu Glu Ala
1               5                   10                  15

Leu Lys Gln Lys Leu Lys
            20


<210> SEQ ID NO 75
<211> LENGTH: 22
<212> TYPE: PRT
<213> ORGANISM: Artificial sequence
<220> FEATURE:
<223> OTHER INFORMATION: synthetic

<400> SEQUENCE: 75

Pro Val Leu Asp Glu Phe Arg Glu Lys Leu Asn Glu Glu Leu Glu Ala
1               5                   10                  15

Leu Lys Gln Lys Leu Lys
            20


<210> SEQ ID NO 76
<211> LENGTH: 22
<212> TYPE: PRT
<213> ORGANISM: Artificial sequence
<220> FEATURE:
<223> OTHER INFORMATION: synthetic
```

<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 76

Pro Val Leu Asp Glu Phe Arg Glu Leu Leu Phe Glu Xaa Leu Glu Ala
1 5 10 15

Leu Lys Gln Lys Leu Lys
20

<210> SEQ ID NO 77
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 77

Pro Val Leu Asp Glu Phe Arg Glu Lys Leu Asn Lys Xaa Leu Glu Ala
1 5 10 15

Leu Lys Gln Lys Leu Lys
20

<210> SEQ ID NO 78
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 78

Pro Val Leu Asp Glu Phe Arg Asp Lys Leu Asn Glu Xaa Leu Glu Ala
1 5 10 15

Leu Lys Gln Lys Leu Lys
20

<210> SEQ ID NO 79
<211> LENGTH: 22
<212> TYPE: PRT
<213> ORGANISM: Artificial sequence
<220> FEATURE:
<223> OTHER INFORMATION: synthetic

<400> SEQUENCE: 79

Pro Val Leu Asp Glu Phe Arg Glu Leu Leu Asn Glu Leu Leu Glu Ala
1 5 10 15

Leu Lys Gln Lys Leu Lys
20

<210> SEQ ID NO 80
<211> LENGTH: 22
<212> TYPE: PRT
<213> ORGANISM: Artificial sequence
<220> FEATURE:
<223> OTHER INFORMATION: synthetic

<400> SEQUENCE: 80

Pro Val Leu Asp Leu Phe Glu Arg Leu Leu Asn Glu Leu Leu Glu Ala
1 5 10 15

Leu Gln Lys Lys Leu Lys
20

<210> SEQ ID NO 81
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 81

Pro Val Leu Asp Glu Phe Arg Glu Lys Leu Asn Trp Xaa Leu Glu Ala
1 5 10 15

Leu Lys Gln Lys Leu Lys
20

<210> SEQ ID NO 82
<211> LENGTH: 20
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 82

Leu Asp Glu Phe Arg Glu Lys Leu Asn Glu Xaa Leu Glu Ala Leu Lys
1 5 10 15

Gln Lys Leu Lys
20

<210> SEQ ID NO 83
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 83

Pro Val Leu Asp Glu Phe Arg Glu Lys Leu Asn Glu Xaa Leu Glu Ala 1 5 10 15

Leu Trp Gln Lys Leu Lys
20

<210> SEQ ID NO 84
<211> LENGTH: 22
<212> TYPE: PRT
<213> ORGANISM: Artificial sequence
<220> FEATURE:
<223> OTHER INFORMATION: synthetic

<400> SEQUENCE: 84

Pro Val Leu Asp Glu Phe Arg Glu Lys Leu Asn Glu Leu Leu Glu Ala
1 5 10 15

Leu Lys Gln Lys Leu Lys
20

<210> SEQ ID NO 85
<211> LENGTH: 21
<212> TYPE: PRT
<213> ORGANISM: Artificial sequence
<220> FEATURE:
<223> OTHER INFORMATION: synthetic

<400> SEQUENCE: 85

Pro Leu Asp Leu Phe Arg Glu Leu Leu Asn Glu Leu Leu Glu Ala Leu
1 5 10 15

Lys Gln Lys Leu Lys
20

<210> SEQ ID NO 86
<211> LENGTH: 22
<212> TYPE: PRT
<213> ORGANISM: Artificial sequence
<220> FEATURE:
<223> OTHER INFORMATION: synthetic

<400> SEQUENCE: 86

Pro Val Leu Glu Leu Phe Glu Arg Leu Leu Asp Glu Leu Leu Asn Ala
1 5 10 15

Leu Gln Lys Lys Leu Lys
20

<210> SEQ ID NO 87
<211> LENGTH: 22
<212> TYPE: PRT
<213> ORGANISM: Artificial sequence
<220> FEATURE:
<223> OTHER INFORMATION: synthetic

<400> SEQUENCE: 87

Pro Leu Leu Glu Leu Leu Lys Glu Leu Leu Gln Glu Leu Leu Glu Ala
1 5 10 15

Leu Lys Gln Lys Leu Lys
20

<210> SEQ ID NO 88
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid -continued
<220> FEATURE:
<221> NAME/KEY: misc_feature
<222> LOCATION: (13)..(13)
<223> OTHER INFORMATION: Xaa can be any naturally occurring amino acid

<400> SEQUENCE: 88

Pro Val Leu Asp Lys Phe Arg Glu Leu Leu Asn Glu Xaa Leu Glu Ala
1               5                   10                  15

Leu Lys Gln Lys Leu Lys
            20

<210> SEQ ID NO 89
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 89

Pro Val Leu Asp Glu Phe Arg Glu Lys Leu Asn Glu Xaa Leu Trp Ala
1               5                   10                  15

Leu Lys Gln Lys Leu Lys
            20

<210> SEQ ID NO 90
<211> LENGTH: 19
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 90

Asp Glu Phe Arg Glu Lys Leu Asn Glu Xaa Leu Glu Ala Leu Lys Gln
1               5                   10                  15

Lys Leu Lys

<210> SEQ ID NO 91
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 91

Pro Val Leu Asp Glu Phe Arg Glu Leu Leu Asn Glu Xaa Leu Glu Ala
1               5                   10                  15

Leu Lys Gln Lys Leu Lys

20

<210> SEQ ID NO 92
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 92

```
Pro Val Leu Asp Glu Phe Arg Glu Leu Tyr Asn Glu Xaa Leu Glu Ala
1               5                   10                  15

Leu Lys Gln Lys Leu Lys
            20
```

<210> SEQ ID NO 93
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 93

```
Pro Val Leu Asp Glu Phe Arg Glu Lys Leu Asn Glu Xaa Leu Lys Ala
1               5                   10                  15

Leu Lys Gln Lys Leu Lys
            20
```

<210> SEQ ID NO 94
<211> LENGTH: 22
<212> TYPE: PRT
<213> ORGANISM: Artificial sequence
<220> FEATURE:
<223> OTHER INFORMATION: synthetic

<400> SEQUENCE: 94

```
Pro Val Leu Asp Glu Phe Arg Glu Lys Leu Asn Glu Ala Leu Glu Ala
1               5                   10                  15

Leu Lys Gln Lys Leu Lys
            20
```

<210> SEQ ID NO 95
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 95

Pro Val Leu Asp Leu Phe Arg Glu Leu Leu Asn Leu Xaa Leu Glu Ala
1               5                   10                  15

Leu Lys Gln Lys Leu Lys
            20

<210> SEQ ID NO 96
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 96

Pro Val Leu Asp Leu Phe Arg Glu Leu Leu Asn Glu Xaa Leu Glu Ala
1               5                   10                  15

Leu Lys Gln Lys Leu Lys
            20

<210> SEQ ID NO 97
<211> LENGTH: 15
<212> TYPE: PRT
<213> ORGANISM: Artificial sequence
<220> FEATURE:
<223> OTHER INFORMATION: synthetic

<400> SEQUENCE: 97

Pro Val Leu Asp Leu Phe Arg Glu Leu Leu Asn Glu Leu Leu Glu
1               5                   10                  15

<210> SEQ ID NO 98
<211> LENGTH: 22
<212> TYPE: PRT
<213> ORGANISM: Artificial sequence
<220> FEATURE:
<223> OTHER INFORMATION: synthetic

<400> SEQUENCE: 98

Pro Val Leu Asp Leu Phe Arg Glu Leu Leu Asn Glu Glu Leu Glu Ala
1               5                   10                  15

Leu Lys Gln Lys Leu Lys
            20

<210> SEQ ID NO 99
<211> LENGTH: 22
<212> TYPE: PRT
<213> ORGANISM: Artificial sequence
<220> FEATURE:
<223> OTHER INFORMATION: synthetic

<400> SEQUENCE: 99

Lys Leu Lys Gln Lys Leu Ala Glu Leu Leu Glu Asn Leu Leu Glu Arg
1               5                   10                  15

Phe Leu Asp Leu Val Pro
            20

<210> SEQ ID NO 100
<211> LENGTH: 22

```
<212> TYPE: PRT
<213> ORGANISM: Artificial sequence
<220> FEATURE:
<223> OTHER INFORMATION: synthetic

<400> SEQUENCE: 100

Pro Val Leu Asp Leu Phe Arg Glu Leu Leu Asn Glu Leu Leu Glu Ala
1               5                   10                  15

Leu Lys Gln Lys Leu Lys
            20


<210> SEQ ID NO 101
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 101

Pro Val Leu Asp Leu Phe Arg Glu Leu Leu Asn Trp Xaa Leu Glu Ala
1               5                   10                  15

Leu Lys Gln Lys Leu Lys
            20


<210> SEQ ID NO 102
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 102

Pro Val Leu Asp Leu Phe Arg Glu Leu Leu Asn Leu Xaa Leu Glu Ala
1               5                   10                  15

Leu Lys Glu Lys Leu Lys
            20


<210> SEQ ID NO 103
<211> LENGTH: 22
<212> TYPE: PRT
<213> ORGANISM: Artificial sequence
<220> FEATURE:
<223> OTHER INFORMATION: synthetic

<400> SEQUENCE: 103

Pro Val Leu Asp Glu Phe Arg Glu Leu Leu Asn Glu Glu Leu Glu Ala
1               5                   10                  15

Leu Lys Gln Lys Leu Lys
            20


<210> SEQ ID NO 104
<211> LENGTH: 15
<212> TYPE: PRT
```

<213> ORGANISM: Artificial sequence
<220> FEATURE:
<223> OTHER INFORMATION: synthetic

<400> SEQUENCE: 104

Pro Leu Leu Asn Glu Leu Leu Glu Ala Leu Lys Gln Lys Leu Lys
1 5 10 15

<210> SEQ ID NO 105
<211> LENGTH: 22
<212> TYPE: PRT
<213> ORGANISM: Artificial sequence
<220> FEATURE:
<223> OTHER INFORMATION: synthetic

<400> SEQUENCE: 105

Pro Ala Ala Asp Ala Phe Arg Glu Ala Ala Asn Glu Ala Ala Glu Ala
1 5 10 15

Ala Lys Gln Lys Ala Lys
20

<210> SEQ ID NO 106
<211> LENGTH: 22
<212> TYPE: PRT
<213> ORGANISM: Artificial sequence
<220> FEATURE:
<223> OTHER INFORMATION: synthetic

<400> SEQUENCE: 106

Pro Val Leu Asp Leu Phe Arg Glu Lys Leu Asn Glu Glu Leu Glu Ala
1 5 10 15

Leu Lys Gln Lys Leu Lys
20

<210> SEQ ID NO 107
<211> LENGTH: 22
<212> TYPE: PRT
<213> ORGANISM: Artificial sequence
<220> FEATURE:
<223> OTHER INFORMATION: synthetic

<400> SEQUENCE: 107

Lys Leu Lys Gln Lys Leu Ala Glu Leu Leu Glu Asn Leu Leu Glu Arg
1 5 10 15

Phe Leu Asp Leu Val Pro
20

<210> SEQ ID NO 108
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 108

Pro Val Leu Asp Leu Phe Arg Trp Leu Leu Asn Glu Xaa Leu Glu Ala
1 5 10 15

Leu Lys Gln Lys Leu Lys
20

<210> SEQ ID NO 109
<211> LENGTH: 22
<212> TYPE: PRT
<213> ORGANISM: Artificial sequence
<220> FEATURE:
<223> OTHER INFORMATION: synthetic

<400> SEQUENCE: 109

```
Pro Val Leu Asp Glu Phe Arg Glu Lys Leu Asn Glu Arg Leu Glu Ala
1               5                   10                  15

Leu Lys Gln Lys Leu Lys
            20
```

<210> SEQ ID NO 110
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 110

```
Pro Val Leu Asp Glu Phe Arg Glu Lys Leu Asn Glu Xaa Xaa Glu Ala
1               5                   10                  15

Leu Lys Gln Lys Leu Lys
            20
```

<210> SEQ ID NO 111
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 111

```
Pro Val Leu Asp Glu Phe Arg Glu Lys Leu Trp Glu Xaa Trp Glu Ala
1               5                   10                  15

Leu Lys Gln Lys Leu Lys
            20
```

<210> SEQ ID NO 112
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 112

Pro Val Leu Asp Glu Phe Arg Glu Lys Leu Asn Glu Xaa Ser Glu Ala
1 5 10 15

Leu Lys Gln Lys Leu Lys
20

<210> SEQ ID NO 113
<211> LENGTH: 22
<212> TYPE: PRT
<213> ORGANISM: Artificial sequence
<220> FEATURE:
<223> OTHER INFORMATION: synthetic

<400> SEQUENCE: 113

Pro Val Leu Asp Glu Phe Arg Glu Lys Leu Asn Glu Pro Leu Glu Ala
1 5 10 15

Leu Lys Gln Lys Leu Lys
20

<210> SEQ ID NO 114
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 114

Pro Val Leu Asp Glu Phe Arg Glu Lys Leu Asn Glu Xaa Met Glu Ala
1 5 10 15

Leu Lys Gln Lys Leu Lys
20

<210> SEQ ID NO 115
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 115

Pro Lys Leu Asp Glu Phe Arg Glu Lys Leu Asn Glu Xaa Leu Glu Ala
1 5 10 15

Leu Lys Gln Lys Leu Lys
20

<210> SEQ ID NO 116
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 116

Pro His Leu Asp Glu Phe Arg Glu Lys Leu Asn Glu Xaa Leu Glu Ala
1 5 10 15

Leu Lys Gln Lys Leu Lys
20

<210> SEQ ID NO 117
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 117

Pro Glu Leu Asp Glu Phe Arg Glu Lys Leu Asn Glu Xaa Leu Glu Ala
1 5 10 15

Leu Lys Gln Lys Leu Lys
20

<210> SEQ ID NO 118
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 118

Pro Val Leu Asp Glu Phe Arg Glu Lys Leu Asn Glu Xaa Leu Glu Ala
1 5 10 15

Leu Glu Gln Lys Leu Lys
20

<210> SEQ ID NO 119
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 119

Pro Val Leu Asp Glu Phe Arg Glu Lys Leu Asn Glu Glu Leu Glu Ala
1 5 10 15

Xaa Lys Gln Lys Leu Lys
20

<210> SEQ ID NO 120
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 120

Pro Val Leu Asp Glu Phe Arg Glu Lys Leu Asn Glu Glu Leu Glu Xaa
1 5 10 15

Leu Lys Gln Lys Leu Lys
20

<210> SEQ ID NO 121
<211> LENGTH: 22
<212> TYPE: PRT
<213> ORGANISM: Artificial sequence
<220> FEATURE:
<223> OTHER INFORMATION: synthetic

<400> SEQUENCE: 121

Pro Val Leu Asp Glu Phe Arg Glu Lys Leu Asn Glu Glu Leu Glu Ala
1 5 10 15

Leu Trp Gln Lys Leu Lys
20

<210> SEQ ID NO 122
<211> LENGTH: 22
<212> TYPE: PRT
<213> ORGANISM: Artificial sequence
<220> FEATURE:
<223> OTHER INFORMATION: synthetic

<400> SEQUENCE: 122

Pro Val Leu Asp Glu Phe Arg Glu Lys Leu Asn Glu Glu Leu Glu Trp
1 5 10 15

Leu Lys Gln Lys Leu Lys
20

<210> SEQ ID NO 123
<211> LENGTH: 22
<212> TYPE: PRT
<213> ORGANISM: Artificial sequence
<220> FEATURE:
<223> OTHER INFORMATION: synthetic

<400> SEQUENCE: 123

Gln Val Leu Asp Leu Phe Arg Glu Leu Leu Asn Glu Leu Leu Glu Ala
1 5 10 15

Leu Lys Gln Lys Leu Lys
20

<210> SEQ ID NO 124
<211> LENGTH: 22
<212> TYPE: PRT
<213> ORGANISM: Artificial sequence

```
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 124

Pro Val Leu Asp Leu Phe Xaa Glu Leu Leu Asn Glu Leu Leu Glu Ala
1               5                   10                  15

Leu Xaa Gln Xaa Leu Xaa
            20


<210> SEQ ID NO 125
<211> LENGTH: 22
<212> TYPE: PRT
<213> ORGANISM: Artificial sequence
<220> FEATURE:
<223> OTHER INFORMATION: synthetic

<400> SEQUENCE: 125

Asn Val Leu Asp Leu Phe Arg Glu Leu Leu Asn Glu Leu Leu Glu Ala
1               5                   10                  15

Leu Lys Gln Lys Leu Lys
            20


<210> SEQ ID NO 126
<211> LENGTH: 22
<212> TYPE: PRT
<213> ORGANISM: Artificial sequence
<220> FEATURE:
<223> OTHER INFORMATION: synthetic

<400> SEQUENCE: 126

Pro Val Leu Asp Leu Phe Arg Glu Leu Leu Asn Glu Leu Gly Glu Ala
1               5                   10                  15

Leu Lys Gln Lys Leu Lys
            20


<210> SEQ ID NO 127
<211> LENGTH: 22
<212> TYPE: PRT
<213> ORGANISM: Artificial sequence
<220> FEATURE:
<223> OTHER INFORMATION: synthetic

<400> SEQUENCE: 127

Pro Val Leu Asp Leu Phe Arg Glu Leu Leu Asn Glu Leu Leu Glu Leu
1               5                   10                  15

Leu Lys Gln Lys Leu Lys
            20
```

-continued

<210> SEQ ID NO 128
<211> LENGTH: 22
<212> TYPE: PRT
<213> ORGANISM: Artificial sequence
<220> FEATURE:
<223> OTHER INFORMATION: synthetic

<400> SEQUENCE: 128

```
Pro Val Leu Asp Leu Phe Arg Glu Leu Leu Asn Glu Leu Leu Glu Phe
1               5                   10                  15

Leu Lys Gln Lys Leu Lys
            20
```

<210> SEQ ID NO 129
<211> LENGTH: 22
<212> TYPE: PRT
<213> ORGANISM: Artificial sequence
<220> FEATURE:
<223> OTHER INFORMATION: synthetic

<400> SEQUENCE: 129

```
Pro Val Leu Glu Leu Phe Asn Asp Leu Leu Arg Glu Leu Leu Glu Ala
1               5                   10                  15

Leu Gln Lys Lys Leu Lys
            20
```

<210> SEQ ID NO 130
<211> LENGTH: 22
<212> TYPE: PRT
<213> ORGANISM: Artificial sequence
<220> FEATURE:
<223> OTHER INFORMATION: synthetic

<400> SEQUENCE: 130

```
Pro Val Leu Glu Leu Phe Asn Asp Leu Leu Arg Glu Leu Leu Glu Ala
1               5                   10                  15

Leu Lys Gln Lys Leu Lys
            20
```

<210> SEQ ID NO 131
<211> LENGTH: 22
<212> TYPE: PRT
<213> ORGANISM: Artificial sequence
<220> FEATURE:
<223> OTHER INFORMATION: synthetic

<400> SEQUENCE: 131

```
Pro Val Leu Glu Leu Phe Lys Glu Leu Leu Asn Glu Leu Leu Asp Ala
1               5                   10                  15

Leu Arg Gln Lys Leu Lys
            20
```

<210> SEQ ID NO 132
<211> LENGTH: 22
<212> TYPE: PRT
<213> ORGANISM: Artificial sequence
<220> FEATURE:
<223> OTHER INFORMATION: synthetic

<400> SEQUENCE: 132

```
Pro Val Leu Asp Leu Phe Arg Glu Leu Leu Glu Asn Leu Leu Glu Ala
1               5                   10                  15

Leu Gln Lys Lys Leu Lys
            20
```

```
<210> SEQ ID NO 133
<211> LENGTH: 22
<212> TYPE: PRT
<213> ORGANISM: Artificial sequence
<220> FEATURE:
<223> OTHER INFORMATION: synthetic

<400> SEQUENCE: 133

Pro Val Leu Glu Leu Phe Glu Arg Leu Leu Glu Asp Leu Leu Gln Ala
1               5                   10                  15

Leu Asn Lys Lys Leu Lys
            20


<210> SEQ ID NO 134
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 134

Pro Val Leu Glu Leu Phe Glu Arg Leu Leu Glu Asp Leu Leu Lys Ala
1               5                   10                  15

Leu Asn Xaa Lys Leu Lys
            20


<210> SEQ ID NO 135
<211> LENGTH: 22
<212> TYPE: PRT
<213> ORGANISM: Artificial sequence
<220> FEATURE:
<223> OTHER INFORMATION: synthetic

<400> SEQUENCE: 135

Asp Val Leu Asp Leu Phe Arg Glu Leu Leu Asn Glu Leu Leu Glu Ala
1               5                   10                  15

Leu Lys Gln Lys Leu Lys
            20


<210> SEQ ID NO 136
<211> LENGTH: 22
<212> TYPE: PRT
<213> ORGANISM: Artificial sequence
<220> FEATURE:
<223> OTHER INFORMATION: synthetic

<400> SEQUENCE: 136

Pro Ala Leu Glu Leu Phe Lys Asp Leu Leu Gln Glu Leu Leu Glu Ala
1               5                   10                  15

Leu Lys Gln Lys Leu Lys
            20


<210> SEQ ID NO 137
<211> LENGTH: 22
<212> TYPE: PRT
<213> ORGANISM: Artificial sequence
<220> FEATURE:
<223> OTHER INFORMATION: synthetic
```

<400> SEQUENCE: 137

Pro Val Leu Asp Leu Phe Arg Glu Leu Leu Asn Glu Gly Leu Glu Ala
1 5 10 15

Glx Lys Gln Lys Leu Lys
20

<210> SEQ ID NO 138
<211> LENGTH: 22
<212> TYPE: PRT
<213> ORGANISM: Artificial sequence
<220> FEATURE:
<223> OTHER INFORMATION: synthetic

<400> SEQUENCE: 138

Pro Val Leu Asp Leu Phe Arg Glu Leu Leu Asn Glu Gly Leu Glu Trp
1 5 10 15

Leu Lys Gln Lys Leu Lys
20

<210> SEQ ID NO 139
<211> LENGTH: 22
<212> TYPE: PRT
<213> ORGANISM: Artificial sequence
<220> FEATURE:
<223> OTHER INFORMATION: synthetic

<400> SEQUENCE: 139

Pro Val Leu Asp Leu Phe Arg Glu Leu Trp Asn Glu Gly Leu Glu Ala
1 5 10 15

Leu Lys Gln Lys Leu Lys
20

<210> SEQ ID NO 140
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 140

Pro Val Leu Asp Leu Phe Arg Glu Leu Leu Asn Glu Gly Leu Glu Ala
1 5 10 15

Leu Xaa Gln Xaa Leu Xaa
20

<210> SEQ ID NO 141
<211> LENGTH: 22
<212> TYPE: PRT
<213> ORGANISM: Artificial sequence
<220> FEATURE:
<223> OTHER INFORMATION: synthetic

<400> SEQUENCE: 141

Pro Val Leu Asp Phe Phe Arg Glu Leu Leu Asn Glu Gly Leu Glu Ala
1               5                   10                  15

Leu Lys Gln Lys Leu Lys
            20

<210> SEQ ID NO 142
<211> LENGTH: 22
<212> TYPE: PRT
<213> ORGANISM: Artificial sequence
<220> FEATURE:
<223> OTHER INFORMATION: synthetic

<400> SEQUENCE: 142

Pro Val Leu Glu Leu Phe Arg Glu Leu Leu Asn Glu Gly Leu Glu Ala
1               5                   10                  15

Leu Lys Gln Lys Leu Lys
            20

<210> SEQ ID NO 143
<211> LENGTH: 22
<212> TYPE: PRT
<213> ORGANISM: Artificial sequence
<220> FEATURE:
<223> OTHER INFORMATION: synthetic

<400> SEQUENCE: 143

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 144
<211> LENGTH: 22
<212> TYPE: PRT
<213> ORGANISM: Artificial sequence
<220> FEATURE:
<223> OTHER INFORMATION: synthetic

<400> SEQUENCE: 144

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 145
<211> LENGTH: 22
<212> TYPE: PRT
<213> ORGANISM: Artificial sequence
<220> FEATURE:
<223> OTHER INFORMATION: synthetic

<400> SEQUENCE: 145

Gly Val Leu Glu Leu Phe Glu Asn Leu Leu Glu Arg Leu Leu Asp Ala
1               5                   10                  15

Leu Gln Lys Lys Leu Lys
            20

<210> SEQ ID NO 146
<211> LENGTH: 22
<212> TYPE: PRT
<213> ORGANISM: Artificial sequence
<220> FEATURE:
<223> OTHER INFORMATION: synthetic

<400> SEQUENCE: 146

```
Pro Val Leu Glu Leu Phe Glu Asn Leu Leu Glu Arg Leu Leu Asp Ala
1               5                   10                  15

Leu Gln Lys Lys Leu Lys
            20
```

<210> SEQ ID NO 147
<211> LENGTH: 22
<212> TYPE: PRT
<213> ORGANISM: Artificial sequence
<220> FEATURE:
<223> OTHER INFORMATION: synthetic

<400> SEQUENCE: 147

```
Pro Val Leu Glu Leu Phe Glu Asn Leu Leu Glu Arg Leu Phe Asp Ala
1               5                   10                  15

Leu Gln Lys Lys Leu Lys
            20
```

<210> SEQ ID NO 148
<211> LENGTH: 22
<212> TYPE: PRT
<213> ORGANISM: Artificial sequence
<220> FEATURE:
<223> OTHER INFORMATION: synthetic

<400> SEQUENCE: 148

```
Pro Val Leu Glu Leu Phe Glu Asn Leu Leu Glu Arg Leu Gly Asp Ala
1               5                   10                  15

Leu Gln Lys Lys Leu Lys
            20
```

<210> SEQ ID NO 149
<211> LENGTH: 22
<212> TYPE: PRT
<213> ORGANISM: Artificial sequence
<220> FEATURE:
<223> OTHER INFORMATION: synthetic

<400> SEQUENCE: 149

```
Pro Val Leu Glu Leu Phe Glu Asn Leu Trp Glu Arg Leu Leu Asp Ala
1               5                   10                  15

Leu Gln Lys Lys Leu Lys
            20
```

<210> SEQ ID NO 150
<211> LENGTH: 22
<212> TYPE: PRT
<213> ORGANISM: Artificial sequence
<220> FEATURE:
<223> OTHER INFORMATION: synthetic

<400> SEQUENCE: 150

```
Pro Leu Leu Glu Leu Phe Glu Asn Leu Leu Glu Arg Leu Leu Asp Ala
1               5                   10                  15

Leu Gln Lys Lys Leu Lys
            20
```

<210> SEQ ID NO 151
<211> LENGTH: 22
<212> TYPE: PRT
<213> ORGANISM: Artificial sequence
<220> FEATURE:

<223> OTHER INFORMATION: synthetic

<400> SEQUENCE: 151

Pro Val Leu Glu Leu Phe Glu Asn Leu Gly Glu Arg Leu Leu Asp Ala
1 5 10 15

Leu Gln Lys Lys Leu Lys
20

<210> SEQ ID NO 152
<211> LENGTH: 22
<212> TYPE: PRT
<213> ORGANISM: Artificial sequence
<220> FEATURE:
<223> OTHER INFORMATION: synthetic

<400> SEQUENCE: 152

Pro Val Phe Glu Leu Phe Glu Asn Leu Leu Glu Arg Leu Leu Asp Ala
1 5 10 15

Leu Gln Lys Lys Leu Lys
20

<210> SEQ ID NO 153
<211> LENGTH: 22
<212> TYPE: PRT
<213> ORGANISM: Artificial sequence
<220> FEATURE:
<223> OTHER INFORMATION: synthetic

<400> SEQUENCE: 153

Ala Val Leu Glu Leu Phe Glu Asn Leu Leu Glu Arg Leu Leu Asp Ala
1 5 10 15

Leu Gln Lys Lys Leu Lys
20

<210> SEQ ID NO 154
<211> LENGTH: 22
<212> TYPE: PRT
<213> ORGANISM: Artificial sequence
<220> FEATURE:
<223> OTHER INFORMATION: synthetic

<400> SEQUENCE: 154

Pro Val Leu Glu Leu Phe Glu Asn Leu Leu Glu Arg Gly Leu Asp Ala
1 5 10 15

Leu Gln Lys Lys Leu Lys
20

<210> SEQ ID NO 155
<211> LENGTH: 22
<212> TYPE: PRT
<213> ORGANISM: Artificial sequence
<220> FEATURE:
<223> OTHER INFORMATION: synthetic

<400> SEQUENCE: 155

Pro Val Leu Glu Leu Phe Leu Asn Leu Trp Glu Arg Leu Leu Asp Ala
1 5 10 15

Leu Gln Lys Lys Leu Lys
20

<210> SEQ ID NO 156
<211> LENGTH: 22
<212> TYPE: PRT
<213> ORGANISM: Artificial sequence -continued
<220> FEATURE:
<223> OTHER INFORMATION: synthetic

<400> SEQUENCE: 156

Pro Val Leu Glu Leu Phe Leu Asn Leu Leu Glu Arg Leu Leu Asp Ala
1 5 10 15

Leu Gln Lys Lys Leu Lys
20

<210> SEQ ID NO 157
<211> LENGTH: 22
<212> TYPE: PRT
<213> ORGANISM: Artificial sequence
<220> FEATURE:
<223> OTHER INFORMATION: synthetic

<400> SEQUENCE: 157

Pro Val Leu Glu Phe Phe Glu Asn Leu Leu Glu Arg Leu Leu Asp Ala
1 5 10 15

Leu Gln Lys Lys Leu Lys
20

<210> SEQ ID NO 158
<211> LENGTH: 22
<212> TYPE: PRT
<213> ORGANISM: Artificial sequence
<220> FEATURE:
<223> OTHER INFORMATION: synthetic

<400> SEQUENCE: 158

Pro Val Leu Glu Leu Phe Leu Asn Leu Leu Glu Arg Leu Leu Asp Trp
1 5 10 15

Leu Gln Lys Lys Leu Lys
20

<210> SEQ ID NO 159
<211> LENGTH: 22
<212> TYPE: PRT
<213> ORGANISM: Artificial sequence
<220> FEATURE:
<223> OTHER INFORMATION: synthetic

<400> SEQUENCE: 159

Pro Val Leu Asp Leu Phe Glu Asn Leu Leu Glu Arg Leu Leu Asp Ala
1 5 10 15

Leu Gln Lys Lys Leu Lys
20

<210> SEQ ID NO 160
<211> LENGTH: 22
<212> TYPE: PRT
<213> ORGANISM: Artificial sequence
<220> FEATURE:
<223> OTHER INFORMATION: synthetic

<400> SEQUENCE: 160

Pro Val Leu Glu Leu Phe Glu Asn Leu Leu Glu Arg Leu Leu Asp Trp
1 5 10 15

Leu Gln Lys Lys Leu Lys
20

<210> SEQ ID NO 161
<211> LENGTH: 22
<212> TYPE: PRT

<213> ORGANISM: Artificial sequence
<220> FEATURE:
<223> OTHER INFORMATION: synthetic

<400> SEQUENCE: 161

Pro Val Leu Glu Leu Phe Glu Asn Leu Leu Glu Arg Leu Leu Glu Ala
1               5                   10                  15

Leu Gln Lys Lys Leu Lys
            20

<210> SEQ ID NO 162
<211> LENGTH: 22
<212> TYPE: PRT
<213> ORGANISM: Artificial sequence
<220> FEATURE:
<223> OTHER INFORMATION: synthetic

<400> SEQUENCE: 162

Pro Val Leu Glu Leu Phe Glu Asn Trp Leu Glu Arg Leu Leu Asp Ala
1               5                   10                  15

Leu Gln Lys Lys Leu Lys
            20

<210> SEQ ID NO 163
<211> LENGTH: 22
<212> TYPE: PRT
<213> ORGANISM: Artificial sequence
<220> FEATURE:
<223> OTHER INFORMATION: synthetic

<400> SEQUENCE: 163

Pro Val Leu Glu Leu Phe Glu Asn Leu Leu Glu Arg Leu Trp Asp Ala
1               5                   10                  15

Leu Gln Lys Lys Leu Lys
            20

<210> SEQ ID NO 164
<211> LENGTH: 22
<212> TYPE: PRT
<213> ORGANISM: Artificial sequence
<220> FEATURE:
<223> OTHER INFORMATION: synthetic

<400> SEQUENCE: 164

Pro Val Leu Glu Leu Phe Glu Asn Leu Leu Glu Arg Leu Leu Asp Ala
1               5                   10                  15

Trp Gln Lys Lys Leu Lys
            20

<210> SEQ ID NO 165
<211> LENGTH: 22
<212> TYPE: PRT
<213> ORGANISM: Artificial sequence
<220> FEATURE:
<223> OTHER INFORMATION: synthetic

<400> SEQUENCE: 165

Pro Val Leu Glu Leu Phe Glu Asn Leu Leu Glu Arg Leu Leu Asp Leu
1               5                   10                  15

Leu Gln Lys Lys Leu Lys
            20

<210> SEQ ID NO 166
<211> LENGTH: 22

<212> TYPE: PRT
<213> ORGANISM: Artificial sequence
<220> FEATURE:
<223> OTHER INFORMATION: synthetic

<400> SEQUENCE: 166

```
Pro Val Leu Glu Leu Phe Leu Asn Leu Leu Glu Lys Leu Leu Asp Ala
1               5                   10                  15

Leu Gln Lys Lys Leu Lys
            20
```

<210> SEQ ID NO 167
<211> LENGTH: 22
<212> TYPE: PRT
<213> ORGANISM: Artificial sequence
<220> FEATURE:
<223> OTHER INFORMATION: synthetic

<400> SEQUENCE: 167

```
Pro Val Leu Glu Leu Phe Glu Asn Gly Leu Glu Arg Leu Leu Asp Ala
1               5                   10                  15

Leu Gln Lys Lys Leu Lys
            20
```

<210> SEQ ID NO 168
<211> LENGTH: 22
<212> TYPE: PRT
<213> ORGANISM: Artificial sequence
<220> FEATURE:
<223> OTHER INFORMATION: synthetic

<400> SEQUENCE: 168

```
Pro Val Leu Glu Leu Phe Glu Gln Leu Leu Glu Lys Leu Leu Asp Ala
1               5                   10                  15

Leu Gln Lys Lys Leu Lys
            20
```

<210> SEQ ID NO 169
<211> LENGTH: 22
<212> TYPE: PRT
<213> ORGANISM: Artificial sequence
<220> FEATURE:
<223> OTHER INFORMATION: synthetic

<400> SEQUENCE: 169

```
Pro Val Leu Glu Leu Phe Glu Asn Leu Leu Glu Lys Leu Leu Asp Ala
1               5                   10                  15

Leu Gln Lys Lys Leu Lys
            20
```

<210> SEQ ID NO 170
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 170

Pro Val Leu Glu Leu Phe Glu Asn Leu Leu Glu Xaa Leu Leu Asp Ala
1 5 10 15

Leu Gln Xaa Xaa Leu Xaa
20

<210> SEQ ID NO 171
<211> LENGTH: 22
<212> TYPE: PRT
<213> ORGANISM: Artificial sequence
<220> FEATURE:
<223> OTHER INFORMATION: synthetic

<400> SEQUENCE: 171

Pro Val Leu Glu Leu Phe Glu Asn Leu Leu Glu Lys Leu Leu Asp Leu
1 5 10 15

Leu Gln Lys Lys Leu Lys
20

<210> SEQ ID NO 172
<211> LENGTH: 22
<212> TYPE: PRT
<213> ORGANISM: Artificial sequence
<220> FEATURE:
<223> OTHER INFORMATION: synthetic

<400> SEQUENCE: 172

Pro Val Leu Glu Leu Phe Leu Asn Leu Leu Glu Arg Leu Gly Asp Ala
1 5 10 15

Leu Gln Lys Lys Leu Lys
20

<210> SEQ ID NO 173
<211> LENGTH: 22
<212> TYPE: PRT
<213> ORGANISM: Artificial sequence
<220> FEATURE:
<223> OTHER INFORMATION: synthetic

<400> SEQUENCE: 173

Pro Val Leu Asp Leu Phe Asp Asn Leu Leu Asp Arg Leu Leu Asp Leu
1 5 10 15

Leu Asn Lys Lys Leu Lys
20

<210> SEQ ID NO 174
<211> LENGTH: 22
<212> TYPE: PRT
<213> ORGANISM: Artificial sequence
<220> FEATURE:
<223> OTHER INFORMATION: synthetic

<400> SEQUENCE: 174

Pro Val Leu Glu Leu Phe Glu Asn Leu Leu Glu Arg Leu Leu Asp Ala
1 5 10 15

Leu Gln Lys Lys Leu Lys
20

<210> SEQ ID NO 175

<211> LENGTH: 22
<212> TYPE: PRT
<213> ORGANISM: Artificial sequence
<220> FEATURE:
<223> OTHER INFORMATION: synthetic

<400> SEQUENCE: 175

Pro Val Leu Glu Leu Phe Glu Asn Leu Leu Glu Arg Leu Leu Glu Leu
1 5 10 15

Leu Asn Lys Lys Leu Lys
20

<210> SEQ ID NO 176
<211> LENGTH: 22
<212> TYPE: PRT
<213> ORGANISM: Artificial sequence
<220> FEATURE:
<223> OTHER INFORMATION: synthetic

<400> SEQUENCE: 176

Pro Val Leu Glu Leu Trp Glu Asn Leu Leu Glu Arg Leu Leu Asp Ala
1 5 10 15

Leu Gln Lys Lys Leu Lys
20

<210> SEQ ID NO 177
<211> LENGTH: 22
<212> TYPE: PRT
<213> ORGANISM: Artificial sequence
<220> FEATURE:
<223> OTHER INFORMATION: synthetic

<400> SEQUENCE: 177

Gly Val Leu Glu Leu Phe Leu Asn Leu Leu Glu Arg Leu Leu Asp Ala
1 5 10 15

Leu Gln Lys Lys Leu Lys
20

<210> SEQ ID NO 178
<211> LENGTH: 22
<212> TYPE: PRT
<213> ORGANISM: Artificial sequence
<220> FEATURE:
<223> OTHER INFORMATION: synthetic

<400> SEQUENCE: 178

Pro Val Leu Glu Leu Phe Asp Asn Leu Leu Glu Lys Leu Leu Glu Ala
1 5 10 15

Leu Gln Lys Lys Leu Arg
20

<210> SEQ ID NO 179
<211> LENGTH: 22
<212> TYPE: PRT
<213> ORGANISM: Artificial sequence
<220> FEATURE:
<223> OTHER INFORMATION: synthetic

<400> SEQUENCE: 179

Pro Val Leu Glu Leu Phe Asp Asn Leu Leu Glu Arg Leu Leu Asp Ala
1 5 10 15

Leu Gln Lys Lys Leu Lys
20

-continued

```
<210> SEQ ID NO 180
<211> LENGTH: 22
<212> TYPE: PRT
<213> ORGANISM: Artificial sequence
<220> FEATURE:
<223> OTHER INFORMATION: synthetic

<400> SEQUENCE: 180

Pro Val Leu Glu Leu Phe Asp Asn Leu Leu Asp Lys Leu Leu Asp Ala
1               5                   10                  15

Leu Gln Lys Lys Leu Arg
            20


<210> SEQ ID NO 181
<211> LENGTH: 22
<212> TYPE: PRT
<213> ORGANISM: Artificial sequence
<220> FEATURE:
<223> OTHER INFORMATION: synthetic

<400> SEQUENCE: 181

Pro Val Leu Glu Leu Phe Glu Asn Leu Leu Glu Arg Trp Leu Asp Ala
1               5                   10                  15

Leu Gln Lys Lys Leu Lys
            20


<210> SEQ ID NO 182
<211> LENGTH: 22
<212> TYPE: PRT
<213> ORGANISM: Artificial sequence
<220> FEATURE:
<223> OTHER INFORMATION: synthetic

<400> SEQUENCE: 182

Pro Val Leu Glu Leu Phe Glu Asn Leu Leu Glu Lys Leu Leu Glu Ala
1               5                   10                  15

Leu Gln Lys Lys Leu Lys
            20


<210> SEQ ID NO 183
<211> LENGTH: 22
<212> TYPE: PRT
<213> ORGANISM: Artificial sequence
<220> FEATURE:
<223> OTHER INFORMATION: synthetic

<400> SEQUENCE: 183

Pro Leu Leu Glu Leu Phe Glu Asn Leu Leu Glu Lys Leu Leu Asp Ala
1               5                   10                  15

Leu Gln Lys Lys Leu Lys
            20


<210> SEQ ID NO 184
<211> LENGTH: 22
<212> TYPE: PRT
<213> ORGANISM: Artificial sequence
<220> FEATURE:
<223> OTHER INFORMATION: synthetic

<400> SEQUENCE: 184

Pro Val Leu Glu Leu Phe Leu Asn Leu Leu Glu Arg Leu Leu Asp Ala
1               5                   10                  15

Trp Gln Lys Lys Leu Lys
            20
```

<210> SEQ ID NO 185
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 185

```
Pro Val Leu Glu Leu Phe Glu Asn Leu Leu Glu Arg Leu Leu Asp Ala
1               5                   10                  15

Leu Gln Xaa Xaa Leu Xaa
            20
```

<210> SEQ ID NO 186
<211> LENGTH: 22
<212> TYPE: PRT
<213> ORGANISM: Artificial sequence
<220> FEATURE:
<223> OTHER INFORMATION: synthetic

<400> SEQUENCE: 186

```
Pro Val Leu Glu Leu Phe Glu Gln Leu Leu Glu Arg Leu Leu Asp Ala
1               5                   10                  15

Leu Gln Lys Lys Leu Lys
            20
```

<210> SEQ ID NO 187
<211> LENGTH: 22
<212> TYPE: PRT
<213> ORGANISM: Artificial sequence
<220> FEATURE:
<223> OTHER INFORMATION: synthetic

<400> SEQUENCE: 187

```
Pro Val Leu Glu Leu Phe Glu Asn Leu Leu Glu Arg Leu Leu Asp Ala
1               5                   10                  15

Leu Asn Lys Lys Leu Lys
            20
```

<210> SEQ ID NO 188
<211> LENGTH: 22
<212> TYPE: PRT
<213> ORGANISM: Artificial sequence
<220> FEATURE:
<223> OTHER INFORMATION: synthetic

<400> SEQUENCE: 188

```
Pro Val Leu Glu Leu Phe Glu Asn Leu Leu Asp Arg Leu Leu Asp Ala
1               5                   10                  15

Leu Gln Lys Lys Leu Lys
            20
```

<210> SEQ ID NO 189
<211> LENGTH: 22
<212> TYPE: PRT

<213> ORGANISM: Artificial sequence
<220> FEATURE:
<223> OTHER INFORMATION: synthetic

<400> SEQUENCE: 189

Asp Val Leu Glu Leu Phe Glu Asn Leu Leu Glu Arg Leu Leu Asp Ala
1 5 10 15

Leu Gln Lys Lys Leu Lys
20

<210> SEQ ID NO 190
<211> LENGTH: 22
<212> TYPE: PRT
<213> ORGANISM: Artificial sequence
<220> FEATURE:
<223> OTHER INFORMATION: synthetic

<400> SEQUENCE: 190

Pro Val Leu Glu Phe Trp Asp Asn Leu Leu Asp Lys Leu Leu Asp Ala
1 5 10 15

Leu Gln Lys Lys Leu Arg
20

<210> SEQ ID NO 191
<211> LENGTH: 18
<212> TYPE: PRT
<213> ORGANISM: Artificial sequence
<220> FEATURE:
<223> OTHER INFORMATION: synthetic

<400> SEQUENCE: 191

Pro Val Leu Asp Leu Leu Arg Glu Leu Leu Glu Glu Leu Lys Gln Lys
1 5 10 15

Leu Lys

<210> SEQ ID NO 192
<211> LENGTH: 18
<212> TYPE: PRT
<213> ORGANISM: Artificial sequence
<220> FEATURE:
<223> OTHER INFORMATION: synthetic

<400> SEQUENCE: 192

Pro Val Leu Asp Leu Phe Lys Glu Leu Leu Glu Glu Leu Lys Gln Lys
1 5 10 15

Leu Lys

<210> SEQ ID NO 193
<211> LENGTH: 18
<212> TYPE: PRT
<213> ORGANISM: Artificial sequence
<220> FEATURE:
<223> OTHER INFORMATION: synthetic

<400> SEQUENCE: 193

Pro Val Leu Asp Leu Phe Arg Glu Leu Leu Glu Glu Leu Lys Gln Lys
1 5 10 15

Leu Lys

<210> SEQ ID NO 194
<211> LENGTH: 18
<212> TYPE: PRT
<213> ORGANISM: Artificial sequence
<220> FEATURE:

<223> OTHER INFORMATION: synthetic

<400> SEQUENCE: 194

Pro Val Leu Glu Leu Phe Arg Glu Leu Leu Glu Glu Leu Lys Gln Lys
1 5 10 15

Leu Lys

<210> SEQ ID NO 195
<211> LENGTH: 18
<212> TYPE: PRT
<213> ORGANISM: Artificial sequence
<220> FEATURE:
<223> OTHER INFORMATION: synthetic

<400> SEQUENCE: 195

Pro Val Leu Glu Leu Phe Lys Glu Leu Leu Glu Glu Leu Lys Gln Lys
1 5 10 15

Leu Lys

<210> SEQ ID NO 196
<211> LENGTH: 18
<212> TYPE: PRT
<213> ORGANISM: Artificial sequence
<220> FEATURE:
<223> OTHER INFORMATION: synthetic

<400> SEQUENCE: 196

Pro Val Leu Asp Leu Phe Arg Glu Leu Leu Glu Glu Leu Lys Asn Lys
1 5 10 15

Leu Lys

<210> SEQ ID NO 197
<211> LENGTH: 18
<212> TYPE: PRT
<213> ORGANISM: Artificial sequence
<220> FEATURE:
<223> OTHER INFORMATION: synthetic

<400> SEQUENCE: 197

Pro Leu Leu Asp Leu Phe Arg Glu Leu Leu Glu Glu Leu Lys Gln Lys
1 5 10 15

Leu Lys

<210> SEQ ID NO 198
<211> LENGTH: 18
<212> TYPE: PRT
<213> ORGANISM: Artificial sequence
<220> FEATURE:
<223> OTHER INFORMATION: synthetic

<400> SEQUENCE: 198

Gly Val Leu Asp Leu Phe Arg Glu Leu Leu Glu Glu Leu Lys Gln Lys
1 5 10 15

Leu Lys

<210> SEQ ID NO 199
<211> LENGTH: 18
<212> TYPE: PRT
<213> ORGANISM: Artificial sequence
<220> FEATURE:
<223> OTHER INFORMATION: synthetic

<400> SEQUENCE: 199

-continued

Pro Val Leu Asp Leu Phe Arg Glu Leu Trp Glu Glu Leu Lys Gln Lys
1               5                   10                  15

Leu Lys

<210> SEQ ID NO 200
<211> LENGTH: 18
<212> TYPE: PRT
<213> ORGANISM: Artificial sequence
<220> FEATURE:
<223> OTHER INFORMATION: synthetic

<400> SEQUENCE: 200

Asn Val Leu Asp Leu Phe Arg Glu Leu Leu Glu Glu Leu Lys Gln Lys
1               5                   10                  15

Leu Lys

<210> SEQ ID NO 201
<211> LENGTH: 18
<212> TYPE: PRT
<213> ORGANISM: Artificial sequence
<220> FEATURE:
<223> OTHER INFORMATION: synthetic

<400> SEQUENCE: 201

Pro Leu Leu Asp Leu Phe Lys Glu Leu Leu Glu Glu Leu Lys Gln Lys
1               5                   10                  15

Leu Lys

<210> SEQ ID NO 202
<211> LENGTH: 18
<212> TYPE: PRT
<213> ORGANISM: Artificial sequence
<220> FEATURE:
<223> OTHER INFORMATION: synthetic

<400> SEQUENCE: 202

Pro Ala Leu Glu Leu Phe Lys Asp Leu Leu Glu Glu Leu Arg Gln Lys
1               5                   10                  15

Leu Arg

<210> SEQ ID NO 203
<211> LENGTH: 18
<212> TYPE: PRT
<213> ORGANISM: Artificial sequence
<220> FEATURE:
<223> OTHER INFORMATION: synthetic

<400> SEQUENCE: 203

Ala Val Leu Asp Leu Phe Arg Glu Leu Leu Glu Glu Leu Lys Gln Lys
1               5                   10                  15

Leu Lys

<210> SEQ ID NO 204
<211> LENGTH: 18
<212> TYPE: PRT
<213> ORGANISM: Artificial sequence
<220> FEATURE:
<223> OTHER INFORMATION: synthetic

<400> SEQUENCE: 204

Pro Val Leu Asp Phe Phe Arg Glu Leu Leu Glu Glu Leu Lys Gln Lys
1               5                   10                  15

Leu Lys

-continued

<210> SEQ ID NO 205
<211> LENGTH: 18
<212> TYPE: PRT
<213> ORGANISM: Artificial sequence
<220> FEATURE:
<223> OTHER INFORMATION: synthetic

<400> SEQUENCE: 205

Pro Val Leu Asp Leu Phe Arg Glu Trp Leu Glu Glu Leu Lys Gln Lys
1 5 10 15

Leu Lys

<210> SEQ ID NO 206
<211> LENGTH: 18
<212> TYPE: PRT
<213> ORGANISM: Artificial sequence
<220> FEATURE:
<223> OTHER INFORMATION: synthetic

<400> SEQUENCE: 206

Pro Leu Leu Glu Leu Leu Lys Glu Leu Leu Glu Glu Leu Lys Gln Lys
1 5 10 15

Leu Lys

<210> SEQ ID NO 207
<211> LENGTH: 18
<212> TYPE: PRT
<213> ORGANISM: Artificial sequence
<220> FEATURE:
<223> OTHER INFORMATION: synthetic

<400> SEQUENCE: 207

Pro Val Leu Glu Leu Leu Lys Glu Leu Leu Glu Glu Leu Lys Gln Lys
1 5 10 15

Leu Lys

<210> SEQ ID NO 208
<211> LENGTH: 18
<212> TYPE: PRT
<213> ORGANISM: Artificial sequence
<220> FEATURE:
<223> OTHER INFORMATION: synthetic

<400> SEQUENCE: 208

Pro Ala Leu Glu Leu Phe Lys Asp Leu Leu Glu Glu Leu Arg Gln Arg
1 5 10 15

Leu Lys

<210> SEQ ID NO 209
<211> LENGTH: 18
<212> TYPE: PRT
<213> ORGANISM: Artificial sequence
<220> FEATURE:
<223> OTHER INFORMATION: synthetic

<400> SEQUENCE: 209

Pro Val Leu Asp Leu Phe Arg Glu Leu Leu Asn Glu Leu Leu Gln Lys
1 5 10 15

Leu Lys

<210> SEQ ID NO 210
<211> LENGTH: 18

<212> TYPE: PRT
<213> ORGANISM: Artificial sequence
<220> FEATURE:
<223> OTHER INFORMATION: synthetic

<400> SEQUENCE: 210

Pro Val Leu Asp Leu Phe Arg Glu Leu Leu Glu Glu Leu Lys Gln Lys
1 5 10 15

Leu Lys

<210> SEQ ID NO 211
<211> LENGTH: 18
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 211

Pro Val Leu Asp Leu Phe Arg Glu Leu Leu Glu Glu Leu Xaa Gln Xaa
1 5 10 15

Leu Xaa

<210> SEQ ID NO 212
<211> LENGTH: 18
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 212

Pro Val Leu Asp Leu Phe Xaa Glu Leu Leu Glu Glu Leu Xaa Gln Xaa
1 5 10 15

Leu Lys

<210> SEQ ID NO 213
<211> LENGTH: 18
<212> TYPE: PRT
<213> ORGANISM: Artificial sequence
<220> FEATURE:
<223> OTHER INFORMATION: synthetic

<400> SEQUENCE: 213

Pro Ala Leu Glu Leu Phe Lys Asp Leu Leu Glu Glu Phe Arg Gln Arg
1 5 10 15

Leu Lys

<210> SEQ ID NO 214
<211> LENGTH: 18
<212> TYPE: PRT
<213> ORGANISM: Artificial sequence
<220> FEATURE:
<223> OTHER INFORMATION: synthetic

<400> SEQUENCE: 214

Pro Val Leu Asp Leu Phe Arg Glu Leu Leu Glu Glu Leu Lys Gln Lys
1 5 10 15

Leu Lys

<210> SEQ ID NO 215
<211> LENGTH: 18
<212> TYPE: PRT
<213> ORGANISM: Artificial sequence
<220> FEATURE:
<223> OTHER INFORMATION: synthetic

<400> SEQUENCE: 215

Pro Val Leu Asp Leu Phe Arg Glu Leu Leu Glu Glu Trp Lys Gln Lys
1 5 10 15

Leu Lys

<210> SEQ ID NO 216
<211> LENGTH: 18
<212> TYPE: PRT
<213> ORGANISM: Artificial sequence
<220> FEATURE:
<223> OTHER INFORMATION: synthetic

<400> SEQUENCE: 216

Pro Val Leu Glu Leu Phe Lys Glu Leu Leu Glu Glu Leu Lys Gln Lys
1 5 10 15

Leu Lys

<210> SEQ ID NO 217
<211> LENGTH: 18
<212> TYPE: PRT
<213> ORGANISM: Artificial sequence
<220> FEATURE:
<223> OTHER INFORMATION: synthetic

<400> SEQUENCE: 217

Pro Val Leu Asp Leu Phe Arg Glu Leu Leu Glu Leu Leu Lys Gln Lys
1 5 10 15

Leu Lys

<210> SEQ ID NO 218
<211> LENGTH: 18
<212> TYPE: PRT
<213> ORGANISM: Artificial sequence
<220> FEATURE:
<223> OTHER INFORMATION: synthetic

<400> SEQUENCE: 218

Pro Val Leu Asp Leu Phe Arg Glu Leu Leu Asn Glu Leu Leu Gln Lys

-continued 1 5 10 15

Leu Lys

<210> SEQ ID NO 219
<211> LENGTH: 18
<212> TYPE: PRT
<213> ORGANISM: Artificial sequence
<220> FEATURE:
<223> OTHER INFORMATION: synthetic

<400> SEQUENCE: 219

Pro Val Leu Asp Leu Phe Arg Glu Leu Leu Asn Glu Leu Trp Gln Lys
1 5 10 15

Leu Lys

<210> SEQ ID NO 220
<211> LENGTH: 18
<212> TYPE: PRT
<213> ORGANISM: Artificial sequence
<220> FEATURE:
<223> OTHER INFORMATION: synthetic

<400> SEQUENCE: 220

Pro Val Leu Asp Leu Phe Arg Glu Leu Leu Glu Glu Leu Gln Lys Lys
1 5 10 15

Leu Lys

<210> SEQ ID NO 221
<211> LENGTH: 18
<212> TYPE: PRT
<213> ORGANISM: Artificial sequence
<220> FEATURE:
<223> OTHER INFORMATION: synthetic

<400> SEQUENCE: 221

Asp Val Leu Asp Leu Phe Arg Glu Leu Leu Glu Glu Leu Lys Gln Lys
1 5 10 15

Leu Lys

<210> SEQ ID NO 222
<211> LENGTH: 18
<212> TYPE: PRT
<213> ORGANISM: Artificial sequence
<220> FEATURE:
<223> OTHER INFORMATION: synthetic

<400> SEQUENCE: 222

Pro Val Leu Asp Ala Phe Arg Glu Leu Leu Glu Ala Leu Leu Gln Leu
1 5 10 15

Lys Lys

<210> SEQ ID NO 223
<211> LENGTH: 18
<212> TYPE: PRT
<213> ORGANISM: Artificial sequence
<220> FEATURE:
<223> OTHER INFORMATION: synthetic

<400> SEQUENCE: 223

Pro Val Leu Asp Ala Phe Arg Glu Leu Leu Glu Ala Leu Ala Gln Leu
1 5 10 15

Lys Lys

<210> SEQ ID NO 224
<211> LENGTH: 18
<212> TYPE: PRT
<213> ORGANISM: Artificial sequence
<220> FEATURE:
<223> OTHER INFORMATION: synthetic

<400> SEQUENCE: 224

Pro Val Leu Asp Leu Phe Arg Glu Gly Trp Glu Glu Leu Lys Gln Lys
1 5 10 15

Leu Lys

<210> SEQ ID NO 225
<211> LENGTH: 18
<212> TYPE: PRT
<213> ORGANISM: Artificial sequence
<220> FEATURE:
<223> OTHER INFORMATION: synthetic

<400> SEQUENCE: 225

Pro Val Leu Asp Ala Phe Arg Glu Leu Ala Glu Ala Leu Ala Gln Leu
1 5 10 15

Lys Lys

<210> SEQ ID NO 226
<211> LENGTH: 18
<212> TYPE: PRT
<213> ORGANISM: Artificial sequence
<220> FEATURE:
<223> OTHER INFORMATION: synthetic

<400> SEQUENCE: 226

Pro Val Leu Asp Ala Phe Arg Glu Leu Gly Glu Ala Leu Leu Gln Leu
1 5 10 15

Lys Lys

<210> SEQ ID NO 227
<211> LENGTH: 18
<212> TYPE: PRT
<213> ORGANISM: Artificial sequence
<220> FEATURE:
<223> OTHER INFORMATION: synthetic

<400> SEQUENCE: 227

Pro Val Leu Asp Leu Phe Arg Glu Leu Gly Glu Glu Leu Lys Gln Lys
1 5 10 15

Leu Lys

<210> SEQ ID NO 228
<211> LENGTH: 18
<212> TYPE: PRT
<213> ORGANISM: Artificial sequence
<220> FEATURE:
<223> OTHER INFORMATION: synthetic

<400> SEQUENCE: 228

Pro Val Leu Asp Leu Phe Arg Glu Gly Leu Glu Glu Leu Lys Gln Lys
1 5 10 15

Leu Lys

<210> SEQ ID NO 229
<211> LENGTH: 18
<212> TYPE: PRT

<213> ORGANISM: Artificial sequence
<220> FEATURE:
<223> OTHER INFORMATION: synthetic

<400> SEQUENCE: 229

Pro Val Leu Asp Leu Phe Arg Glu Leu Leu Glu Glu Gly Lys Gln Lys
1 5 10 15

Leu Lys

<210> SEQ ID NO 230
<211> LENGTH: 18
<212> TYPE: PRT
<213> ORGANISM: Artificial sequence
<220> FEATURE:
<223> OTHER INFORMATION: synthetic

<400> SEQUENCE: 230

Pro Val Leu Glu Leu Phe Glu Arg Leu Leu Glu Asp Leu Gln Lys Lys
1 5 10 15

Leu Lys

<210> SEQ ID NO 231
<211> LENGTH: 18
<212> TYPE: PRT
<213> ORGANISM: Artificial sequence
<220> FEATURE:
<223> OTHER INFORMATION: synthetic

<400> SEQUENCE: 231

Pro Val Leu Asp Leu Phe Arg Glu Leu Leu Glu Lys Leu Glu Gln Lys
1 5 10 15

Leu Lys

<210> SEQ ID NO 232
<211> LENGTH: 18
<212> TYPE: PRT
<213> ORGANISM: Artificial sequence
<220> FEATURE:
<223> OTHER INFORMATION: synthetic

<400> SEQUENCE: 232

Pro Leu Leu Glu Leu Phe Lys Glu Leu Leu Glu Glu Leu Lys Gln Lys
1 5 10 15

Leu Lys

<210> SEQ ID NO 233
<211> LENGTH: 18
<212> TYPE: PRT
<213> ORGANISM: Artificial sequence
<220> FEATURE:
<223> OTHER INFORMATION: synthetic

<400> SEQUENCE: 233

Leu Asp Asp Leu Leu Gln Lys Trp Ala Glu Ala Phe Asn Gln Leu Leu
1 5 10 15

Lys Lys

<210> SEQ ID NO 234
<211> LENGTH: 18
<212> TYPE: PRT
<213> ORGANISM: Artificial sequence
<220> FEATURE:
<223> OTHER INFORMATION: synthetic

<400> SEQUENCE: 234

Glu Trp Leu Lys Ala Phe Tyr Glu Lys Val Leu Glu Lys Leu Lys Glu
1 5 10 15

Leu Phe

<210> SEQ ID NO 235
<211> LENGTH: 18
<212> TYPE: PRT
<213> ORGANISM: Artificial sequence
<220> FEATURE:
<223> OTHER INFORMATION: synthetic

<400> SEQUENCE: 235

Glu Trp Leu Glu Ala Phe Tyr Lys Lys Val Leu Glu Lys Leu Lys Glu
1 5 10 15

Leu Phe

<210> SEQ ID NO 236
<211> LENGTH: 18
<212> TYPE: PRT
<213> ORGANISM: Artificial sequence
<220> FEATURE:
<223> OTHER INFORMATION: synthetic

<400> SEQUENCE: 236

Asp Trp Leu Lys Ala Phe Tyr Asp Lys Val Ala Glu Lys Leu Lys Glu
1 5 10 15

Ala Phe

<210> SEQ ID NO 237
<211> LENGTH: 18
<212> TYPE: PRT
<213> ORGANISM: Artificial sequence
<220> FEATURE:
<223> OTHER INFORMATION: synthetic

<400> SEQUENCE: 237

Asp Trp Phe Lys Ala Phe Tyr Asp Lys Val Phe Glu Lys Phe Lys Glu
1 5 10 15

Phe Phe

<210> SEQ ID NO 238
<211> LENGTH: 18
<212> TYPE: PRT
<213> ORGANISM: Artificial sequence
<220> FEATURE:
<223> OTHER INFORMATION: synthetic

<400> SEQUENCE: 238

Gly Ile Lys Lys Phe Leu Gly Ser Ile Trp Lys Phe Ile Lys Ala Phe
1 5 10 15

Val Gly

<210> SEQ ID NO 239
<211> LENGTH: 18
<212> TYPE: PRT
<213> ORGANISM: Artificial sequence
<220> FEATURE:
<223> OTHER INFORMATION: synthetic

<400> SEQUENCE: 239

Asp Trp Phe Lys Ala Phe Tyr Asp Lys Val Ala Glu Lys Phe Lys Glu
1 5 10 15

Ala Phe

<210> SEQ ID NO 240
<211> LENGTH: 18
<212> TYPE: PRT
<213> ORGANISM: Artificial sequence
<220> FEATURE:
<223> OTHER INFORMATION: synthetic

<400> SEQUENCE: 240

Asp Trp Leu Lys Ala Phe Tyr Asp Lys Val Ala Glu Lys Leu Lys Glu
1 5 10 15

Ala Phe

<210> SEQ ID NO 241
<211> LENGTH: 18
<212> TYPE: PRT
<213> ORGANISM: Artificial sequence
<220> FEATURE:
<223> OTHER INFORMATION: synthetic

<400> SEQUENCE: 241

Asp Trp Leu Lys Ala Phe Tyr Asp Lys Val Phe Glu Lys Phe Lys Glu
1 5 10 15

Phe Phe

<210> SEQ ID NO 242
<211> LENGTH: 18
<212> TYPE: PRT
<213> ORGANISM: Artificial sequence
<220> FEATURE:
<223> OTHER INFORMATION: synthetic

<400> SEQUENCE: 242

Glu Trp Leu Glu Ala Phe Tyr Lys Lys Val Leu Glu Lys Leu Lys Glu
1 5 10 15

Leu Pro

<210> SEQ ID NO 243
<211> LENGTH: 18
<212> TYPE: PRT
<213> ORGANISM: Artificial sequence
<220> FEATURE:
<223> OTHER INFORMATION: synthetic

<400> SEQUENCE: 243

Asp Trp Phe Lys Ala Phe Tyr Asp Lys Phe Phe Glu Lys Phe Lys Glu
1 5 10 15

Phe Phe

<210> SEQ ID NO 244
<211> LENGTH: 18
<212> TYPE: PRT
<213> ORGANISM: Artificial sequence
<220> FEATURE:
<223> OTHER INFORMATION: synthetic

<400> SEQUENCE: 244

Glu Trp Leu Lys Ala Phe Tyr Glu Lys Val Leu Glu Lys Leu Lys Glu
1 5 10 15

Leu Phe

-continued

<210> SEQ ID NO 245
<211> LENGTH: 18
<212> TYPE: PRT
<213> ORGANISM: Artificial sequence
<220> FEATURE:
<223> OTHER INFORMATION: synthetic

<400> SEQUENCE: 245

Glu Trp Leu Lys Ala Glu Tyr Glu Lys Val Glu Glu Lys Leu Lys Glu
1 5 10 15

Leu Phe

<210> SEQ ID NO 246
<211> LENGTH: 18
<212> TYPE: PRT
<213> ORGANISM: Artificial sequence
<220> FEATURE:
<223> OTHER INFORMATION: synthetic

<400> SEQUENCE: 246

Glu Trp Leu Lys Ala Glu Tyr Glu Lys Val Leu Glu Lys Leu Lys Glu
1 5 10 15

Leu Phe

<210> SEQ ID NO 247
<211> LENGTH: 18
<212> TYPE: PRT
<213> ORGANISM: Artificial sequence
<220> FEATURE:
<223> OTHER INFORMATION: synthetic

<400> SEQUENCE: 247

Glu Trp Leu Lys Ala Phe Tyr Lys Lys Val Leu Glu Lys Leu Lys Glu
1 5 10 15

Leu Phe

<210> SEQ ID NO 248
<211> LENGTH: 15
<212> TYPE: PRT
<213> ORGANISM: Artificial sequence
<220> FEATURE:
<223> OTHER INFORMATION: synthetic

<400> SEQUENCE: 248

Pro Val Leu Asp Leu Phe Arg Glu Leu Leu Glu Gln Lys Leu Lys
1 5 10 15

<210> SEQ ID NO 249
<211> LENGTH: 16
<212> TYPE: PRT
<213> ORGANISM: Artificial sequence
<220> FEATURE:
<223> OTHER INFORMATION: synthetic

<400> SEQUENCE: 249

Pro Val Leu Asp Leu Phe Arg Glu Leu Leu Glu Glu Leu Lys Gln Lys
1 5 10 15

<210> SEQ ID NO 250
<211> LENGTH: 16
<212> TYPE: PRT
<213> ORGANISM: Artificial sequence
<220> FEATURE:
<223> OTHER INFORMATION: synthetic

<400> SEQUENCE: 250

```
Pro Val Leu Asp Leu Phe Arg Glu Leu Leu Glu Lys Leu Lys Gln Lys
1               5                   10                  15


<210> SEQ ID NO 251
<211> LENGTH: 15
<212> TYPE: PRT
<213> ORGANISM: Artificial sequence
<220> FEATURE:
<223> OTHER INFORMATION: synthetic

<400> SEQUENCE: 251

Pro Val Leu Asp Leu Phe Arg Glu Leu Leu Glu Lys Leu Gln Lys
1               5                   10                  15


<210> SEQ ID NO 252
<211> LENGTH: 16
<212> TYPE: PRT
<213> ORGANISM: Artificial sequence
<220> FEATURE:
<223> OTHER INFORMATION: synthetic

<400> SEQUENCE: 252

Pro Val Leu Asp Leu Phe Arg Glu Leu Leu Glu Ala Leu Lys Gln Lys
1               5                   10                  15


<210> SEQ ID NO 253
<211> LENGTH: 16
<212> TYPE: PRT
<213> ORGANISM: Artificial sequence
<220> FEATURE:
<223> OTHER INFORMATION: synthetic

<400> SEQUENCE: 253

Pro Val Leu Asp Leu Phe Glu Asn Leu Leu Glu Arg Leu Lys Gln Lys
1               5                   10                  15


<210> SEQ ID NO 254
<211> LENGTH: 16
<212> TYPE: PRT
<213> ORGANISM: Artificial sequence
<220> FEATURE:
<223> OTHER INFORMATION: synthetic

<400> SEQUENCE: 254

Pro Val Leu Asp Leu Phe Arg Glu Leu Leu Asn Glu Leu Lys Gln Lys
1               5                   10                  15


<210> SEQ ID NO 255
<211> LENGTH: 18
<212> TYPE: PRT
<213> ORGANISM: Artificial sequence
<220> FEATURE:
<223> OTHER INFORMATION: synthetic

<400> SEQUENCE: 255

Asp Trp Leu Lys Ala Phe Tyr Asp Lys Val Ala Glu Lys Leu Lys Glu
1               5                   10                  15

Ala Phe


<210> SEQ ID NO 256
<211> LENGTH: 18
<212> TYPE: PRT
<213> ORGANISM: Artificial sequence
<220> FEATURE:
<223> OTHER INFORMATION: synthetic
```

<400> SEQUENCE: 256

Asp Trp Leu Lys Ala Phe Tyr Asp Lys Val Ala Glu Lys Leu Lys Glu
1 5 10 15

Ala Phe

<210> SEQ ID NO 257
<211> LENGTH: 18
<212> TYPE: PRT
<213> ORGANISM: Artificial sequence
<220> FEATURE:
<223> OTHER INFORMATION: synthetic

<400> SEQUENCE: 257

Asp Trp Leu Lys Ala Phe Tyr Asp Lys Val Ala Glu Lys Leu Lys Glu
1 5 10 15

Ala Phe

<210> SEQ ID NO 258
<211> LENGTH: 18
<212> TYPE: PRT
<213> ORGANISM: Artificial sequence
<220> FEATURE:
<223> OTHER INFORMATION: synthetic

<400> SEQUENCE: 258

Asp Trp Phe Lys Ala Phe Tyr Asp Lys Val Ala Glu Lys Leu Lys Glu
1 5 10 15

Ala Phe

<210> SEQ ID NO 259
<211> LENGTH: 18
<212> TYPE: PRT
<213> ORGANISM: Artificial sequence
<220> FEATURE:
<223> OTHER INFORMATION: synthetic

<400> SEQUENCE: 259

Asp Trp Leu Lys Ala Phe Tyr Asp Lys Val Ala Glu Lys Phe Lys Glu
1 5 10 15

Ala Phe

<210> SEQ ID NO 260
<211> LENGTH: 18
<212> TYPE: PRT
<213> ORGANISM: Artificial sequence
<220> FEATURE:
<223> OTHER INFORMATION: synthetic

<400> SEQUENCE: 260

Asp Trp Phe Lys Ala Phe Tyr Asp Lys Val Ala Glu Lys Phe Lys Glu
1 5 10 15

Ala Phe

<210> SEQ ID NO 261
<211> LENGTH: 18
<212> TYPE: PRT
<213> ORGANISM: Artificial sequence
<220> FEATURE:
<223> OTHER INFORMATION: synthetic

<400> SEQUENCE: 261

Asp Trp Leu Lys Ala Phe Tyr Asp Lys Val Phe Glu Lys Phe Lys Glu
1 5 10 15

Phe Phe

<210> SEQ ID NO 262
<211> LENGTH: 18
<212> TYPE: PRT
<213> ORGANISM: Artificial sequence
<220> FEATURE:
<223> OTHER INFORMATION: synthetic

<400> SEQUENCE: 262

Asp Trp Leu Lys Ala Phe Tyr Asp Lys Phe Phe Glu Lys Phe Lys Glu
1 5 10 15

Phe Phe

<210> SEQ ID NO 263
<211> LENGTH: 18
<212> TYPE: PRT
<213> ORGANISM: Artificial sequence
<220> FEATURE:
<223> OTHER INFORMATION: synthetic

<400> SEQUENCE: 263

Asp Trp Phe Lys Ala Phe Tyr Asp Lys Phe Phe Glu Lys Phe Lys Glu
1 5 10 15

Phe Phe

<210> SEQ ID NO 264
<211> LENGTH: 18
<212> TYPE: PRT
<213> ORGANISM: Artificial sequence
<220> FEATURE:
<223> OTHER INFORMATION: synthetic

<400> SEQUENCE: 264

Asp Trp Leu Lys Ala Phe Tyr Asp Lys Val Ala Glu Lys Leu Lys Glu
1 5 10 15

Phe Phe

<210> SEQ ID NO 265
<211> LENGTH: 18
<212> TYPE: PRT
<213> ORGANISM: Artificial sequence
<220> FEATURE:
<223> OTHER INFORMATION: synthetic

<400> SEQUENCE: 265

Asp Trp Leu Lys Ala Phe Tyr Asp Lys Val Phe Glu Lys Phe Lys Glu
1 5 10 15

Ala Phe

<210> SEQ ID NO 266
<211> LENGTH: 18
<212> TYPE: PRT
<213> ORGANISM: Artificial sequence
<220> FEATURE:
<223> OTHER INFORMATION: synthetic

<400> SEQUENCE: 266

Asp Trp Leu Lys Ala Phe Tyr Asp Lys Val Phe Glu Lys Leu Lys Glu
1 5 10 15

Phe Phe

<210> SEQ ID NO 267
<211> LENGTH: 18
<212> TYPE: PRT
<213> ORGANISM: Artificial sequence
<220> FEATURE:
<223> OTHER INFORMATION: synthetic

<400> SEQUENCE: 267

Asp Trp Leu Lys Ala Phe Tyr Asp Lys Val Ala Glu Lys Phe Lys Glu
1 5 10 15

Phe Phe

<210> SEQ ID NO 268
<211> LENGTH: 18
<212> TYPE: PRT
<213> ORGANISM: Artificial sequence
<220> FEATURE:
<223> OTHER INFORMATION: synthetic

<400> SEQUENCE: 268

Asp Trp Leu Lys Ala Phe Tyr Asp Lys Val Phe Glu Lys Phe Lys Glu
1 5 10 15

Phe Phe

<210> SEQ ID NO 269
<211> LENGTH: 18
<212> TYPE: PRT
<213> ORGANISM: Artificial sequence
<220> FEATURE:
<223> OTHER INFORMATION: synthetic

<400> SEQUENCE: 269

Glu Trp Leu Lys Leu Phe Tyr Glu Lys Val Leu Glu Lys Phe Lys Glu
1 5 10 15

Ala Phe

<210> SEQ ID NO 270
<211> LENGTH: 18
<212> TYPE: PRT
<213> ORGANISM: Artificial sequence
<220> FEATURE:
<223> OTHER INFORMATION: synthetic

<400> SEQUENCE: 270

Glu Trp Leu Lys Ala Phe Tyr Asp Lys Val Ala Glu Lys Phe Lys Glu
1 5 10 15

Ala Phe

<210> SEQ ID NO 271
<211> LENGTH: 18
<212> TYPE: PRT
<213> ORGANISM: Artificial sequence
<220> FEATURE:
<223> OTHER INFORMATION: synthetic

<400> SEQUENCE: 271

Glu Trp Leu Lys Ala Phe Tyr Asp Lys Val Ala Glu Lys Leu Lys Glu
1 5 10 15

Phe Phe

<210> SEQ ID NO 272
<211> LENGTH: 18
<212> TYPE: PRT
<213> ORGANISM: Artificial sequence
<220> FEATURE:
<223> OTHER INFORMATION: synthetic

<400> SEQUENCE: 272

Glu Trp Leu Lys Ala Phe Tyr Asp Lys Val Phe Glu Lys Phe Lys Glu
1 5 10 15

Ala Phe

<210> SEQ ID NO 273
<211> LENGTH: 18
<212> TYPE: PRT
<213> ORGANISM: Artificial sequence
<220> FEATURE:
<223> OTHER INFORMATION: synthetic

<400> SEQUENCE: 273

Glu Trp Leu Lys Ala Phe Tyr Asp Lys Val Phe Glu Lys Leu Lys Glu
1 5 10 15

Phe Phe

<210> SEQ ID NO 274
<211> LENGTH: 18
<212> TYPE: PRT
<213> ORGANISM: Artificial sequence
<220> FEATURE:
<223> OTHER INFORMATION: synthetic

<400> SEQUENCE: 274

Glu Trp Leu Lys Ala Phe Tyr Asp Lys Val Ala Glu Lys Phe Lys Glu
1 5 10 15

Phe Phe

<210> SEQ ID NO 275
<211> LENGTH: 18
<212> TYPE: PRT
<213> ORGANISM: Artificial sequence
<220> FEATURE:
<223> OTHER INFORMATION: synthetic

<400> SEQUENCE: 275

Glu Trp Leu Lys Ala Phe Tyr Asp Lys Val Phe Glu Lys Phe Lys Glu
1 5 10 15

Phe Phe

<210> SEQ ID NO 276
<211> LENGTH: 14
<212> TYPE: PRT
<213> ORGANISM: Artificial sequence
<220> FEATURE:
<223> OTHER INFORMATION: synthetic

<400> SEQUENCE: 276

Ala Phe Tyr Asp Lys Val Ala Glu Lys Leu Lys Glu Ala Phe
1 5 10

<210> SEQ ID NO 277
<211> LENGTH: 14
<212> TYPE: PRT
<213> ORGANISM: Artificial sequence
<220> FEATURE:
<223> OTHER INFORMATION: synthetic

<400> SEQUENCE: 277

Ala Phe Tyr Asp Lys Val Ala Glu Lys Phe Lys Glu Ala Phe 1 5 10

<210> SEQ ID NO 278
<211> LENGTH: 14
<212> TYPE: PRT
<213> ORGANISM: Artificial sequence
<220> FEATURE:
<223> OTHER INFORMATION: synthetic

<400> SEQUENCE: 278

Ala Phe Tyr Asp Lys Val Ala Glu Lys Phe Lys Glu Ala Phe
1 5 10

<210> SEQ ID NO 279
<211> LENGTH: 14
<212> TYPE: PRT
<213> ORGANISM: Artificial sequence
<220> FEATURE:
<223> OTHER INFORMATION: synthetic

<400> SEQUENCE: 279

Ala Phe Tyr Asp Lys Phe Phe Glu Lys Phe Lys Glu Phe Phe
1 5 10

<210> SEQ ID NO 280
<211> LENGTH: 14
<212> TYPE: PRT
<213> ORGANISM: Artificial sequence
<220> FEATURE:
<223> OTHER INFORMATION: synthetic

<400> SEQUENCE: 280

Ala Phe Tyr Asp Lys Phe Phe Glu Lys Phe Lys Glu Phe Phe
1 5 10

<210> SEQ ID NO 281
<211> LENGTH: 14
<212> TYPE: PRT
<213> ORGANISM: Artificial sequence
<220> FEATURE:
<223> OTHER INFORMATION: synthetic

<400> SEQUENCE: 281

Ala Phe Tyr Asp Lys Val Ala Glu Lys Phe Lys Glu Ala Phe
1 5 10

<210> SEQ ID NO 282
<211> LENGTH: 14
<212> TYPE: PRT
<213> ORGANISM: Artificial sequence
<220> FEATURE:
<223> OTHER INFORMATION: synthetic

<400> SEQUENCE: 282

Ala Phe Tyr Asp Lys Val Ala Glu Lys Leu Lys Glu Phe Phe
1 5 10

<210> SEQ ID NO 283
<211> LENGTH: 14
<212> TYPE: PRT
<213> ORGANISM: Artificial sequence
<220> FEATURE:
<223> OTHER INFORMATION: synthetic

<400> SEQUENCE: 283

Ala Phe Tyr Asp Lys Val Phe Glu Lys Phe Lys Glu Ala Phe
1 5 10

<210> SEQ ID NO 284
<211> LENGTH: 14
<212> TYPE: PRT
<213> ORGANISM: Artificial sequence
<220> FEATURE:
<223> OTHER INFORMATION: synthetic

<400> SEQUENCE: 284

Ala Phe Tyr Asp Lys Val Phe Glu Lys Leu Lys Glu Phe Phe
1 5 10

<210> SEQ ID NO 285
<211> LENGTH: 14
<212> TYPE: PRT
<213> ORGANISM: Artificial sequence
<220> FEATURE:
<223> OTHER INFORMATION: synthetic

<400> SEQUENCE: 285

Ala Phe Tyr Asp Lys Val Ala Glu Lys Phe Lys Glu Phe Phe
1 5 10

<210> SEQ ID NO 286
<211> LENGTH: 14
<212> TYPE: PRT
<213> ORGANISM: Artificial sequence
<220> FEATURE:
<223> OTHER INFORMATION: synthetic

<400> SEQUENCE: 286

Lys Ala Phe Tyr Asp Lys Val Phe Glu Lys Phe Lys Glu Phe
1 5 10

<210> SEQ ID NO 287
<211> LENGTH: 14
<212> TYPE: PRT
<213> ORGANISM: Artificial sequence
<220> FEATURE:
<223> OTHER INFORMATION: synthetic

<400> SEQUENCE: 287

Leu Phe Tyr Glu Lys Val Leu Glu Lys Phe Lys Glu Ala Phe
1 5 10

<210> SEQ ID NO 288
<211> LENGTH: 14
<212> TYPE: PRT
<213> ORGANISM: Artificial sequence
<220> FEATURE:
<223> OTHER INFORMATION: synthetic

<400> SEQUENCE: 288

Ala Phe Tyr Asp Lys Val Ala Glu Lys Phe Lys Glu Ala Phe
1 5 10

<210> SEQ ID NO 289
<211> LENGTH: 14
<212> TYPE: PRT
<213> ORGANISM: Artificial sequence
<220> FEATURE:
<223> OTHER INFORMATION: synthetic

<400> SEQUENCE: 289

Ala Phe Tyr Asp Lys Val Ala Glu Lys Leu Lys Glu Phe Phe
1 5 10

<210> SEQ ID NO 290
<211> LENGTH: 14
<212> TYPE: PRT
<213> ORGANISM: Artificial sequence
<220> FEATURE:
<223> OTHER INFORMATION: synthetic

<400> SEQUENCE: 290

Ala Phe Tyr Asp Lys Val Phe Glu Lys Phe Lys Glu Ala Phe
1 5 10

<210> SEQ ID NO 291
<211> LENGTH: 14
<212> TYPE: PRT
<213> ORGANISM: Artificial sequence
<220> FEATURE:
<223> OTHER INFORMATION: synthetic

<400> SEQUENCE: 291

Ala Phe Tyr Asp Lys Val Phe Glu Lys Leu Lys Glu Phe Phe
1 5 10

<210> SEQ ID NO 292
<211> LENGTH: 14
<212> TYPE: PRT
<213> ORGANISM: Artificial sequence
<220> FEATURE:
<223> OTHER INFORMATION: synthetic

<400> SEQUENCE: 292

Ala Phe Tyr Asp Lys Val Ala Glu Lys Phe Lys Glu Phe Phe
1 5 10

<210> SEQ ID NO 293
<211> LENGTH: 14
<212> TYPE: PRT
<213> ORGANISM: Artificial sequence
<220> FEATURE:
<223> OTHER INFORMATION: synthetic

<400> SEQUENCE: 293

Ala Phe Tyr Asp Lys Val Phe Glu Lys Phe Lys Glu Phe Phe
1 5 10

<210> SEQ ID NO 294
<211> LENGTH: 18
<212> TYPE: PRT
<213> ORGANISM: Artificial sequence
<220> FEATURE:
<223> OTHER INFORMATION: synthetic

<400> SEQUENCE: 294

Asp Trp Leu Lys Ala Leu Tyr Asp Lys Val Ala Glu Lys Leu Lys Glu
1 5 10 15

Ala Leu

<210> SEQ ID NO 295
<211> LENGTH: 18
<212> TYPE: PRT
<213> ORGANISM: Artificial sequence
<220> FEATURE:
<223> OTHER INFORMATION: synthetic

<400> SEQUENCE: 295

Asp Trp Phe Lys Ala Phe Tyr Glu Lys Val Ala Glu Lys Leu Lys Glu
1 5 10 15

Phe Phe

<210> SEQ ID NO 296
<211> LENGTH: 18
<212> TYPE: PRT
<213> ORGANISM: Artificial sequence
<220> FEATURE:
<223> OTHER INFORMATION: synthetic

<400> SEQUENCE: 296

Asp Trp Phe Lys Ala Phe Tyr Glu Lys Phe Phe Glu Lys Phe Lys Glu
1 5 10 15

Phe Phe

<210> SEQ ID NO 297
<211> LENGTH: 18
<212> TYPE: PRT
<213> ORGANISM: Artificial sequence
<220> FEATURE:
<223> OTHER INFORMATION: synthetic

<400> SEQUENCE: 297

Glu Trp Leu Lys Ala Leu Tyr Glu Lys Val Ala Glu Lys Leu Lys Glu
1 5 10 15

Ala Leu

<210> SEQ ID NO 298
<211> LENGTH: 18
<212> TYPE: PRT
<213> ORGANISM: Artificial sequence
<220> FEATURE:
<223> OTHER INFORMATION: synthetic

<400> SEQUENCE: 298

Glu Trp Leu Lys Ala Phe Tyr Glu Lys Val Ala Glu Lys Leu Lys Glu
1 5 10 15

Ala Phe

<210> SEQ ID NO 299
<211> LENGTH: 18
<212> TYPE: PRT
<213> ORGANISM: Artificial sequence
<220> FEATURE:
<223> OTHER INFORMATION: synthetic

<400> SEQUENCE: 299

Glu Trp Phe Lys Ala Phe Tyr Glu Lys Val Ala Glu Lys Leu Lys Glu
1 5 10 15

Phe Phe

<210> SEQ ID NO 300
<211> LENGTH: 18
<212> TYPE: PRT
<213> ORGANISM: Artificial sequence
<220> FEATURE:
<223> OTHER INFORMATION: synthetic

<400> SEQUENCE: 300

Glu Trp Leu Lys Ala Phe Tyr Glu Lys Val Phe Glu Lys Phe Lys Glu
1 5 10 15

Phe Phe

<210> SEQ ID NO 301
<211> LENGTH: 18
<212> TYPE: PRT
<213> ORGANISM: Artificial sequence
<220> FEATURE:
<223> OTHER INFORMATION: synthetic

<400> SEQUENCE: 301

Glu Trp Leu Lys Ala Phe Tyr Glu Lys Phe Phe Glu Lys Phe Lys Glu
1 5 10 15

Phe Phe

<210> SEQ ID NO 302
<211> LENGTH: 18
<212> TYPE: PRT
<213> ORGANISM: Artificial sequence
<220> FEATURE:
<223> OTHER INFORMATION: synthetic

<400> SEQUENCE: 302

Glu Trp Phe Lys Ala Phe Tyr Glu Lys Phe Phe Glu Lys Phe Lys Glu
1 5 10 15

Phe Phe

<210> SEQ ID NO 303
<211> LENGTH: 18
<212> TYPE: PRT
<213> ORGANISM: Artificial sequence
<220> FEATURE:
<223> OTHER INFORMATION: synthetic

<400> SEQUENCE: 303

Asp Phe Leu Lys Ala Trp Tyr Asp Lys Val Ala Glu Lys Leu Lys Glu
1 5 10 15

Ala Trp

<210> SEQ ID NO 304
<211> LENGTH: 18
<212> TYPE: PRT
<213> ORGANISM: Artificial sequence
<220> FEATURE:
<223> OTHER INFORMATION: synthetic

<400> SEQUENCE: 304

Glu Phe Leu Lys Ala Trp Tyr Glu Lys Val Ala Glu Lys Leu Lys Glu
1 5 10 15

Ala Trp

<210> SEQ ID NO 305
<211> LENGTH: 18
<212> TYPE: PRT
<213> ORGANISM: Artificial sequence
<220> FEATURE:
<223> OTHER INFORMATION: synthetic

<400> SEQUENCE: 305

Asp Phe Trp Lys Ala Trp Tyr Asp Lys Val Ala Glu Lys Leu Lys Glu
1 5 10 15

Trp Trp

<210> SEQ ID NO 306
<211> LENGTH: 18
<212> TYPE: PRT
<213> ORGANISM: Artificial sequence -continued
<220> FEATURE:
<223> OTHER INFORMATION: synthetic

<400> SEQUENCE: 306

Glu Phe Trp Lys Ala Trp Tyr Glu Lys Val Ala Glu Lys Leu Lys Glu
1               5                   10                  15

Trp Trp

<210> SEQ ID NO 307
<211> LENGTH: 18
<212> TYPE: PRT
<213> ORGANISM: Artificial sequence
<220> FEATURE:
<223> OTHER INFORMATION: synthetic

<400> SEQUENCE: 307

Asp Lys Leu Lys Ala Phe Tyr Asp Lys Val Phe Glu Trp Ala Lys Glu
1               5                   10                  15

Ala Phe

<210> SEQ ID NO 308
<211> LENGTH: 18
<212> TYPE: PRT
<213> ORGANISM: Artificial sequence
<220> FEATURE:
<223> OTHER INFORMATION: synthetic

<400> SEQUENCE: 308

Asp Lys Trp Lys Ala Val Tyr Asp Lys Phe Ala Glu Ala Phe Lys Glu
1               5                   10                  15

Phe Leu

<210> SEQ ID NO 309
<211> LENGTH: 18
<212> TYPE: PRT
<213> ORGANISM: Artificial sequence
<220> FEATURE:
<223> OTHER INFORMATION: synthetic

<400> SEQUENCE: 309

Glu Lys Leu Lys Ala Phe Tyr Glu Lys Val Phe Glu Trp Ala Lys Glu
1               5                   10                  15

Ala Phe

<210> SEQ ID NO 310
<211> LENGTH: 18
<212> TYPE: PRT
<213> ORGANISM: Artificial sequence
<220> FEATURE:
<223> OTHER INFORMATION: synthetic

<400> SEQUENCE: 310

Glu Lys Trp Lys Ala Val Tyr Glu Lys Phe Ala Glu Ala Phe Lys Glu
1               5                   10                  15

Phe Leu

<210> SEQ ID NO 311
<211> LENGTH: 18
<212> TYPE: PRT
<213> ORGANISM: Artificial sequence
<220> FEATURE:
<223> OTHER INFORMATION: synthetic

<400> SEQUENCE: 311

Asp Trp Leu Lys Ala Phe Val Asp Lys Phe Ala Glu Lys Phe Lys Glu
1 5 10 15

Ala Tyr

<210> SEQ ID NO 312
<211> LENGTH: 18
<212> TYPE: PRT
<213> ORGANISM: Artificial sequence
<220> FEATURE:
<223> OTHER INFORMATION: synthetic

<400> SEQUENCE: 312

Glu Lys Trp Lys Ala Val Tyr Glu Lys Phe Ala Glu Ala Phe Lys Glu
1 5 10 15

Phe Leu

<210> SEQ ID NO 313
<211> LENGTH: 18
<212> TYPE: PRT
<213> ORGANISM: Artificial sequence
<220> FEATURE:
<223> OTHER INFORMATION: synthetic

<400> SEQUENCE: 313

Asp Trp Leu Lys Ala Phe Val Tyr Asp Lys Val Phe Lys Leu Lys Glu
1 5 10 15

Phe Phe

<210> SEQ ID NO 314
<211> LENGTH: 18
<212> TYPE: PRT
<213> ORGANISM: Artificial sequence
<220> FEATURE:
<223> OTHER INFORMATION: synthetic

<400> SEQUENCE: 314

Glu Trp Leu Lys Ala Phe Val Tyr Glu Lys Val Phe Lys Leu Lys Glu
1 5 10 15

Phe Phe

<210> SEQ ID NO 315
<211> LENGTH: 18
<212> TYPE: PRT
<213> ORGANISM: Artificial sequence
<220> FEATURE:
<223> OTHER INFORMATION: synthetic

<400> SEQUENCE: 315

Asp Trp Leu Arg Ala Phe Tyr Asp Lys Val Ala Glu Lys Leu Lys Glu
1 5 10 15

Ala Phe

<210> SEQ ID NO 316
<211> LENGTH: 18
<212> TYPE: PRT
<213> ORGANISM: Artificial sequence
<220> FEATURE:
<223> OTHER INFORMATION: synthetic

<400> SEQUENCE: 316

Glu Trp Leu Arg Ala Phe Tyr Glu Lys Val Ala Glu Lys Leu Lys Glu
1 5 10 15

Ala Phe

<210> SEQ ID NO 317
<211> LENGTH: 18
<212> TYPE: PRT
<213> ORGANISM: Artificial sequence
<220> FEATURE:
<223> OTHER INFORMATION: synthetic

<400> SEQUENCE: 317

Asp Trp Leu Lys Ala Phe Tyr Asp Arg Val Ala Glu Lys Leu Lys Glu
1 5 10 15

Ala Phe

<210> SEQ ID NO 318
<211> LENGTH: 18
<212> TYPE: PRT
<213> ORGANISM: Artificial sequence
<220> FEATURE:
<223> OTHER INFORMATION: synthetic

<400> SEQUENCE: 318

Glu Trp Leu Lys Ala Phe Tyr Glu Arg Val Ala Glu Lys Leu Lys Glu
1 5 10 15

Ala Phe

<210> SEQ ID NO 319
<211> LENGTH: 18
<212> TYPE: PRT
<213> ORGANISM: Artificial sequence
<220> FEATURE:
<223> OTHER INFORMATION: synthetic

<400> SEQUENCE: 319

Asp Trp Leu Lys Ala Phe Tyr Asp Lys Val Ala Glu Arg Leu Lys Glu
1 5 10 15

Ala Phe

<210> SEQ ID NO 320
<211> LENGTH: 18
<212> TYPE: PRT
<213> ORGANISM: Artificial sequence
<220> FEATURE:
<223> OTHER INFORMATION: synthetic

<400> SEQUENCE: 320

Glu Trp Leu Lys Ala Phe Tyr Glu Lys Val Ala Glu Arg Leu Lys Glu
1 5 10 15

Ala Phe

<210> SEQ ID NO 321
<211> LENGTH: 18
<212> TYPE: PRT
<213> ORGANISM: Artificial sequence
<220> FEATURE:
<223> OTHER INFORMATION: synthetic

<400> SEQUENCE: 321

Asp Trp Leu Lys Ala Phe Tyr Asp Lys Val Ala Glu Lys Leu Arg Glu
1 5 10 15

Ala Phe

<210> SEQ ID NO 322

<211> LENGTH: 18
<212> TYPE: PRT
<213> ORGANISM: Artificial sequence
<220> FEATURE:
<223> OTHER INFORMATION: synthetic

<400> SEQUENCE: 322

Glu Trp Leu Lys Ala Phe Tyr Glu Lys Val Ala Glu Lys Leu Arg Glu
1 5 10 15

Ala Phe

<210> SEQ ID NO 323
<211> LENGTH: 18
<212> TYPE: PRT
<213> ORGANISM: Artificial sequence
<220> FEATURE:
<223> OTHER INFORMATION: synthetic

<400> SEQUENCE: 323

Asp Trp Leu Lys Ala Phe Tyr Asp Arg Val Ala Glu Arg Leu Lys Glu
1 5 10 15

Ala Phe

<210> SEQ ID NO 324
<211> LENGTH: 18
<212> TYPE: PRT
<213> ORGANISM: Artificial sequence
<220> FEATURE:
<223> OTHER INFORMATION: synthetic

<400> SEQUENCE: 324

Glu Trp Leu Lys Ala Phe Tyr Glu Arg Val Ala Glu Arg Leu Lys Glu
1 5 10 15

Ala Phe

<210> SEQ ID NO 325
<211> LENGTH: 18
<212> TYPE: PRT
<213> ORGANISM: Artificial sequence
<220> FEATURE:
<223> OTHER INFORMATION: synthetic

<400> SEQUENCE: 325

Asp Trp Leu Arg Ala Phe Tyr Asp Lys Val Ala Glu Lys Leu Arg Glu
1 5 10 15

Ala Phe

<210> SEQ ID NO 326
<211> LENGTH: 18
<212> TYPE: PRT
<213> ORGANISM: Artificial sequence
<220> FEATURE:
<223> OTHER INFORMATION: synthetic

<400> SEQUENCE: 326

Glu Trp Leu Arg Ala Phe Tyr Glu Lys Val Ala Glu Lys Leu Arg Glu
1 5 10 15

Ala Phe

<210> SEQ ID NO 327
<211> LENGTH: 18
<212> TYPE: PRT
<213> ORGANISM: Artificial sequence
<220> FEATURE:

-continued

<223> OTHER INFORMATION: synthetic

<400> SEQUENCE: 327

Asp Trp Leu Arg Ala Phe Tyr Asp Arg Val Ala Glu Lys Leu Lys Glu
1 5 10 15

Ala Phe

<210> SEQ ID NO 328
<211> LENGTH: 18
<212> TYPE: PRT
<213> ORGANISM: Artificial sequence
<220> FEATURE:
<223> OTHER INFORMATION: synthetic

<400> SEQUENCE: 328

Glu Trp Leu Arg Ala Phe Tyr Glu Arg Val Ala Glu Lys Leu Lys Glu
1 5 10 15

Ala Phe

<210> SEQ ID NO 329
<211> LENGTH: 18
<212> TYPE: PRT
<213> ORGANISM: Artificial sequence
<220> FEATURE:
<223> OTHER INFORMATION: synthetic

<400> SEQUENCE: 329

Asp Trp Leu Lys Ala Phe Tyr Asp Lys Val Ala Glu Arg Leu Arg Glu
1 5 10 15

Ala Phe

<210> SEQ ID NO 330
<211> LENGTH: 18
<212> TYPE: PRT
<213> ORGANISM: Artificial sequence
<220> FEATURE:
<223> OTHER INFORMATION: synthetic

<400> SEQUENCE: 330

Glu Trp Leu Lys Ala Phe Tyr Glu Lys Val Ala Glu Arg Leu Arg Glu
1 5 10 15

Ala Phe

<210> SEQ ID NO 331
<211> LENGTH: 18
<212> TYPE: PRT
<213> ORGANISM: Artificial sequence
<220> FEATURE:
<223> OTHER INFORMATION: synthetic

<400> SEQUENCE: 331

Asp Trp Leu Arg Ala Phe Tyr Asp Lys Val Ala Glu Arg Leu Lys Glu
1 5 10 15

Ala Phe

<210> SEQ ID NO 332
<211> LENGTH: 18
<212> TYPE: PRT
<213> ORGANISM: Artificial sequence
<220> FEATURE:
<223> OTHER INFORMATION: synthetic

<400> SEQUENCE: 332

-continued

```
Glu Trp Leu Arg Ala Phe Tyr Glu Lys Val Ala Glu Arg Leu Lys Glu
1               5                   10                  15

Ala Phe


<210> SEQ ID NO 333
<211> LENGTH: 18
<212> TYPE: PRT
<213> ORGANISM: Artificial sequence
<220> FEATURE:
<223> OTHER INFORMATION: synthetic

<400> SEQUENCE: 333

Phe Ala Glu Lys Phe Lys Glu Ala Val Lys Asp Tyr Phe Ala Lys Phe
1               5                   10                  15

Trp Asp


<210> SEQ ID NO 334
<211> LENGTH: 18
<212> TYPE: PRT
<213> ORGANISM: Artificial sequence
<220> FEATURE:
<223> OTHER INFORMATION: synthetic

<400> SEQUENCE: 334

Asp Trp Phe Lys Ala Phe Tyr Asp Lys Val Ala Glu Lys Phe Lys Glu
1               5                   10                  15

Ala Phe


<210> SEQ ID NO 335
<211> LENGTH: 18
<212> TYPE: PRT
<213> ORGANISM: Artificial sequence
<220> FEATURE:
<223> OTHER INFORMATION: synthetic

<400> SEQUENCE: 335

Asp Trp Leu Lys Ala Phe Tyr Asp Lys Val Ala Glu Lys Leu Lys Glu
1               5                   10                  15

Ala Phe


<210> SEQ ID NO 336
<211> LENGTH: 34
<212> TYPE: PRT
<213> ORGANISM: Artificial sequence
<220> FEATURE:
<223> OTHER INFORMATION: synthetic

<400> SEQUENCE: 336

Pro Ala Leu Glu Asp Leu Arg Gln Gly Leu Leu Pro Val Leu Glu Ser
1               5                   10                  15

Phe Lys Val Phe Leu Ser Ala Leu Glu Glu Tyr Thr Lys Lys Leu Asn
            20                  25                  30

Thr Gln


<210> SEQ ID NO 337
<211> LENGTH: 23
<212> TYPE: DNA
<213> ORGANISM: Artificial sequence
<220> FEATURE:
<223> OTHER INFORMATION: synthetic

<400> SEQUENCE: 337

gccagtatgc aagggagctc atg                                          23
```

<210> SEQ ID NO 338
<211> LENGTH: 25
<212> TYPE: PRT
<213> ORGANISM: Artificial sequence
<220> FEATURE:
<223> OTHER INFORMATION: synthetic

<400> SEQUENCE: 338

Gly Ala Ser Thr Ala Met Gly Ala Thr Cys Ala Asn Cys Ala Arg Gly
1 5 10 15

Gly Glu Gly Cys Leu Cys Ala Met Gly
20 25

<210> SEQ ID NO 339
<211> LENGTH: 23
<212> TYPE: DNA
<213> ORGANISM: Artificial sequence
<220> FEATURE:
<223> OTHER INFORMATION: synthetic

<400> SEQUENCE: 339
gccagtatgc aatggagctc atg 23

<210> SEQ ID NO 340
<211> LENGTH: 25
<212> TYPE: PRT
<213> ORGANISM: Artificial sequence
<220> FEATURE:
<223> OTHER INFORMATION: synthetic

<400> SEQUENCE: 340

Gly Ala Ser Thr Ala Met Gly Ala Thr Cys Ala Asn Cys Ala Met Gly
1 5 10 15

Gly Glu Gly Cys Leu Cys Ala Thr Gly
20 25

<210> SEQ ID NO 341
<211> LENGTH: 26
<212> TYPE: PRT
<213> ORGANISM: Artificial sequence
<220> FEATURE:
<223> OTHER INFORMATION: synthetic

<400> SEQUENCE: 341

Trp Asp Arg Val Lys Asp Leu Ala Thr Val Tyr Val Asp Val Leu Lys
1 5 10 15

Asp Ser Gly Arg Asp Tyr Val Ser Gln Phe
20 25

<210> SEQ ID NO 342
<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (20)..(20)
<223> OTHER INFORMATION: Xaa = Hydroxyproline

<400> SEQUENCE: 342

Leu Lys Leu Leu Asp Asn Trp Asp Ser Val Thr Ser Thr Phe Ser Lys
1 5 10 15

Leu Arg Glu Xaa Leu

20

<210> SEQ ID NO 343
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa = Hydroxyproline
<220> FEATURE:
<221> NAME/KEY: misc_feature
<222> LOCATION: (19)..(19)
<223> OTHER INFORMATION: Xaa = Hydroxyproline

<400> SEQUENCE: 343

Pro Val Thr Xaa Glu Phe Trp Asp Asn Leu Glu Lys Glu Thr Glu Gly
1 5 10 15

Leu Arg Xaa Glu Met Ser
20

<210> SEQ ID NO 344
<211> LENGTH: 11
<212> TYPE: PRT
<213> ORGANISM: Artificial sequence
<220> FEATURE:
<223> OTHER INFORMATION: synthetic

<400> SEQUENCE: 344

Lys Asp Leu Glu Glu Val Lys Ala Lys Val Gln
1 5 10

<210> SEQ ID NO 345
<211> LENGTH: 11
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: Xaa = Hydroxyproline

<400> SEQUENCE: 345

Lys Asp Leu Glu Glu Val Lys Ala Lys Val Xaa
1 5 10

<210> SEQ ID NO 346
<211> LENGTH: 22
<212> TYPE: PRT
<213> ORGANISM: Artificial sequence
<220> FEATURE:
<223> OTHER INFORMATION: synthetic

<400> SEQUENCE: 346

Pro Tyr Leu Asp Asp Phe Gln Lys Lys Trp Gln Glu Glu Met Glu Leu
1 5 10 15

Tyr Arg Gln Lys Val Glu
20

<210> SEQ ID NO 347
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: Xaa = Hydroxyproline

<400> SEQUENCE: 347

Pro Leu Arg Ala Glu Leu Gln Glu Gly Ala Arg Gln Lys Leu His Glu
1 5 10 15

Leu Xaa Glu Lys Leu Ser
20

<210> SEQ ID NO 348
<211> LENGTH: 22
<212> TYPE: PRT
<213> ORGANISM: Artificial sequence
<220> FEATURE:
<223> OTHER INFORMATION: synthetic

<400> SEQUENCE: 348

Pro Leu Gly Glu Glu Met Arg Asp Arg Ala Arg Ala His Val Asp Ala
1 5 10 15

Leu Arg Thr His Leu Ala
20

<210> SEQ ID NO 349
<211> LENGTH: 22
<212> TYPE: PRT
<213> ORGANISM: Artificial sequence
<220> FEATURE:
<223> OTHER INFORMATION: synthetic

<400> SEQUENCE: 349

Pro Tyr Ser Asp Glu Leu Arg Gln Arg Leu Ala Ala Arg Leu Glu Ala
1 5 10 15

Leu Lys Glu Asn Gly Gly
20

<210> SEQ ID NO 350
<211> LENGTH: 22
<212> TYPE: PRT
<213> ORGANISM: Artificial sequence
<220> FEATURE:
<223> OTHER INFORMATION: synthetic

<400> SEQUENCE: 350

Ala Arg Leu Ala Glu Tyr His Ala Lys Ala Thr Glu His Leu Ser Thr
1 5 10 15

Leu Ser Glu Lys Ala Lys
20

<210> SEQ ID NO 351
<211> LENGTH: 11
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa = Hydroxyproline

<400> SEQUENCE: 351

Pro Ala Leu Glu Asp Leu Arg Xaa Gly Leu Leu
1 5 10

<210> SEQ ID NO 352
<211> LENGTH: 22
<212> TYPE: PRT
<213> ORGANISM: Artificial sequence
<220> FEATURE:
<223> OTHER INFORMATION: synthetic

<400> SEQUENCE: 352

Pro Val Leu Glu Ser Phe Lys Val Ser Phe Leu Ser Ala Leu Glu Glu
1 5 10 15

Tyr Thr Lys Lys Leu Asn
20

<210> SEQ ID NO 353
<211> LENGTH: 21
<212> TYPE: PRT
<213> ORGANISM: Artificial sequence
<220> FEATURE:
<223> OTHER INFORMATION: synthetic

<400> SEQUENCE: 353

Pro Val Leu Glu Ser Phe Val Ser Phe Leu Ser Ala Leu Glu Glu Tyr
1 5 10 15

Thr Lys Lys Leu Asn
20

<210> SEQ ID NO 354
<211> LENGTH: 24
<212> TYPE: PRT
<213> ORGANISM: Artificial sequence
<220> FEATURE:
<223> OTHER INFORMATION: synthetic

<400> SEQUENCE: 354

Thr Val Leu Leu Leu Thr Ile Cys Ser Leu Glu Gly Ala Leu Val Arg
1 5 10 15

Arg Gln Ala Lys Glu Pro Cys Val
20

<210> SEQ ID NO 355
<211> LENGTH: 12
<212> TYPE: PRT
<213> ORGANISM: Artificial sequence
<220> FEATURE:
<223> OTHER INFORMATION: synthetic

<400> SEQUENCE: 355

Gln Thr Val Thr Asp Tyr Gly Lys Asp Leu Met Glu
1 5 10

<210> SEQ ID NO 356
<211> LENGTH: 20
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: Xaa = Hydroxyproline

<400> SEQUENCE: 356

Lys Val Lys Ser Pro Glu Leu Xaa Ala Glu Ala Lys Ser Tyr Phe Glu
1 5 10 15

Lys Ser Lys Glu
20

```
<210> SEQ ID NO 357
<211> LENGTH: 24
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Hydroxyproline
<220> FEATURE:
<221> NAME/KEY: misc_feature
<222> LOCATION: (20)..(20)
<223> OTHER INFORMATION: Xaa can be any naturally occurring amino acid

<400> SEQUENCE: 357

Val Leu Thr Leu Ala Leu Val Ala Val Ala Gly Ala Arg Ala Glu Val
1               5                   10                  15

Ser Ala Asp Xaa Val Ala Thr Val
            20


<210> SEQ ID NO 358
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Hydroxyproline
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid

<400> SEQUENCE: 358

Asn Asn Ala Lys Glu Ala Val Glu His Leu Xaa Lys Ser Glu Leu Thr
1               5                   10                  15

Xaa Xaa Leu Asn Ala Leu
            20


<210> SEQ ID NO 359
<211> LENGTH: 25
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: Xaa = Hydroxyproline

<400> SEQUENCE: 359

Leu Pro Val Leu Val Trp Leu Ser Ile Val Leu Glu Gly Pro Ala Pro
1               5                   10                  15

Ala Xaa Gly Thr Pro Asp Val Ser Ser
            20                  25


<210> SEQ ID NO 360
<211> LENGTH: 26
<212> TYPE: PRT
<213> ORGANISM: Artificial sequence
<220> FEATURE:
<223> OTHER INFORMATION: synthetic
```

<400> SEQUENCE: 360

Leu Pro Val Leu Val Val Val Leu Ser Ile Val Leu Glu Gly Pro Ala
1 5 10 15

Pro Ala Gln Gly Thr Pro Asp Val Ser Ser
20 25

<210> SEQ ID NO 361
<211> LENGTH: 21
<212> TYPE: PRT
<213> ORGANISM: Artificial sequence
<220> FEATURE:
<223> OTHER INFORMATION: synthetic

<400> SEQUENCE: 361

Ala Leu Asp Lys Leu Lys Glu Phe Gly Asn Thr Leu Glu Asp Lys Ala
1 5 10 15

Arg Glu Leu Ile Ser
20

<210> SEQ ID NO 362
<211> LENGTH: 22
<212> TYPE: PRT
<213> ORGANISM: Artificial sequence
<220> FEATURE:
<223> OTHER INFORMATION: synthetic

<400> SEQUENCE: 362

Val Val Ala Leu Leu Ala Leu Leu Ala Ser Ala Arg Ala Ser Glu Ala
1 5 10 15

Glu Asp Ala Ser Leu Leu
20

<210> SEQ ID NO 363
<211> LENGTH: 25
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: Xaa = Hydroxyproline

<400> SEQUENCE: 363

His Leu Arg Lys Leu Arg Lys Arg Leu Leu Arg Asp Ala Asp Asp Leu
1 5 10 15

Gln Lys Arg Leu Ala Val Tyr Xaa Ala
20 25

<210> SEQ ID NO 364
<211> LENGTH: 22
<212> TYPE: PRT
<213> ORGANISM: Artificial sequence
<220> FEATURE:
<223> OTHER INFORMATION: synthetic

<400> SEQUENCE: 364

Ala Gln Ala Trp Gly Glu Arg Leu Arg Ala Arg Met Glu Glu Met Gly
1 5 10 15

Ser Arg Thr Arg Asp Arg
20

<210> SEQ ID NO 365
<211> LENGTH: 20

```
<212> TYPE: PRT
<213> ORGANISM: Artificial sequence
<220> FEATURE:
<223> OTHER INFORMATION: synthetic

<400> SEQUENCE: 365

Leu Asp Glu Val Lys Glu Gln Val Ala Glu Val Arg Ala Lys Leu Glu
1               5                   10                  15

Glu Gln Ala Gln
            20


<210> SEQ ID NO 366
<211> LENGTH: 37
<212> TYPE: PRT
<213> ORGANISM: Artificial sequence
<220> FEATURE:
<223> OTHER INFORMATION: synthetic

<400> SEQUENCE: 366

Asp Trp Leu Lys Ala Phe Tyr Asp Lys Val Ala Glu Lys Leu Lys Glu
1               5                   10                  15

Ala Phe Pro Asp Trp Ala Lys Ala Ala Tyr Asp Lys Ala Ala Glu Lys
            20                  25                  30

Ala Lys Glu Ala Ala
        35


<210> SEQ ID NO 367
<211> LENGTH: 21
<212> TYPE: PRT
<213> ORGANISM: Artificial sequence
<220> FEATURE:
<223> OTHER INFORMATION: synthetic

<400> SEQUENCE: 367

Pro Val Leu Asp Leu Phe Arg Glu Leu Leu Asn Glu Leu Leu Glu Ala
1               5                   10                  15

Leu Lys Gln Lys Leu
            20


<210> SEQ ID NO 368
<211> LENGTH: 22
<212> TYPE: PRT
<213> ORGANISM: Artificial sequence
<220> FEATURE:
<223> OTHER INFORMATION: synthetic

<400> SEQUENCE: 368

Pro Val Leu Asp Leu Phe Arg Glu Leu Leu Asn Glu Leu Leu Glu Ala
1               5                   10                  15

Leu Lys Gln Lys Leu Ala
            20


<210> SEQ ID NO 369
<211> LENGTH: 22
<212> TYPE: PRT
<213> ORGANISM: Artificial sequence
<220> FEATURE:
<223> OTHER INFORMATION: synthetic

<400> SEQUENCE: 369

Pro Val Leu Asp Leu Phe Arg Glu Leu Leu Asn Glu Leu Leu Glu Ala
1               5                   10                  15

Leu Lys Gln Lys Leu Ala
            20
```

<210> SEQ ID NO 370
<211> LENGTH: 22
<212> TYPE: PRT
<213> ORGANISM: Artificial sequence
<220> FEATURE:
<223> OTHER INFORMATION: synthetic

<400> SEQUENCE: 370

Pro Val Leu Asp Leu Phe Arg Glu Leu Leu Asn Glu Leu Leu Glu Ala
1 5 10 15

Leu Lys Lys Leu Leu Lys
20

<210> SEQ ID NO 371
<211> LENGTH: 22
<212> TYPE: PRT
<213> ORGANISM: Artificial sequence
<220> FEATURE:
<223> OTHER INFORMATION: synthetic

<400> SEQUENCE: 371

Pro Val Leu Asp Leu Phe Arg Glu Leu Leu Asn Glu Leu Leu Glu Ala
1 5 10 15

Leu Lys Lys Leu Leu Ala
20

<210> SEQ ID NO 372
<211> LENGTH: 22
<212> TYPE: PRT
<213> ORGANISM: Artificial sequence
<220> FEATURE:
<223> OTHER INFORMATION: synthetic

<400> SEQUENCE: 372

Pro Leu Leu Asp Leu Phe Arg Glu Leu Leu Asn Glu Leu Leu Glu Ala
1 5 10 15

Leu Lys Lys Leu Leu Ala
20

<210> SEQ ID NO 373
<211> LENGTH: 26
<212> TYPE: PRT
<213> ORGANISM: Artificial sequence
<220> FEATURE:
<223> OTHER INFORMATION: synthetic

<400> SEQUENCE: 373

Glu Val Arg Ser Lys Leu Glu Glu Trp Phe Ala Ala Phe Arg Glu Phe
1 5 10 15

Ala Glu Glu Phe Leu Ala Arg Leu Lys Ser
20 25

<210> SEQ ID NO 374
<211> LENGTH: 20
<212> TYPE: PRT
<213> ORGANISM: Artificial sequence
<220> FEATURE:
<223> OTHER INFORMATION: synthetic

<400> SEQUENCE: 374

Ser Cys Val Arg Ala Cys Gly Ala Asp Ser Tyr Glu Met Glu Glu Asp
1 5 10 15

Gly Val Arg Lys

20

<210> SEQ ID NO 375
<211> LENGTH: 19
<212> TYPE: PRT
<213> ORGANISM: Artificial sequence
<220> FEATURE:
<223> OTHER INFORMATION: synthetic

<400> SEQUENCE: 375

Val Trp Ser Tyr Gly Val Thr Val Trp Glu Leu Met Thr Phe Gly Ser
1 5 10 15

Lys Pro Tyr

<210> SEQ ID NO 376
<211> LENGTH: 9
<212> TYPE: PRT
<213> ORGANISM: Artificial sequence
<220> FEATURE:
<223> OTHER INFORMATION: synthetic

<400> SEQUENCE: 376

Arg Met Phe Pro Asn Ala Pro Tyr Leu
1 5

<210> SEQ ID NO 377
<211> LENGTH: 19
<212> TYPE: PRT
<213> ORGANISM: Artificial sequence
<220> FEATURE:
<223> OTHER INFORMATION: synthetic

<400> SEQUENCE: 377

Ser Gly Gln Ala Arg Met Phe Pro Asn Ala Pro Tyr Leu Pro Ser Cys
1 5 10 15

Leu Glu Ser

<210> SEQ ID NO 378
<211> LENGTH: 23
<212> TYPE: PRT
<213> ORGANISM: Artificial sequence
<220> FEATURE:
<223> OTHER INFORMATION: synthetic

<400> SEQUENCE: 378

Ser Gly Gln Ala Arg Met Phe Pro Asn Ala Pro Tyr Leu Pro Ser Cys
1 5 10 15

Leu Glu Ser Gln Pro Thr Ile
20

<210> SEQ ID NO 379
<211> LENGTH: 6
<212> TYPE: PRT
<213> ORGANISM: Artificial sequence
<220> FEATURE:
<223> OTHER INFORMATION: synthetic

<400> SEQUENCE: 379

Arg Pro Ala Pro Gly Ser
1 5

<210> SEQ ID NO 380
<211> LENGTH: 7
<212> TYPE: PRT
<213> ORGANISM: Artificial sequence
<220> FEATURE:
<223> OTHER INFORMATION: synthetic

<400> SEQUENCE: 380

Pro Pro Ala His Gly Val Thr
1 5

<210> SEQ ID NO 381
<211> LENGTH: 5
<212> TYPE: PRT
<213> ORGANISM: Artificial sequence
<220> FEATURE:
<223> OTHER INFORMATION: synthetic

<400> SEQUENCE: 381

Pro Asp Thr Arg Pro
1 5

<210> SEQ ID NO 382
<211> LENGTH: 20
<212> TYPE: DNA
<213> ORGANISM: Artificial sequence
<220> FEATURE:
<223> OTHER INFORMATION: synthetic

<400> SEQUENCE: 382
tccatgacgt tcctgacgtt 20

<210> SEQ ID NO 383
<211> LENGTH: 9
<212> TYPE: PRT
<213> ORGANISM: Artificial sequence
<220> FEATURE:
<223> OTHER INFORMATION: synthetic

<400> SEQUENCE: 383

Ala Ser Met Thr Asn Met Glu Leu Met
1 5

<210> SEQ ID NO 384
<211> LENGTH: 11
<212> TYPE: PRT
<213> ORGANISM: Artificial sequence
<220> FEATURE:
<223> OTHER INFORMATION: synthetic

<400> SEQUENCE: 384

Cys Ser Ser Ser Ile Ile Asn Phe Glu Lys Leu
1 5 10

<210> SEQ ID NO 385
<211> LENGTH: 8
<212> TYPE: PRT
<213> ORGANISM: Artificial sequence
<220> FEATURE:
<223> OTHER INFORMATION: synthetic

<400> SEQUENCE: 385

Ser Ile Ile Asn Phe Glu Lys Leu
1 5

-continued

<210> SEQ ID NO 386
<211> LENGTH: 10
<212> TYPE: PRT
<213> ORGANISM: Artificial sequence
<220> FEATURE:
<223> OTHER INFORMATION: synthetic

<400> SEQUENCE: 386

Cys Ser Ser Ser Ile Ile Asn Phe Glu Lys
1 5 10